United States Patent
Brooks et al.

(10) Patent No.: US 8,658,636 B2
(45) Date of Patent: Feb. 25, 2014

(54) TRPV4 ANTAGONISTS

(75) Inventors: Carl A. Brooks, King of Prussia, PA (US); Mui Cheung, King of Prussia, PA (US); Hilary S. Eidam, King of Prussia, PA (US); Ryan M. Fox, King of Prussia, PA (US); Mark A. Hilfiker, King of Prussia, PA (US); Eric S. Manas, King of Prussia, PA (US); Guosen Ye, King of Prussia, PA (US)

(73) Assignee: GlaxoSmithKline, LLC, Philadelphia, PA (US)

( * ) Notice: Subject to any disclaimer, the term of this patent is extended or adjusted under 35 U.S.C. 154(b) by 89 days.

(21) Appl. No.: 13/635,952

(22) PCT Filed: Mar. 23, 2011

(86) PCT No.: PCT/US2011/029579
§ 371 (c)(1),
(2), (4) Date: Sep. 19, 2012

(87) PCT Pub. No.: WO2011/119701
PCT Pub. Date: Sep. 29, 2011

(65) Prior Publication Data
US 2013/0012499 A1    Jan. 10, 2013

Related U.S. Application Data

(60) Provisional application No. 61/316,432, filed on Mar. 23, 2010.

(51) Int. Cl.
| | | |
|---|---|---|
| C07D 401/14 | (2006.01) |
| A61K 31/4453 | (2006.01) |
| C07D 413/14 | (2006.01) |
| A61K 31/5355 | (2006.01) |
| C07D 223/02 | (2006.01) |
| A61K 31/55 | (2006.01) |
| C07D 215/14 | (2006.01) |
| A61P 9/00 | (2006.01) |
| A61P 11/00 | (2006.01) |
| A61P 13/00 | (2006.01) |

(52) U.S. Cl.
USPC .......... 514/217.04; 514/235.2; 514/314; 514/316; 540/597; 544/128; 546/187; 546/194

(58) Field of Classification Search
USPC .......... 514/316, 235.2, 217.04, 314; 540/597; 544/128; 546/187, 194
See application file for complete search history.

(56) References Cited

U.S. PATENT DOCUMENTS

| 6,169,097 B1 | 1/2001 | Janssens et al. |
| 2003/0113336 A1* | 6/2003 | Harris et al. ............... 424/178.1 |
| 2005/0070574 A1 | 3/2005 | Farina et al. |
| 2007/0129363 A1 | 6/2007 | Chapdelaine et al. |

FOREIGN PATENT DOCUMENTS

| WO | WO2007/071055 A1 | 6/2007 |
| WO | WO 2011119693 A1 * | 9/2011 |

* cited by examiner

*Primary Examiner* — James O Wilson
*Assistant Examiner* — Oluwafemi Masha
(74) *Attorney, Agent, or Firm* — Linda E. Hall; John L. Lemanowicz

(57) ABSTRACT

The present invention relates to quinoline analogs, pharmaceutical compositions containing them and their use as TRPV4 antagonists.

8 Claims, No Drawings

TRPV4 ANTAGONISTS

This application is a 371 of International Application No. PCT/US2011/029579, filed Mar. 23, 2011, which claims the benefit of U.S. Provisional Application No. 61/316,432, filed Mar. 23, 2010, which is incorporated herein in its entirety.

FIELD OF THE INVENTION

The present invention relates to quinoline analogs, pharmaceutical compositions containing them and their use as TRPV4 antagonists.

BACKGROUND OF THE INVENTION

TRPV4 is a member of the Transient Receptor Potential (TRP) superfamily of cation channels and is activated by heat, demonstrating spontaneous activity at 528 temperatures (Guler et al., 2002. *J Neurosci* 22: 6408-6414). Consistent with its polymodal activation property TRPV4 is also activated by hypotonicity and physical cell stress/pressure (Strotmann et al., 2000. *Nat Cell Biol* 2: 695-702), through a mechanism involving phospholipase A2 activation, arachidonic acid and epoxyeicosatrienoic acid generation (Vriens et al., 2004. *Proc Natl Acad Sci USA* 101: 396-401), In addition, amongst other mechanisms proposed, tyrosine kinase activity may also regulate TRPV4 (Wegierski et al., 2009. *J Biol Chem*. 284: 2923-33).

Heart failure results in the decreased ability of the left ventricle to pump blood into the peripheral circulation as indicated by a reduced ejection fraction and/or left ventricular dialation. This increases the left ventricular end diastolic pressure resulting in enhanced pulmonary blood pressures. This places the septal barrier, which separates the circulatory aqueous environment and the alveolar airspaces of the lung, at risk. Increased pulmonary pressure results in the flow of fluid from the pulmonary circulation into the alveolar space resulting in lung edema/congestion, as is observed in patients with congestive heart failure.

TRPV4 is expressed in the lung (Delany et al., 2001. *Physiol. Genomics* 4: 165-174) and has been shown to mediate $Ca^{2+}$ entry in isolated endothelial cells and in intact lungs (Jian et al., 2009 *Am J Respir Cell Mol Biol* 38: 386-92). Endothelial cells are responsible for forming the capillary vessels that mediate oxygen/carbon dioxide exchange and contribute to the septal barrier in the lung. Activation of TRPV4 channels results in contraction of endothelial cells in culture and cardiovascular collapse in vivo (Willette et al., 2008 *J Pharmacol Exp Ther* 325: 466-74), at least partially due to the enhanced filtration at the septal barrier evoking lung edema and hemorrage (Alvarez et al., 2006. *Circ Res* 99: 988-95). Indeed filtration at the septal barrier is increased in response to increased vascular and/or airway pressures and this response is dependent on the activity of TRPV4 channels (Jian et al., 2008 *Am J Respir Cell Mol Biol* 38: 386-92). Overall this suggests a clinical benefit of inhibiting TRPV4 function in the treatment of heart failure associated lung congestion.

Additional benefit is suggested in inhibiting TRPV4 function in pulmonary-based pathologies presenting with symptoms including lung edema/congestion, infection, inflammation, pulmonary remodeling and/or altered airway reactivity. A genetic link between TRPV4 and chronic obstructive pulmonary disorder (COPD) has recently been identified (Zhu et al., 2009. *Hum Mol Genetics,* 18: 2053-62) suggesting potential efficacy for TRPV4 modulation in treatment of COPD with or without coincident emphysema. Enhanced TRPV4 activity is also a key driver in ventilator-induced lung injury (Hamanaka et al., 2007. *Am J Physiol* 293: L923-32) and it is suggested that TRPV4 activation may underlie pathologies involved in acute respiratory distress syndrome (ARDS), pulmonary fibrosis and asthma (Liedtke & Simon, 2004. *Am J Physiol* 287: 269-71). A potential clinical benefit for TRPV4 blockers in the treatment of sinusitis, as well as allergic and non-allergic rhinitis is also supported (Bhargave et al., 2008. *Am J Rhinol* 22:7-12).

In addition, TRPV4 channels have recently been implicated in urinary bladder function (Thorneloe et al., 2008. *J Pharmacol Exp Ther* 326: 432-42) and are likely to provide therapeutic benefit for conditions of bladder overactivity, characterized by an increased urge to urinate and an enhancement of micturition frequency. These data suggest a clinically beneficial effect of inhibiting TRPV4, located on multiple cell types, on urinary bladder function that is likely to be effective in bladder disorders such as overactive bladder, interstitial cystitis and painful bladder syndrome.

Furthermore TRPV4 has in recent years been implicated in a number of other physiological/pathophysiological processes in which TRPV4 antagonists are likely to provide significant clinical benefit. These include various aspects of pain (Todaka et al., 2004. *J Biol Chem* 279: 35133-35138; Grant et al., 2007. *J Physiol* 578: 715-733; Alessandri-Haber et al., 2006. *J Neurosci* 26: 3864-3874), genetic motor neuron disorders (Auer-Grumbach et al., 2009. *Nat Genet*. PMID: 20037588; Deng et al., 2009. *Nat Genet* PMID: 20037587; Landouré et al., 2009. *Nat Genet* PMID: 20037586), cardiovascular disease (Earley et al., 2005. *Circ Res* 97: 1270-9; Yang et al., 2006. *Am. J Physiol.* 290:L1267-L1276), and bone related disorders; including osteoarthritis (Muramatsu et al., 2007. *J. Biol. Chem.* 282: 32158-67), genetic gain-of function mutations (Krakow et al., 2009. *Am J Hum Genet* 84: 307-15; Rock et al., 2008 *Nat Genet* 40: 999-1003) and osteoclast differentiation (Masuyama et al. 2008. *Cell Metab* 8: 257-65).

SUMMARY OF THE INVENTION

In one aspect this invention provides for quinoline analogs, pharmaceutically acceptable salts thereof, and pharmaceutical compositions containing them.

In a second aspect, this invention provides for the use of the compounds of Formula (I) as TRPV4 antagonists.

In another aspect, this invention provides for the use of the compounds of Formula (I) for treating and preventing conditions associated with TRPV4 imbalance.

In yet another aspect, this invention provides for the use of the compounds of Formula (I) for the treatment or prevention of atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, pulmonary fibrosis, sinusitis/rhinitis, asthma, overactive bladder, pain, motor neuron disorders, genetic gain of function disorders, cardiovascular disease, renal dysfunction, osteoarthritis crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence.

The TRPV4 antagonist may be administered alone or in conjunction with one or more other therapeutic agents, eg. agents being selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, beta blocker, aldosterone antagonists, iontropes, NSAIDS, nitric oxide donors, calcium channel modulators, muscarinic antagonists, steroidal anti-inflammatory drugs, bronchodilators, anti-histamines, leukotriene antagonist, HMG-CoA reductase inhibitors, dual non-selective β-adrenoceptor and α₁-adrenoceptor antagonists, type-5 phosphodiesterase inhibitors, and renin inhibitors.

Other aspects and advantages of the present invention are described further in the following detailed description of the preferred embodiments thereof.

DETAILED DESCRIPTION OF THE INVENTION

The present invention provides for compounds of Formula (I):

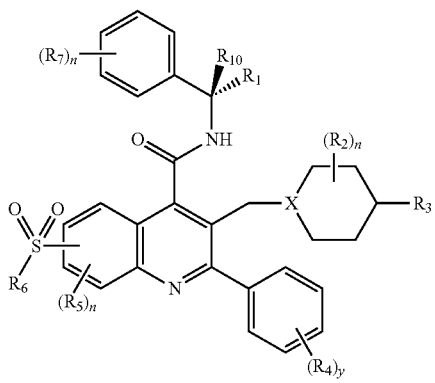

wherein:

$R_1$ is independently H, $CF_3$, or Me;

$R_2$ is independently OH, $OC_{1-4}$ alkyl, $C_{1-4}$ alkyl, $CH_2OH$, F, $CH_2OC_{1-4}$ alkyl, $CF_3$, or $CF_2H$;

$R_3$ is morpholinyl, piperidinyl, pyrrolidinyl, or hexahydroazepinyl; all of which may be unsubstituted or substituted by one or two $R_8$;

or $R_3$ is $N(C_{1-6}$ alkyl$)_2$, wherein $C_{1-6}$ alkyl may be unsubstituted or substituted by OH or —$OCH_3$, $R_4$ is $CF_3$, halo, OMe, or $C_{1-3}$ alkyl;

$R_5$ is

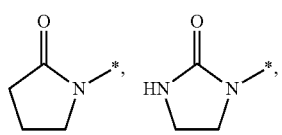

halo, cyano, $CF_3$, $C_{1-5}$ alkyl, $C_{2-4}$ alkenyl, pyrrolidinyl, morpholinyl, piperidinyl, phenyl, pyridyl, pyrazolyl, pyrrolyl, piperazinyl, pyrimidinyl, OH, O—$C_{1-4}$alkyl-$OR_6$, $OCF_3$, $OCH_2CF_3$, $OCH_2CN$, $OR_6$, or $CH_2R_9$;

wherein the

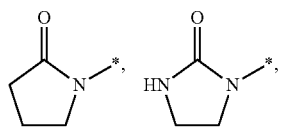

pyrrolidinyl, morpholinyl, piperidinyl, phenyl, pyridyl, pyrazolyl, pyrrolyl, piperazinyl or pyrimidinyl may be unsubstituted or substituted with one or two halo, OH, $OR_6$ or $R_6$;

$R_6$ is independently $C_{1-4}$ alkyl, $C_{3-6}$ cycloalkyl;

$R_7$ is independently halo, methyl, or OMe;

$R_8$ is independently OH, $OC_{1-4}$ alkyl, $C_{1-4}$ alkyl, $CH_2OH$, F, $CH_2OC_{1-4}$ alkyl, $CF_3$, or $CF_2H$;

$R_9$ is independently pyrrolidinyl, morpholinyl, or piperidinyl;

$R_{10}$ is independently H, $CF_3$, or Me;

n is independently 0, 1, or 2;

X is N or C;

y is 1 or 2;

or a pharmaceutically acceptable salt thereof.

"Alkyl" refers to a monovalent saturated hydrocarbon chain having the specified number of member atoms. For example, $C_{1-4}$ alkyl refers to an alkyl group having from 1 to 4 member atoms. Alkyl groups may be straight or branched. Representative branched alkyl groups have one, two, or three branches. Alkyl includes methyl, ethyl, propyl (n-propyl and isopropyl), and butyl (n-butyl, isobutyl, and t-butyl).

"Cycloalkyl" refers to a monovalent saturated or unsaturated hydrocarbon ring having the specified number of member atoms. For example, $C_{3-6}$ cycloalkyl refers to a cycloalkyl group having from 3 to 6 member atoms. Unsaturated cycloalkyl groups have one or more carbon-carbon double bonds within the ring. Cycloalkyl groups are not aromatic. Cycloalkyl includes cyclopropyl, cyclopropenyl, cyclobutyl, cyclobutenyl, cyclopentyl, cyclopentenyl, cyclohexyl, and cyclohexenyl.

When used herein, the terms 'halogen' and 'halo' mean fluorine, chlorine, bromine and iodine, and fluoro, chloro, bromo, and iodo, respectively.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

With regard to stereoisomers, the compounds of Formula (I) may have one or more asymmetric carbon atom and may occur as racemates, racemic mixtures and as individual enantiomers or diastereomers. All such isomeric forms are included within the present invention, including mixtures thereof.

As used herein, "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The skilled artisan will appreciate that pharmaceutically acceptable salts of the compounds according to Formula (I) may be prepared. These pharmaceutically acceptable salts may be prepared in situ during the final isolation and purification of the compound, or by separately treating the purified compound in its free acid or free base form with a suitable base or acid, respectively.

In certain embodiments, compounds according to Formula (I) may contain an acidic functional group and are, therefore, capable of forming pharmaceutically acceptable base addition salts by treatment with a suitable base. Examples of such bases include a) hydroxides, carbonates, and bicarbonates of sodium, potassium, lithium, calcium, magnesium, aluminium, and zinc; and b) primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically acceptable acid addition salts by treatment with a suitable acid. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, succinic acid, malic acid, malonic acid, tartaric acid, citric acid, salicylic acid, benzoic acid, tannic acid, formic acid, stearic acid, lactic acid, ascorbic acid, methylsulfonic acid, p-toluenesulfonic acid, oleic acid, lauric acid, and the like.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed for crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as 2H, 3H, 11C, 13C, 14C, 15N, 17O, 18O, 31P, 32P, 35S, 18F, 36Cl, 123I and 125I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as 3H, 14C are incorporated, are useful in drug and/or substrate tissue distribution assays. Tritiated, i.e., 3H, and carbon-14, i.e., 14C, isotopes are particularly preferred for their ease of preparation and detectability. 11C and 18F isotopes are particularly useful in PET (positron emission tomography), and 125I isotopes are particularly useful in SPECT (single photon emission computerized tomography), all useful in brain imaging. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Representative Embodiments

In one embodiment:

$R_1$ is independently H, $CF_3$, or Me;

$R_2$ is independently OH, $OC_{1-4}$ alkyl, $C_{1-4}$ alkyl, $CH_2OH$, F, $CH_2OC_{1-4}$ alkyl, $CF_3$, or $CF_2H$;

$R_3$ is morpholinyl, piperidinyl, pyrrolidinyl, or hexahydroazepinyl; all of which may be unsubstituted or substituted by one or two $R_8$;

or $R_3$ is $N(C_{1-6}alkyl)_2$, wherein $C_{1-6}$ alkyl may be unsubstituted or substituted by OH or —$OCH_3$, $R_4$ is $CF_3$, halo, OMe, or $C_{1-3}$ alkyl;

$R_5$ is

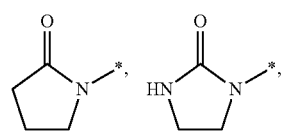

halo, cyano, $CF_3$, $C_{1-5}$ alkyl, $C_{2-4}$ alkenyl, pyrrolidinyl, morpholinyl, piperidinyl, phenyl, pyridyl, pyrazolyl, pyrrolyl, piperazinyl, pyrimidinyl, OH, O—$C_{1-4}$alkyl-$OR_6$, $OCF_3$, $OCH_2CF_3$, $OCH_2CN$, $OR_6$, or $CH_2R_9$;

wherein the

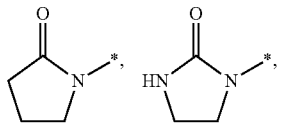

pyrrolidinyl, morpholinyl, piperidinyl, phenyl, pyridyl, pyrazolyl, pyrrolyl, piperazinyl or pyrimidinyl may be unsubstituted or substituted with one or two halo, OH, $OR_6$ or $R_6$;
$R_6$ is independently $C_{1-4}$ alkyl, $C_{3-6}$ cycloalkyl;
$R_7$ is independently halo, methyl, or OMe;
$R_8$ is independently OH, $OC_{1-4}$ alkyl, $C_{1-4}$ alkyl, $CH_2OH$, F, $CH_2OC_{1-4}$ alkyl, $CF_3$, or $CF_2H$;
$R_9$ is independently pyrrolidinyl, morpholinyl, or piperidinyl;
$R_{10}$ is independently H, $CF_3$, or Me;
n is independently 0, 1, or 2;
X is N or C; and
y is 1 or 2.

In another embodiment:
$R_1$ is independently $CF_3$, or Me;
$R_2$ is independently OH, $OC_{1-4}$ alkyl, $C_{1-4}$ alkyl, $CH_2OH$, F, $CH_2OC_{1-4}$ alkyl, $CF_3$, or $CF_2H$;
$R_3$ is morpholinyl, piperidinyl, pyrrolidinyl, or hexahydroazepinyl; all of which may be unsubstituted or substituted by one or two $R_8$;
or $R_3$ is $N(C_{1-6}alkyl)_2$, wherein $C_{1-6}$ alkyl may be unsubstituted or substituted by OH or —$OCH_3$,
$R_4$ is $CF_3$ or halo;
$R_5$ is

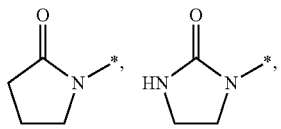

halo, cyano, $CF_3$, $C_{1-5}$ alkyl, $C_{2-4}$ alkenyl, pyrrolidinyl, morpholinyl, piperidinyl, phenyl, pyridyl, pyrazolyl, pyrrolyl, piperazinyl, pyrimidinyl, OH, O—$C_{1-4}$alkyl-$OR_6$, $OCF_3$, $OCH_2CF_3$, $OCH_2CN$, $OR_6$, or $CH_2R_9$;
wherein the

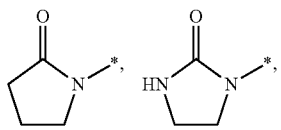

pyrrolidinyl, morpholinyl, piperidinyl, phenyl, pyridyl, pyrazolyl, pyrrolyl, piperazinyl or pyrimidinyl may be unsubstituted or substituted with one or two, $OR_6$ or $R_6$;
$R_6$ is independently $C_{1-4}$ alkyl or $C_{3-6}$ cycloalkyl;
$R_7$ is independently halo, methyl, or OMe;
$R_8$ is independently OH, $OC_{1-4}$ alkyl, $C_{1-4}$ alkyl, $CH_2OH$, F, $CH_2OC_{1-4}$ alkyl, $CF_3$, or $CF_2H$;
$R_9$ is independently pyrrolidinyl, morpholinyl, or piperidinyl;
$R_{10}$ is H;
n is independently 0, or 1;
X is N or C; and
y is 1 or 2.

In another embodiment:
$R_1$ is independently $CF_3$, or Me;
$R_2$ is independently $C_{1-4}$ alkyl, $CF_3$, or $CF_2H$;
$R_3$ is morpholinyl, piperidinyl, pyrrolidinyl, or hexahydroazepinyl; all of which may be unsubstituted or substituted by one or two $R_8$;
or $R_3$ is $N(C_{1-6}$ alkyl$)_2$, wherein $C_{1-6}$ alkyl may be unsubstituted or substituted by OH or —$OCH_3$;
$R_4$ is $CF_3$ or halo;
$R_5$ is halo, cyano, $CF_3$, $C_{1-5}$ alkyl, $C_{2-4}$ alkenyl, OH, O—$C_{1-4}$ alkyl-$OR_6$, $OCF_3$, $OCH_2CF_3$, $OCH_2CN$, or $OR_6$;
$R_6$ is independently $C_{1-4}$ alkyl, or $C_{3-6}$ cycloalkyl;
$R_7$ is independently halo, methyl, or OMe;
$R_8$ is independently OH, $OC_{1-4}$ alkyl, $C_{1-4}$ alkyl, $CH_2OH$, F, $CH_2OC_{1-4}$ alkyl, $CF_3$, or $CF_2H$;
$R_{10}$ is H;
n is independently 0, or 1;
X is N; and
y is 1 or 2.

In another embodiment:
$R_1$ is independently $CF_3$, or Me;
$R_2$ is independently $C_{1-4}$ alkyl;
$R_3$ is morpholinyl, piperidinyl, pyrrolidinyl, or hexahydroazepinyl; all of which may be unsubstituted or substituted by one or two $R_8$;
$R_4$ is $CF_3$ or halo;
$R_5$ is halo, cyano, $CF_3$, $C_{1-5}$ alkyl, $C_{2-4}$ alkenyl, OH, O—$C_{1-4}$ alkyl-$OR_6$, $OCF_3$, $OCH_2CF_3$, $OCH_2CN$, or $OR_6$;
$R_6$ is independently $C_{1-4}$ alkyl, or $C_{3-6}$ cycloalkyl;
n is 0 for $R_7$;
$R_8$ is independently OH, $C_{1-4}$ alkyl, F, $CF_3$, or $CF_2H$;
$R_{10}$ is H;
n is independently 0, or 1;
X is N; and
y is 1 or 2.

It is to be understood that the present invention covers all combinations of particular groups described hereinabove. Specific examples of compounds of the present invention include the following:

3-(1,4'-bipiperidin-1'-ylmethyl)-6-(methylsulfonyl)-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-6-(methylsulfonyl)-N-[(1S)-1-phenylethyl]-2-[3-(trifluoromethyl)phenyl]-4-quinolinecarboxamide;

3-(1,4'-bipiperidin-1'-ylmethyl)-6-(ethylsulfonyl)-7-(methyloxy)-2-[3-(trifluoromethyl)phenyl]-N-[(1R)-2,2,2-trifluoro-1-phenylethyl]-4-quinolinecarboxamide;

3-(1,4'-bipiperidin-1-ylmethyl)-7-(methyloxy)-6-(methylsulfonyl)-N-[(1S)-1-phenylethyl]-2-[3-(trifluoromethyl)phenyl]-4-quinolinecarboxamide;

3-(1,4'-bipiperidin-1'-ylmethyl)-7-(methyloxy)-6-(methylsulfonyl)-2-[3-trifluoromethyl)phenyl]-N-[(1R)-2,2,2-trifluoro-1-phenylethyl]-4-quinolinecarboxamide;

7-(methyloxy)-6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

7-(methyloxy)-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-6-(ethylsulfonyl)-7-(methyloxy)-N-[(1S)-1-phenylethyl]-2-[3-(trifluoromethyl)phenyl]-4-quinolinecarboxamide;

6-(ethylsulfonyl)-7-(methyloxy)-3-{[4-(4-morpholinyl)-1-piperidinyl]methyl}-N-[(1S)-1-phenylethyl]-2-[3-(trifluoromethyl)phenyl]-4-quinolinecarboxamide;

3-(1,4'-bipiperidin-1'-ylmethyl)-6-[(1-methylethyl)sulfonyl]-7-(methyloxy)-N-[(1S)-1-phenylethyl]-2-[3-(trifluoromethyl)phenyl]-4-quinolinecarboxamide;

6-[(1-methylethyl)sulfonyl]-7-(methyloxy)-3-{[4-(4-morpholinyl)-1-piperidinyl]methyl}-N-[(1S)-1-phenylethyl]-2-[3-(trifluoromethyl)phenyl]-4-quinolinecarboxamide;

6-(ethylsulfonyl)-7-(methyloxy)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

7-(ethyloxy)-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-7-(ethyloxy)-6-(methylsulfonyl)-N-[(1S)-1-phenylethyl]-2-[3-(trifluoromethyl)phenyl]-4-quinolinecarboxamide;

3-(1,4'-bipiperidin-1'-ylmethyl)-7-(ethyloxy)-6-(methylsulfonyl)-2-[3-(trifluoromethyl)phenyl]-N-[(1R)-2,2,2-trifluoro-1-phenylethyl]-4-quinolinecarboxamide;

7-(ethyloxy)-6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

3-(1,4'-bipiperidin-1'-ylmethyl)-7-[(1-methylethyl)oxy]-6-(methylsulfonyl)-N-[(1S)-1-phenylethyl]-2-[3-(trifluoromethyl)phenyl]-4-quinolinecarboxamide;

3-(1,4'-bipiperidin-1'-ylmethyl)-7-[(1-methylethyl)oxy]-6-(methylsulfonyl)-2-[3-(trifluoromethyl)phenyl]-N-[(1R)-2,2,2-trifluoro-1-phenylethyl]-4-quinolinecarboxamide;

7-[(1-methylethyl)oxy]-6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

7-[(1-methylethyl)oxy]-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-6-[(1-methylethyl)sulfonyl]-7-(methyloxy)-2-[3-(trifluoromethyl)phenyl]-N-[(1R)-2,2,2-trifluoro-1-phenylethyl]-4-quinolinecarboxamide;

6-[(1-methylethyl)sulfonyl]-7-(methyloxy)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

7-(ethyloxy)-6-[(1-methylethyl)sulfonyl]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-7-(ethyloxy)-6-[(1-methylethyl)sulfonyl]-2-[3-(trifluoromethyl)phenyl]-N-[(1R)-2,2,2-trifluoro-1-phenylethyl]-4-quinolinecarboxamide;

7-(ethyloxy)-6-[(1-methylethyl)sulfonyl]-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;

7-(ethyloxy)-6-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-7-(ethyloxy)-6-(ethylsulfonyl)-N-[(1S)-1-phenylethyl]-2-[3-(trifluoromethyl)phenyl]-4-quinolinecarboxamide;

3-(1,4'-bipiperidin-1'-ylmethyl)-7-(ethyloxy)-6-(ethylsulfonyl)-2-[3-(trifluoromethyl)phenyl]-N-[(1R)-2,2,2-trifluoro-1-phenylethyl]-4-quinolinecarboxamide;

7-(ethyloxy)-6-(ethylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

7-(ethyloxy)-6-(ethylsulfonyl)-N-[(1S)-1-phenylethyl]-3-{[4-(1-pyrrolidinyl)-1-piperidinyl]methyl}-2-[3-(trifluoromethyl)phenyl]-4-quinolinecarboxamide;

7-(ethyloxy)-6-(ethylsulfonyl)-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-6-(ethylsulfonyl)-7-[(1-methylethyl)oxy]-N-[(1S)-1-phenylethyl]-2-[3-(trifluoromethyl)phenyl]-4-quinolinecarboxamide;

3-(1,4'-bipiperidin-1'-ylmethyl)-6-(ethylsulfonyl)-7-[(1-methylethyl)oxy]-2-[3-(trifluoromethyl)phenyl]-N-[(1R)-2,2,2-trifluoro-1-phenylethyl]-4-quinolinecarboxamide;

6-(ethylsulfonyl)-7-[(1-methylethyl)oxy]-3-{[4-(4-morpholinyl)-1-piperidinyl]methyl}-N-[(1S)-1-phenylethyl]-2-[3-(trifluoromethyl)phenyl]-4-quinolinecarboxamide;

6-(ethylsulfonyl)-7-[(1-methylethyl)oxy]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

6-(ethylsulfonyl)-7-[(1-methylethyl)oxy]-N-[(1S)-1-phenylethyl]-3-{[4-(1-pyrrolidinyl)-1-piperidinyl]methyl}-2-[3-(trifluoromethyl)phenyl]-4-quinolinecarboxamide;

6-(ethylsulfonyl)-7-[(1-methylethyl)oxy]-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;

6-[(1-methylethyl)sulfonyl]-3-{[3-methyl-4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

6-[(1-methylethyl)sulfonyl]-3-{[3-methyl-4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;

3-[(3'-methyl-1,4'-bipiperidin-1'-yl)methyl]-6-[(1-methylethyl)sulfonyl]-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-7-(methylsulfonyl)-N-[(1S)-1-phenylethyl]-2-[3-(trifluoromethyl)phenyl]-4-quinolinecarboxamide;

3-(1,4'-bipiperidin-1'-ylmethyl)-7-(methylsulfonyl)-2-[3-(trifluoromethyl)phenyl]-N-[(1R)-2,2,2-trifluoro-1-phenylethyl]-4-quinolinecarboxamide;

7-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

7-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-7-(ethylsulfonyl)-N-(1-methyl-1-phenylethyl)-2-[3-(trifluoromethyl)phenyl]-4-quinolinecarboxamide;

3-(1,4'-bipiperidin-1'-ylmethyl)-7-(ethylsulfonyl)-N-[(1S)-1-phenylethyl]-2-[3-(trifluoromethyl)phenyl]-4-quinolinecarboxamide;

7-(ethylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

7-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-7-(ethylsulfonyl)-2-[3-(trifluoromethyl)phenyl]-N-[(1R)-2,2,2-trifluoro-1-phenylethyl]-4-quinolinecarboxamide;

6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-6-(ethylsulfonyl)-N-[(1S)-1-phenylethyl]-2-[3-(trifluoromethyl)phenyl]-4-quinolinecarboxamide;

3-(1,4'-bipiperidin-1'-ylmethyl)-6-(ethylsulfonyl)-2-[3-(trifluoromethyl)phenyl]-N-[(1R)-2,2,2-trifluoro-1-phenylethyl]-4-quinolinecarboxamide;

6-(ethylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

6-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-6-[(1-methylethyl)sulfonyl]-N-[(1S)-1-phenylethyl]-2-[3-(trifluoromethyl)phenyl]-4-quinolinecarboxamide;

3-(1,4'-bipiperidin-1'-ylmethyl)-6-[(1-methylethyl)sulfonyl]-2-[3-(trifluoromethyl)phenyl]-N-[(1R)-2,2,2-trifluoro-1-phenylethyl]-4-quinolinecarboxamide;

6-[(1-methylethyl)sulfonyl]-3-{[4-(4-morpholinyl)-1-piperidinyl]methyl}-N-[(1S)-1-phenylethyl]-2-[3-(trifluoromethyl)phenyl]-4-quinolinecarboxamide;

7-chloro-6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

7-chloro-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

6-[(1-methylethyl)sulfonyl]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

6-[(1-methylethyl)sulfonyl]-3-{[4-(4-morpholinyl)-1-piperidinyl]methyl}-2-[3-(trifluoromethyl)phenyl]-N-[(1S)-2,2,2-trifluoro-1-phenylethyl]-4-quinolinecarboxamide;

3-(1,4'-bipiperidin-1'-ylmethyl)-7-chloro-6-(methylsulfonyl)-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-7-chloro-6-(methylsulfonyl)-N-[(1S)-1-phenylethyl]-2-[3-(trifluoromethyl)phenyl]-4-quinolinecarboxamide;

3-(1,4'-bipiperidin-1'-ylmethyl)-7-chloro-6-(ethylsulfonyl)-N-[(1S)-1-phenylethyl]-2-[3-(trifluoromethyl)phenyl]-4-quinolinecarboxamide;

3-(1,4'-bipiperidin-1'-ylmethyl)-7-chloro-6-(ethylsulfonyl)-2-[3-(trifluoromethyl)phenyl]-N-[(1R)-2,2,2-trifluoro-1-phenylethyl]-4-quinolinecarboxamide;

7-chloro-6-(ethylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

7-chloro-6-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-7-chloro-6-[(1-methylethyl)sulfonyl]-N-[(1S)-1-phenylethyl]-2-[3-(trifluoromethyl)phenyl]-4-quinolinecarboxamide;

3-(1,4'-bipiperidin-1'-ylmethyl)-7-chloro-6-[(1-methylethyl)sulfonyl]-2-[3-(trifluoromethyl)phenyl]-N-[(1R)-2,2,2-trifluoro-1-phenylethyl]-4-quinolinecarboxamide;

7-chloro-6-[(1-methylethyl)sulfonyl]-3-{[4-(4-morpholinyl)-1-piperidinyl]methyl}-N-[(1S)-1-phenylethyl]-2-[3-(trifluoromethyl)phenyl]-4-quinolinecarboxamide;

72)7-chloro-6-[(1-methylethyl)sulfonyl]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

6-(methylsulfonyl)-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;

6-(methylsulfonyl)-N-[(1S)-1-phenylethyl]-3-{[4-(1-pyrrolidinyl)-1-piperidinyl]methyl}-2-[3-(trifluoromethyl)phenyl]-4-quinolinecarboxamide;

3-({4-[(3S)-3-fluoro-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-({4-[(3S)-3-fluoro-1-pyrrolidinyl]-1-piperidinyl}methyl)-6-(methylsulfonyl)-N-[(1S)-1-phenylethyl]-2-[3-(trifluoromethyl)phenyl]-4-quinolinecarboxamide;

3-[(4,4-difluoro-1,4'-bipiperidin-1'-yl)methyl]-6-(methylsulfonyl)-2-[3-(trifluoromethyl)phenyl]-N-[(1R)-2,2,2-trifluoro-1-phenylethyl]-4-quinolinecarboxamide;

3-[(4,4-difluoro-1,4'-bipiperidin-1'-yl)methyl]-6-(methylsulfonyl)-N-[(1S)-1-phenylethyl]-2-[3-(trifluoromethyl)phenyl]-4-quinolinecarboxamide;

3-{[(3S)-3-hydroxy-1,4'-bipiperidin-1-yl]methyl}-6-(methylsulfonyl)-2-[3-(trifluoromethyl)phenyl]-N-[(1R)-2,2,2-trifluoro-1-phenylethyl]-4-quinolinecarboxamide;

3-{[(3S)-3-hydroxy-1,4'-bipiperidin-1-yl]methyl}-6-(methylsulfonyl)-N-[(1S)-1-phenylethyl]-2-[3-(trifluoromethyl)phenyl]-4-quinolinecarboxamide;

3-{[(3R)-3-hydroxy-1,4'-bipiperidin-1'-yl]methyl}-6-(methylsulfonyl)-2-[3-(trifluoromethyl)phenyl]-N-[(1R)-2,2,2-trifluoro-1-phenylethyl]-4-quinolinecarboxamide;

3-{[(3R)-3-hydroxy-1,4'-bipiperidin-1'-yl]methyl}-6-(methylsulfonyl)-N-[(1S)-1-phenylethyl]-2-[3-(trifluoromethyl)phenyl]-4-quinolinecarboxamide;

6-(methylsulfonyl)-2-[3-(trifluoromethyl)phenyl]-3-({4-[2-(trifluoromethyl)-1-pyrrolidinyl]-1-piperidinyl}methyl)-N-[(1R)-2,2,2-trifluoro-1-phenylethyl]-4-quinolinecarboxamide;

6-(methylsulfonyl)-N-[(1S)-1-phenylethyl]-2-[3-(trifluoromethyl)phenyl]-3-({4-[2-(trifluoromethyl)-1-pyrrolidinyl]-1-piperidinyl}methyl)-4-quinolinecarboxamide;

3-{[3-(methyloxy)-1,4'-bipiperidin-1'-yl]methyl}-6-(methylsulfonyl)-2-[3-(trifluoromethyl)phenyl]-N-[(1R)-2,2,2-trifluoro-1-phenylethyl]-4-quinolinecarboxamide;

3-[(4-fluoro-1,4'-bipiperidin-1'-yl)methyl]-6-(methylsulfonyl)-2-[3-(trifluoromethyl)phenyl]-N-[(1R)-2,2,2-trifluoro-1-phenylethyl]-4-quinolinecarboxamide;

3-{[4-(diethylamino)-1-piperidinyl]methyl}-6-(methylsulfonyl)-2-[3-(trifluoromethyl)phenyl]-N-[(1R)-2,2,2-trifluoro-1-phenylethyl]-4-quinolinecarboxamide;

6-(methylsulfonyl)-3-{[4-(4-morpholinyl)-1-piperidinyl]methyl}-2-[4-(trifluoromethyl)phenyl]-N-[(1R)-2,2,2-trifluoro-1-phenylethyl]-4-quinolinecarboxamide;

6-(methylsulfonyl)-3-{[4-(4-morpholinyl)-1-piperidinyl]methyl}-N-[(1S)-1-phenylethyl]-2-[4-(trifluoromethyl)phenyl]-4-quinolinecarboxamide;

3-(1,4'-bipiperidin-1'-ylmethyl)-6-(methylsulfonyl)-2-[4-(trifluoromethyl)phenyl]-N-[(1R)-2,2,2-trifluoro-1-phenylethyl]-4-quinolinecarboxamide;

3-(1,4'-bipiperidin-1'-ylmethyl)-6-(methylsulfonyl)-N-[(1S)-1-phenylethyl]-2-[4-(trifluoromethyl)phenyl]-4-quinolinecarboxamide;

6-(methylsulfonyl)-3-{[4-(1-pyrrolidinyl)-1-piperidinyl]methyl}-2-[4-(trifluoromethyl)phenyl]-N-[(1R)-2,2,2-trifluoro-1-phenylethyl]-4-quinolinecarboxamide;

6-(methylsulfonyl)-N-[(1S)-1-phenylethyl]-3-{[4-(1-pyrrolidinyl)-1-piperidinyl]methyl}-2-[4-(trifluoromethyl)phenyl]-4-quinolinecarboxamide;

3-(1,4'-bipiperidin-1'-ylmethyl)-2-[4-(methyloxy)phenyl]-6-(methylsulfonyl)-N-[(1R)-2,2,2-trifluoro-1-phenylethyl]-4-quinolinecarboxamide;

2-(3,4-dichlorophenyl)-6-(methylsulfonyl)-3-{[4-(4-morpholinyl)-1-piperidinyl]methyl}-N-[(1R)-2,2,2-trifluoro-1-phenylethyl]-4-quinolinecarboxamide;

2-(3,4-dichlorophenyl)-6-(methylsulfonyl)-3-{[4-(4-morpholinyl)-1-piperidinyl]methyl}-N-[(1S)-1-phenylethyl]-4-quinolinecarboxamide;

3-(1,4'-bipiperidin-1'-ylmethyl)-2-(3,4-dichlorophenyl)-6-(methylsulfonyl)-N-[(1R)-2,2,2-trifluoro-1-phenylethyl]-4-quinolinecarboxamide;

3-(1,4'-bipiperidin-1'-ylmethyl)-2-(3,4-dichlorophenyl)-6-(methylsulfonyl)-N-[(1S)-1-phenylethyl]-4-quinolinecarboxamide;

2-(3,4-dichlorophenyl)-6-(methylsulfonyl)-3-{[4-(1-pyrrolidinyl)-1-piperidinyl]methyl}-N-[(1R)-2,2,2-trifluoro-1-phenylethyl]-4-quinolinecarboxamide;

2-(3,4-dichlorophenyl)-6-(methylsulfonyl)-N-[(1S)-1-phenylethyl]-3-{[4-(1-pyrrolidinyl)-1-piperidinyl]methyl}-4-quinolinecarboxamide;

6-[(1-methylethyl)sulfonyl]-7-(methyloxy)-3-{[4-(4-morpholinyl)-1-piperidinyl]methyl}-2-[3-(trifluoromethyl)phenyl]-N-[(1S)-2,2,2-trifluoro-1-phenylethyl]-4-quinolinecarboxamide;

3-{[4-(3,3-difluoro-1-pyrrolidinyl)-1-piperidinyl]methyl}-6-(methylsulfonyl)-2-[3-(trifluoromethyl)phenyl]-N-[(1R)-2,2,2-trifluoro-1-phenylethyl]-4-quinolinecarboxamide;

3-{[4-(3,3-difluoro-1-pyrrolidinyl)-1-piperidinyl]methyl}-6-(methylsulfonyl)-N-[(1S)-1-phenylethyl]-2-[3-(trifluoromethyl)phenyl]-4-quinolinecarboxamide;

3-({4-[(3R)-3-hydroxy-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-({4-[(3S)-3-hydroxy-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

2-(3-bromophenyl)-6-(methylsulfonyl)-3-{[4-(4-morpholinyl)-1-piperidinyl]methyl}-N-[(1R)-2,2,2-trifluoro-1-phenylethyl]-4-quinolinecarboxamide;

6-[(1-methylethyl)sulfonyl]-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;

6-[(1-methylethyl)sulfonyl]-N-[(1S)-1-phenylethyl]-3-{[4-(1-pyrrolidinyl)-1-piperidinyl]methyl}-2-[3-(trifluoromethyl)phenyl]-4-quinolinecarboxamide;

2-(3-bromophenyl)-6-(methylsulfonyl)-3-{[4-(4-morpholinyl)-1-piperidinyl]methyl}-N-[(1S)-1-phenylethyl]-4-quinolinecarboxamide;

3-(1,4'-bipiperidin-1'-ylmethyl)-2-(3-bromophenyl)-6-(methylsulfonyl)-N-[(1R)-2,2,2-trifluoro-1-phenylethyl]-4-quinolinecarboxamide;

3-(1,4'-bipiperidin-1'-ylmethyl)-2-(3-bromophenyl)-6-(methylsulfonyl)-N-[(1S)-1-phenylethyl]-4-quinolinecarboxamide;

2-(3-bromophenyl)-6-(methylsulfonyl)-3-{[4-(1-pyrrolidinyl)-1-piperidinyl]methyl}-N-[(1R)-2,2,2-trifluoro-1-phenylethyl]-4-quinolinecarboxamide;

2-(3-bromophenyl)-6-(methylsulfonyl)-N-[(1S)-1-phenylethyl]-3-{[4-(1-pyrrolidinyl)-1-piperidinyl]methyl}-4-quinolinecarboxamide;

3-(1,4'-bipiperidin-1-ylmethyl)-6-(methylsulfonyl)-2-[3-(trifluoromethyl)phenyl]-N-[(1S)-2,2,2-trifluoro-1-phenylethyl]-4-quinolinecarboxamide;

3-({4-[(2R)-2-methyl-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-[(3-fluoro-1,4'-bipiperidin-1'-yl)methyl]-6-(methylsulfonyl)-2-[3-(trifluoromethyl)phenyl]-N-[(1R)-2,2,2-trifluoro-1-phenylethyl]-4-quinolinecarboxamide;

3-({4-[(2S)-2-methyl-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-({4-[(2S)-2-(hydroxymethyl)-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-({4-[(2R)-2-(hydroxymethyl)-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-{[3-(hydroxymethyl)-1,4'-bipiperidin-1-yl]methyl}-6-(methylsulfonyl)-2-[3-(trifluoromethyl)phenyl]-N-[(1R)-2,2,2-trifluoro-1-phenylethyl]-4-quinolinecarboxamide;

3-[(4-{methyl[2-(methyloxy)ethyl]amino}-1-piperidinyl)methyl]-6-(methylsulfonyl)-2-[3-(trifluoromethyl)phenyl]-N-[(1R)-2,2,2-trifluoro-1-phenylethyl]-4-quinolinecarboxamide;

3-({[4-ethyl(propyl)amino]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-({[4-methyl(2-methylpropyl)amino]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-{[4-(hexahydro-1H-azepin-1-yl)-1-piperidinyl]methyl}-6-(methylsulfonyl)-2-[3-(trifluoromethyl)phenyl]-N-[(1R)-2,2,2-trifluoro-1-phenylethyl]-4-quinolinecarboxamide;

3-{[4-(methyloxy)-1,4'-bipiperidin-1-yl]methyl}-6-(methylsulfonyl)-2-[3-(trifluoromethyl)phenyl]-N-[(1R)-2,2,2-trifluoro-1-phenylethyl]-4-quinolinecarboxamide;

3-({[4-methyl(propyl)amino]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-[(4-{(2S)-2-[(methyloxy)methyl]-1-pyrrolidinyl}-1-piperidinyl)methyl]-6-(methylsulfonyl)-2-[3-(trifluoromethyl)phenyl]-N-[(1R)-2,2,2-trifluoro-1-phenylethyl]-4-quinolinecarboxamide;

3-({4-[(2-hydroxyethyl)(methyl)amino]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

6-(ethylsulfonyl)-7-(methyloxy)-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;

6-(ethylsulfonyl)-7-(methyloxy)-N-[(1S)-1-phenylethyl]-3-{[4-(1-pyrrolidinyl)-1-piperidinyl]methyl}-2-[3-(trifluoromethyl)phenyl]-4-quinolinecarboxamide;

6-(ethylsulfonyl)-3-[(4-fluoro-1,4'-bipiperidin-1'-yl)methyl]-7-(methyloxy)-2-[3-(trifluoromethyl)phenyl]-N-[(1R)-2,2,2-trifluoro-1-phenylethyl]-4-quinolinecarboxamide; and 6-(ethylsulfonyl)-3-[(4-fluoro-1,4'-bipiperidin-1'-yl)methyl]-7-(methyloxy)-N-[(1S)-1-phenylethyl]-2-[3-(trifluoromethyl)phenyl]-4-quinolinecarboxamide;
or a pharmaceutically acceptable salt thereof.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general formula (I) and pharmaceutically acceptable derivatives and salts thereof may be accomplished as outlined below in Schemes 1-8. In the following description, the groups are as defined above for compounds of formula (I) unless otherwise indicated. Starting materials are commercially available or are made from commercially available starting materials using methods known to those skilled in the art.

As shown in Scheme 1, the compounds of Formula I can be prepared in a multi-step sequence from substituted methyl 3-methyl-2-phenyl-4-quinolinecarboxylates. The substituted methyl 3-methyl-2-phenyl-4-quinolinecarboxylate is treated with N-bromosuccinimide and benzoyl peroxide to form an appropriately substituted bromomethyl quinoline, which can undergo displacement with an appropriate amine in acetonitrile to afford the corresponding tertiary amine. The methyl ester can be hydrolyzed under standard conditions, for example by treatment with KOH in methanol/water. Coupling of the acid with an appropriate benzylamine under standard conditions, for example, EDC/HOBT or T3P, provides compounds of Formula I.

Scheme 1

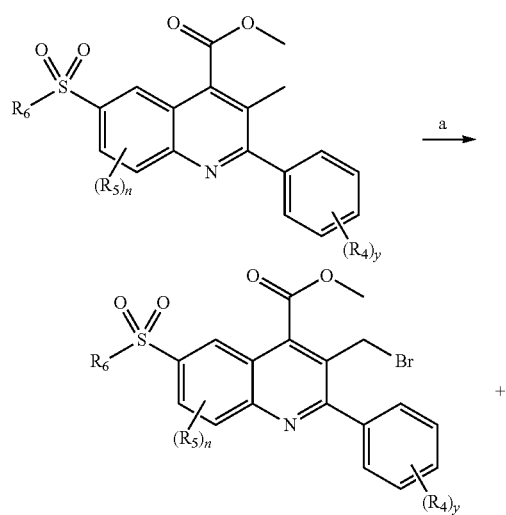

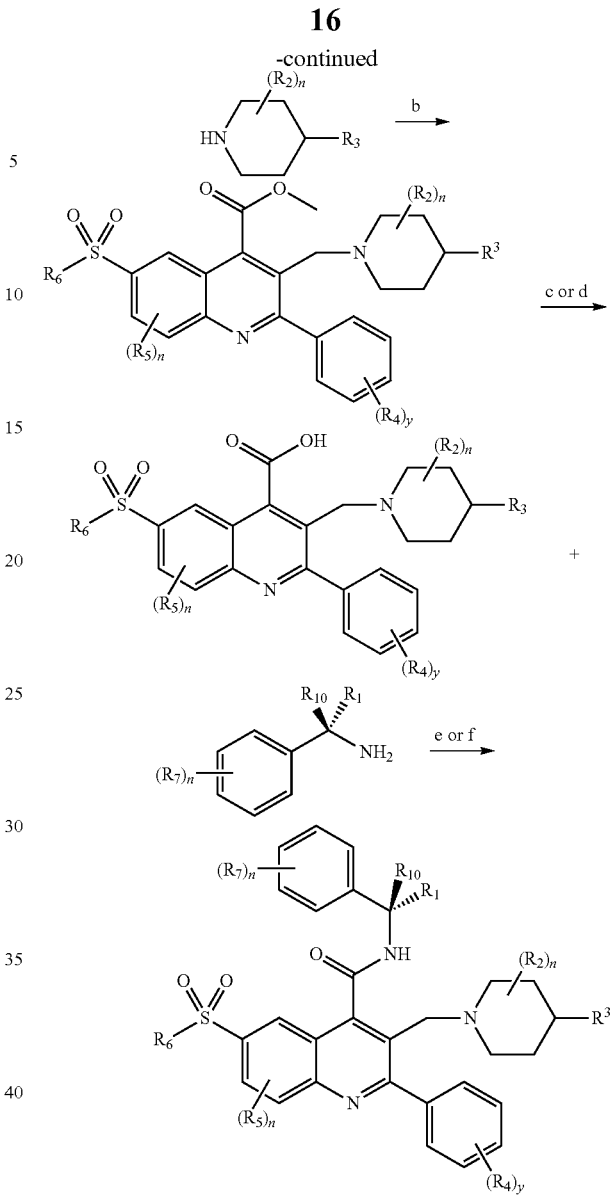

a) benzoyl peroxide, NBS, CCl$_4$, b) CH$_3$CN or i-Pr$_2$NEt, CH$_3$CN; c) KOH, MeOH/H$_2$O; d) 3N NaOH, MeOH/THF; e) HOBT, EDC, i-Pr$_2$NEt, DMF/THF; f) T3P, i-Pr$_2$NEt, CH$_2$Cl$_2$ The substituted methyl 3-methyl-2-phenyl-4-quinolinecarboxylate employed in Scheme 1 can be prepared using the multi-step sequence described in Scheme 2. The substituted 3-methyl-2-phenyl-4-quinolinecarboxylic acid can be formed by reaction of an appropriately substituted 1H-indole-2,3-dione with KOH in refluxing ethanol. This compound can be converted to a substituted methyl 3-methyl-6-(alkylthio)-2-phenyl-4-quinolinecarboxylate in a two-step procedure wherein the acid is converted to the methyl ester via an acid chloride intermediate (oxalyl chloride, DMF, then MeOH). The fluoroquinoline can be displaced with an appropriate thiol nucleophile to afford methyl 3-methyl-6-(alkylthio)-2-phenyl-4-quinolinecarboxylates.

Methyl 3-methyl-6-(alkylthio)-2-phenyl-4-quinolinecarboxylates can also be accessed in a one-pot procedure by displacement of the fluoride with an appropriate thiolate nucleophile, followed by esterification with iodomethane. Alternatively, thioether intermediates can be accessed directly using an appropriately substituted thioalkyl isatin under standard conditions. Methyl 3-methyl-6-(alkylthio)-2-phenyl-4-quinolinecarboxylates can be converted to the required sulfones using standard oxidation procedures, for example, oxone or m-CPBA in suitable solvents.

Scheme 2

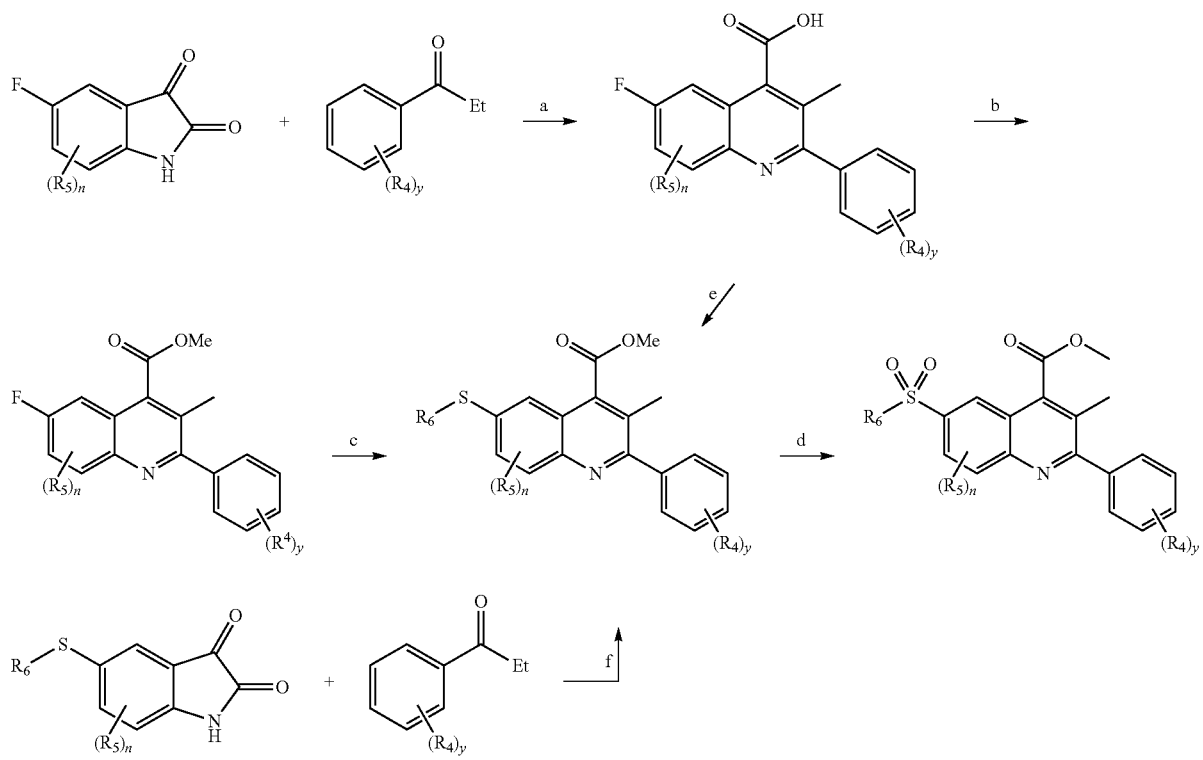

a) KOH, H₂O/EtOH; b) (COCl)₂, DMF, CH₂Cl₂, then MeOH; c) R₆SNa, DMF, then NaH, MeI; d) oxone, THF/H₂O or m-CPBA, CH₂Cl₂; e) R₆SNa, DMSO, then MeI; f) i) KOH, H₂O/EtOH; ii) (COCl)₂, DMF, CH₂Cl₂, then MeOH.

Alternatively, when $R_5$ is alkoxy, the substituted methyl 3-methyl-2-phenyl-4-quinolinecarboxylate can be prepared via the multistep sequence outlined in Scheme 3. An appropriately substituted 6-fluoro-3-methyl-7-(methyloxy)-2-phenyl-4-quinolinecarboxylic acid can be prepared from the appropriately substituted aniline, the appropriately substituted benzaldehyde, and 2-oxobutanoic acid. This intermediate can be converted to the substituted methyl 3-methyl-7-(methoxy)-6-(alkylthio)-2-phenyl-4-quinolinecarboxylate by nucleophilic aromatic substitution with the appropriate alkylthiolate nucleophile, and methylation of the resultant carboxylate with iodomethane. The substituted methyl 3-methyl-7-(methoxy)-6-(alkylthio)-2-phenyl-4-quinolinecarboxylate can be oxidized using standard conditions, for example, m-CPBA in CH₂Cl₂, to afford the substituted methyl 3-methyl-7-(methoxy)-6-(alkylsulfonyl)-2-phenyl-4-quinolinecarboxylate, which can be elaborated to the compounds of Formula I using the procedure described in Scheme 1. The 7-methoxy group can be converted to other substitutions using procedures known to those skilled in the art. For example, the substituted methyl 3-methyl-7-(methoxy)-6-(alkylsulfonyl)-2-phenyl-4-quinolinecarboxylate can be demethylated by treatment with HBr in AcOH. The substituted 3-methyl-7-hydroxy-6-(alkylsulfonyl)-2-phenyl-4-quinolinecarboxylic acid can be treated with oxalyl chloride in the presence of DMF to form the ester. Formation of the methyl 3-methyl-7-alkoxy-6-(alkylsulfonyl)-2-phenyl-4-quinolinecarboxylate can be accomplished by alkylation of the hydroxyl quinoline with an appropriately substituted alkyl halide such as alkyl iodide in the presence of base such as cesium carbonate.

Scheme 3

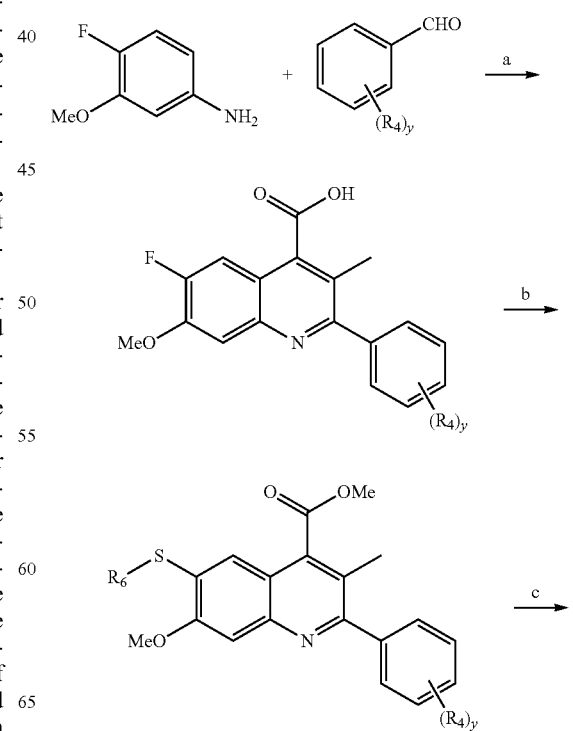

-continued

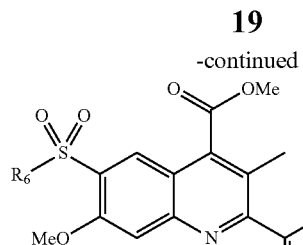

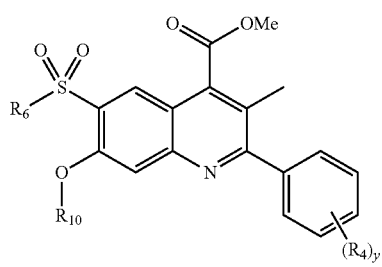

a) 2-oxobutanoic acid, EtOH; b) R₆SNa, NaH, DMSO, then MeI; c) m-CPBA, CH₂Cl₂; d) i) HBr, AcOH, ii) (COCl)₂, DMF, CH₂Cl₂, then MeOH, iii) R₁₀I, Cs₂CO₃, DMF.

As known to those skilled in the art, the substituted methyl 3-methyl-6-(alkylsulfonyl)-2-phenyl-4-quinolinecarboxylate can also be accessed by reordering the steps detailed in Scheme 3 as illustrated in Scheme 4.

Scheme 4

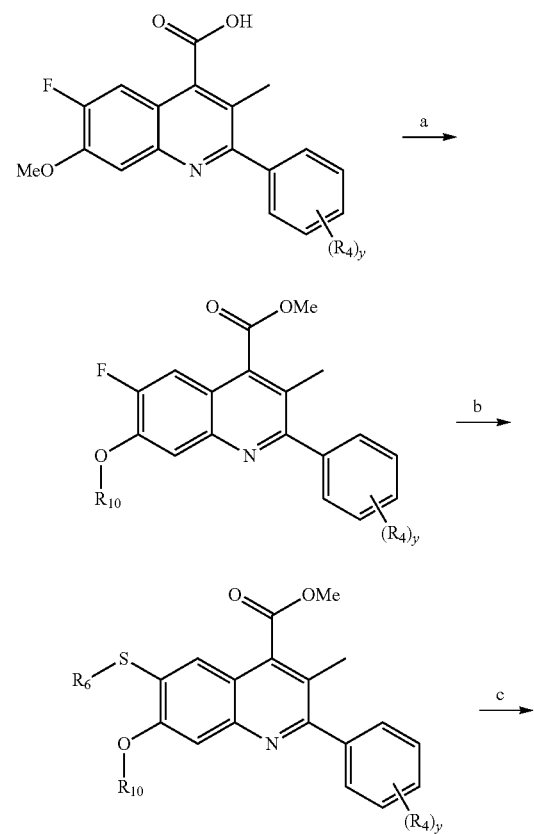

-continued

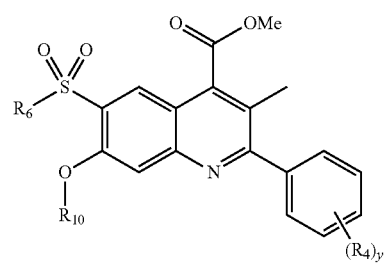

a) i) HBr, AcOH, ii) (COCl)₂, DMF, CH₂Cl₂, then MeOH, iii) R₁₀I, Cs₂CO₃, DMF; b) R₆SNa, NaH, DMSO, then MeI; c) oxone, THF/H₂O.

Methyl 3-methyl-6-(alkylsulfonyl)-2-phenyl-4-quinolinecarboxylates can be prepared via the multistep sequence outlined in Scheme 5. Substituted 3-methyl-2-phenyl-4-quinolinecarboxylic acids can be formed by reaction of an appropriately substituted 1H-indole-2,3-dione with KOH in refluxing ethanol. This intermediate can be converted to the substituted methyl 3-methyl-2-phenyl-4-quinolinecarboxylate by treatment with oxalyl chloride in the presence of DMF, and methanolysis of the resulting acid chloride. The substituted methyl 3-methyl-6-bromo-2-phenyl-4-quinolinecarboxylate can undergo a Cu-mediated coupling with an appropriate alkyl sulfinate to install the requisite alkyl sulfone. The resulting substituted methyl 3-methyl-6-(alkylsulfonyl)-2-phenyl-4-quinolinecarboxylate can be converted to the compounds of Formula I using the method described in Scheme 1.

Scheme 5

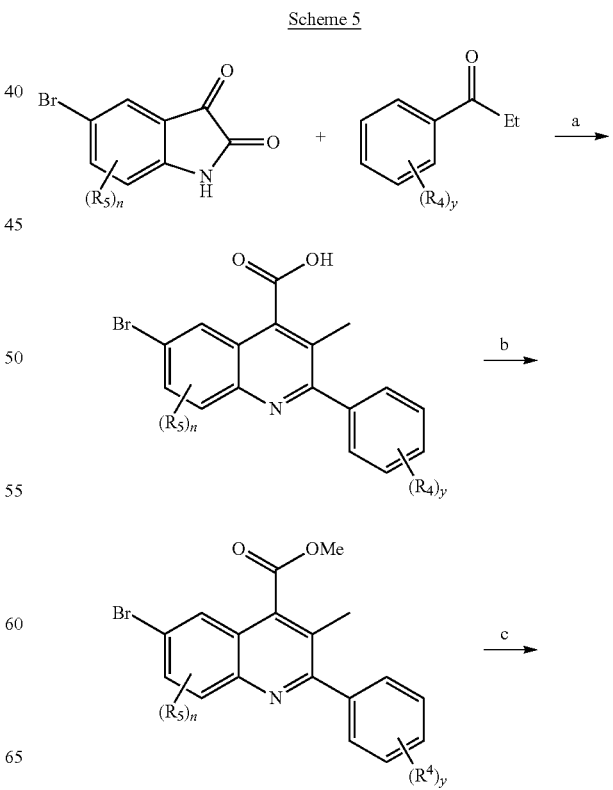

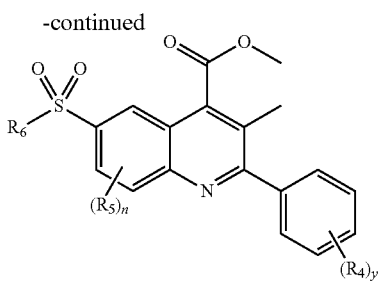

a) KOH, H₂O/EtOH; b) (COCl)₂, DMF, CH₂Cl₂, then MeOH; c) R₆SO₂Na, CuI, DMSO.

When $R_5$ is alkoxy, the substituted methyl 3-methyl-6-(alkylsulfonyl)-2-phenyl-4-quinolinecarboxylate can also be accessed via the multistep sequence outlined in Scheme 6. An appropriately substituted 6-bromo-3-methyl-7-(methyloxy)-2-phenyl-4-quinolinecarboxylic acid can be prepared from the appropriately substituted aniline, the appropriately substituted benzaldehyde, and 2-oxobutanoic acid. Incorporation of the alkylsulfone can be accomplished by Cu-mediated coupling of an appropriate sodium sulfinate. The resulting carboxylic acid can be converted to the corresponding methyl ester by treatment with oxalyl chloride in DMF, followed by methanolysis of the resulting acid chloride to afford the 3-methyl-6-(alkylsulfonyl)-7-(methyloxy)-2-phenyl-4-quinolinecarboxylate. Alternatively, as known to those skilled in the art, the order of steps can be modified, and the substituted 6-bromo-3-methyl-7-(methyloxy)-2-phenyl-4-quinolinecarboxylic acid can be converted to the methyl ester using standard conditions (for example, oxalyl chloride in DMF, then MeOH). The substituted methyl 3-methyl-6-(alkylsulfonyl)-7-(methyloxy)-2-phenyl-4-quinolinecarboxylate can be then be generated from the corresponding quinoline bromide using a Cu-mediated coupling reaction to install the alkylsulfone. The resulting substituted methyl 3-methyl-6-(alkylsulfonyl)-2-phenyl-4-quinolinecarboxylate can be converted to the compounds of Formula I using the method described in Scheme 1. Alternatively, the substituted methyl 3-methyl-7-(methoxy)-6-(alkylsulfonyl)-2-phenyl-4-quinolinecarboxylate can be demethylated by treatment with HBr in AcOH. The substituted 3-methyl-7-hydroxy-6-(alkylsulfonyl)-2-phenyl-4-quinolinecarboxylic acid can be treated with oxalyl chloride in the presence of DMF to form the ester. Formation of the methyl 3-methyl-7-alkoxy-6-(alkylsulfonyl)-2-phenyl-4-quinolinecarboxylate can be accomplished by alkylation of the hydroxyl quinoline with an appropriately substituted alkyl iodide in the presence of cesium carbonate. The resulting substituted methyl 3-methyl-7-alkoxy-6-(alkylsulfonyl)-2-phenyl-4-quinolinecarboxylate can be converted to the compounds of Formula I using the method described in Scheme 1.

Scheme 6

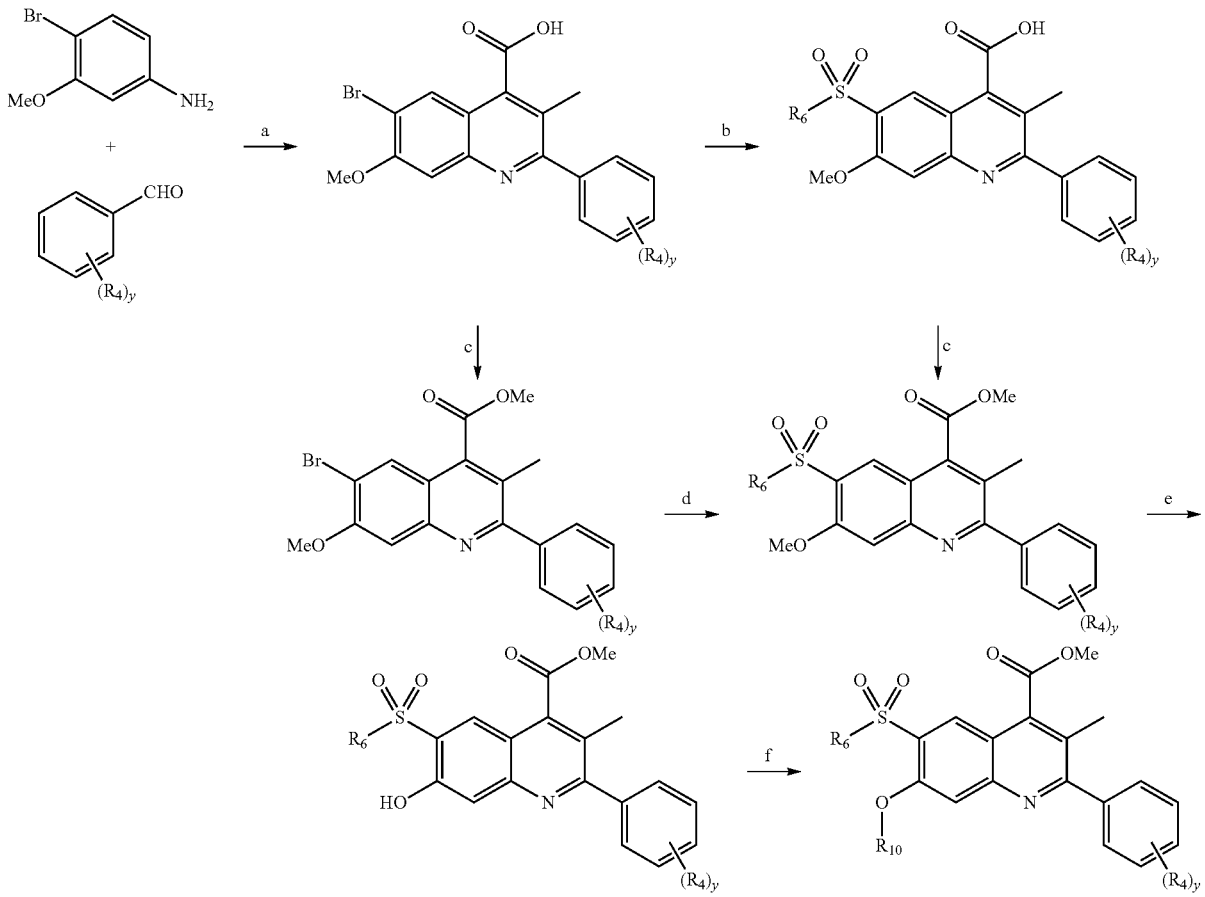

a) 2-oxobutanoic acid, EtOH; b) R₆SO₂Na, CuI, then MeI; c) (COCl)₂, DMF; d) R₆SO₂Na, CuI; e) i) HBr, AcOH, ii) (COCl)₂, DMF, CH₂Cl₂, then MeOH; f) R₁₀I, Cs₂CO₃, DMF.

The compounds of Formula I can also be formed using the multistep sequence outlined in Scheme 7. The substituted 3-methyl-7-(alkylthio)-2-phenyl-4-quinolinecarboxylic acid is formed by reaction of the appropriately substituted benzaldehyde, the appropriate 3-(alkylthio)aniline, and 2-oxobutanoic acid in refluxing ethanol. Oxidation of this intermediate using m-CPBA provides the substituted methyl 3-methyl-7-(alkylsulfonyl)-2-[3-(trifluoromethyl)phenyl]-4-quinolinecarboxylate. The resulting intermediate is treated with N-bromosuccinimide and benzoyl peroxide in carbon tetrachloride, followed by an appropriate amine in acetonitrile to afford the corresponding tertiary amine. The methyl ester can be hydrolyzed with KOH in methanol/water. The acid is then coupled with the appropriate benzylamine in the presence of T3P to provide compounds of Formula I.

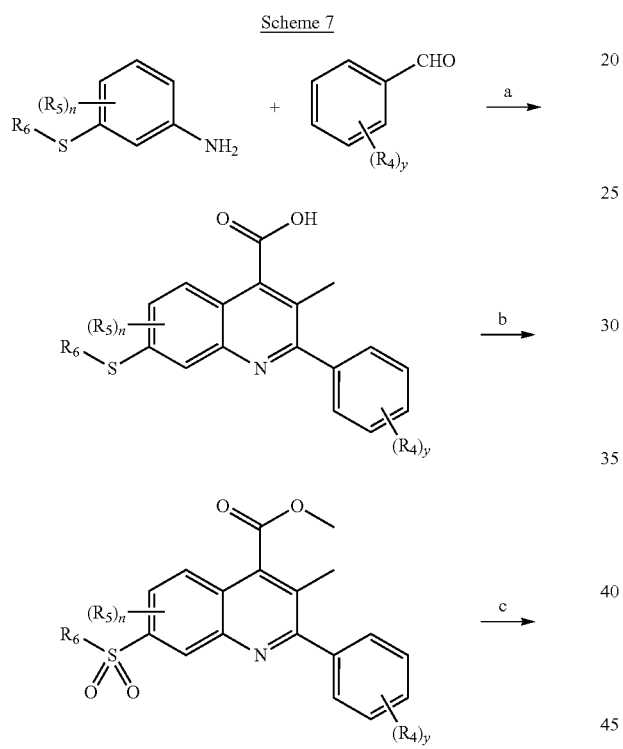

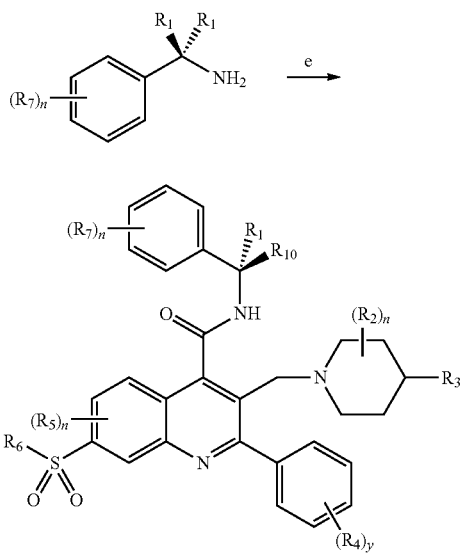

a) 2-oxobutanoic acid, EtOH; b) i) (COCl)$_2$, DMF, CH$_2$Cl$_2$, then MeOH, ii) m-CPBA, CH$_2$Cl$_2$; c) i) benzoyl peroxide, NBS, CCl$_4$, ii) amine, CH$_3$CN; d) KOH, MeOH/H$_2$O; e) T3P, i-Pr$_2$NEt, CH$_2$Cl$_2$.

The compounds of Formula I can also be prepared as outlined in Scheme 8. An appropriately substituted methyl 3-methyl-2-phenyl-4-quinolinecarboxylate can be treated with NBS in the presence of benzoyl peroxide to provide a substituted methyl 3-bromomethyl-2-phenyl-4-quinolinecarboxylate. Reaction with an appropriately substituted 4-piperidone affords an intermediate methyl 6-(alkylsulfonyl)-3-[(4-oxo-1-piperidinyl)methyl]-2-phenyl-4-quinolinecarboxylate, which can be treated with sodium hydroxide to provide the corresponding acid. The intermediate acid can be coupled with an appropriately substituted benzylamine to afford a substituted 6-(methylsulfonyl)-3-[(4-oxo-1-piperidinyl)methyl]-2-phenyl-N-(phenylmethyl)-4-quinolinecarboxamide. Conversion of the 4-oxopiperidine to an appropriate amine (R$_3$) can be accomplished by reductive amination in the presence of sodium triacetoxyborohydride to afford compounds of Formula I.

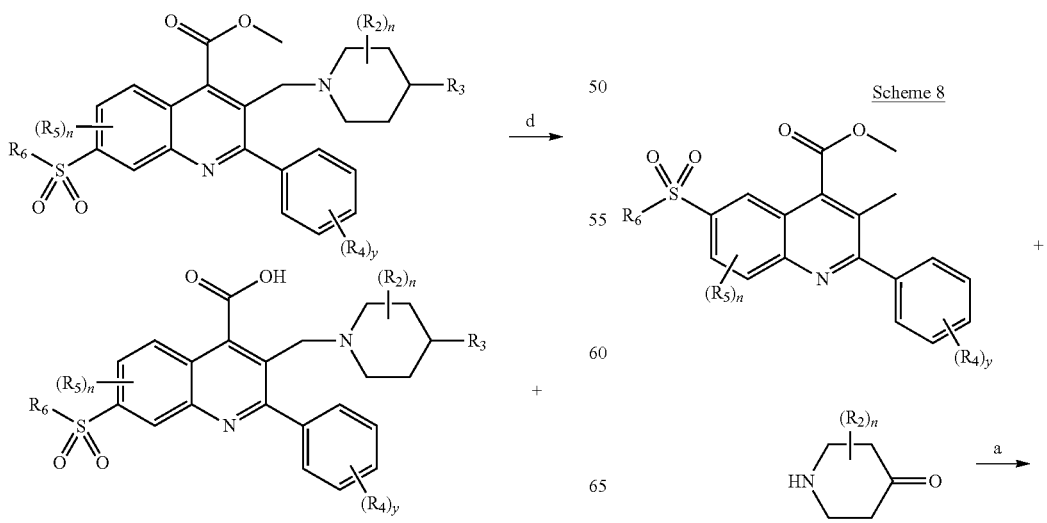

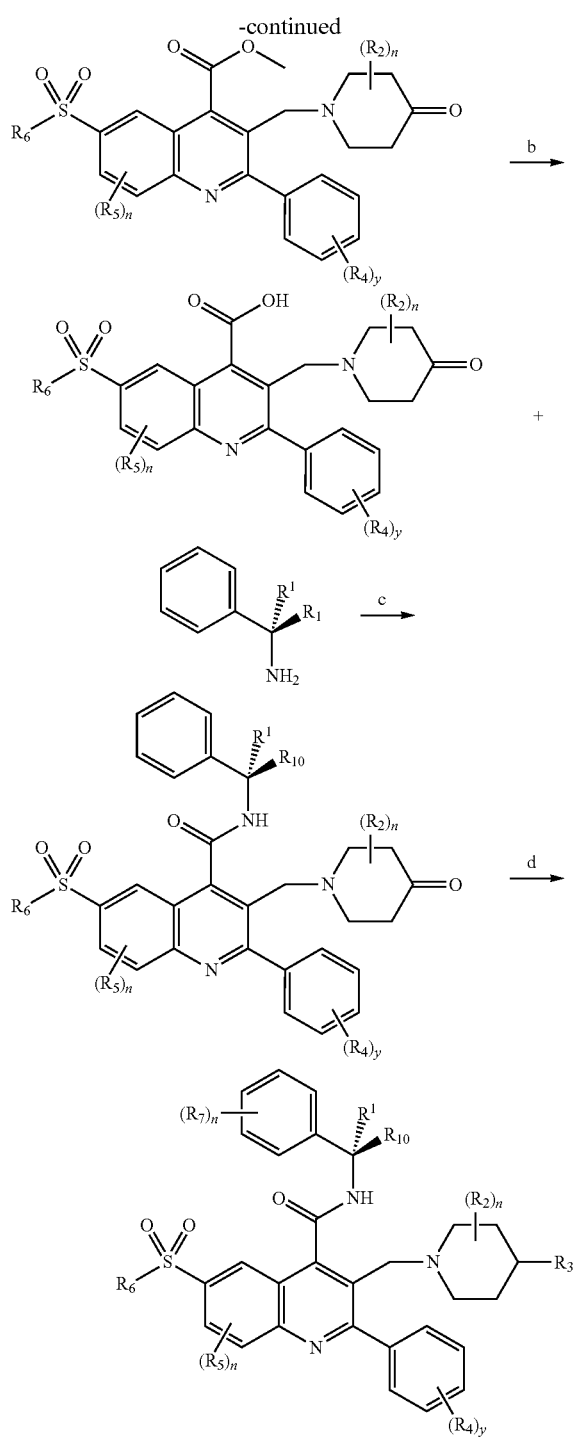

a) i) benzoyl peroxide, NBS, CCl₄, ii) 4-piperidone, i-Pr₂NEt, CH₃CN; b) NaOH, MeOH/H₂O; c) T3P, i-Pr₂NEt, CH₂Cl₂; d) amine, NaBH(OAc)₃, AcOH, CH₂Cl₂.

Biological Activity

As stated above, the compounds according to Formula I are TRPV4 antagonists, and are useful in the treatment or prevention of atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, pulmonary fibrosis, sinusitis/rhinitis, asthma, overactive bladder, pain, motor neuron disorders, genetic gain of function disorders, cardiovascular disease, renal dysfunction, osteoarthritis crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence.

The biological activity of the compounds according to Formula I can be determined using any suitable assay for determining the activity of a candidate compound as a TRPV4 antagonist, as well as tissue and in vivo models.

The biological activity of the compounds of Formula (I) are demonstrated by the following tests.

Ligand-Gated Assay:

TRP channel activation/opening results in an influx of divalent and monovalent cations including calcium. The resulting changes in intracellular calcium are monitored using a calcium selective fluorescent dye Fluo4 (MDS Analytical Technologies). Dye loaded cells were initially exposed to test compound to verify a lack of agonist activity. Cells were subsequently activated by addition of an agonist and inhibition of the agonist-induced activation was recorded. Human embryonic kidney 293 cells stably expressing the macrophage scavenger receptor class II (HEK-293-MSR-II) and transduced with 1% BacMam (J. P. Condreay, S. M. Witherspoon, W. C. Clay and T. A. Kost, Proc Natl Acad Sci 96 (1999), pp. 127-132) virus expressing the human TRPV4 gene were plated at 15000 cells/well in a volume of 50 uL in a 384 well poly-D lysine coated plate. Cells were incubated for 24 hours at 37 degrees and 5% $CO_2$. Media was then aspirated using a Tecan Plate-washer and replaced with 20 uL of dye loading buffer: HBSS, 500 uM Brilliant Black (MDS Analytical Technologies), 2 uM Fluo-4. Dye loaded plates were then incubated in the dark at room temperature for 1-1.5 hours. 10 uL of test compound diluted in HBSS+0.01% Chaps was added to the plate, incubated for 10 min at room temperature in the dark and then 10 uL of agonist was added at a final conc. equal to the agonist EC80. Calcium release was measured using the FLIPRtetra (MDS Analytical Technologies).

All examples described herein possessed TRPV4 biological activity with $pIC_{50}$ ranges above 6.0.

Hypotonicity Assay (BHK Cells):

BHK/AC9_DMEM/F12 conditioned (Baby Hamster Kidney) cells were transduced with 2% BacMam virus expressing the human TRPV4 gene and were plated at 10K cells per well in a volume of 50 uL in 384 well poly-D-lysine coated plates. Cells were incubated for 18-24 hours at 37 degrees and 5% $CO_2$. The following day, the media was aspirated using a Tecan Plate-washer and replaced with 20 uL of dye loading buffer: HBSS buffer, 2.5 mM Probenecid, 500 uM Brilliant Black, 2 uM Fluo-4. The dye loaded cells were incubated for 1-1.5 hours at room temperature in the dark. 10 uL of test compound diluted in HBSS/H₂O (~1:2.3)+0.01% Chaps was added to the plate, incubated for 10 min at room temperature in the dark, and then 10 uL of hypotonic buffer (H₂O+1.5 mM CaCl₂+~68 mM NaCl; 140 mOsm stock/260 mOsm FAC) was used to test the inhibition of the hypotonicity-induced activation. Reaction was measured on a heated stage (37 degrees) using the FLIPRtetra.

All examples described herein possessed BHK biological activity with $pIC_{50}$ ranges above 4.0

Methods of Use

The compounds of the invention are TRPV4 antagonists, and are useful in the treatment or prevention of atherosclerosis, disorders related to atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, pulmonary fibrosis, sinusitis/rhinitis, asthma, overactive bladder, pain, motor neuron disorders, genetic gain of function disorders, cardiovascular disease, renal dysfunction and osteoarthritis. Accordingly, in another aspect the invention is directed to methods of treating such conditions.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per dose. Preferred dosages are 10-500 mg BID per person.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

The compounds may be administered alone or in conjunction with one or more other therapeutic agents, said agents being selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, beta blocker, aldosterone antagonists, iontropes, NSAIDS, nitric oxide donors, calcium channel modulators, muscarinic antagonists, steroidal anti-inflammatory drugs, bronchodilators, anti-histamines, leukotriene antagonist, HMG-CoA reductase inhibitors, dual non-selective $\beta$-adrenoceptor and $\alpha_1$-adrenoceptor antagonists, type-5 phosphodiesterase inhibitors, and renin inhibitors.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

In the Examples:

Chemical shifts are expressed in parts per million (ppm) units. Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Flash column chromatography was performed on silica gel.

The naming program used is ACD Name Pro 6.02 or Chem Draw.

The following abbreviations and terms had the indicated meanings throughout:

| Abbreviation | Meaning |
| --- | --- |
| AcOH | acetic acid |
| aq | aqueous |
| Brine | saturated aqueous NaCl |
| $CCl_4$ | carbon tetrachloride |
| $CH_2Cl_2$ | methylene chloride |
| $CH_3CN$ or MeCN | acetonitrile |
| $CH_3I$ | methyl iodide |

-continued

| Abbreviation | Meaning |
|---|---|
| CH₃SNa | sodium methyl mercaptide |
| (COCl)₂ | oxalyl chloride |
| Cs₂CO₃ | cesium carbonate |
| CuI | copper(I) iodide |
| d | day |
| DCE | dichloroethane |
| DMF | N,N-dimethylformamide |
| DMSO | dimethylsulfoxide |
| EDC | 1-[3-(dimethylamino)propyl]-3-ethylcarbodiimide hydrochloride |
| Equiv | equivalents |
| Et | ethyl |
| EtI | ethyl iodide |
| Et₃N | triethylamine |
| EtOH | ethanol |
| Et₂O | diethyl ether |
| EtOAc | ethyl acetate |
| EtSNa | sodium ethanethiolate |
| h, hr | hour |
| HBr | hydrobromic acid |
| HCl | hydrochloric acid |
| HOBt | 1-hydroxybenzotriazole |
| H₂SO₄ | sulfuric acid |
| i-PrI | 2-iodopropane |
| i-PrOH | isopropanol |
| i-Pr₂NEt | N',N'-diisopropylethylamine |
| i-PrSNa | sodium 2-propanethiolate |
| K₂CO₃ | potassium carbonate |
| KOH | potassium hydroxide |
| LCMS | liquid chromatography-mass spectroscopy |
| m-CPBA | meta-chloroperoxybenzoic acid |
| Me | methyl |
| MeI | methyl iodide |
| MeOH or CH₃OH | methanol |
| MgSO₄ | magnesium sulfate |
| Min | minute |
| MS | mass spectrum |
| μw | microwave |
| NaBH(OAc)₃ | sodium triacetoxyborohydride |
| n-BuLi | butyllithium |
| Na₂CO₃ | sodium carbonate |
| NaH | sodium hydride |
| NaHCO₃ | sodium bicarbonate |
| NaOH | sodium hydroxide |
| Na₂SO₄ | sodium sulfate |
| NBS | N-bromosuccinimide |
| NH₂OH•HCl | hydroxylamine hydrochloride |
| NH₄Cl | ammonium chloride |
| NH₄OH | ammonium hydroxide |
| Pd/C | palladium on carbon |
| Ph | phenyl |
| rt | room temperature |
| satd | saturated |
| SCX | strong cation exchange |
| SPE | solid phase extraction |
| T3P | propylphosphonic anhydride |
| TFA | trifluoroacetic acid |
| THF | tetrahydrofuran |
| $t_R$ | retention time |

Intermediate Preparation 1

5-(methylthio)-1H-indole-2,3-dione

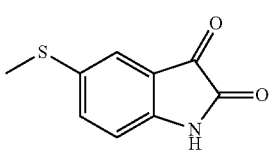

A mixture of 4-(methylthio)aniline (13.92 g, 100 mmol) and diethyl ethanedioate (17.42 g, 100 mmol) in acetic acid (50 mL) was stirred at 90° C. for 8 h. The mixture was cooled to room temperature and allowed to stand overnight, at which time the product had crystallized. The crystals were collected by filtration and washed with minimal acetic acid. The crystals were dissolved in 5% sodium hydroxide (150 mL), and the solution was heated to 90° C. Air was bubbled through the solution continuously, forming a yellow solution. After 8 hours, the solution was cooled and acidified with concentrated HCl. The precipitate was collected by filtration and was washed with water and dried to afford 5-(methylthio)-1H-indole-2,3-dione (1.9 g, 10% yield). MS (m/z) 194.0 (M+H⁺).

Intermediate Preparation 2

6-chloro-5-fluoro-1H-indole-2,3-dione

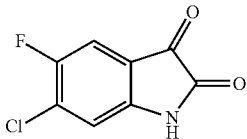 [SMILES: O=C1Nc2cc(Cl)c(F)cc2C1=O]

N-(3-chloro-4-fluorophenyl)-2-(hydroxyimino)ethanamide

Hydroxylamine hydrochloride (22.24 g, 320 mmol) in water (50 mL) was added to a suspension of 2,2,2-trichloro-1-ethoxyethanol (23.21 g, 120 mmol) and sodium sulfate (128 g, 900 mmol) in water (150 mL) and 2N HCl (100 mL). The mixture was stirred at 60° C. for 20 min. 3-Chloro-4-fluoroaniline (14.56 g, 100 mmol) in 2N HCl (100 mL) was added, and the mixture was heated to 90° C. for 2 h. The mixture was cooled to room temperature. The solid was collected by filtration, washed with water, and air dried to afford N-(3-chloro-4-fluorophenyl)-2-(hydroxyimino)ethanamide (19.45 g, 90% yield). This material was used in the next step without further purification.

6-chloro-5-fluoro-1H-indole-2,3-dione

To concentrated H₂SO₄ (100 ml) at 65° C. was added N-(3-chloro-4-fluorophenyl)-2-(hydroxyimino)ethanamide (19.45 g, 90 mmol) portionwise. The mixture was heated at 90° C. for 1.5 h. The mixture was cooled to room temperature, poured onto ice, and stirred for 10 min. The solid was collected by filtration, washed with water, and air dried to afford 6-chloro-5-fluoro-1H-indole-2,3-dione and 4-chloro-5-fluoro-1H-indole-2,3-dione as a mixture of regioisomers (15.5 g, 86% yield). This material was used without further purification.

Intermediate Preparation 3

3-(ethylthio)aniline

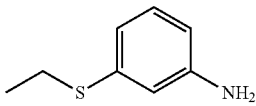

To a solution of 3-aminobenzenethiol (5.0 g, 39.9 mmol) in N,N-dimethylformamide (50 mL) was added potassium carbonate (6.62 g, 47.9 mmol) and iodoethane (3.19 mL, 39.9 mmol). The mixture was stirred at room temperature overnight. The reaction mixture was diluted with water and extracted with ethyl acetate (3 times). The combined organic extracts were washed with brine (2 times), dried over $Na_2SO_4$, filtered, and concentrated in vacuo. The residue was purified via column chromatography (ISCO, 0-30% ethyl acetate/hexanes) to afford 3-(ethylthio)aniline (5.12 g, 84% yield). MS (m/z) 154.1 (M+H⁺).

Intermediate Preparation 4

4-fluoro-1,4'-bipiperidine

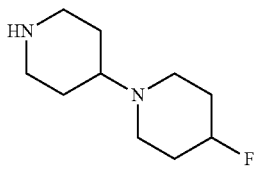

1,1-dimethylethyl 4-hydroxy-1,4'-bipiperidine-1'-carboxylate

A mixture of 1,1-dimethylethyl 4-oxo-1-piperidinecarboxylate (3.15 g, 15.8 mmol), 4-piperidinol (1.0 g, 9.88 mmol), and acetic acid (0.8 mL) in methylene chloride (30 mL) was stirred for 3 h at room temperature. Sodium triacetoxyborohydride (3.35 g, 15.8 mmol) was added and the mixture was stirred at room temperature for 18 h. The solvent was removed under reduced pressure, and the residue was dissolved in methylene chloride and washed with 1N HCl. The aqueous phase was extracted with ether (3×10 mL) and adjusted to pH 9-10 with 1N NaOH. The basic aqueous mixture was extracted with methylene chloride (3×10 mL). The combined organic extracts were concentrated in vacuo to afford 1,1-dimethylethyl 4-hydroxy-1,4'-bipiperidine-1'-carboxylate (1.1 g, 39% yield). This material was used in the next step without further purification.

1,1-dimethylethyl 4-fluoro-1,4'-bipiperidine-1'-carboxylate

Deoxo-Fluor® was added to a solution of 1,1-dimethylethyl 4-hydroxy-1,4'-bipiperidine-1'-carboxylate (0.500 g, 1.76 mmol) dropwise at −78° C. The mixture was maintained at −78° C. for 30 min before it was warmed to room temperature and stirred for 2 h. The mixture was washed with saturated aqueous sodium bicarbonate. The organic phase was dried over $Na_2SO_4$, filtered, and concentrated in vacuo. The crude material was purified via column chromatography (1:200 methanol/methylene chloride) to afford 1,1-dimethylethyl 4-fluoro-1,4'-bipiperidine-1'-carboxylate (0.300 g, 60% yield) as a colorless oil.

4-fluoro-1,4'-bipiperidine

A mixture of 1,1-dimethylethyl 4-fluoro-1,4'-bipiperidine-1'-carboxylate (0.300 g, 1.047 mmol) in 10 mL of 4N HCl/dioxane was stirred at room temperature for 18 h. The solid material was collected by filtration, washed with ether and dried to afford 4-fluoro-1,4'-bipiperidine (0.261 g, 96% yield). MS (m/z) 187 (M+H⁺).

Intermediate Preparation 4

(3S)-1-(4-piperidinyl)-3-pyrrolidinol

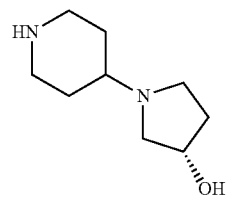 [SMILES: O[C@H]1CCN(C2CCNCC2)C1]

phenylmethyl 4-[(3S)-3-hydroxy-1-pyrrolidinyl]-1-piperidinecarboxylate

A solution of phenylmethyl 4-oxo-1-piperidinecarboxylate (1 g, 4.29 mmol) and (3S)-3-pyrrolidinol (0.411 g, 4.72 mmol) in 1,2-dichloroethane (14.29 mL) was treated at room temperature under air with sodium triacetoxyborohydride (1.363 g, 6.43 mmol) and glacial acetic acid (0.245 mL, 4.29 mmol). After 16 h, the mixture was diluted with 1N NaOH (75 mL) and extracted with methylene chloride (3×75 mL). The combined organic extracts were washed with brine (1×75 mL), dried over $Na_2SO_4$, filtered, and concentrated in vacuo to afford phenylmethyl 4-[(3S)-3-hydroxy-1-pyrrolidinyl]-1-piperidinecarboxylate (1.35 g, 98% yield). This material was used in the next step without further purification. MS (m/z) 305.0 (M+H⁺).

(3S)-1-(4-piperidinyl)-3-pyrrolidinol

Phenylmethyl 4-[(3S)-3-hydroxy-1-pyrrolidinyl]-1-piperidinecarboxylate (1.33 g, 4.37 mmol) was dissolved in methanol (11.65 ml) and 1,4-cyclohexadiene (2.91 ml) was added. The mixture was flushed with nitrogen and palladium on carbon (10%) (0.023 g, 0.218 mmol) was added. The reaction mixture was heated in an 80° C. oil bath at reflux for 1 h. The mixture was filtered through Celite®, washed with MeOH, and the filtrate was concentrated to afford (3S)-1-(4-piperidinyl)-3-pyrrolidinol (0.670 g, 81% yield). MS (m/z) 171.0 (M+H⁺).

The following diamines were prepared using procedures analogous to those described in Intermediate Preparation 4 using phenylmethyl 4-oxo-1-piperidinecarboxylate and the specified pyrrolidine or piperidine as starting materials. As is appreciated by those skilled in the art, these analogous examples may involve variations in general reaction conditions.

| Diamine | Pyrrolidine or Piperidine Starting Material | MS (m/z) (M + H)⁺ |
|---|---|---|
| 4-[2-(trifluoromethyl)-1-pyrrolidinyl]piperidine | 2-(trifluoromethyl)pyrrolidine | 223.1 |
| 4,4-difluoro-1,4'-bipiperidine | 4,4-difluoropiperidine | 205.1 |

Intermediate Preparation 5

(1R)-2,2,2-trifluoro-1-phenylethanamine

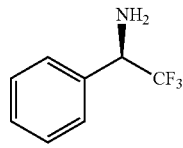

L-Tartaric acid (36 g, 240.0 mmol) was added to a solution of 2,2,2-trifluoro-1-phenylethanamine (40 g, 228.57 mmol) in isopropanol (400 mL). The solution was heated to reflux for 30 min. The mixture was cooled and the solid was collected by filtration. The material was diluted with $Na_2CO_3/H_2O$ and the aqueous mixture was extracted with methylene chloride (3×100 mL). The combined organic extracts were dried over $K_2CO_3$ and concentrated under reduced pressure to afford (1R)-2,2,2-trifluoro-1-phenylethanamine (12.5 g, 31% yield) as a white solid.

Intermediate Preparation 6 methyl 3-methyl-6-(methylsulfonyl)-2-[3-(trifluoromethyl)phenyl]-4-quinolinecarboxylate

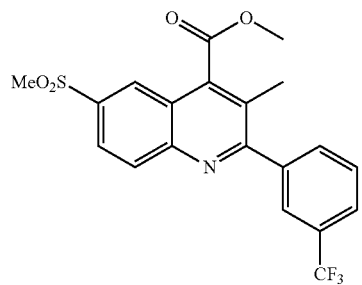 [SMILES: COC(=O)c1c(C)c(-c2cccc(C(F)(F)F)c2)nc2ccc(S(C)(=O)=O)cc12]

6-bromo-3-methyl-2-[3-(trifluoromethyl)phenyl]-4-quinolinecarboxylic acid

5-Bromoisatin (198 g, 788 mmol) was dissolved in ethanol (1.2 L) in a 6 L conical jacketed lab reactor equipped with a mechanical stirrer and an internal temperature probe. A solution of KOH (265 g, 4730 mmol) in water (0.480 L) was added slowly via addition funnel over ca. 1 hour, such that the vessel temperature was maintained at 20° C. 1-[3-(Trifluoromethyl)phenyl]-1-propanone (159 g, 788 mmol) was added in one portion and the reactor was heated to reflux for 1 h. The reaction mixture was cooled to 20° C. and acidified to pH~2 by addition of 450 mL of concentrated HCl. An additional 1.5 L of 50% $EtOH/H_2O$ was added to facilitate filtration. The slurry was filtered and the filter cake was rinsed twice with 1 L portions of 50% EtOH/water. The solid was dried in vacuo to give 6-bromo-3-methyl-2-[3-(trifluoromethyl)phenyl]-4-quinolinecarboxylic acid (281.7 g, 87% yield) as a fine off-white solid. MS (m/z) 412.7 (M+H$^+$).

methyl 6-bromo-3-(methyl)-2-[3-(trifluoromethyl)phenyl]-4-quinolinecarboxylate

A solution of 6-bromo-3-methyl-2-[3-(trifluoromethyl)phenyl]-4-quinolinecarboxylic acid (50 g, 122 mmol) in dichloromethane (700 mL) was cooled to 0° C., and DMF (1.416 mL, 18.28 mmol) was added. To the cooled solution, oxalyl chloride (16.01 mL, 183 mmol) was added dropwise (slowly) and the mixture was stirred at 0° C. for 1 h. Methanol was added and after 2 h the mixture was warmed to room temperature overnight. The solvent was removed under reduced pressure. The residue was treated with water (200 mL) and saturated aqueous $NaHCO_3$ (300 mL) and extracted with methylene chloride (500 mL). The aqueous phase was extracted with methylene chloride (300 mL). The organic phase was washed with saturated aqueous $NaHCO_3$ and brine, dried, filtered, and concentrated. The resulting solid was combined with material from a separate experiment (51 g) and the material was suspended in 400-500 mL of acetonitrile. The mixture was heated to 75° C. until the solid completely dissolved. The mixture was cooled, and the resulting precipitate was collected by filtration and dried. The filtrate was concentrated and the recrystallization procedure was repeated to give additional product. Both batches were combined to afford methyl 6-bromo-3-(methyl)-2-[3-(trifluoromethyl)phenyl]-4-quinolinecarboxylate (79 g, 73% overall yield). MS (m/z) 426.0 (M+H$^+$).

methyl 3-methyl-6-(methylsulfonyl)-2-[3-(trifluoromethyl)phenyl]-4-quinolinecarboxylate Methyl 6-bromo-3-methyl-2-[3-(trifluoromethyl)phenyl]-4-quinolinecarboxylate (50 g, 118 mmol) was combined with copper(I) iodide (44.9 g, 236 mmol) and sodium methylsulfinate (24.07 g, 236 mmol) in a 2 L round bottom flask and the vessel was purged with $N_2$ (3×). The solids were suspended in dimethyl sulfoxide (400 mL), the atmosphere was exchanged for nitrogen (3×Vac/N2 purges), and the reaction was heated to 120° C. overnight. The reaction was cooled to 50° C., and iodomethane (50.2 g, 354 mmol) was added. The reaction was stirred for 2 hours at 50° C. and cooled to RT. The crude reaction mixture was added slowly 1 L of water with stirring over 30 minutes. The resulting yellow slurry was filtered through a buchner funnel. The filter cake was washed with 3×500 mL water and dried overnight. The solids were suspended in 625 mL $CH_2Cl_2$, and the suspension was stirred for ca. 30 min. The solids were purified by flash chromatography eluting with 100% $CH_2Cl_2 \rightarrow 40\%$ $EtOAc/CH_2Cl_2$. Fractions containing the product were further purified by trituration with MeOH. Mixed fractions were repurified using the same conditions and combined with the previously isolated solid to provide 31.9 g (64%) of the product as a white solid. MS (m/z) 423.7 (M+H$^+$).

Intermediate Preparation 7 methyl 3-methyl-6-[(1-methylethyl)sulfonyl]-7-(methyloxy)-2-[3-(trifluoromethyl)phenyl]-4-quinolinecarboxylate

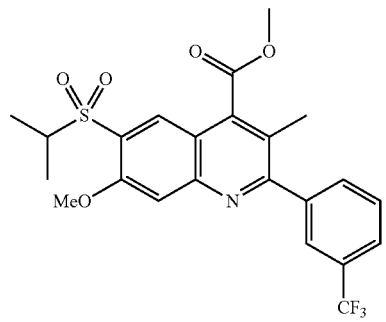 [SMILES: COC(=O)c1c(C)c(-c2cccc(C(F)(F)F)c2)nc2cc(OC)c(S(=O)(=O)C(C)C)cc12]

(2E)-N-[4-bromo-3-(methyloxy)phenyl]-2-(hydroxyimino)ethanamide

A mixture of 4-bromo-3-(methyloxy)aniline (50 g, 247 mmol), HCl (100 mL) and dioxane (150 mL) in $H_2O$ (500 mL) was stirred at 50° C. 2,2,2-Trichloro-1,1-ethanediol (81.7 g, 494 mmol), $Na_2SO_4$ (526 g, 3705 mmol) and $H_2O$ (1 L) were added to the mixture followed by $NH_2OH \cdot HCl$ (103 g, 1482 mmol in 100 mL of $H_2O$). The mixture was stirred at 80° C. for 1 h, cooled to room temperature, filtered and washed with $H_2O$ to yield (2E)-N-[4-bromo-3-(methyloxy)phenyl]-2-(hydroxyimino)ethanamide (75 g) as a yellow solid. MS (m/z) 273 (M+H$^+$).

5-bromo-6-(methyloxy)-1H-indole-2,3-dione

Concentrated $H_2SO_4$ (400 mL) was heated to 50° C. and portions of (2E)-N-[4-bromo-3-(methyloxy)phenyl]-2-(hydroxyimino)ethanamide (75 g, 275 mmol) were added while keeping the internal temperature below 70° C. After complete addition, the mixture was heated to 80° C. for 1 h, then poured into ice, filtered and washed with $H_2O$ to yield 5-bromo-6-(methyloxy)-1H-indole-2,3-dione (75 g) of a red solid. MS (m/z) 257.9 (M+H$^+$).

6-bromo-3-methyl-7-(methyloxy)-2-[3-(trifluoromethyl)phenyl]-4-quinolinecarboxylic acid A solution of 5-bromo-6-(methyloxy)-1H-indole-2,3-dione (75 g, 293 mmol), KOH (98.5 g, 1760 mmol) in EtOH (500 mL) and $H_2O$ (150 mL) was stirred followed by the addition of 1-[3-(trifluoromethyl)phenyl]-1-propanone (59 g, 293 mmol) in one portion. After refluxing for 16 h, the mixture was evaporated to remove EtOH and pH adjusted to 3 with 2N HCl. Following filtration to yield the crude product, the material was refluxed in EtOH (1 L) for 1 h, filtered and dried to yield 6-bromo-3-methyl-7-(methyloxy)-2-[3-(trifluoromethyl)phenyl]-4-quinolinecarboxylic acid (57 g, 44% yield) as an off white solid. MS (m/z) 440 (M+H$^+$).

methyl 6-bromo-3-methyl-7-(methyloxy)-2-[3-(trifluoromethyl)phenyl]-4-quinolinecarboxylate To a 2 L flask was added 6-bromo-3-methyl-7-(methyloxy)-2-[3-(trifluoromethyl)phenyl]-4-quinolinecarboxylic acid (82.5 g, 187 mmol), DMSO (1249 mL), cesium carbonate (67.2 g, 206 mmol) and methyl iodide (23.44 ml, 375 mmol). The mixture was stirred at room temperature for 2 h. To the resulting slurry was added water (500 mL). The mixture became warm and was cooled with an ice/water bath. Stirring was continued an additional 30 min, then filtered and washed with $H_2O$ (2 L). The resulting solid was dried under reduced pressure then azeotroped with toluene two times to afford methyl 6-bromo-3-methyl-7-(methyloxy)-2-[3-(trifluoromethyl)phenyl]-4-quinolinecarboxylate (72.3 g, 85% yield) as a tan solid. MS (m/z) 456 (M+H$^+$).

methyl 3-methyl-6-[(1-methylethyl)sulfonyl]-7-(methyloxy)-2-[3-(trifluoromethyl)phenyl]-4-quinolinecarboxylate To a solution of methyl 6-bromo-3-methyl-7-(methyloxy)-2-[3-(trifluoromethyl)phenyl]-4-quinolinecarboxylate (72 g, 159 mmol) in dimethyl sulfoxide (1057 mL) was added copper(I) iodide (60.4 g, 317 mmol) and isopropyl sulfinic acid sodium salt (41.3 g, 317 mmol). The mixture was evacuated and purged with $N_2$ three times and then heated at 120° C. for 6 h, then cooled to 65° C. Stirring was continued at 65° C. overnight then cooled to room temperature and MeI (39.6 mL, 634 mmol) was added. After stirring for 1 h, the mixture was diluted with DCM (750 mL) and water (1 L), followed by vigorous stirring for 30 min. The mixture was then filtered over celite and washed with DCM. The two layers were separated and the aqueous layer was extracted twice with DCM. The DCM extracts were washed 2× brine, dried over $Na_2SO_4$, filtered and concentrated to afford a thick dark residue. To the residue was added MeOH (500 mL) and the solvent was removed under reduced pressure until a precipitate formed. This solution was then heated to reflux with stirring and then allowed to cool slowly overnight. The following day, the mixture was filtered and washed with MeOH (100 mL) to give 44 g of an off white solid. The filtrate was concentrated and the process was repeated to give an additional 20 g. The resulting off white solids were a mixture of product, the acid of the product, and some unreacted starting material. The 44 g crop was dissolved in DCM (500 mL) and washed with 2N NaOH (400 mL). The DCM was separated and the aqueous layer extracted 2 times with DCM (100 ml). The combined DCM extracts were dried over $Na_2SO_4$ and concentrated under reduced pressure to afford a light yellow residue. The same procedure was repeated with the 20 g crop. This process removed the acid from the mixture. The first residue was dissolved in DCM (100 mL) and this mixture was heated to reflux and hexanes (500 mL) was added. The mixture was again heated to reflux making sure all the material was in solution. The solution was allowed to stir at reflux without a condenser. This reduced the amount of DCM in the solution allowing the product to crystallize. Once solid material began to appear in the solution, the solution was allowed to slowly cool to room temperature then filtered and washed with hexanes. The same procedure was repeated with the other residue. The two solids were combined in a 1 L flask and the DCM/Hex procedure was repeated. The filter cake was transferred into a 1 L flask and dried under reduced pressure to afford methyl 3-methyl-6-[(1-methylethyl)sulfonyl]-7-(methyloxy)-2-[3-(trifluoromethyl)phenyl]-4-quinolinecarboxylate (53 g, 69% yield) as a white solid. $^1$H NMR (400 MHz, DMSO-d$_6$) δ 8.24 (s, 1H), 7.99-8.05 (m, 2H), 7.92 (d, J=8.03 Hz, 1H), 7.76-7.84 (m, 2H), 4.09 (s, 6H), 3.83 (quin, J=6.78 Hz, 1H), 2.37 (s, 3H), 1.21 (s, 3H), 1.20 (s, 3H); MS (m/z) 482.1 (M+H$^+$).

Example 1

3-(1,4'-bipiperidin-1'-ylmethyl)-6-(methylsulfonyl)-2-[3-(trifluoromethyl)phenyl]-N-[(1R)-2,2,2-trifluoro-1-phenylethyl]-4-quinolinecarboxamide

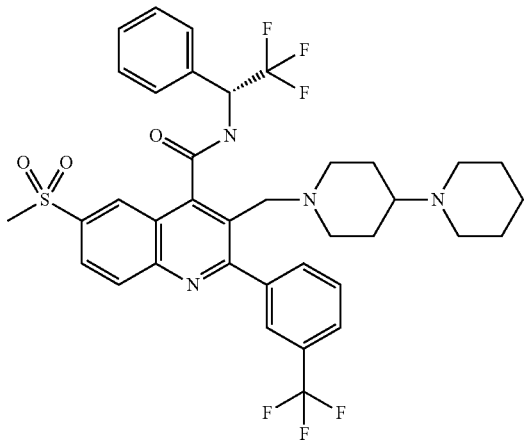 [SMILES: CS(=O)(=O)c1ccc2nc(-c3cccc(C(F)(F)F)c3)c(CN3CCC(N4CCCCC4)CC3)c(C(=O)N[C@H](c3ccccc3)C(F)(F)F)c2c1]

Route 1:

3-methyl-6-(methylthio)-2-[3-(trifluoromethyl)phenyl]-4-quinolinecarboxylic acid Potassium hydroxide (3.31 g, 59.0 mmol) in water (10 mL) was added slowly to a suspension of 5-(methylthio)-1H-indole-2,3-dione (1.9 g, 9.83 mmol) in ethanol (25 mL). 1-[3-(Trifluoromethyl)phenyl]-1-propanone (1.99 g, 9.83 mmol) was added and the mixture was heated to reflux for 1 h. The solvent was removed under reduced pressure, the residue was dissolved in water, and the aqueous mixture was washed with ether (3 times). The aqueous phase was chilled and was acidified to pH 3 with concentrated HCl. The solid material was collected by filtration, washed with water, and air dried to afford 3-methyl-6-(methylthio)-2-[3-(trifluoromethyl)phenyl]-4-quinolinecarboxylic acid (2.5 g, 67% yield). MS (m/z) 378.0 (M+H$^+$).

methyl 3-methyl-6-(methylthio)-2-[3-(trifluoromethyl)phenyl]-4-quinolinecarboxylate DMF (5 drops) was added to a suspension of 3-methyl-6-(methylthio)-2-[3-(trifluoromethyl)phenyl]-4-quinolinecarboxylic acid (2.1 g, 5.56 mmol) in dichloromethane (100 mL). Oxalyl chloride (0.731 mL, 8.35 mmol) was added slowly and the mixture was stirred for 1 h. The solvent was removed under reduced pressure, the residue was redissolved in methanol (50 mL), and triethylamine (1.55 mL, 11.13 mmol) was added slowly. The mixture was stirred overnight at room temperature. The solvent was removed under reduced pressure, the residue was diluted with aqueous saturated NaHCO$_3$, and the aqueous mixture was extracted with ethyl acetate (3 times). The combined organic extracts were washed with brine, dried over Na$_2$SO$_4$, filtered, and concentrated in vacuo. The residue was purified via column chromatography (ISCO, 0-30% ethyl acetate/hexanes) to give methyl 3-methyl-6-(methylthio)-2-[3-(trifluoromethyl)phenyl]-4-quinolinecarboxylate (1.5 g, 69% yield). $^1$H NMR (400 MHz, DMSO-d$_6$) δ 7.95-8.04 (m, 3H), 7.88 (d, J=8.03 Hz, 1H), 7.69-7.81 (m, 2H), 7.41 (d, J=2.01 Hz, 1H), 4.08 (s, 3H), 2.62 (s, 3H), 2.35 (s, 3H); MS (m/z) 392.1 (M+H$^+$).

methyl 3-methyl-6-(methylsulfonyl)-2-[3-(trifluoromethyl)phenyl]-4-quinolinecarboxylate A solution of methyl 3-methyl-6-(methylthio)-2-[3-(trifluoromethyl)phenyl]-4-quinolinecarboxylate (1.5 g, 3.83 mmol) and 3-chloroperoxybenzoic acid (1.46 g, 8.43 mmol) in dichloromethane (50 mL) was stirred overnight. Saturated aqueous sodium bicarbonate and sodium sulfate were added and the mixture was stirred for 30 min. The aqueous mixture was extracted with methylene chloride (3 times). The combined organic extracts were washed with brine, dried over Na$_2$SO$_4$, filtered, and concentrated in vacuo. The residue was purified via column chromatography (ISCO, 10-40% ethyl acetate/hexanes) to afford methyl 3-methyl-6-(methylsulfonyl)-2-[3-(trifluoromethyl)phenyl]-4-quinolinecarboxylate (1.22 g, 75% yield). $^1$H NMR (400 MHz, DMSO-d$_6$) δ 8.31-8.39 (m, 2H), 8.26-8.31 (m, 1H), 8.00-8.08 (m, 2H), 7.93 (d, J=7.78 Hz, 1H), 7.80 (t, J=7.65 Hz, 1H), 4.12 (s, 3H), 3.40 (s, 3H), 2.42 (s, 3H); MS (m/z) 424.0 (M+H$^+$).

methyl 3-(bromomethyl)-6-(methylsulfonyl)-2-[3-(trifluoromethyl)phenyl]-4-quinolinecarboxylate Methyl 3-methyl-6-(methylsulfonyl)-2-[3-(trifluoromethyl)phenyl]-4-quinolinecarboxylate (1.22 g, 2.88 mmol), NBS (0.667 g, 3.75 mmol) and diphenylperoxyanhydride (0.070 g, 0.288 mmol) in carbon tetrachloride (50 mL) were heated to 100° C. and stirred overnight. The mixture was cooled to room temperature, and the solvent was removed in vacuo to afford methyl 3-(bromomethyl)-6-(methylsulfonyl)-2-[3-(trifluoromethyl)phenyl]-4-quinolinecarboxylate. This material was used without further purification. MS (m/z) 502.0 (M+H$^+$).

methyl 3-(1,4'-bipiperidin-1'-ylmethyl)-6-(methylsulfonyl)-2-[3-(trifluoromethyl)phenyl]-4-quinolinecarboxylate A suspension of methyl 3-(bromomethyl)-6-(methylsulfonyl)-2-[3-(trifluoromethyl)phenyl]-4-quinolinecarboxylate (1.45 g, 2.88 mmol) and 1,4'-bipiperidine (0.630 g, 3.74 mmol) in acetonitrile (10 mL) was stirred for 3 hours. The solvent was removed under reduced pressure. The residue was dissolved in DMSO and was purified via HPLC (Biotage, 0-50% MeCN/H$_2$O with 0.1% TFA). Fractions containing the product were neutralized with saturated aqueous NaHCO$_3$ and extracted with methylene chloride (three times). The combined organic extracts were washed with brine, dried over Na$_2$SO$_4$, filtered, and concentrated in vacuo to afford methyl 3-(1,4'-bipiperidin-1'-ylmethyl)-6-(methylsulfonyl)-2-[3-(trifluoromethyl)phenyl]-4-quinolinecarboxylate (2.47 g, 87% yield). $^1$H NMR (400 MHz, DMSO-d$_6$) δ 8.43 (d, J=1.76 Hz, 1H), 8.37 (d, J=8.78 Hz, 1H), 8.27-8.33 (m, 1H), 8.00 (s, 1H), 7.89-7.96 (m, 2H), 7.76-7.82 (m, 1H), 4.04 (s, 3H), 3.66 (s, 2H), 3.39 (s, 3H), 2.54-2.71 (m, 3H), 2.31-2.47 (m, 4H), 1.82 (br. s., 2H), 1.53 (d, J=10.04 Hz, 2H), 1.45 (br. s., 4H), 1.21-1.40 (m, 4H); MS (m/z) 590.2 (M+H$^+$).

3-(1,4'-bipiperidin-1'-ylmethyl)-6-(methylsulfonyl)-2-[3-(trifluoromethyl)phenyl]-4-quinolinecarboxylic acid Potassium hydroxide (0.699 g, 12.46 mmol) in water (10 mL) was added to a solution of methyl 3-(1,4'-bipiperidin-1'-ylmethyl)-6-(methylsulfonyl)-2-[3-(trifluoromethyl)phenyl]-4-quinolinecarboxylate (1.47 g, 2.493 mmol) in methanol (30 mL). The mixture was heated to reflux for 5 h before the solvent was removed under reduced pressure. The residue was acidified to pH 5-6 with 2N HCl, and the mixture was allowed to stand overnight at room temperature. The solvent was collected by filtration, washed with water, and dried via azeotrope with benzene to give 3-(1,4'-bipiperidin-1'-ylmethyl)-6-(methylsulfonyl)-2-[3-(trifluoromethyl)phenyl]-4-quinolinecarboxylic acid (0.69 g, 48% yield). $^1$H NMR (400 MHz, DMSO-d$_6$) δ 8.57 (d, J=1.51 Hz, 1H), 8.09-8.15 (m, 3H), 7.91 (d, J=7.53 Hz, 1H), 7.80 (d, J=7.78 Hz, 1H), 7.69 (t, J=7.65 Hz, 1H), 3.51 (s, 2H), 3.28 (s, 3H), 2.48 (br. s., 2H), 2.33 (br. s., 4H), 2.04 (br. s., 1H), 1.84 (t, J=11.29 Hz, 2H), 1.43 (br. s., 6H), 1.29-1.38 (m, 2H), 0.95-1.11 (m, 2H); MS (m/z) 576.2 (M+H$^+$).

3-(1,4'-bipiperidin-1'-ylmethyl)-6-(methylsulfonyl)-2-[3-(trifluoromethyl)phenyl]-N-[(1R)-2,2,2-trifluoro-1-phenylethyl]-4-quinolinecarboxamide A mixture of 3-(1,4'-bipiperidin-1'-ylmethyl)-6-(methylsulfonyl)-2-[3-(trifluoromethyl)phenyl]-4-quinolinecarboxylic acid (0.100 g, 0.174 mmol), (1R)-2,2,2-trifluoro-1- phenylethanamine (0.046 g, 0.261 mmol), EDC (133 mg, 0.695 mmol), HOBT (26.6 mg, 0.174 mmol), and N,N-diisopropylethylamine (0.303 mL, 1.737 mmol) in N,N-dimethylformamide (2 mL) and tetrahydrofuran (2 mL) was stirred at 50° C. overnight. The solvent was removed in vacuo. The residue was dissolved in DMSO and purified via HPLC (Waters, 20-60% MeCN/H$_2$O with 0.1% TFA). The fractions containing the product were neutralized with saturated aqueous NaHCO$_3$ and extracted with methylene chloride (3 times). The combined organic extracts were washed with brine, dried over Na$_2$SO$_4$, filtered, and concentrated in vacuo to afford 3-(1,4'-bipiperidin-1'-ylmethyl)-6-(methylsulfonyl)-2-[3-(trifluoromethyl)phenyl]-N-[(1R)-2,2,2-trifluoro-1-phenylethyl]-4-quinolinecarboxamide (0.040 g, 30% yield). $^1$H NMR (400 MHz, CDCl$_3$) δ 10.22 (br. s., 1H), 8.75 (s, 1H), 8.31 (d, J=9.03 Hz, 1H), 8.23 (dd, J=2.01, 8.78 Hz, 1H), 7.77-7.84 (m, 2H), 7.65-7.72 (m, 2H), 7.54-7.60 (m, 2H), 7.46 (dd, J=1.76, 5.02 Hz, 3H), 6.26 (br. s., 1H), 3.60-3.78 (m, 2H), 3.15 (s, 3H), 2.66 (br. s., 1H), 2.38 (br. s., 4H), 2.18 (br. s., 1H), 2.12 (br. s., 1H), 1.53-1.64 (m, 10H), 1.37-1.46 (m, 2H); MS (m/z) 733.3 (M+H$^+$). Human TRPV4 FLIPR pIC50=8.5

Route 2:

Alternatively, methyl 3-methyl-6-(methylsulfonyl)-2-[3-(trifluoromethyl)phenyl]-4-quinolinecarboxylate was prepared using 5-bromoisatin as described in the Intermediate Preparation 6 instead of 5-(methylthio)-1H-indole-2,3-dione as described in the Example 1, Route 1.

Methyl 3-methyl-6-(methylsulfonyl)-2-[3-(trifluoromethyl)phenyl]-4-quinolinecarboxylate was then converted to 3-(1,4'-bipiperidin-1-ylmethyl)-6-(methylsulfonyl)-2-[3-(trifluoromethyl)phenyl]-N-[(1R)-2,2,2-trifluoro-1-phenylethyl]-4-quinolinecarboxamide via bromination, amine displacement, hydrolysis and amide coupling procedures analogous to those as described in Example 1, Route 1.

The following compound was prepared using procedures analogous to those described in Example 1 substituting (1R)-2,2,2-trifluoro-1-phenylethanamine with (1S)-1-phenylethanamine. As is appreciated by those skilled in the art, this analogous example may involve variations in general reaction conditions.

Example 3

3-(1,4'-bipiperidin-1'-ylmethyl)-6-(ethylsulfonyl)-7-(methyloxy)-2-[3-(trifluoromethyl)phenyl]-N-[(1R)-2,2,2-trifluoro-1-phenylethyl]-4-quinolinecarboxamide

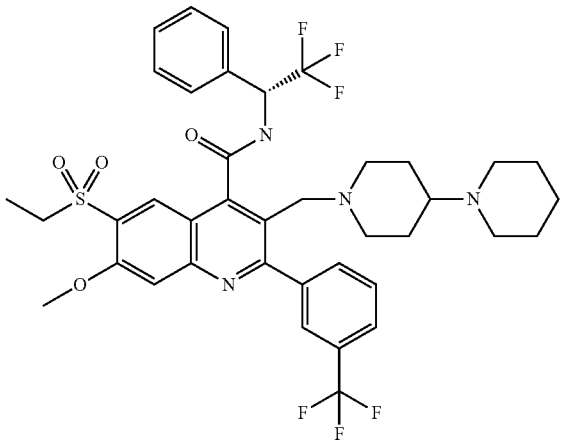 [SMILES: CCS(=O)(=O)c1cc2c(C(=O)N[C@H](c3ccccc3)C(F)(F)F)c(CN3CCC(N4CCCCC4)CC3)c(-c3cccc(C(F)(F)F)c3)nc2cc1OC]

6-fluoro-3-methyl-7-(methyloxy)-2-[3-(trifluoromethyl)phenyl]-4-quinolinecarboxylic acid A solution of the 4-fluoro-3-(methyloxy)aniline (11.29 g, 80 mmol) and 3-(trifluoromethyl)benzaldehyde (13.93 g, 80 mmol) in ethanol (200 mL) was heated to reflux for 1 h. 2-Oxobutanoic acid (8.17 g, 80 mmol) was added portionwise. The reaction mixture was stirred at reflux for additional 3 h, cooled to room temperature, and stirred at room temperature overnight. The solid was collected by filtration, washed with ethanol, and air dried to give 6-fluoro-3-methyl-7-(methyloxy)-2-[3-(trifluoromethyl)phenyl]-4-quinolinecarboxylic acid (16.05 g, 53% yield). $^1$H NMR (400 MHz, DMSO-d$_6$) δ 14.35 (br. s., 1H), 7.93-8.00 (m, 2H), 7.85-7.91 (m, J=7.78 Hz, 1H), 7.74-7.81 (m, 1H), 7.68-7.73 (m, J=8.53 Hz, 1H), 7.54 (d, J=12.05 Hz, 1H), 4.03 (s, 3H), 2.38 (s, 3H); MS (m/z) 380.1 (M+H$^+$).

| Ex | Name | Structure | MS (m/z) |
|---|---|---|---|
| 2 | 3-(1,4'-bipiperidin-1'-ylmethyl)-6-(methylsulfonyl)-N-[(1S)-1-phenylethyl]-2-[3-(trifluoromethyl)phenyl]-4-quinolinecarboxamide | | 679.3 (M + H$^+$) | methyl 6-(ethylthio)-3-methyl-7-(methyloxy)-2-[3-(trifluoromethyl)phenyl]-4-quinolinecarboxylate Sodium hydride (1.27 g, 31.6 mmol) was added portionwise to a suspension of 6-fluoro-3-methyl-7-(methyloxy)-2-[3-(trifluoromethyl)phenyl]-4-quinolinecarboxylic acid (8.0 g, 21.09 mmol) in dimethyl sulfoxide (50 mL). The mixture was stirred for 20 min. Sodium ethanethiolate (2.168 g, 23.20 mmol) was added and the resulting mixture was stirred at 100° C. for 1 h. The mixture was cooled to room temperature, iodomethane (3.96 mL, 63.3 mmol) was added, and the mixture was stirred for 2 h. The reaction mixture was diluted with water and extracted three times with methylene chloride. The combined organic extracts were washed with brine (two times), dried over $Na_2SO_4$, filtered, and concentrated in vacuo. The residue was purified via column chromatography (ISCO, 330 g silica, 0-10% ethyl acetate/methylene chloride) to afford methyl 6-(ethylthio)-3-methyl-7-(methyloxy)-2-[3-(trifluoromethyl)phenyl]-4-quinolinecarboxylate (7.05 g, 77% yield, about 70% pure). MS (m/z) 436.1 (M+H$^+$).

methyl 6-(ethylsulfonyl)-3-methyl-7-(methyloxy)-2-[3-(trifluoromethyl)phenyl]-4-quinolinecarboxylate A solution of methyl 6-(ethylthio)-3-methyl-7-(methyloxy)-2-[3-(trifluoromethyl)phenyl]-4-quinolinecarboxylate (7.05 g, 11.33 mmol) and 3-chloroperoxybenzoic acid (5.11 g, 22.7 8 mmol) in dichloromethane (50 mL) was stirred overnight. Saturated aqueous $NaHCO_3$ and $Na_2S_2O_3$ were added slowly, and the mixture was stirred for 30 min and extracted three times with methylene chloride. The combined organic extracts were washed with brine, dried over $Na_2SO_4$, filtered, and concentrated in vacuo. The residue was purified via column chromatography (ISCO, 0-15% ethyl acetate/methylene chloride) to give methyl 6-(ethylsulfonyl)-3-methyl-7-(methyloxy)-2-[3-(trifluoromethyl)phenyl]-4-quinolinecarboxylate (3.4 g, 64% yield). $^1$H NMR (400 MHz, DMSO-d$_6$) δ 8.24 (s, 1H), 7.98-8.05 (m, 2H), 7.92 (d, J=8.03 Hz, 1H), 7.76-7.85 (m, 2H), 4.10 (s, 3H), 4.09 (s, 3H), 3.54 (q, J=7.53 Hz, 2H), 2.37 (s, 3H), 1.15 (t, J=7.40 Hz, 3H); MS (m/z) 468.1 (M+H$^+$).

methyl 3-(bromomethyl)-6-(ethylsulfonyl)-7-(methyloxy)-2-[3-(trifluoromethyl)phenyl]-4-quinolinecarboxylate A mixture of 6-(ethylsulfonyl)-3-methyl-7-(methyloxy)-2-[3-(trifluoromethyl)phenyl]-4-quinolinecarboxylate (3.4 g, 7.27 mmol), NBS (1.683 g, 9.46 mmol) and diphenylperoxyanhydride (0.176 g, 0.727 mmol) in carbon tetrachloride (60 mL) was heated to 100° C. and stirred overnight. The mixture was cooled to room temperature and the solvent was removed under reduced pressure to give methyl 3-(bromomethyl)-6-(ethylsulfonyl)-7-(methyloxy)-2-[3-(trifluoromethyl)phenyl]-4-quinolinecarboxylate. This material was used without further purification. MS (m/z) 548.0 (M+H$^+$).

methyl 3-(1,4'-bipiperidin-1'-ylmethyl)-6-(ethylsulfonyl)-7-(methyloxy)-2-[3-(trifluoromethyl)phenyl]-4-quinolinecarboxylate A suspension of methyl 3-(bromomethyl)-6-(ethylsulfonyl)-7-(methyloxy)-2-[3-(trifluoromethyl)phenyl]-4-quinolinecarboxylate (1.983 g, 3.63 mmol) and 1,4'-bipiperidine (0.794 g, 4.72 mmol) in acetonitrile (30 mL) was stirred for 3 h at room temperature. The solvent was removed under reduced pressure and the residue was dissolved in DMSO and purified via HPLC (Biotage RP, 0-50% MeCN/H$_2$O with 0.1% TFA). The fractions containing the product were neutralized with saturated aqueous $NaHCO_3$ and extracted with methylene chloride. The combined organic extracts were washed with brine, dried over $Na_2SO_4$, filtered, and concentrated to afford methyl 3-(1,4'-bipiperidin-1'-ylmethyl)-6-(ethylsulfonyl)-7-(methyloxy)-2-[3-(trifluoromethyl)phenyl]-4-quinolinecarboxylate (2.1 g, 91% yield). $^1$H NMR (400 MHz, DMSO-d$_6$) δ 8.37 (s, 1H), 7.98 (s, 1H), 7.90 (t, J=8.03 Hz, 2H), 7.74-7.83 (m, 2H), 4.10 (s, 3H), 4.01 (s, 3H), 3.61 (s, 2H), 3.54 (q, J=7.45 Hz, 2H), 2.63 (d, J=9.79 Hz, 2H), 2.30-2.43 (m, 3H), 2.01-2.13 (m, 1H), 1.80 (t, J=11.29 Hz, 2H), 1.39-1.60 (m, 6H), 1.22-1.39 (m, 5H), 1.15 (t, J=7.40 Hz, 3H); MS (m/z) 634.3 (M+H$^+$).

3-(1,4'-bipiperidin-1'-ylmethyl)-6-(ethylsulfonyl)-7-(methyloxy)-2-[3-(trifluoromethyl)phenyl]-4-quinolinecarboxylic acid Potassium hydroxide (1.86 g, 33.1 mmol) was added to a solution of methyl 3-(1,4'-bipiperidin-1'-ylmethyl)-6-(ethylsulfonyl)-7-(methyloxy)-2-[3-(trifluoromethyl)phenyl]-4-quinolinecarboxylate (2.1 g, 3.31 mmol) in methanol (60 mL) and water (20 mL). The mixture was heated to reflux overnight. The reaction mixture was cooled to room temperature and diluted with water. The methanol was removed in vacuo. The solid precipitate was collected by filtration, washed with cold water, and air dried to afford 3-(1,4'-bipiperidin-1'-ylmethyl)-6-(ethylsulfonyl)-7-(methyloxy)-2-[3-(trifluoromethyl)phenyl]-4-quinolinecarboxylic acid (2.0 g, 92% yield) as the potassium salt. $^1$H NMR (400 MHz, DMSO-d$_6$) δ 8.52 (s, 1H), 8.11 (s, 1H), 7.91 (d, J=7.78 Hz, 1H), 7.79 (d, J=7.78 Hz, 1H), 7.67 (t, J=7.78 Hz, 1H), 7.55 (s, 1H), 4.04 (s, 3H), 3.42-3.52 (m, 4H), 2.33 (br. s., 4H), 2.03 (t, J=11.80 Hz, 1H), 1.82 (t, J=11.29 Hz, 2H), 1.39-1.48 (m, 6H), 1.30-1.39 (m, 2H), 1.12 (t, J=7.40 Hz, 3H), 0.97-1.09 (m, 2H); MS (m/z) 620.2 (M+H$^+$).

3-(1,4'-bipiperidin-1'-ylmethyl)-6-(ethylsulfonyl)-7-(methyloxy)-2-[3-(trifluoromethyl)phenyl]-N-[(1R)-2,2,2-trifluoro-1-phenylethyl]-4-quinolinecarboxamide T3P (2,4,6-tripropyl-1,3,5,2,4,6-trioxatriphosphorinane 2,4,6-trioxide, 0.253 mL of a 50% solution in ethyl acetate, 0.425 mmol) was added to a solution of 3-(1,4'-bipiperidin-1'-ylmethyl)-6-(ethylsulfonyl)-7-(methyloxy)-2-[3-(trifluoromethyl)phenyl]-4-quinolinecarboxylic acid (0.200 g, 0.304 mmol), (1R)-2,2,2-trifluoro-1-phenylethanamine (0.069 g, 0.395 mmol), N,N-diisopropylethylamine (10.60 µL, 0.061 mmol) in dichloromethane (2 mL) at 0° C. The mixture was stirred at 0° C. for 2 h, warmed to room temperature, and stirred overnight. The reaction mixture was diluted with saturated $NaHCO_3$ and extracted with methylene chloride (three times). The combined organic extracts were washed with brine (two times), dried over $Na_2SO_4$, filtered, and concentrated in vacuo. The residue was dissolved in DMSO and purified via HPLC (Waters, Sunfire, 30×75 mm column, 50 mL/min, 20-60% MeCN/H$_2$O with 0.1% TFA). The fractions containing the product were neutralized with saturated aqueous $NaHCO_3$ and extracted with methylene chloride (three times). The combined organic extracts were washed with brine (two times), dried over $Na_2SO_4$, filtered, and concentrated to afford 3-(1,4'-bipiperidin-1'-ylmethyl)-6-(ethylsulfonyl)-7-(methyloxy)-2-[3-(trifluoromethyl)phenyl]-N-[(1R)-2,2,2-trifluoro-1-phenylethyl]-4-quinolinecarboxamide (0.160 g, 65% yield). $^1$H NMR (400 MHz, DMSO-d$_6$) δ 10.05 (br. s., 1H), 8.50 (br. s., 1H), 7.97 (br. s., 1H), 7.87 (d, J=7.53 Hz, 2H), 7.80 (s, 1H), 7.71-7.78

(m, 1H), 7.65 (br. s., 2H), 7.42-7.51 (m, 3H), 6.22 (quin, J=8.60 Hz, 1H), 4.10 (s, 3H), 3.40-3.61 (m, 3H), 3.12-3.27 (m, 1H), 2.05-2.44 (m, 6H), 1.58-1.82 (m, 2H), 1.03-1.52 (m, 12H), 0.77-1.00 (m, 2H); MS (m/z) 777.2 (M+H$^+$).
Human TRPV4 FLIPR pIC50=8.2

The following compounds were prepared using procedures analogous to those described in Example 3 using an appropriate thiolate, substituting 1,4'-bipiperidine with 4-morpholinopiperidine, and replacing (1R)-2,2,2-trifluoro-1-phenylethanamine with an appropriate benzylamine when necessary. As is appreciated by those skilled in the art, these analogous examples may involve variations in general reaction conditions.

| Ex | Name | Structure | MS (m/z) |
|---|---|---|---|
| 4 | 3-(1,4'-bipiperidin-1'-ylmethyl)-7-(methyloxy)-6-(methylsulfonyl)-N-[(1S)-1-phenylethyl]-2-[3-(trifluoromethyl)phenyl]-4-quinolinecarboxamide | 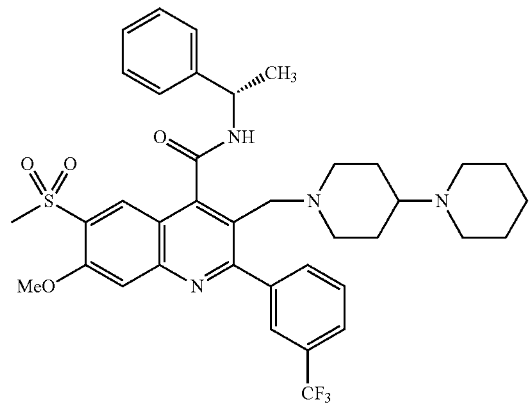 | 709.3 (M + H$^+$) |
| 5 | 3-(1,4'-bipiperidin-1'-ylmethyl)-7-(methyloxy)-6-(methylsulfonyl)-2-[3-(trifluoromethyl)phenyl]-N-[(1R)-2,2,2-trifluoro-1-phenylethyl]-4-quinolinecarboxamide | 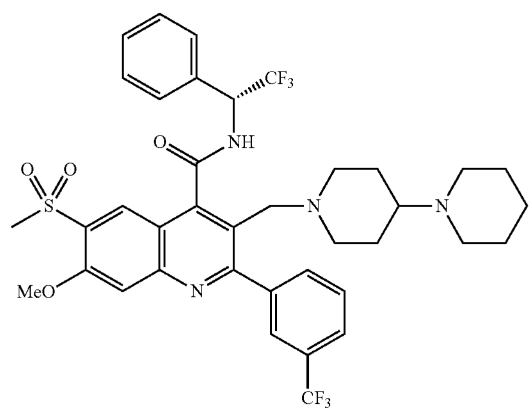 [SMILES: COc1cc2nc(-c3cccc(C(F)(F)F)c3)c(CN3CCC(N4CCCCC4)CC3)c(C(=O)N[C@H](c3ccccc3)C(F)(F)F)c2cc1S(C)(=O)=O] | 763.3 (M + H$^+$) |
| 6 | 7-(methyloxy)-6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide | 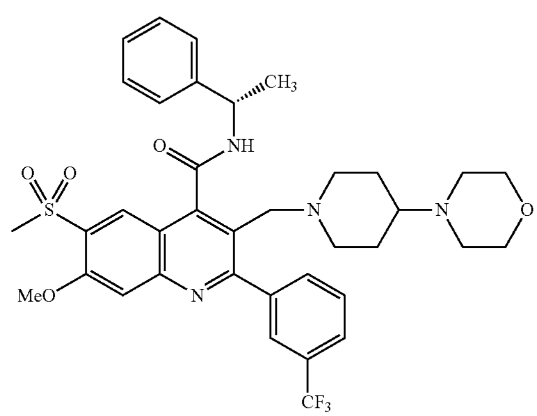 | 711.2 (M + H$^+$) |

-continued

| Ex | Name | Structure | MS (m/z) |
|---|---|---|---|
| 7 | 7-(methyloxy)-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide | 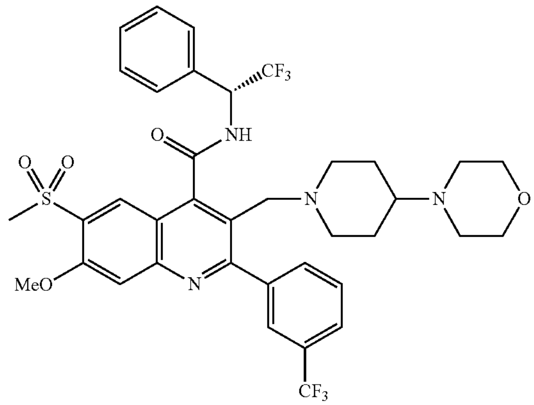 | 765.2 (M + H$^+$) |
| 8 | 3-(1,4'-bipiperidin-1'-ylmethyl)-6-(ethylsulfonyl)-7-(methyloxy)-N-[(1S)-1-phenylethyl]-2-[3-(trifluoromethyl)phenyl]-4-quinolinecarboxamide | 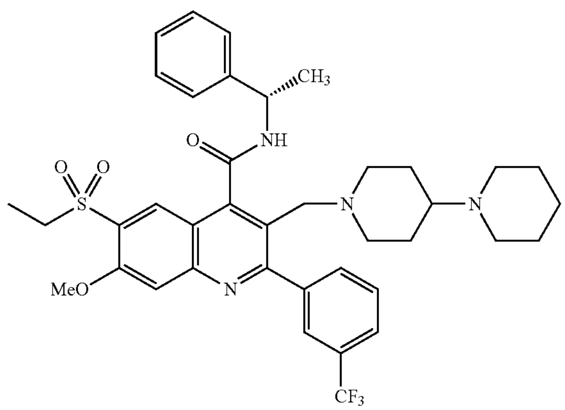 [SMILES: CCS(=O)(=O)c1cc2c(C(=O)N[C@@H](C)c3ccccc3)c(CN3CCC(N4CCCCC4)CC3)c(-c3cccc(C(F)(F)F)c3)nc2cc1OC] | 723.3 (M + H$^+$) |
| 9 | 6-(ethylsulfonyl)-7-(methyloxy)-3-{[4-(4-morpholinyl)-1-piperidinyl]methyl}-N-[(1S)-1-phenylethyl]-2-[3-(trifluoromethyl)phenyl]-4-quinolinecarboxamide | 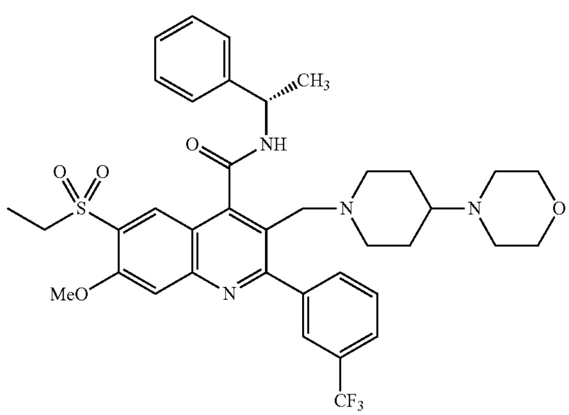 [SMILES: CCS(=O)(=O)c1cc2c(C(=O)N[C@@H](C)c3ccccc3)c(CN3CCC(N4CCOCC4)CC3)c(-c3cccc(C(F)(F)F)c3)nc2cc1OC] | 725.3 (M + H$^+$) |

| Ex | Name | Structure | MS (m/z) |
|---|---|---|---|
| 10 | 3-(1,4'-bipiperidin-1'-ylmethyl)-6-[(1-methylethyl)sulfonyl]-7-(methyloxy)-N-[(1S)-1-phenylethyl]-2-[3-(trifluoromethyl)phenyl]-4-quinolinecarboxamide | 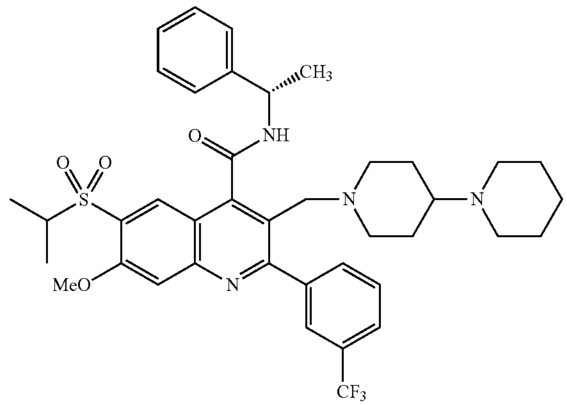 [SMILES: COc1cc2nc(-c3cccc(C(F)(F)F)c3)c(CN3CCC(N4CCCCC4)CC3)c(C(=O)N[C@@H](C)c3ccccc3)c2cc1S(=O)(=O)C(C)C] | 737.2 (M + H⁺) |
| 11 | 6-[(1-methylethyl)sulfonyl]-7-(methyloxy)-3-{[4-(4-morphlinyl)-1-piperidinyl]methyl}-N-[(1S)-1-phenylethyl]-2-[3-(trifluoromethyl)phenyl]-4-quinolinecarboxamide | 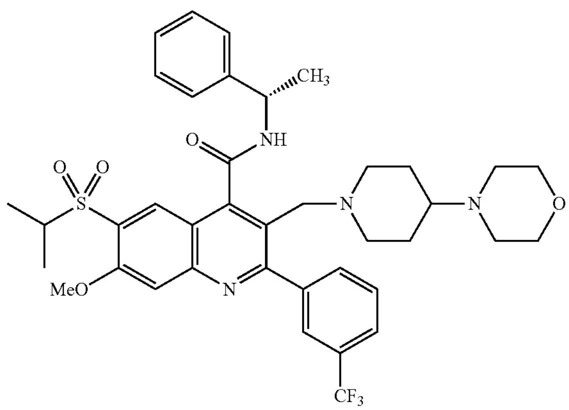 [SMILES: COc1cc2nc(-c3cccc(C(F)(F)F)c3)c(CN3CCC(N4CCOCC4)CC3)c(C(=O)N[C@@H](C)c3ccccc3)c2cc1S(=O)(=O)C(C)C] | 739.3 (M + H⁺) |

Example 12

6-(ethylsulfonyl)-7-(methyloxy)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide

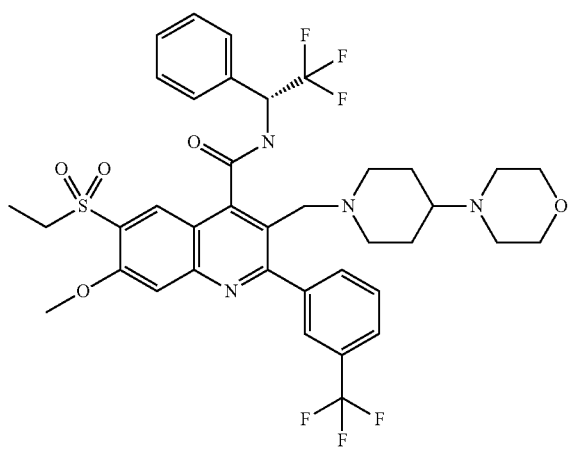 [SMILES: CCS(=O)(=O)c1cc2c(C(=O)N[C@H](c3ccccc3)C(F)(F)F)c(CN3CCC(N4CCOCC4)CC3)c(-c3cccc(C(F)(F)F)c3)nc2cc1OC]

6-fluoro-3-methyl-7-(methyloxy)-2-[3-(trifluoromethyl)phenyl]-4-quinolinecarboxylic acid A solution of the 4-fluoro-3-(methyloxy)aniline (11.29 g, 80 mmol) and 3-(trifluoromethyl)benzaldehyde (13.93 g, 80 mmol) in ethanol (200 mL) was heated to reflux for 1 h. 2-Oxobutanoic acid (8.17 g, 80 mmol) was added portionwise. The reaction mixture was stirred at reflux for an additional 3 h, cooled to room temperature, and stirred overnight. The solid was collected by filtration, washed with ethanol, and air dried to give 6-fluoro-3-methyl-7-(methyloxy)-2-[3-(trifluoromethyl)phenyl]-4-quinolinecarboxylic acid (16.05 g, 53% yield). $^1$H NMR (400 MHz, DMSO-d$_6$) δ 14.35 (br. s., 1H), 7.93-8.00 (m, 2H), 7.85-7.91 (m, J=7.78 Hz, 1H), 7.74-7.81 (m, 1H), 7.68-7.73 (m, J=8.53 Hz, 1H), 7.54 (d, J=12.05 Hz, 1H), 4.03 (s, 3H), 2.38 (s, 3H); MS (m/z) 380.1 (M+H⁺).

methyl 6-(ethylthio)-3-methyl-7-(methyloxy)-2-[3-(trifluoromethyl)phenyl]-4-quinolinecarboxylate Sodium hydride (1.27 g, 31.6 mmol) was added portionwise to a suspension of 6-fluoro-3-methyl-7-(methyloxy)-2-[3-(trifluoromethyl)phenyl]-4-quinolinecarboxylic acid (8.0 g, 21.09 mmol) in dimethyl sulfoxide (50 mL). The mixture was stirred for 20 min. Sodium ethanethiolate (2.168 g, 23.20 mmol) was added and the resulting mixture was stirred at 100° C. for 1 h. The mixture was cooled to room temperature, iodomethane (3.96 mL, 63.3 mmol) was added, and the mixture was stirred for 2 h. The reaction mixture was diluted with water and was extracted with methylene chloride (three times). The combined organic extracts were washed with brine (two times), dried over $Na_2SO_4$, filtered, and concentrated in vacuo. The residue was purified via column chromatography (ISCO, 330 g silica, 0-10% ethyl acetate/methylene chloride) to afford methyl 6-(ethylthio)-3-methyl-7-(methyloxy)-2-[3-(trifluoromethyl)phenyl]-4-quinolinecarboxylate (7.05 g, 77% yield, about 70% pure). MS (m/z) 436.1 (M+H$^+$).

methyl 6-(ethylsulfonyl)-3-methyl-7-(methyloxy)-2-[3-(trifluoromethyl)phenyl]-4-quinolinecarboxylate A solution of methyl 6-(ethylthio)-3-methyl-7-(methyloxy)-2-[3-(trifluoromethyl)phenyl]-4-quinolinecarboxylate (7.05 g, 11.33 mmol) and 3-chloroperoxybenzoic acid (5.11 g, 22.78 mmol) in dichloromethane (50 mL) was stirred overnight. Saturated aqueous $NaHCO_3$ and $Na_2S_2O_3$ were added slowly. The mixture was stirred for 30 min and extracted with methylene chloride (three times). The combined organic extracts were washed with brine, dried over $Na_2SO_4$, filtered, and concentrated. The residue was purified via column chromatography (ISCO, 0-15% ethyl acetate/methylene chloride) to give methyl 6-(ethylsulfonyl)-3-methyl-7-(methyloxy)-2-[3-(trifluoromethyl)phenyl]-4-quinolinecarboxylate (3.4 g, 64% yield). $^1$H NMR (400 MHz, DMSO-d$_6$) δ 8.24 (s, 1H), 7.98-8.05 (m, 2H), 7.92 (d, J=8.03 Hz, 1H), 7.76-7.85 (m, 2H), 4.10 (s, 3H), 4.09 (s, 3H), 3.54 (q, J=7.53 Hz, 2H), 2.37 (s, 3H), 1.15 (t, J=7.40 Hz, 3H); MS (m/z) 468.1 (M+H$^+$).

methyl 3-(bromomethyl)-6-(ethylsulfonyl)-7-(methyloxy)-2-[3-(trifluoromethyl)phenyl]-4-quinolinecarboxylate A mixture of 6-(ethylsulfonyl)-3-methyl-7-(methyloxy)-2-[3-(trifluoromethyl)phenyl]-4-quinolinecarboxylate (3.4 g, 7.27 mmol), NBS (1.683 g, 9.46 mmol) and diphenylperoxyanhydride (0.176 g, 0.727 mmol) in carbon tetrachloride (60 mL) was heated to 100° C. and stirred overnight. The mixture was cooled to room temperature and the solvent was removed under reduced pressure to give methyl 3-(bromomethyl)-6-(ethylsulfonyl)-7-(methyloxy)-2-[3-(trifluoromethyl)phenyl]-4-quinolinecarboxylate. This material was used without further purification. MS (m/z) 548.0 (M+H$^+$).

methyl 6-(ethylsulfonyl)-7-(methyloxy)-3-{[4-(4-morpholinyl)-1-piperidinyl]methyl}-2-[3-(trifluoromethyl)phenyl]-4-quinolinecarboxylate A suspension of methyl 3-(bromomethyl)-6-(ethylsulfonyl)-7-(methyloxy)-2-[3-(trifluoromethyl)phenyl]-4-quinolinecarboxylate (1.983 g, 3.63 mmol) and 4-(4-piperidinyl)morpholine (0.803 g, 4.72 mmol) in acetonitrile (30 mL) was stirred for 3 hours. The solvent was removed under reduced pressure. The residue was dissolved in DMSO and purified via reverse phase HPLC (Biotage RP, 0-50% MeCN/H$_2$O with 0.1% TFA). The fractions containing the product were neutralized with saturated aqueous $NaHCO_3$ and extracted with methylene chloride (3 times). The combined organic extracts were washed with brine, dried over $Na_2SO_4$, filtered, and concentrated in vacuo to afford methyl 6-(ethylsulfonyl)-7-(methyloxy)-3-{[4-(4-morpholinyl)-1-piperidinyl]methyl}-2-[3-(trifluoromethyl)phenyl]-4-quinolinecarboxylate (2.0 g, 87% yield). $^1$H NMR (400 MHz, DMSO-d$_6$) δ 8.38 (s, 1H), 7.98 (s, 1H), 7.90 (t, J=7.91 Hz, 2H), 7.75-7.84 (m, 2H), 4.10 (s, 3H), 4.01 (s, 3H), 3.61 (s, 2H), 3.50-3.58 (m, 6H), 2.63 (d, J=11.04 Hz, 2H), 2.38 (br. s., 4H), 1.93-2.08 (m, 1H), 1.81 (t, J=10.92 Hz, 2H), 1.61 (d, J=11.54 Hz, 2H), 1.22-1.30 (m, 2H), 1.15 (t, J=7.40 Hz, 3H); MS (m/z) 636.2 (M+H$^+$).

6-(ethylsulfonyl)-7-(methyloxy)-3-{[4-(4-morpholinyl)-1-piperidinyl]methyl}-2-[3-(trifluoromethyl)phenyl]-4-quinolinecarboxylic acid Potassium hydroxide was added to a solution of methyl 6-(ethylsulfonyl)-7-(methyloxy)-3-{[4-(4-morpholinyl)-1-piperidinyl]methyl}-2-[3-(trifluoromethyl)phenyl]-4-quinolinecarboxylate (2.0 g, 3.15 mmol) in methanol (60 mL) and water (20 mL) and reaction mixture was heated to reflux overnight. The mixture was cooled to room temperature and diluted with water. The methanol was removed under reduced pressure. The solid was collected by filtration, washed with cold water, and air dried to afford 6-(ethylsulfonyl)-7-(methyloxy)-3-{[4-(4-morpholinyl)-1-piperidinyl]methyl}-2-[3-(trifluoromethyl)phenyl]-4-quinolinecarboxylic acid (2.0 g, 96% yield) as the potassium salt. $^1$H NMR (400 MHz, DMSO-d$_6$) δ 8.53 (s, 1H), 8.13 (s, 1H), 7.92 (d, J=7.53 Hz, 1H), 7.79 (d, J=7.78 Hz, 1H), 7.68 (t, J=7.78 Hz, 1H), 7.55 (s, 1H), 4.04 (s, 3H), 3.49-3.55 (m, 4H), 3.43-3.49 (m, 4H), 2.53-2.57 (m, 2H), 2.33-2.38 (m, 4H), 1.93-2.04 (m, 1H), 1.84 (t, J=11.04 Hz, 2H), 1.52 (d, J=11.29 Hz, 2H), 1.12 (t, J=7.28 Hz, 3H), 0.95-1.08 (m, 2H); MS (m/z) 622.2 (M+H$^+$).

6-(ethylsulfonyl)-7-(methyloxy)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide A solution of 6-(ethylsulfonyl)-7-(methyloxy)-3-{[4-(4-morpholinyl)-1-piperidinyl]methyl}-2-[3-(trifluoromethyl)phenyl]-4-quinolinecarboxylic acid (0.200 g, 0.303 mmol), (1R)-2,2,2-trifluoro-1-phenylethanamine (0.069 g, 0.393 mmol), N,N-diisopropylethylamine (10.57 µL, 0.061 mmol) and 2,4,6-tripropyl-1,3,5,2,4,6-trioxatriphosphorinane 2,4,6-trioxide (0.252 mL as a 50% solution in ethyl acetate, 0.424 mmol) in dichloromethane (2 mL) was stirred at 0° C. for 2 h, then warmed to room temperature overnight. The solution was diluted with saturated aqueous $NaHCO_3$ and extracted with methylene chloride (3 times). The combined organic extracts were washed with brine, dried over $Na_2SO_4$, filtered, and concentrated in vacuo. The residue was dissolved in DMSO and purified via HPLC (Waters, Sunfire, 30×75 mm column, 50 mL/min, 20-60% MeCN/H$_2$O with 0.1% TFA). The fractions containing the product were neutralized with saturated aqueous $NaHCO_3$ and extracted with methylene chloride (three times). The combined organic extracts were washed with brine, dried over $Na_2SO_4$, filtered, and concentrated to afford 6-(ethylsulfonyl)-7-(methyloxy)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide (0.166 g, 67% yield). $^1$H NMR (400 MHz, CHLOROFORM-d) δ 9.79 (br. s., 1H), 8.78 (s, 1H), 7.81 (s, 1H), 7.76-7.80 (m, 1H), 7.65-7.69 (m, 2H), 7.60 (s, 1H), 7.53-7.59 (m, 2H), 7.42-7.49 (m, 3H), 6.20-6.31 (m, 1H), 4.11 (s, 3H), 3.65-3.71 (m, 4H), 3.54-3.65 (m, 2H), 3.47 (q, J=7.28 Hz, 2H), 2.59-2.71 (m, 1H), 2.38-2.46 (m, 4H), 2.17-2.28 (m, 1H), 2.04 (t, J=11.04 Hz, 1H), 1.49-1.65 (m, 6H), 1.32 (t, J=7.53 Hz, 3H); MS (m/z) 779.2 (M+H$^+$).

Example 13

7-(ethyloxy)-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide

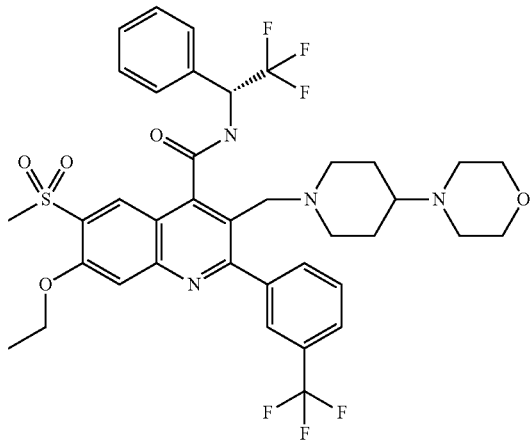 [SMILES: CCOc1cc2nc(-c3cccc(C(F)(F)F)c3)c(CN3CCC(N4CCOCC4)CC3)c(C(=O)N[C@H](c3ccccc3)C(F)(F)F)c2cc1S(C)(=O)=O]

6-fluoro-3-methyl-7-(methyloxy)-2-[3-(trifluoromethyl)phenyl]-4-quinolinecarboxylic acid A solution of the 4-fluoro-3-(methyloxy)aniline (11.29 g, 80 mmol) and 3-(trifluoromethyl)benzaldehyde (13.93 g, 80 mmol) in ethanol (200 mL) was heated to reflux for 1 h. 2-Oxobutanoic acid (8.17 g, 80 mmol) was added portionwise. The reaction mixture was stirred at reflux for additional 3 h, cooled to room temperature, and stirred overnight. The solid was collected by filtration, washed with ethanol, and dried to afford 6-fluoro-3-methyl-7-(methyloxy)-2-[3-(trifluoromethyl)phenyl]-4-quinolinecarboxylic acid (16.05 g, 53% yield). $^1$H NMR (400 MHz, DMSO-$d_6$) δ 7.94-7.98 (m, 2H), 7.88 (d, J=7.78 Hz, 1H), 7.74-7.80 (m, 1H), 7.71 (d, J=8.53 Hz, 1H), 7.54 (d, J=12.05 Hz, 1H), 4.03 (s, 3H), 2.38 (s, 3H); MS (m/z) 380.1 (M+H$^+$).

methyl 3-methyl-7-(methyloxy)-6-(methylthio)-2-[3-(trifluoromethyl)phenyl]-4-quinolinecarboxylate Sodium hydride (0.949 g, 23.73 mmol) was added portionwise to a suspension of 6-fluoro-3-methyl-7-(methyloxy)-2-[3-(trifluoromethyl)phenyl]-4-quinolinecarboxylic acid (6.0 g, 15.82 mmol) in dimethyl sulfoxide (50 mL). After 20 min, sodium thiomethoxide (1.44 g, 17.40 mmol) was added. The reaction mixture was heated to 100° C. for 2 h. The mixture was cooled to room temperature, and iodomethane (4.95 mL, 79 mmol) was added. The reaction mixture was stirred for 2 h, diluted with ether, and extracted with methylene chloride (three times). The combined organic extracts were washed with brine (2 times), dried over Na$_2$SO$_4$, filtered, and concentrated. The residue was purified via column chromatography (ISCO, 330 g silica, 0-15% ethyl acetate/hexanes) to give methyl 3-methyl-7-(methyloxy)-6-(methylthio)-2-[3-(trifluoromethyl)phenyl]-4-quinolinecarboxylate (5.48 g, 82% yield). $^1$H NMR (400 MHz, DMSO-$d_6$) δ 7.94-8.01 (m, 2H), 7.87 (d, J=7.28 Hz, 1H), 7.77 (d, J=7.53 Hz, 1H), 7.49 (s, 1H), 7.24 (s, 1H), 4.07 (s, 3H), 4.01 (s, 3H), 2.53 (s, 3H), 2.34 (s, 3H); MS (m/z) 422.1 (M+H$^+$).

methyl 3-methyl-7-(methyloxy)-6-(methylsulfonyl)-2-[3-(trifluoromethyl)phenyl]-4-quinolinecarboxylate A solution of methyl 3-methyl-7-(methyloxy)-6-(methylthio)-2-[3-(trifluoromethyl)phenyl]-4-quinolinecarboxylate (4.5 g, 8.54 mmol) and 3-chloroperoxybenzoic acid (3.85 g, 17.17 mmol) in dichloromethane (50 mL) was stirred overnight. Saturated aqueous NaHCO$_3$ and Na$_2$S$_2$O$_3$ were added slowly and the resulting mixture was stirred for 30 min. The mixture was extracted with methylene chloride (3 times). The combined organic extracts were washed with brine (2 times), dried over Na$_2$SO$_4$, filtered, and concentrated in vacuo. The residue was purified via column chromatography (ISCO, 0-15% ethyl acetate/methylene chloride) to give methyl 3-methyl-7-(methyloxy)-6-(methylsulfonyl)-2-[3-(trifluoromethyl)phenyl]-4-quinolinecarboxylate (2.74 g, 71% yield). $^1$H NMR (400 MHz, DMSO-$d_6$) δ8.25 (s, 1H), 7.99-8.06 (m, 2H), 7.92 (d, J=7.78 Hz, 1H), 7.82 (s, 1H), 7.76-7.82 (m, 1H), 4.11 (s, 3H), 4.09 (s, 3H), 3.41 (s, 3H), 2.38 (s, 3H); MS (m/z) 454.1 (M+H$^+$).

7-hydroxy-3-methyl-6-(methylsulfonyl)-2-[3-(trifluoromethyl)phenyl]-4-quinolinecarboxylic acid A solution of methyl 3-methyl-7-(methyloxy)-6-(methylsulfonyl)-2-[3-(trifluoromethyl)phenyl]-4-quinolinecarboxylate (4.95 g, 10.92 mmol) and hydrobromic acid (30 mL, 552 mmol) in acetic acid (30 mL) was heated to reflux for 5 d. The mixture was cooled to room temperature and diluted with water. The solid precipitate was collected by filtration, washed with water, and air dried to afford 7-hydroxy-3-methyl-6-(methylsulfonyl)-2-[3-(trifluoromethyl)phenyl]-4-quinolinecarboxylic acid (4.22 g, 91% yield). $^1$H NMR (400 MHz, DMSO-$d_6$) δ14.51 (br. s., 1H), 11.77 (s, 1H), 8.32 (s, 1H), 7.95-8.00 (m, 2H), 7.90 (d, J=7.78 Hz, 1H), 7.78 (t, J=7.78 Hz, 1H), 7.54 (s, 1H), 3.41 (s, 3H), 2.36 (s, 3H); MS (m/z) 426.0 (M+H$^+$).

methyl 7-hydroxy-3-methyl-6-(methylsulfonyl)-2-[3-(trifluoromethyl)phenyl]-4-quinolinecarboxylate DMF (5 drops) was added to a suspension of 7-hydroxy-3-methyl-6-(methylsulfonyl)-2-[3-(trifluoromethyl)phenyl]-4-quinolinecarboxylic acid (6.92 g, 16.27 mmol) in dichloromethane (120 mL) at 0° C. Oxalyl chloride (2.14 mL, 24.40 mmol) was added slowly. After 1 h at 0° C., the mixture was warmed to room temperature and additional oxalyl chloride (2.14 mL, 24.40 mmol) was added. The mixture was warmed to room temperature and stirred overnight. Methanol (30 mL) was added and the mixture stirred overnight. The solvent was removed under reduced pressure, the residue was diluted with water, and the aqueous mixture was treated with saturated aqueous NaHCO$_3$. The mixture was extracted with methylene chloride (three times). The combined organic extracts were washed with brine (2 times), dried over Na$_2$SO$_4$, filtered, and concentrated to afford methyl 7-hydroxy-3-methyl-6-(methylsulfonyl)-2-[3-(trifluoromethyl)phenyl]-4-quinolinecarboxylate (6.0 g, 84% yield). $^1$H NMR (400 MHz, DMSO-$d_6$) δ 11.85 (br. s., 1H), 8.18 (s, 1H), 7.95-8.02 (m, 2H), 7.91 (d, J=7.78 Hz, 1H), 7.78 (t, J=7.78 Hz, 1H), 7.55 (s, 1H), 4.07 (s, 3H), 3.41 (s, 3H), 2.32 (s, 3H); MS (m/z) 440.0 (M+H$^+$).

7-(ethyloxy)-3-methyl-6-(methylsulfonyl)-2-[3-(trifluoromethyl)phenyl]-4-quinolinecarboxylic acid Iodoethane (1.10 mL, 13.65 mL) was slowly added to a mixture of methyl 7-hydroxy-3-methyl-6-(methylsulfonyl)-

2-[3-(trifluoromethyl)phenyl]-4-quinolinecarboxylate (3.0 g, 6.83 mmol) and Cs$_2$CO$_3$ (6.67 g, 20.48 mmol) in N,N-dimethylformamide (30 mL) at room temperature. The reaction mixture was stirred overnight, quenched with saturated NH$_4$Cl, and extracted with methylene chloride (three times). The combined organic extracts were washed with brine (two times), dried over Na$_2$SO$_4$, filtered, and concentrated in vacuo. The residue was purified via column chromatography (ISCO, 120 g silica, 0-20% ethyl acetate/methylene chloride) to afford 7-(ethyloxy)-3-methyl-6-(methylsulfonyl)-2-[3-(trifluoromethyl)phenyl]-4-quinolinecarboxylic acid (2.92 g, 91% yield). $^1$H NMR (400 MHz, DMSO-d$_6$) δ8.25 (s, 1H), 7.98-8.06 (m, 2H), 7.92 (d, J=8.03 Hz, 1H), 7.76-7.83 (m, 2H), 4.40 (q, J=6.94 Hz, 2H), 4.09 (s, 3H), 2.37 (s, 3H), 1.47 (t, J=6.90 Hz, 3H); MS (m/z) 468.1 (M+H$^+$).

methyl 3-(bromomethyl)-7-(ethyloxy)-6-(methylsulfonyl)-2-[3-(trifluoromethyl)phenyl]-4-quinolinecarboxylate A suspension of methyl 7-(ethyloxy)-3-methyl-6-(methylsulfonyl)-2-[3-(trifluoromethyl)phenyl]-4-quinolinecarboxylate (2.92 g, 6.25 mmol), NBS (1.445 g, 8.12 mmol) and diphenylperoxyanhydride (0.151 g, 0.625 mmol) in carbon tetrachloride (30 mL) was heated to 100° C. and stirred overnight. The mixture was cooled to room temperature and the solvent was removed under reduced pressure to give methyl 3-(bromomethyl)-7-(ethyloxy)-6-(methylsulfonyl)-2-[3-(trifluoromethyl)phenyl]-4-quinolinecarboxylate. This material was used without further purification. MS (m/z) 548.0 (M+H$^+$).

methyl 7-(ethyloxy)-6-(methylsulfonyl)-3-{[4-(4-morpholinyl)-1-piperidinyl]methyl}-2-[3-(trifluoromethyl)phenyl]-4-quinolinecarboxylate A suspension of methyl 3-(bromomethyl)-7-(ethyloxy)-6-(methylsulfonyl)-2-[3-(trifluoromethyl)phenyl]-4-quinolinecarboxylate (1.705 g, 3.12 mmol) and -(4-piperidinyl)morpholine (0.691 g, 4.06 mmol) in acetonitrile (30 mL) was stirred for 3 h. The solvent was removed under reduced pressure, and the residue was dissolved in DMSO and purified via HPLC (Biotage RP, 0-50% MeCN/H$_2$O with 0.1% TFA). The fractions containing the product were neutralized with saturated aqueous NaHCO$_3$ and were extracted with methylene chloride (three times). The combined organic extracts were washed with brine (two times), dried over Na$_2$SO$_4$, filtered, and concentrated in vacuo to afford methyl 7-(ethyloxy)-6-(methylsulfonyl)-3-{[4-(4-morpholinyl)-1-piperidinyl]methyl}-2-[3-(trifluoromethyl)phenyl]-4-quinolinecarboxylate (1.54 g, 78% yield). $^1$H NMR (400 MHz, DMSO-d$_6$) δ8.40 (s, 1H), 7.98 (s, 1H), 7.87-7.94 (m, 2H), 7.76-7.81 (m, 2H), 4.40 (q, J=6.94 Hz, 2H), 4.01 (s, 3H), 3.61 (s, 2H), 3.53 (br. s., 4H), 3.42 (s, 3H), 2.62 (d, J=11.29 Hz, 2H), 2.38 (br. s., 4H), 1.93-2.05 (m, 1H), 1.81 (t, J=11.04 Hz, 2H), 1.62 (d, J=12.05 Hz, 2H), 1.47 (t, J=6.90 Hz, 3H), 1.18-1.30 (m, 2H); MS (m/z) 636.2 (M+H$^+$).

7-(ethyloxy)-6-(methylsulfonyl)-3-{[4-(4-morpholinyl)-1-piperidinyl]methyl}-2-[3-(trifluoromethyl)phenyl]-4-quinolinecarboxylic acid Potassium hydroxide (1.36 g, 2.42 mmol) was added to a solution of methyl 7-(ethyloxy)-6-(methylsulfonyl)-3-{[4-(4-morpholinyl)-1-piperidinyl]methyl}-2-[3-(trifluoromethyl)phenyl]-4-quinolinecarboxylate (1.54 g, 2.423 mmol) in methanol (60 mL) and water (20 mL). The reaction mixture was heated to reflux overnight. The mixture was cooled to room temperature, diluted with water, and concentrated in vacuo to remove methanol. The solid precipitate was collected by filtration, washed with cold water, and dried to afford 7-(ethyloxy)-6-(methylsulfonyl)-3-{[4-(4-morpholinyl)-1-piperidinyl]methyl}-2-[3-(trifluoromethyl)phenyl]-4-quinolinecarboxylic acid (1.6 g, >99% yield) as the potassium salt. $^1$H NMR (400 MHz, DMSO-d$_6$) δ8.14 (s, 1H), 7.92 (d, J=7.53 Hz, 1H), 7.79 (d, J=7.78 Hz, 1H), 7.68 (t, J=7.78 Hz, 1H), 7.52 (s, 1H), 4.34 (q, J=6.94 Hz, 2H), 3.49-3.55 (m, 4H), 3.44 (s, 2H), 3.17 (s, 3H), 2.53 (br. s., 2H), 2.31-2.38 (m, 4H), 1.93-2.02 (m, 1H), 1.85 (t, J=11.29 Hz, 2H), 1.52 (d, J=11.04 Hz, 2H), 1.46 (t, J=7.03 Hz, 3H), 0.94-1.07 (m, 2H); MS (m/z) 622.2 (M+H$^+$).

7-(ethyloxy)-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide 7-(ethyloxy)-6-(methylsulfonyl)-3-{[4-(4-morpholinyl)-1-piperidinyl]methyl}-2-[3-(trifluoromethyl)phenyl]-4-quinolinecarboxylic acid (0.200 g, 0.303 mmol), (1R)-2,2,2-trifluoro-1-phenylethanamine (0.069 g, 0.393 mmol), N,N-diisopropylethylamine (10.57 µL, 0.061 mmol) and 2,4,6-tripropyl-1,3,5,2,4,6-trioxatriphosphorinane 2,4,6-trioxide (0.252 mL of a 50% solution in ethyl acetate, 0.424 mmol) in dichloromethane (2 mL) was stirred at 0° C. for 2 h. The solution was warmed to room temperature overnight. The solution was diluted with saturated aqueous NaHCO$_3$ and extracted with methylene chloride (3 times). The combined organic extracts were washed with brine (two times), dried over Na$_2$SO$_4$, filtered, and concentrated in vacuo. The residue was dissolved in DMSO and purified via HPLC (Waters, Sunfire, 30×75 mm column, 50 mL/min, 20-60% MeCN/H$_2$O with 0.1% TFA). The fractions containing the product were neutralized with saturated aqueous NaHCO$_3$ and extracted with CH$_2$Cl$_2$ (3 times). The combined organic extracts were washed with brine (2 times), dried over Na$_2$SO$_4$, filtered, and concentrated in vacuo to afford 7-(ethyloxy)-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide (0.086 g, 35% yield). $^1$H NMR (400 MHz, CDCl$_3$) δ9.88 (br. s., 1H), 8.79 (s, 1H), 7.81 (s, 1H), 7.78 (d, J=6.02 Hz, 1H), 7.64-7.69 (m, 2H), 7.53-7.60 (m, 3H), 7.43-7.48 (m, 3H), 6.25 (quin, J=7.65 Hz, 1H), 4.36 (q, J=6.94 Hz, 2H), 3.66-3.71 (m, 4H), 3.53-3.65 (m, 2H), 3.33 (s, 3H), 2.64 (br. s., 1H), 2.38-2.46 (m, 4H), 2.20 (br. s., 1H), 2.04 (t, J=10.92 Hz, 1H), 1.56-1.66 (m, 9H); MS (m/z) 779.3 (M+H$^+$).

The following compounds were prepared using procedures analogous to those described in Example 13 using an appropriate alkyl iodide, substituting 4-morpholinopiperidine with 1,4'-bipiperidine, and replacing (1R)-2,2,2-trifluoro-1-phenylethanamine with an appropriate benzylamine when necessary. As is appreciated by those skilled in the art, these analogous examples may involve variations in general reaction conditions.

| Ex | Name | Structure | MS (m/z) |
|---|---|---|---|
| 14 | 3-(1,4'-bipiperidin-1'-ylmethyl)-7-(ethyloxy)-6-(methylsulfonyl)-N-[(1S)-1-phenylethyl]-2-[3-(trifluoromethyl)phenyl]-4-quinolinecarboxamide | 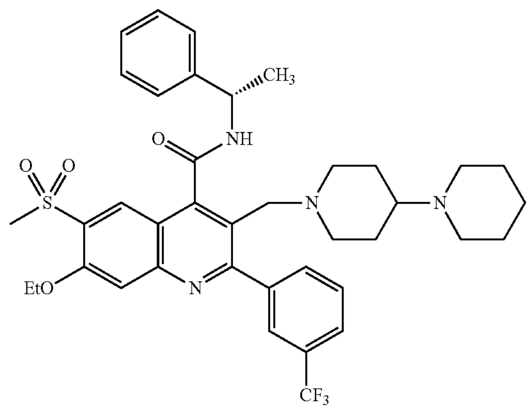 | 723.3 (M + H⁺) |
| 15 | 3-(1,4'-bipiperidin-1'-ylmethyl)-7-(ethyloxy)-6-(methylsulfonyl)-2-[3-(trifluoromethyl)phenyl]-N-[(1R)-2,2,2-trifluoro-1-phenylethyl]-4-quinolinecarboxamide | 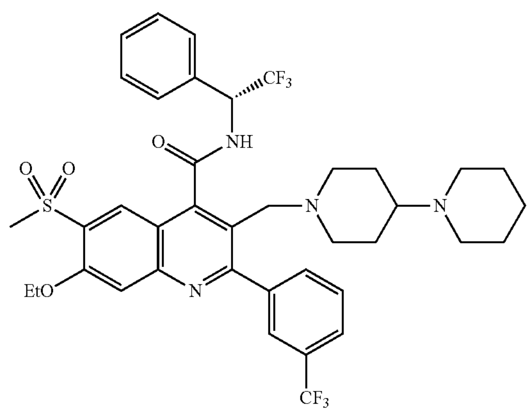 | 777.3 (M + H⁺) |
| 16 | 7-(ethyloxy)-6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide | 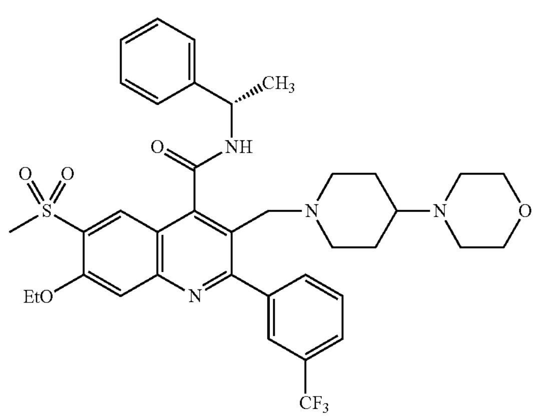 | 725.3 (M + H⁺) |

-continued

| Ex | Name | Structure | MS (m/z) |
|---|---|---|---|
| 17 | 3-(1,4'-bipiperidin-1'-ylmethyl)-7-[(1-methylethyl)oxy]-6-(methylsulfonyl)-N-[(1S)-1-phenylethyl]-2-[3-(trifluoromethyl)phenyl]-4-quinolinecarboxamide | 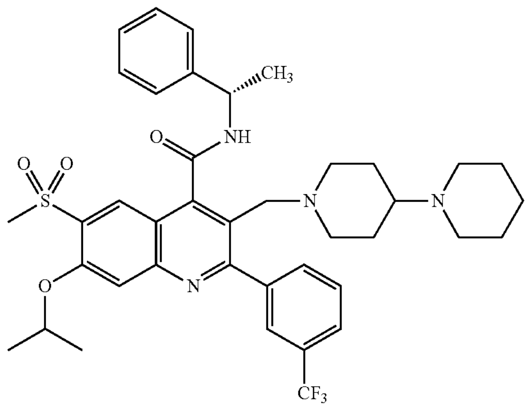 [SMILES: CC(C)Oc1cc2nc(-c3cccc(C(F)(F)F)c3)c(CN3CCC(N4CCCCC4)CC3)c(C(=O)N[C@@H](C)c3ccccc3)c2cc1S(C)(=O)=O] | 737.3 (M + H⁺) |
| 18 | 3-(1,4'-bipiperidin-1'-ylmethyl)-7-[(1-methylethyl)oxy]-6-(methylsulfonyl)-2-[3-(trifluoromethyl)phenyl]-N-[(1R)-2,2,2-trifluoro-1-phenylethyl]-4-quinolinecarboxamide | 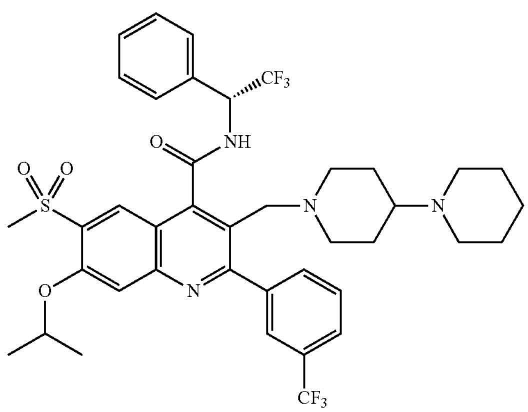 [SMILES: CC(C)Oc1cc2nc(-c3cccc(C(F)(F)F)c3)c(CN3CCC(N4CCCCC4)CC3)c(C(=O)N[C@H](c3ccccc3)C(F)(F)F)c2cc1S(C)(=O)=O] | 791.3 (M + H⁺) |
| 19 | 7-[(1-methylethyl)oxy]-6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide | 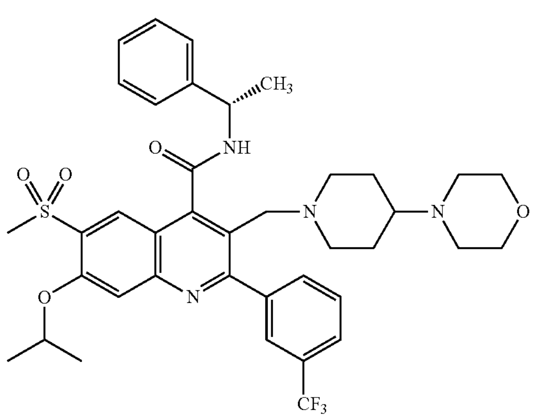 [SMILES: CC(C)Oc1cc2nc(-c3cccc(C(F)(F)F)c3)c(CN3CCC(N4CCOCC4)CC3)c(C(=O)N[C@@H](C)c3ccccc3)c2cc1S(C)(=O)=O] | 739.3 (M + H⁺) |

Example 20

7-[(1-methylethyl)oxy]-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide

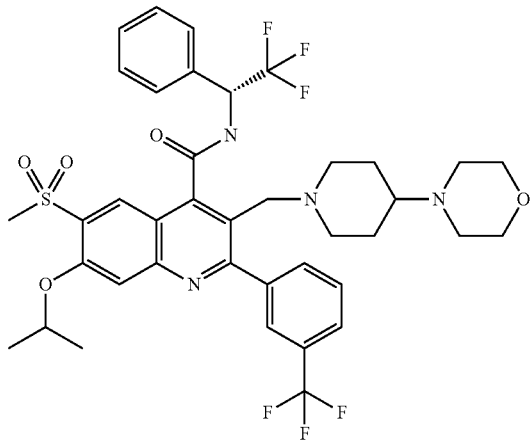 [SMILES: CC(C)Oc1cc2nc(-c3cccc(C(F)(F)F)c3)c(CN3CCC(N4CCOCC4)CC3)c(C(=O)N[C@H](c3ccccc3)C(F)(F)F)c2cc1S(C)(=O)=O]

6-fluoro-3-methyl-7-(methyloxy)-2-[3-(trifluoromethyl)phenyl]-4-quinolinecarboxylic acid A solution of 4-fluoro-3-(methyloxy)aniline (11.29 g, 80 mmol) and 3-(trifluoromethyl)benzaldehyde (13.93 g, 80 mmol) in ethanol (200 mL) was heated to reflux for 1 h. 2-Oxobutanoic acid (8.17 g, 80 mmol) was added portionwise. The reaction mixture was stirred at reflux for additional 3 h and cooled to room temperature overnight. The solid was collected by filtration, washed with ethanol, and dried to afford 6-fluoro-3-methyl-7-(methyloxy)-2-[3-(trifluoromethyl)phenyl]-4-quinolinecarboxylic acid (16.05 g, 53% yield). $^1$H NMR (400 MHz, DMSO-$d_6$) δ 7.94-7.98 (m, 2H), 7.88 (d, J=7.78 Hz, 1H), 7.74-7.80 (m, 1H), 7.71 (d, J=8.53 Hz, 1H), 7.54 (d, J=12.05 Hz, 1H), 4.03 (s, 3H), 2.38 (s, 3H); MS (m/z) 380.1 (M+H$^+$).

methyl 3-methyl-7-(methyloxy)-6-(methylthio)-2-[3-(trifluoromethyl)phenyl]-4-quinolinecarboxylate Sodium hydride (0.949 g, 23.73 mmol) was added portionwise to a suspension of 6-fluoro-3-methyl-7-(methyloxy)-2-[3-(trifluoromethyl)phenyl]-4-quinolinecarboxylic acid (6.0 g, 15.82 mmol) in dimethyl sulfoxide (50 mL). After 20 min, sodium thiomethoxide (1.44 g, 17.40 mmol) was added. The reaction mixture was heated to 100° C. for 2 h. The mixture was cooled to room temperature and iodomethane (4.95 mL, 79 mmol) was added. The reaction mixture was stirred for 2 h, diluted with ether, and extracted with methylene chloride (three times). The combined organic extracts were washed with brine (2 times), dried over Na$_2$SO$_4$, filtered, and concentrated. The residue was purified via column chromatography (ISCO, 330 g silica, 0-15% ethyl acetate/hexanes) to give methyl 3-methyl-7-(methyloxy)-6-(methylthio)-2-[3-(trifluoromethyl)phenyl]-4-quinolinecarboxylate (5.48 g, 82% yield). $^1$H NMR (400 MHz, DMSO-$d_6$) δ 7.94-8.01 (m, 2H), 7.87 (d, J=7.28 Hz, 1H), 7.77 (d, J=7.53 Hz, 1H), 7.49 (s, 1H), 7.24 (s, 1H), 4.07 (s, 3H), 4.01 (s, 3H), 2.53 (s, 3H), 2.34 (s, 3H); MS (m/z) 422.1 (M+H$^+$).

methyl 3-methyl-7-(methyloxy)-6-(methylsulfonyl)-2-[3-(trifluoromethyl)phenyl]-4-quinolinecarboxylate A solution of methyl 3-methyl-7-(methyloxy)-6-(methylthio)-2-[3-(trifluoromethyl)phenyl]-4-quinolinecarboxylate (4.5 g, 8.54 mmol) and 3-chloroperoxybenzoic acid (3.85 g, 17.17 mmol) in dichloromethane (50 mL) was stirred overnight. Saturated aqueous NaHCO$_3$ and Na$_2$S$_2$O$_3$ were added slowly and the resulting mixture was stirred for 30 min. The mixture was extracted with methylene chloride (3 times). The combined organic extracts were washed with brine (2 times), dried over Na$_2$SO$_4$, filtered, and concentrated in vacuo. The residue was purified via column chromatography (ISCO, 0-15% ethyl acetate/methylene chloride) to give methyl 3-methyl-7-(methyloxy)-6-(methylsulfonyl)-2-[3-(trifluoromethyl)phenyl]-4-quinolinecarboxylate (2.74 g, 71% yield). $^1$H NMR (400 MHz, DMSO-$d_6$) δ 8.25 (s, 1H), 7.99-8.06 (m, 2H), 7.92 (d, J=7.78 Hz, 1H), 7.82 (s, 1H), 7.76-7.82 (m, 1H), 4.11 (s, 3H), 4.09 (s, 3H), 3.41 (s, 3H), 2.38 (s, 3H); MS (m/z) 454.1 (M+H$^+$).

7-hydroxy-3-methyl-6-(methylsulfonyl)-2-[3-(trifluoromethyl)phenyl]-4-quinolinecarboxylic acid A solution of methyl 3-methyl-7-(methyloxy)-6-(methylsulfonyl)-2-[3-(trifluoromethyl)phenyl]-4-quinolinecarboxylate (4.95 g, 10.92 mmol) and hydrobromic acid (30 mL, 552 mmol) in acetic acid (30 mL) was heated to reflux for 5 days. The mixture was cooled to room temperature and diluted with water. The solid precipitate was collected by filtration, washed with water, and air dried to afford 7-hydroxy-3-methyl-6-(methylsulfonyl)-2-[3-(trifluoromethyl)phenyl]-4-quinolinecarboxylic acid (4.22 g, 91% yield). $^1$H NMR (400 MHz, DMSO-$d_6$) δ14.51 (br. s., 1H), 11.77 (s, 1H), 8.32 (s, 1H), 7.95-8.00 (m, 2H), 7.90 (d, J=7.78 Hz, 1H), 7.78 (t, J=7.78 Hz, 1H), 7.54 (s, 1H), 3.41 (s, 3H), 2.36 (s, 3H); MS (m/z) 426.0 (M+H$^+$).

methyl 7-hydroxy-3-methyl-6-(methylsulfonyl)-2-[3-(trifluoromethyl)phenyl]-4-quinolinecarboxylate DMF (5 drops) was added to a suspension of 7-hydroxy-3-methyl-6-(methylsulfonyl)-2-[3-(trifluoromethyl)phenyl]-4-quinolinecarboxylic acid (6.92 g, 16.27 mmol) in dichloromethane (120 mL) at 0° C. Oxalyl chloride (2.14 mL, 24.40 mmol) was added slowly. After 1 h at 0° C., the mixture was warmed to room temperature, and additional oxalyl chloride (2.14 mL, 24.40 mmol) was added. The mixture was warmed to room temperature and stirred overnight. Methanol (30 mL) was added and the mixture was stirred overnight. The solvent was removed under reduced pressure, the residue was diluted with water, and the aqueous mixture was treated with saturated aqueous NaHCO$_3$. The mixture was extracted with methylene chloride (three times). The combined organic extracts were washed with brine (2 times), dried over Na$_2$SO$_4$, filtered, and concentrated to afford methyl 7-hydroxy-3-methyl-6-(methylsulfonyl)-2-[3-(trifluoromethyl)

phenyl]-4-quinolinecarboxylate (6.0 g, 84% yield). $^1$H NMR (400 MHz, DMSO-d$_6$) δ11.85 (br. s., 1H), 8.18 (s, 1H), 7.95-8.02 (m, 2H), 7.91 (d, J=7.78 Hz, 1H), 7.78 (t, J=7.78 Hz, 1H), 7.55 (s, 1H), 4.07 (s, 3H), 3.41 (s, 3H), 2.32 (s, 3H); MS (m/z) 440.0 (M+H$^+$).

methyl 3-methyl-7-[(1-methylethyl)oxy]-6-(methylsulfonyl)-2-[3-(trifluoromethyl)phenyl]-4-quinolinecarboxylate 2-Iodopropane (2.32 g, 13.65 mmol) was added to a mixture of methyl methyl 7-hydroxy-3-methyl-6-(methylsulfonyl)-2-[3-(trifluoromethyl)phenyl]-4-quinolinecarboxylate (3.0 g, 6.83 mmol) and Cs$_2$CO$_3$ (6.67 g, 20.48 mmol) in N,N-dimethylformamide (30 mL). The mixture was stirred at room temperature overnight. The reaction mixture was diluted with saturated aqueous NH$_4$Cl and extracted with methylene chloride (three times). The combined organic extracts were washed with brine, dried over Na$_2$SO$_4$, filtered, and concentrated in vacuo. The residue was purified via column chromatography (ISCO, 120 g silica, 0-20% ethyl acetate/methylene chloride) to afford methyl 3-methyl-7-[(1-methylethyl)oxy]-6-(methylsulfonyl)-2-[3-(trifluoromethyl)phenyl]-4-quinolinecarboxylate (2.97 g, 90% yield). $^1$H NMR (400 MHz, DMSO-d$_6$) δ8.25 (d, J=1.00 Hz, 1H), 7.97-8.05 (m, 2H), 7.92 (d, J=7.78 Hz, 1H), 7.75-7.84 (m, 2H), 5.11 (dt, J=5.93, 11.98 Hz, 1H), 4.05-4.11 (m, 3H), 3.41 (s, 3H), 2.36 (s, 3H), 1.42-1.45 (m, 3H), 1.42 (s, 3H); MS (m/z) 482.1 (M+H$^+$).

methyl 3-(bromomethyl)-7-[(1-methylethyl)oxy]-6-(methylsulfonyl)-2-[3-(trifluoromethyl)phenyl]-4-quinolinecarboxylate A mixture of methyl 3-methyl-7-[(1-methylethyl)oxy]-6-(methylsulfonyl)-2-[3-(trifluoromethyl)phenyl]-4-quinolinecarboxylate (2.97 g, 6.17 mmol), NBS (1.427 g, 8.02 mmol) and diphenylperoxyanhydride (0.149 g, 0.617 mmol) in carbon tetrachloride (30 mL) was heated to 100° C. and stirred overnight. The mixture was cooled to room temperature, and the solvent was removed under reduced pressure to give methyl 3-(bromomethyl)-7-[(1-methylethyl)oxy]-6-(methylsulfonyl)-2-[3-(trifluoromethyl)phenyl]-4-quinolinecarboxylate. This material was used without further purification. MS (m/z) 562.0 (M+H$^+$).

methyl 7-[(1-methylethyl)oxy]-6-(methylsulfonyl)-3-{[4-(4-morpholinyl)-1-piperidinyl]methyl}-2-[3-(trifluoromethyl)phenyl]-4-quinolinecarboxylate A suspension of methyl 3-(bromomethyl)-7-[(1-methylethyl)oxy]-6-(methylsulfonyl)-2-[3-(trifluoromethyl)phenyl]-4-quinolinecarboxylate (1.732 g, 3.09 mmol) and 4-(4-piperidinyl)morpholine (0.684 g, 4.02 mmol) in acetonitrile (30 mL) was stirred for 3 h. The solvent was removed under reduced pressure, and the residue was purified via HPLC (Biotage RP, 0-50% MeCN/H$_2$O with 0.1% TFA). The fractions containing the product were neutralized with saturated aqueous NaHCO$_3$, and extracted with methylene chloride (three times). The combined organic extracts were washed with brine, dried over Na$_2$SO$_4$, filtered, and concentrated to afford methyl 7-[(1-methylethyl)oxy]-6-(methylsulfonyl)-3-{[4-(4-morpholinyl)-1-piperidinyl]methyl}-2-[3-(trifluoromethyl)phenyl]-4-quinolinecarboxylate (1.6 g, 80% yield). $^1$H NMR (400 MHz, DMSO-d$_6$) δ8.40 (s, 1H), 7.98 (s, 1H), 7.87-7.93 (m, 2H), 7.75-7.83 (m, 2H), 5.11 (dt, J=6.02, 12.05 Hz, 1H), 4.00 (s, 3H), 3.61 (s, 2H), 3.51-3.56 (m, 4H), 3.41 (s, 3H), 2.62 (d, J=11.29 Hz, 2H), 2.38 (br. s., 4H), 1.95-2.05 (m, 1H), 1.81 (t, J=10.92 Hz, 2H), 1.62 (d, J=12.55 Hz, 2H), 1.43 (s, 3H), 1.41 (s, 3H), 1.20-1.29 (m, 2H); MS (m/z) 650.2 (M+H$^+$).

7-[(1-methylethyl)oxy]-6-(methylsulfonyl)-3-{[4-(4-morpholinyl)-1-piperidinyl]methyl}-2-[3-(trifluoromethyl)phenyl]-4-quinolinecarboxylic acid Potassium hydroxide (1.38 g, 24.63 mmol) was added to a solution of methyl 7-[(1-methylethyl)oxy]-6-(methylsulfonyl)-3-{[4-(4-morpholinyl)-1-piperidinyl]methyl}-2-[3-(trifluoromethyl)phenyl]-4-quinolinecarboxylate (1.6 g, 2.463 mmol) in methanol (60 mL) and water (20 mL). The reaction mixture was heated to reflux overnight, cooled to room temperature and diluted with water. The methanol was removed under reduced pressure. The residual mixture was acidified to pH 6 with 2N HCl and extracted with methylene chloride (three times). The combined organic extracts were washed with brine, dried over Na$_2$SO$_4$, filtered, and concentrated to afford 7-[(1-methylethyl)oxy]-6-(methylsulfonyl)-3-{[4-(4-morpholinyl)-1-piperidinyl]methyl}-2-[3-(trifluoromethyl)phenyl]-4-quinolinecarboxylic acid (1.5 g, 96% yield). $^1$H NMR (400 MHz, DMSO-d$_6$) δ8.82 (s, 1H), 8.03 (s, 1H), 7.91 (t, J=7.91 Hz, 2H), 7.79 (t, J=7.78 Hz, 1H), 7.70 (s, 1H), 5.08 (dt, J=5.93, 11.98 Hz, 1H), 4.11 (br. s., 2H), 3.56 (br. s., 4H), 3.38 (s, 3H), 2.99 (d, J=11.29 Hz, 2H), 2.53-2.59 (m, 1H), 2.42 (br. s., 4H), 2.34 (br. s., 1H), 1.78 (d, J=12.30 Hz, 2H), 1.43 (s, 3H), 1.41 (s, 3H), 1.22-1.39 (m, 3H); MS (m/z) 636.2 (M+H$^+$).

7-[(1-methylethyl)oxy]-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide A solution of 7-[(1-methylethyl)oxy]-6-(methylsulfonyl)-3-{[4-(4-morpholinyl)-1-piperidinyl]methyl}-2-[3-(trifluoromethyl)phenyl]-4-quinolinecarboxylic acid (0.200 mg, 0.315 mmol), (1R)-2,2,2-trifluoro-1-phenylethanamine (0.072 g, 0.409 mmol), N,N-diisopropylethylamine (10.99 µL, 0.063 mmol), and 2,4,6-tripropyl-1,3,5,2,4,6-trioxatriphosphorinane 2,4,6-trioxide (0.262 mL of a 50% solution in ethyl acetate, 0.440 mmol) in dichloromethane (2 mL) was stirred at 0° C. for 2 h. The solution was warmed to room temperature overnight, diluted with saturated aqueous NaHCO$_3$, and extracted with methylene chloride (three times). The combined organic extracts were washed with brine, dried over Na$_2$SO$_4$, filtered and concentrated in vacuo. The residue was purified via HPLC (Waters, Sunfire 30×100 mm, 25-60% CH$_3$CN/H$_2$O with 0.1% TFA) to afford 7-[(1-methylethyl)oxy]-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide (0.137 g, 52% yield). $^1$H NMR (400 MHz, CHLOROFORM-d) δ9.85 (br. s., 1H), 8.79 (s, 1H), 7.81 (s, 1H), 7.75-7.80 (m, 1H), 7.64-7.69 (m, 2H), 7.52-7.59 (m, 3H), 7.42-7.48 (m, 3H), 6.25 (t, J=6.90 Hz, 1H), 4.91 (dt, J=6.02, 12.05 Hz, 1H), 3.65-3.72 (m, 5H), 3.52-3.65 (m, 2H), 3.31 (s, 3H), 2.64 (br. s., 1H), 2.38-2.45 (m, 4H), 2.20 (br. s., 1H), 2.03 (t, J=10.67 Hz, 1H), 1.66 (br. s., 4H), 1.59 (d, J=11.54 Hz, 2H), 1.54 (s, 3H), 1.53 (s, 3H); MS (m/z) 793.3 (M+H⁺).
Human TRPV4 FLIPR pIC50=8.2

Example 21

3-(1,4'-bipiperidin-1'-ylmethyl)-6-[(1-methylethyl) sulfonyl]-7-(methyloxy)-2-[3-(trifluoromethyl)phenyl]-N-[(1R)-2,2,2-trifluoro-1-phenylethyl]-4-quinolinecarboxamide

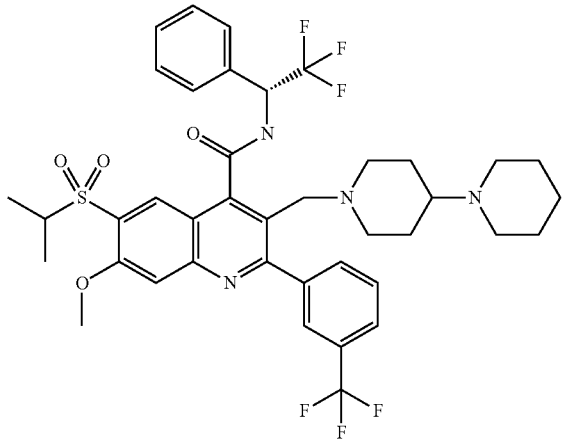 [SMILES: COc1cc2nc(-c3cccc(C(F)(F)F)c3)c(CN3CCC(N4CCCCC4)CC3)c(C(=O)N[C@H](c3ccccc3)C(F)(F)F)c2cc1S(=O)(=O)C(C)C]

6-fluoro-3-methyl-7-(methyloxy)-2-[3-(trifluoromethyl)phenyl]-4-quinolinecarboxylic acid A solution of 4-fluoro-3-(methyloxy)aniline (13.6 g, 96 mmol) and 3-(trifluoromethyl)benzaldehyde (16.78 g, 96 mmol) in ethanol (200 mL) was heated to reflux for 1 h. 2-Oxobutanoic acid (9.84 g, 96 mmol) was added portionwise. The reaction mixture was stirred at reflux for an additional 3 h, cooled to room temperature, and stirred overnight. The solid was collected by filtration, washed with ethanol, and air dried to afford 6-fluoro-3-methyl-7-(methyloxy)-2-[3-(trifluoromethyl)phenyl]-4-quinolinecarboxylic acid (17.9 g, 49% yield). ¹H NMR (400 MHz, DMSO-d₆)™ 14.34 (br. s., 1H), 7.93-7.98 (m, 2H), 7.88 (d, J=7.78 Hz, 1H), 7.77 (t, J=7.65 Hz, 1H), 7.71 (d, J=8.53 Hz, 1H), 7.54 (d, J=12.05 Hz, 1H), 4.03 (s, 3H), 2.38 (s, 3H); MS (m/z) 380.1 (M+H⁺).

methyl 3-methyl-6-[(1-methylethyl)thio]-7-(methyloxy)-2-[3-(trifluoromethyl)phenyl]-4-quinolinecarboxylate Sodium hydride (1.265 g, 31.6 mmol) was added to a suspension of 6-fluoro-3-methyl-7-(methyloxy)-2-[3-(trifluoromethyl)phenyl]-4-quinolinecarboxylic acid (8.0 g, 21.09 mmol) in dimethyl sulfoxide (50 mL), and the mixture was stirred for 20 min. Sodium 2-propanethiolate (2.53 g, 23.20 mmol) was added, and the resulting mixture was stirred at 100° C. overnight. The mixture was cooled to room temperature, treated with NaH (1.27 g of 60% dispersion in mineral oil, 31.6 mmol) and sodium 2-propanethiolate (2.53 g, 23.20 mmol), and heated at 100° C. for an additional 4 hours. The reaction mixture was cooled to room temperature. Iodomethane (3.96 mL, 63.3 mmol) was added, and the mixture was stirred for 2 hours. The mixture was diluted with water and extracted with methylene chloride (three times). The combined organic extracts were washed with brine, dried over Na₂SO₄, filtered, and concentrated in vacuo. The residue was purified via column chromatography (ISCO, 330 g silica, 0-10% ethyl acetate/methylene chloride) to afford methyl 3-methyl-6-[(1-methylethyl)thio]-7-(methyloxy)-2-[3-(trifluoromethyl)phenyl]-4-quinolinecarboxylate (5.5 g, 58% yield). This material was used in the next step without further purification. MS (m/z) 450.1 (M+H⁺).

methyl 3-methyl-6-[(1-methylethyl)sulfonyl]-7-(methyloxy)-2-[3-(trifluoromethyl)phenyl]-4-quinolinecarboxylate A solution of methyl 3-methyl-6-[(1-methylethyl)thio]-7-(methyloxy)-2-[3-(trifluoromethyl)phenyl]-4-quinolinecarboxylate (5.5 g, 4.04 mmol) and 3-chloroperoxybenzoic acid (1.819 g, 8.12 mmol) in dichloromethane (50 mL) was stirred overnight. Saturated aqueous NaHCO₃ and Na₂S₂O₃ were added slowly, and the mixture was stirred for 30 min before it was extracted with methylene chloride (three times). The combined organic extracts were washed with brine (two times), dried over Na₂SO₄, filtered, and concentrated in vacuo. The residue was purified via column chromatography (ISCO, 0-15% ethyl acetate/methylene chloride) to afford methyl 3-methyl-6-[(1-methylethyl)sulfonyl]-7-(methyloxy)-2-[3-(trifluoromethyl)phenyl]-4-quinolinecarboxylate (1.76 g, 91% yield). ¹H NMR (400 MHz, DMSO-d₆) δ8.24 (s, 1H), 7.99-8.05 (m, 2H), 7.92 (d, J=8.03 Hz, 1H), 7.76-7.84 (m, 2H), 4.09 (s, 6H), 3.83 (quin, J=6.78 Hz, 1H), 2.37 (s, 3H), 1.21 (s, 3H), 1.20 (s, 3H); MS (m/z) 482.1 (M+H⁺).

methyl 3-(bromomethyl)-6-[(1-methylethyl)sulfonyl]-7-(methyloxy)-2-[3-(trifluoromethyl)phenyl]-4-quinolinecarboxylate A mixture of methyl 3-methyl-6-[(1-methylethyl)sulfonyl]-7-(methyloxy)-2-[3-(trifluoromethyl)phenyl]-4-quinolinecarboxylate (1.76 g, 3.66 mmol), NBS (0.846 g, 4.75 mmol) and diphenylperoxyanhydride (0.089 g, 0.366 mmol) in carbon tetrachloride (60 mL) was heated to 100° C. and stirred overnight. The mixture was cooled to room temperature, and the solvent was removed under reduced pressure to afford methyl 3-(bromomethyl)-6-[(1-methylethyl)sulfonyl]-7-(methyloxy)-2-[3-(trifluoromethyl)phenyl]-4-quinolinecarboxylate. This material was used without further purification. MS (m/z) 562.0 (M+H⁺).

methyl 3-(1,4'-bipiperidin-1'-ylmethyl)-6-[(1-methylethyl)sulfonyl]-7-(methyloxy)-2-[3-(trifluoromethyl)phenyl]-4-quinolinecarboxylate A suspension of methyl 3-(bromomethyl)-6-[(1-methylethyl)sulfonyl]-7-(methyloxy)-2-[3-(trifluoromethyl)phenyl]-4-quinolinecarboxylate (1.025 g, 1.83 mmol) and 1,4'-bipiperidine (0.400 g, 2.379 mmol) in acetonitrile (10 mL) was stirred for 3 h. The solvent was removed under reduced pressure. The residue was dissolved in DMSO and purified via HPLC (Biotage RP, 0-50% MeCN/H₂O with 0.1% TFA). The fractions containing the product were neutralized with saturated aqueous NaHCO₃ and extracted with methylene chloride (three times). The combined organic extracts were washed with brine (two times), dried over Na₂SO₄, filtered, and concentrated to afford methyl 3-(1,4'-bipiperidin-1-ylmethyl)-6-[(1-methylethyl)sulfonyl]-7-(methyloxy)-2-[3-(trifluoromethyl)phenyl]-4-quinolinecarboxylate (0.94 g, 79% yield). ¹H NMR (400 MHz, DMSO-d₆) δ8.37 (s, 1H), 7.98 (s, 1H), 7.87-7.94 (m, 2H), 7.82 (s, 1H), 7.75-7.81 (m, 1H), 4.09 (s, 3H), 4.02 (s, 3H), 3.83 (quin, J=6.84 Hz, 1H), 3.61 (br. s., 2H), 2.65 (br. s., 2H), 2.31-2.44 (m, 2H), 2.07 (br. s., 1H), 1.76-1.91 (m, 2H), 1.65-1.75 (m, 1H), 1.41-1.61 (m, 6H), 1.24-1.39 (m, 5H), 1.22 (s, 3H), 1.21 (s, 3H); MS (m/z) 648.2 (M+H+).

3-(1,4'-bipiperidin-1'-ylmethyl)-6-[(1-methylethyl)sulfonyl]-7-(methyloxy)-2-[3-(trifluoromethyl)phenyl]-4-quinolinecarboxylic acid Potassium hydroxide (0.814 g, 14.51 mmol) was added to a solution of methyl 3-(1,4'-bipiperidin-1-ylmethyl)-6-[(1-methylethyl)sulfonyl]-7-(methyloxy)-2-[3-(trifluoromethyl)phenyl]-4-quinolinecarboxylate (0.94 g, 1.451 mmol) in methanol (60 mL) and water. The reaction mixture was heated to reflux overnight, cooled to room temperature, and diluted with water. The methanol was removed under reduced pressure, the residue was acidified to pH 6, and the mixture was extracted with methylene chloride (three times). The combined organic extracts were washed with brine (two times), dried over $Na_2SO_4$, filtered, and concentrated in vacuo to afford 3-(1,4'-bipiperidin-1'-ylmethyl)-6-[(1-methylethyl)sulfonyl]-7-(methyloxy)-2-[3-(trifluoromethyl)phenyl]-4-quinolinecarboxylic acid (0.73 g, 79% yield). $^1$H NMR (400 MHz, DMSO-$d_6$) δ 8.67 (s, 1H), 8.13 (s, 1H), 8.02 (d, J=7.53 Hz, 1H), 7.87 (d, J=8.03 Hz, 1H), 7.75 (t, J=7.65 Hz, 1H), 7.63 (s, 1H), 4.05 (s, 3H), 3.77 (dt, J=6.81, 13.74 Hz, 1H), 3.55 (br. s., 2H), 3.02 (br. s., 2H), 2.79 (br. s., 3H), 2.05 (br. s., 3H), 1.76-1.96 (m, 6H), 1.40-1.55 (m, 3H), 1.23-1.30 (m, 2H), 1.20 (s, 3H), 1.18 (s, 3H); MS (m/z) 634.2 (M+H+).

3-(1,4'-bipiperidin-1'-ylmethyl)-6-[(1-methylethyl)sulfonyl]-7-(methyloxy)-2-[3-(trifluoromethyl)phenyl]-N-[(1R)-2,2,2-trifluoro-1-phenylethyl]-4-quinolinecarboxamide A solution of 3-(1,4'-bipiperidin-1'-ylmethyl)-6-[(1-methylethyl)sulfonyl]-7-(methyloxy)-2-[3-(trifluoromethyl)phenyl]-4-quinolinecarboxylic acid (0.330 g, 0.521 mmol), (1R)-2,2,2-trifluoro-1-phenylethanamine (0.143 g, 0.677 mmol), N,N-diisopropylethylamine (0.018 mL, 0.104 mmol), and 2,4,6-tripropyl-1,3,5,2,4,6-trioxatriphosphorinane 2,4,6-trioxide (0.434 mL in a 50% ethyl acetate solution, 0.729 mmol) in dichloromethane (4 mL) was stirred at 0° C. for 2 h. The solution was warmed to room temperature and stirred overnight. The reaction mixture was diluted with saturated aqueous $NaHCO_3$ and extracted with methylene chloride (three times). The combined organic extracts were washed with brine, dried over $Na_2SO_4$, filtered, and concentrated in vacuo. The residue was dissolved in DMSO and was purified via HPLC (Waters, Sunfire, 30×75 mm column, 50 mL/min, 20-60% MeCN/$H_2O$ with 0.1% TFA). The fractions containing the product were neutralized with saturated aqueous $NaHCO_3$ and extracted with methylene chloride (three times). The combined organic extracts were washed with brine, dried over $Na_2SO_4$, filtered, and concentrated in vacuo to afford 3-(1,4'-bipiperidin-1-ylmethyl)-6-[(1-methylethyl)sulfonyl]-7-(methyloxy)-2-[3-(trifluoromethyl)phenyl]-N-[(1R)-2,2,2-trifluoro-1-phenylethyl]-4-quinolinecarboxamide (0.341 g, 79% yield). $^1$H NMR (400 MHz, CDCl$_3$) δ 10.03 (br. s., 1H), 8.80 (s, 1H), 7.75-7.82 (m, 2H), 7.64-7.68 (m, 2H), 7.59 (s, 1H), 7.53-7.58 (m, 2H), 7.42-7.47 (m, 3H), 6.21-6.31 (m, 1H), 4.09 (s, 3H), 3.76-3.85 (m, 1H), 3.60-3.69 (m, 1H), 3.52-3.60 (m, 1H), 2.67 (br. s., 1H), 2.40 (br. s., 4H), 2.17-2.27 (m, 1H), 2.14 (br. s., 1H), 1.50-1.71 (m, 9H), 1.42 (br. s., 2H), 1.32-1.39 (m, 6H), 1.15-1.28 (m, 1H); MS (m/z) 791.3 (M+H+).
Human TRPV4 FLIPR pIC50=8.4

Example 22

6-[(1-methylethyl)sulfonyl]-7-(methyloxy)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide

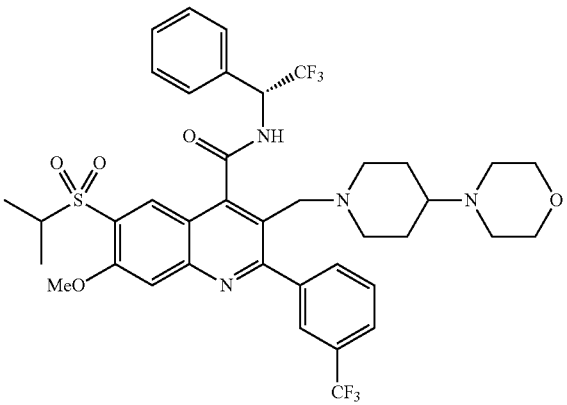 [SMILES: COc1cc2nc(-c3cccc(C(F)(F)F)c3)c(CN3CCC(N4CCOCC4)CC3)c(C(=O)N[C@H](c3ccccc3)C(F)(F)F)c2cc1S(=O)(=O)C(C)C]

Route 1:

6-fluoro-3-methyl-7-(methyloxy)-2-[3-(trifluoromethyl)phenyl]-4-quinolinecarboxylic acid A solution of 4-fluoro-3-(methyloxy)aniline (13.6 g, 96 mmol) and 3-(trifluoromethyl)benzaldehyde (16.78 g, 96 mmol) in ethanol (200 mL) was heated to reflux for 1 h. 2-Oxobutanoic acid (9.84 g, 96 mmol) was added portionwise. The reaction mixture was stirred at reflux for an additional 3 h, cooled to room temperature, and stirred overnight. The solid was collected by filtration, washed with ethanol, and air dried to afford 6-fluoro-3-methyl-7-(methyloxy)-2-[3-(trifluoromethyl)phenyl]-4-quinolinecarboxylic acid (17.9 g, 49% yield). $^1$H NMR (400 MHz, DMSO-$d_6$) δ14.34 (br. s., 1H), 7.93-7.98 (m, 2H), 7.88 (d, J=7.78 Hz, 1H), 7.77 (t, J=7.65 Hz, 1H), 7.71 (d, J=8.53 Hz, 1H), 7.54 (d, J=12.05 Hz, 1H), 4.03 (s, 3H), 2.38 (s, 3H); MS (m/z) 380.1 (M+H+).

methyl 3-methyl-6-[(1-methylethyl)thio]-7-(methyloxy)-2-[3-(trifluoromethyl)phenyl]-4-quinolinecarboxylate Sodium hydride (1.265 g, 31.6 mmol) was added to a suspension of 6-fluoro-3-methyl-7-(methyloxy)-2-[3-(trifluoromethyl)phenyl]-4-quinolinecarboxylic acid (8.0 g, 21.09 mmol) in dimethyl sulfoxide (50 mL), and the mixture was stirred for 20 min. Sodium 2-propanethiolate (2.53 g, 23.20 mmol) was added, and the resulting mixture was stirred at 100° C. overnight. The mixture was cooled to room temperature, treated with additional portions of NaH (1.27 g of 60% dispersion in mineral oil, 31.6 mmol) and sodium 2-propanethiolate (2.53 g, 23.20 mmol), and heated at 100° C. for an additional 4 hours. The reaction mixture was cooled to room temperature. Iodomethane (3.96 mL, 63.3 mmol) was added, and the mixture was stirred for 2 hours. The mixture was diluted with water and extracted with methylene chloride (three times). The combined organic extracts were washed with brine, dried over $Na_2SO_4$, filtered, and concentrated in vacuo. The residue was purified via column chromatography (ISCO, 330 g silica, 0-10% ethyl acetate/methylene chloride) to afford methyl 3-methyl-6-[(1-methylethyl)thio]-7-(methyloxy)-2-[3-(trifluoromethyl)phenyl]-4-quinolinecarboxylate (5.5 g, 58% yield). This material was used in the next step without further purification. MS (m/z) 450.1 (M+H$^+$).

methyl 3-methyl-6-[(1-methylethyl)sulfonyl]-7-(methyloxy)-2-[3-(trifluoromethyl)phenyl]-4-quinolinecarboxylate A solution of methyl 3-methyl-6-[(1-methylethyl)thio]-7-(methyloxy)-2-[3-(trifluoromethyl)phenyl]-4-quinolinecarboxylate (5.5 g, 4.04 mmol) and 3-chloroperoxybenzoic acid (1.819 g, 8.12 mmol) in dichloromethane (50 mL) was stirred overnight. Saturated aqueous NaHCO$_3$ and Na$_2$S$_2$O$_3$ were added slowly, and the mixture was stirred for 30 min before it was extracted with methylene chloride (three times). The combined organic extracts were washed with brine (two times), dried over Na$_2$SO$_4$, filtered, and concentrated in vacuo. The residue was purified via column chromatography (ISCO, 0-15% ethyl acetate/methylene chloride) to afford methyl 3-methyl-6-[(1-methylethyl)sulfonyl]-7-(methyloxy)-2-[3-(trifluoromethyl)phenyl]-4-quinolinecarboxylate (1.76 g, 91% yield). $^1$H NMR (400 MHz, DMSO-d$_6$) δ 8.24 (s, 1H), 7.99-8.05 (m, 2H), 7.92 (d, J=8.03 Hz, 1H), 7.76-7.84 (m, 2H), 4.09 (s, 6H), 3.83 (quin, J=6.78 Hz, 1H), 2.37 (s, 3H), 1.21 (s, 3H), 1.20 (s, 3H); MS (m/z) 482.1 (M+H$^+$).

methyl 3-(bromomethyl)-6-[(1-methylethyl)sulfonyl]-7-(methyloxy)-2-[3-(trifluoromethyl)phenyl]-4-quinolinecarboxylate A mixture of methyl 3-methyl-6-[(1-methylethyl)sulfonyl]-7-(methyloxy)-2-[3-(trifluoromethyl)phenyl]-4-quinolinecarboxylate (1.76 g, 3.66 mmol), NBS (0.846 g, 4.75 mmol) and diphenylperoxyanhydride (0.089 g, 0.366 mmol) in carbon tetrachloride (60 mL) was heated to 100° C. and stirred overnight. The mixture was cooled to room temperature, and the solvent was removed under reduced pressure to afford methyl 3-(bromomethyl)-6-[(1-methylethyl)sulfonyl]-7-(methyloxy)-2-[3-(trifluoromethyl)phenyl]-4-quinolinecarboxylate. This material was used in the next reaction without further purification. MS (m/z) 562.0 (M+H$^+$).

methyl 6-[(1-methylethyl)sulfonyl]-7-(methyloxy)-3-{[4-(4-morpholinyl)-1-piperidinyl]methyl}-2-[3-(trifluoromethyl)phenyl]-4-quinolinecarboxylate A suspension of methyl 3-(bromomethyl)-6-[(1-methylethyl)sulfonyl]-7-(methyloxy)-2-[3-(trifluoromethyl)phenyl]-4-quinolinecarboxylate (1.025 g, 1.83 mmol) and 4-(4-piperidinyl)morpholine (0.405 g, 2.379 mmol) in acetonitrile (10 mL) was stirred for 3 h. The solvent was removed under reduced pressure, and the residue was dissolved in DMSO and purified via HPLC (Biotage RP, 0-50% MeCN/H$_2$O with 0.1% TFA). The fractions containing the product were neutralized with saturated aqueous NaHCO$_3$ and extracted with methylene chloride (three times). The combined organic extracts were washed with brine (two times), dried over Na$_2$SO$_4$, filtered, and concentrated in vacuo to afford methyl 6-[(1-methylethyl)sulfonyl]-7-(methyloxy)-3-{[4-(4-morpholinyl)-1-piperidinyl]methyl}-2-[3-(trifluoromethyl)phenyl]-4-quinolinecarboxylate (0.77 g, 65% yield). $^1$H NMR (400 MHz, DMSO-d$_6$) δ 8.37 (s, 1H), 7.98 (s, 1H), 7.87-7.94 (m, 2H), 7.81 (s, 1H), 7.79 (d, J=7.78 Hz, 1H), 4.09 (s, 3H), 4.01 (s, 3H), 3.83 (quin, J=6.78 Hz, 1H), 3.61 (s, 2H), 3.53 (br. s., 4H), 2.59-2.69 (m, 2H), 2.38 (br. s., 4H), 2.00 (t, J=10.54 Hz, 1H), 1.77-1.86 (m, 2H), 1.62 (d, J=11.04 Hz, 2H), 1.24-1.30 (m, 2H), 1.22 (s, 3H), 1.21 (s, 3H); MS (m/z) 650.2 (M+H$^+$).

6-[(1-methylethyl)sulfonyl]-7-(methyloxy)-3-{[4-(4-morpholinyl)-1-piperidinyl]methyl}-2-[3-(trifluoromethyl)phenyl]-4-quinolinecarboxylic acid Potassium hydroxide (0.665 g, 11.85 mmol) was added to a solution of methyl 6-[(1-methylethyl)sulfonyl]-7-(methyloxy)-3-{[4-(4-morpholinyl)-1-piperidinyl]methyl}-2-[3-(trifluoromethyl)phenyl]-4-quinolinecarboxylate (0.77 g, 1.185 mmol) in methanol (60 mL) and water (20 mL). The reaction mixture was heated to reflux overnight, cooled to room temperature, and diluted with water. The methanol was removed under reduced pressure, and the residue was acidified to about pH 6 with 2N HCl and extracted with methylene chloride (three times). The combined organic extracts were washed twice with brine, dried over Na$_2$SO$_4$, filtered, and concentrated to afford 6-[(1-methylethyl)sulfonyl]-7-(methyloxy)-3-{[4-(4-morpholinyl)-1-piperidinyl]methyl}-2-[3-(trifluoromethyl)phenyl]-4-quinolinecarboxylic acid (0.67 g, 89% yield). $^1$H NMR (400 MHz, DMSO-d$_6$) δ 8.81 (s, 1H), 8.03 (s, 1H), 7.91 (t, J=6.53 Hz, 2H), 7.76-7.82 (m, 1H), 7.70 (s, 1H), 4.05-4.12 (m, 5H), 3.81 (dt, J=6.87, 13.61 Hz, 1H), 3.57 (br. s., 4H), 3.01 (d, J=9.79 Hz, 2H), 2.41-2.49 (m, 4H), 2.31-2.40 (m, 1H), 1.78 (d, J=11.54 Hz, 2H), 1.24-1.41 (m, 4H), 1.22 (s, 3H), 1.20 (s, 3H); MS (m/z) 636.2 (M+H$^+$).

6-[(1-methylethyl)sulfonyl]-7-(methyloxy)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide A solution of 6-[(1-methylethyl)sulfonyl]-7-(methyloxy)-3-{[4-(4-morpholinyl)-1-piperidinyl]methyl}-2-[3-(trifluoromethyl)phenyl]-4-quinolinecarboxylic acid (0.220 g, 0.346 mmol), (1R)-2,2,2-trifluoro-1-phenylethanamine (0.095 g, 0.450 mmol), N,N-diisopropylethylamine (0.012 mL, 0.069 mmol) and 2,4,6-tripropyl-1,3,5,2,4,6-trioxatriphosphorinane 2,4,6-trioxide (0.288 mL of a 50% solution in ethyl acetate, 0.485 mmol) in dichloromethane (4 mL) was stirred at 0° C. for 2 h. The reaction mixture was warmed to room temperature and stirred overnight. The solution was diluted with saturated aqueous NaHCO$_3$ and extracted with methylene chloride (three times). The combined organic extracts were washed twice with brine, dried over Na$_2$SO$_4$, filtered, and concentrated in vacuo. The residue was dissolved in DMSO and purified via HPLC (Waters, Sunfire, 30×75 mm column, 50 mL/min, 20-60% MeCN/H$_2$O with 0.1% TFA). The fractions containing the product were neutralized with saturated aqueous NaHCO$_3$ and extracted with methylene chloride (three times). The combined organic extracts were washed twice with brine, dried over Na$_2$SO$_4$, filtered, and concentrated in vacuo to afford 6-[(1-methylethyl)sulfonyl]-7-(methyloxy)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide (0.218 g, 75% yield). $^1$H NMR (400 MHz, CDCl$_3$) δ 9.71 (br. s., 1H), 8.77 (s, 1H), 7.82 (s, 1H), 7.77 (d, J=6.78 Hz, 1H), 7.63-7.69 (m, 2H), 7.59 (s, 1H), 7.53-7.58 (m, 2H), 7.42-7.47 (m, 3H), 6.19-6.29 (m, 1H), 4.08 (s, 3H), 3.80 (quin, J=6.84 Hz, 1H), 3.64-3.71 (m, 4H), 3.53-3.64 (m, 2H), 2.62 (br. s., 1H), 2.38-2.46 (m, 4H), 2.16-2.27 (m, 1H), 2.03 (t, J=10.92 Hz, 1H), 1.56-1.71 (m, 3H), 1.47-1.56 (m, 1H), 1.36 (s, 3H), 1.34 (s, 3H), 1.22-1.32 (m, 1H), 1.08-1.22 (m, 1H); MS (m/z) 793.2 (M+H⁺).

Human TRPV4 FLIPR pIC50=8.2

Route 2:

Alternatively, methyl 3-methyl-6-[(1-methylethyl)sulfonyl]-7-(methyloxy)-2-[3-(trifluoromethyl)phenyl]-4-quinolinecarboxylate was prepared using 4-bromo-3-(methyloxy) aniline (procedures described for the synthesis of Intermediate Preparation 7).

Methyl 3-methyl-6-[(1-methylethyl)sulfonyl]-7-(methyloxy)-2-[3-(trifluoromethyl)phenyl]-4-quinolinecarboxylate was then converted to 6-[(1-methylethyl)sulfonyl]-7-(methyloxy)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide via bromination, amine displacement, hydrolysis and amide coupling procedures analogous to those as described in Example 22, Route 1.

Example 23

7-(ethyloxy)-6-[(1-methylethyl)sulfonyl]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide

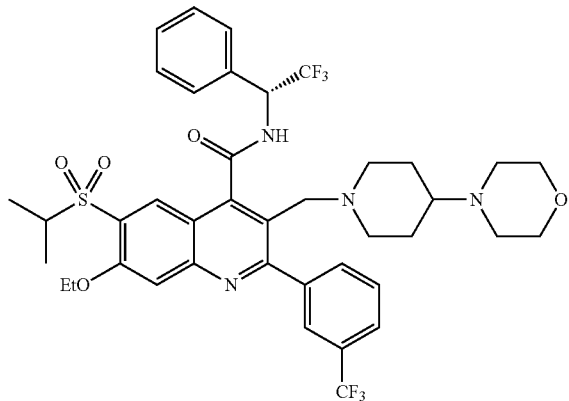 [SMILES: CCOc1cc2nc(-c3cccc(C(F)(F)F)c3)c(CN3CCC(N4CCOCC4)CC3)c(C(=O)N[C@H](c3ccccc3)C(F)(F)F)c2cc1S(=O)(=O)C(C)C]

6-bromo-3-methyl-7-(methyloxy)-2-[3-(trifluoromethyl)phenyl]-4-quinolinecarboxylic acid 3-(Trifluoromethyl)benzaldehyde (21.54 g, 124 mmol) was added to a solution of 4-bromo-3-(methyloxy)aniline (25 g, 124 mmol) in ethanol (300 mL) dropwise. The mixture was stirred at reflux for 1 h, and 2-oxobutanoic acid (12.63 g, 124 mmol) was added portionwise. The reaction mixture was stirred at reflux for additional 3 h, cooled to room temperature, and stirred overnight. The mixture was filtered to collect the precipitate, and the solid was washed with ethanol and dried to give 6-bromo-3-methyl-7-(methyloxy)-2-[3-(trifluoromethyl)phenyl]-4-quinolinecarboxylic acid (42.6 g, 78% yield). This material was used without further purification. MS (m/z) 442.0 (M+H⁺).

methyl 6-bromo-3-methyl-7-(methyloxy)-2-[3-(trifluoromethyl)phenyl]-4-quinolinecarboxylate DMF (5 drops) was added to a suspension of 6-bromo-3-methyl-7-(methyloxy)-2-[3-(trifluoromethyl)phenyl]-4-quinolinecarboxylic acid (42.6 g, 97 mmol) in dichloromethane (500 mL) at 0° C. Oxalyl chloride (12.71 mL, 145 mmol) was added slowly. The mixture was stirred at 0° C. for 1 h. MeOH (30 mL) was added, and the resulting mixture was stirred at 0° C. for 2 h and allowed to warm to room temperature overnight. The solvent was removed under reduced pressure. The residue was diluted with water, treated with saturated aqueous NaHCO₃, and extracted with methylene chloride. The combined organic extracts were washed with brine, dried over Na₂SO₄, filtered and concentrated in vacuo. The crude material was purified via column chromatography (ISCO, 330 g silica, 40-100% methylene chloride/hexanes) to afford methyl 6-bromo-3-methyl-7-(methyloxy)-2-[3-(trifluoromethyl)phenyl]-4-quinolinecarboxylate (29.8 g, 68% yield). ¹H NMR (400 MHz, DMSO-d₆) δ 8.05 (s, 1H), 7.96-8.01 (m, 2H), 7.89 (d, J=7.78 Hz, 1H), 7.77 (t, J=7.65 Hz, 1H), 7.65 (s, 1H), 4.08 (s, 3H), 4.03 (s, 3H), 2.34 (s, 3H); MS (m/z) 455.0 (M+H⁺).

methyl 3-methyl-6-[(1-methylethyl)sulfonyl]-7-(methyloxy)-2-[3-(trifluoromethyl)phenyl]-4-quinolinecarboxylate To a solution of methyl 6-bromo-3-methyl-7-(methyloxy)-2-[3-(trifluoromethyl)phenyl]-4-quinolinecarboxylate (10.0 g, 22.01 mmol) in dimethyl sulfoxide (200 mL) was added copper(I) iodide (8.39 g, 44.0 mmol) and sodium isopropanesulfinate (5.73 g, 44.0 mmol). The mixture was evacuated, purged with N₂ three times, and heated at 120° C. overnight. The mixture was cooled to room temperature, treated with iodomethane (4.13 mL, 66.0 mmol), and stirred for 1 h. The reaction mixture was diluted with methylene chloride (150 mL) and water (150 mL), stirred for 30 min, and filtered through Celite®. The filtrate was extracted with methylene chloride, and the organic phase was washed with brine, dried over Na₂SO₄, filtered, and concentrated. The material was purified via column chromatography (ISCO, 0-30% ethyl acetate/methylene chloride) to give methyl 3-methyl-6-[(1-methylethyl)sulfonyl]-7-(methyloxy)-2-[3-(trifluoromethyl)phenyl]-4-quinolinecarboxylate (9.55 g, 90% yield). ¹H NMR (400 MHz, DMSO-d₆) δ8.24 (s, 1H), 7.99-8.05 (m, 2H), 7.91 (s, 1H), 7.76-7.84 (m, 2H), 4.09 (s, 6H), 3.83 (quin, J=6.84 Hz, 1H), 2.37 (s, 3H), 1.21 (s, 3H), 1.20 (s, 3H); MS (m/z) 482.1 (M+H⁺).

7-hydroxy-3-methyl-6-[(1-methylethyl)sulfonyl]-2-[3-(trifluoromethyl)phenyl]-4-quinolinecarboxylic acid Hydrobromic acid (80 mL, 1467 mmol) was added slowly to a solution of methyl 3-methyl-6-[(1-methylethyl)sulfonyl]-7-(methyloxy)-2-[3-(trifluoromethyl)phenyl]-4-quinolinecarboxylate (14.13 g, 29.3 mmol) in acetic acid (30 mL). The mixture was heated to reflux for 5 days. The mixture was cooled to room temperature and diluted with water. The solids were collected by filtration, washed with water, and dried to afford 7-hydroxy-3-methyl-6-[(1-methylethyl)sulfonyl]-2-[3-(trifluoromethyl)phenyl]-4-quinolinecarboxylic acid (12.5 g, 94% yield). ¹H NMR (400 MHz, DMSO-d₆) δ11.73 (br. s., 1H), 8.31 (s, 1H), 7.94-8.00 (m, 2H), 7.91 (d, J=7.78 Hz, 1H), 7.79 (t, J=7.65 Hz, 1H), 7.54 (s, 1H), 3.91 (dt, J=6.81, 13.74 Hz, 1H), 2.35 (s, 3H), 1.22 (s, 3H), 1.21 (s, 3H); MS (m/z) 454.1 (M+H⁺).

methyl 7-hydroxy-3-methyl-6-[(1-methylethyl)sulfonyl]-2-[3-(trifluoromethyl)phenyl]-4-quinolinecarboxylate DMF (5 drops) was added to a suspension of 7-hydroxy-3-methyl-6-[(1-methylethyl)sulfonyl]-2-[3-(trifluoromethyl)phenyl]-4-quinolinecarboxylic acid (12.5 g, 27.6 mmol) in dichloromethane (120 mL). Oxalyl chloride (3.62 mL, 41.4 mmol) was added slowly. The mixture was stirred at room temperature for 1 h. Methanol (30 mL) was added, and the mixture was stirred overnight at room temperature. The solvent was removed under reduced pressure to provide methyl 7-hydroxy-3-methyl-6-[(1-methylethyl)sulfonyl]-2-[3-(trifluoromethyl)phenyl]-4-quinolinecarboxylate. This material was used without further purification. MS (m/z) 468.1 (M+H$^+$).

methyl 7-(ethyloxy)-3-methyl-6-[(1-methylethyl)
sulfonyl]-2-[3-(trifluoromethyl)phenyl]-4-quinolinecarboxylate Iodoethane (3.35 mL, 41.4 mmol) was added slowly to a mixture of methyl 7-hydroxy-3-methyl-6-[(1-methylethyl)sulfonyl]-2-[3-(trifluoromethyl)phenyl]-4-quinolinecarboxylate (12.90 g, 27.6 mmol) and cesium carbonate (27.0 g, 83 mmol) in dimethyl sulfoxide (150 mL) at room temperature. The mixture was stirred at room temperature overnight. The mixture was diluted with water and extracted with methylene chloride. The phases were separated, and the organic phase was washed with brine, dried over Na$_2$SO$_4$, filtered, and concentrated. The crude material was purified via column chromatography (ISCO, 330 g silica, 0-20% ethyl acetate/methylene chloride) to afford a solid residue that was triturated from methanol to give methyl 7-(ethyloxy)-3-methyl-6-[(1-methylethyl)sulfonyl]-2-[3-(trifluoromethyl)phenyl]-4-quinolinecarboxylate (11.39 g, 83% yield). $^1$H NMR (400 MHz, DMSO-d$_6$) δ8.24 (s, 1H), 7.98-8.04 (m, 2H), 7.91 (d, J=7.78 Hz, 1H), 7.76-7.82 (m, 2H), 4.39 (q, J=7.03 Hz, 2H), 4.09 (s, 3H), 3.85 (quin, J=6.84 Hz, 1H), 2.36 (s, 3H), 1.44 (t, J=7.03 Hz, 3H), 1.23 (s, 3H), 1.21 (s, 3H); MS (m/z) 496.1 (M+H$^+$).

methyl 3-(bromomethyl)-7-(ethyloxy)-6-[(1-methylethyl)sulfonyl]-2-[3-(trifluoromethyl)phenyl]-4-quinolinecarboxylate A suspension of methyl 7-(ethyloxy)-3-methyl-6-[(1-methylethyl)sulfonyl]-2-[3-(trifluoromethyl)phenyl]-4-quinolinecarboxylate (9.5 g, 19.17 mmol), N-bromosuccinimide (4.09 g, 23.01 mmol), and benzoyl peroxide (0.464 g, 1.917 mmol) in carbon tetrachloride (100 mL) was heated to reflux (100° C.) overnight. The reaction mixture was concentrated in vacuo to give methyl 3-(bromomethyl)-7-(ethyloxy)-6-[(1-methylethyl)sulfonyl]-2-[3-(trifluoromethyl)phenyl]-4-quinolinecarboxylate. This material was used without further purification. MS (m/z) 576.0 (M+H$^+$).

methyl 7-(ethyloxy)-6-[(1-methylethyl)sulfonyl]-3-{[4-(4-morpholinyl)-1-piperidinyl]methyl}-2-[3-(trifluoromethyl)phenyl]-4-quinolinecarboxylate A solution of methyl 3-(bromomethyl)-7-(ethyloxy)-6-[(1-methylethyl)sulfonyl]-2-[3-(trifluoromethyl)phenyl]-4-quinolinecarboxylate (3.5 g, 6.09 mmol), 4-(4-piperidinyl) morpholine (1.778 g, 7.31 mmol), and N,N-diisopropylethylamine (2.13 mL, 12.19 mmol) in acetonitrile (50 mL) was stirred at room temperature for 1.5 h. The solvent was removed under reduced pressure, and the residue was partitioned between a 10% sodium carbonate solution and methylene chloride. The organic phase was separated and washed with Na$_2$CO$_3$. The organic phase was extracted with 2N HCl (three times). The aqueous extracts were cooled in an ice bath and adjusted to pH 12 with 6N NaOH. The precipitated solid was extracted with methylene chloride (three times). The combined organic extracts were washed with brine, dried over Na$_2$SO$_4$, filtered, and concentrated to afford methyl 7-(ethyloxy)-6-[(1-methylethyl)sulfonyl]-3-{[4-(4-morpholinyl)-1-piperidinyl]methyl}-2-[3-(trifluoromethyl)phenyl]-4-quinolinecarboxylate (1.3 g, 31% yield) as a yellow solid. This material was used without further purification. MS (m/z) 664.2 (M+H$^+$).

7-(ethyloxy)-6-[(1-methylethyl)sulfonyl]-3-{[4-(4-morpholinyl)-1-piperidinyl]methyl}-2-[3-(trifluoromethyl)phenyl]-4-quinolinecarboxylic acid A stirred suspension of methyl 7-(ethyloxy)-6-[(1-methylethyl)sulfonyl]-3-{[4-(4-morpholinyl)-1-piperidinyl]methyl}-2-[3-(trifluoromethyl)phenyl]-4-quinolinecarboxylate (1.3 g, 1.959 mmol) and potassium hydroxide (0.879 g, 15.67 mmol) in methanol (15 mL) and water (3.75 mL) was heated to reflux for 20 h. The mixture was cooled to room temperature, and the solvent was removed under reduced pressure. The resulting yellow oil was partitioned between water and methylene chloride and cooled in an ice bath. The pH was adjusted to 5/6 with 2N HCl and the organic phase was separated. The aqueous phase was extracted twice more with methylene chloride. The combined organic extracts were washed with brine, dried, and concentrated to afford 7-(ethyloxy)-6-[(1-methylethyl)sulfonyl]-3-{[4-(4-morpholinyl)-1-piperidinyl]methyl}-2-[3-(trifluoromethyl)phenyl]-4-quinolinecarboxylic acid (1.3 g, 97% yield) as a yellow solid. $^1$H NMR (400 MHz, DMSO-d$_6$) δ8.81 (s, 1H), 8.01 (s, 1H), 7.86-7.94 (m, 2H), 7.75-7.82 (m, 1H), 7.67 (s, 1H), 4.37 (q, J=6.80 Hz, 2H), 4.10 (br. s., 2H), 3.84 (quin, J=6.80 Hz, 1H), 3.56 (br. s., 4H), 3.02 (d, J=11.08 Hz, 2H), 2.52-2.63 (m, 2H), 2.44 (br. s., 4H), 2.33 (br. s., 1H), 1.79 (d, J=12.34 Hz, 2H), 1.44 (t, J=6.92 Hz, 3H), 1.26-1.39 (m, 2H), 1.23 (s, 3H), 1.21 (s, 3H); MS (m/z) 650.2 (M+H$^+$).

7-(ethyloxy)-6-[(1-methylethyl)sulfonyl]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide T3P in ethyl acetate (1.273 mL of a 50% solution, 2.001 mmol) was added to a stirred solution of 7-(ethyloxy)-6-[(1-methylethyl)sulfonyl]-3-{[4-(4-morpholinyl)-1-piperidinyl]methyl}-2-[3-(trifluoromethyl)phenyl]-4-quinolinecarboxylic acid (1 g, 1.539 mmol), [(1R)-2,2,2-trifluoro-1-phenylethyl]amine (0.391 g, 1.847 mmol), and N,N-diisopropylethylamine (0.538 mL, 3.08 mmol) in dichloromethane (10 mL). The reaction mixture was stirred for 16 h, diluted with saturated aqueous sodium bicarbonate, and extracted with methylene chloride (three times). The combined organic extracts were washed with saturated sodium bicarbonate, brine, dried, and concentrated in vacuo. The residue was purified via column chromatography (ISCO, 0-5% methanol/methylene chloride) to afford 7-(ethyloxy)-6-[(1-methylethyl)sulfonyl]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide (0.450 g, 34% yield) as a light yellow solid. $^1$H NMR (400 MHz, DMSO-d$_6$) δ10.00 (br. s., 1H), 8.48 (br. s., 1H), 7.97 (s, 1H), 7.86 (d, J=7.55 Hz, 2H), 7.71-7.78 (m, 2H), 7.60-7.68 (m, 2H), 7.42-7.47 (m, 3H), 6.20 (quin, J=8.81 Hz, 1H), 4.39 (q, J=6.80 Hz, 2H), 3.72-3.86 (m, 1H), 3.50 (br. s., 4H), 3.44 (br. s., 1H), 3.18 (br. s., 1H), 2.39 (br. s., 1H), 2.33 (br. s., 1H), 2.26 (br. s., 4H), 2.11 (br. s., 1H), 1.68 (br. s., 2H), 1.53 (br. s., 1H), 1.44 (t, J=6.80 Hz, 3H), 1.12-1.37 (m, 7H), 0.74-0.99 (m, 2H); MS (m/z) 807.2 (M+H$^+$).

Human TRPV4 FLIPR pIC50=8.2

The following compounds were prepared using procedures analogous to those described in Example 23 substituting 4-morpholinopiperidine with 1,4'-bipiperidine or 4-(1-pyrrolidinyl)piperidine when necessary. As is appreciated by those skilled in the art, these analogous examples may involve variations in general reaction conditions.

| Ex | Name | Structure | MS (m/z) |
|---|---|---|---|
| 24 | 3-(1,4'-bipiperidin-1'-ylmethyl)-7-(ethyloxy)-6-[(1-methylethyl)sulfonyl]-2-[3-(trifluoromethyl)phenyl]-N-[(1R)-2,2,2-trifluoro-1-phenylethyl]-4-quinolinecarboxamide | 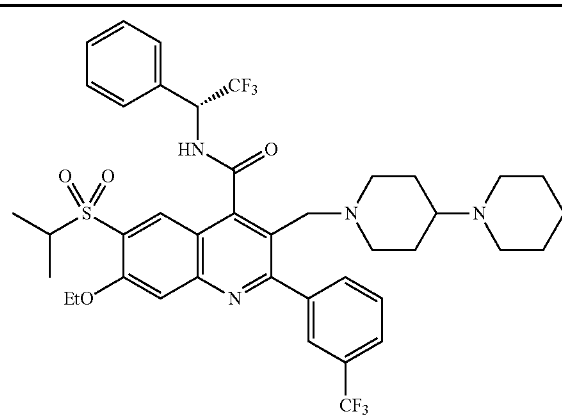 | 805.3 (M + H+) |
| 25 | 7-(ethyloxy)-6-[(1-methylethyl)sulfonyl]-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide | 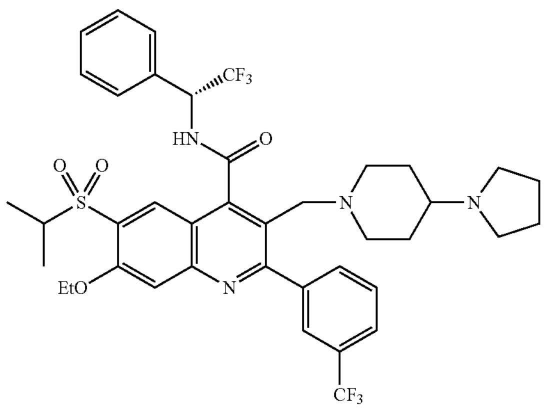 [SMILES: CCOc1cc2nc(-c3cccc(C(F)(F)F)c3)c(CN3CCC(N4CCCC4)CC3)c(C(=O)N[C@H](c3ccccc3)C(F)(F)F)c2cc1S(=O)(=O)C(C)C] | 791.2 (M + H+) |

Example 26

7-(ethyloxy)-6-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide

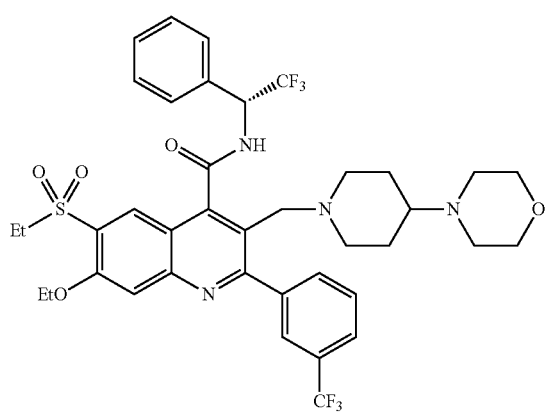 [SMILES: CCOc1cc2nc(-c3cccc(C(F)(F)F)c3)c(CN3CCC(N4CCOCC4)CC3)c(C(=O)N[C@H](c3ccccc3)C(F)(F)F)c2cc1S(=O)(=O)CC]

6-fluoro-3-methyl-7-(methyloxy)-2-[3-(trifluoromethyl)phenyl]-4-quinolinecarboxylic acid To a solution of 4-fluoro-3-(methyloxy)aniline (25.0 g, 177 mmol) in ethanol (300 mL) was added 3-(trifluoromethyl)benzaldehyde (30.8 g, 177 mmol) dropwise. The mixture was stirred at reflux for 1 h, and 2-oxobutanoic acid (18.08 g, 177 mmol) was added portionwise. The reaction mixture was stirred at reflux for an additional 3 h, cooled to room temperature, and stirred overnight. The solid precipitate was collected by filtration, washed with ethanol, and air dried to give 6-fluoro-3-methyl-7-(methyloxy)-2-[3-(trifluoromethyl)phenyl]-4-quinolinecarboxylic acid (29.1 g, 43% yield). $^1$H NMR (400 MHz, DMSO-$d_6$) δ14.34 (br. s., 1H), 7.94-7.98 (m, 2H), 7.88 (d, J=7.78 Hz, 1H), 7.77 (t, J=7.65 Hz, 1H), 7.71 (d, J=8.53 Hz, 1H), 7.54 (d, J=12.05 Hz, 1H), 4.03 (s, 3H), 2.38 (s, 3H); MS (m/z) 380.1 (M+H+).

6-fluoro-7-hydroxy-3-methyl-2-[3-(trifluoromethyl)phenyl]-4-quinolinecarboxylic acid To a solution of 6-fluoro-3-methyl-7-(methyloxy)-2-[3-(trifluoromethyl)phenyl]-4-quinolinecarboxylic acid (19.5 g, 51.4 mmol) in acetic acid (50 mL) was added hydrobromic acid (140 mL, 2.57 mol) slowly. The resulting mixture was heated to reflux for 5 days. The mixture was cooled to room temperature, diluted with water and filtered. The filter cake was washed with water and air dried to afford 6-fluoro-7-hydroxy-3-methyl-2-[3-(trifluoromethyl)phenyl]-4-quinolinecarboxylic acid (18.57 g, 99% yield). $^1$H NMR (400 MHz, DMSO-d$_6$) δ14.27 (br. s., 1H), 11.04 (s, 1H), 7.90-7.95 (m, 2H), 7.87 (d, J=7.78 Hz, 1H), 7.76 (t, J=7.65 Hz, 1H), 7.50 (d, J=2.76 Hz, 1H), 7.47 (s, 1H), 2.34 (s, 3H); MS (m/z) 366.0 (M+H$^+$).

methyl 6-fluoro-7-hydroxy-3-methyl-2-[3-(trifluoromethyl)phenyl]-4-quinolinecarboxylate To a suspension of 6-fluoro-7-hydroxy-3-methyl-2-[3-(trifluoromethyl)phenyl]-4-quinolinecarboxylic acid (9.0 g, 24.64 mmol) in dichloromethane (120 mL) at 0° C. was added 5 drops of DMF. Oxalyl chloride (3.24 mL, 37.0 mmol) was added slowly. The mixture was stirred at 0° C. for 1 h. The mixture was warmed to room temperature, and an additional portion of oxalyl chloride (3.24 mL, 37.0 mmol) was added. The reaction mixture was stirred overnight. Methanol (50 mL) was added and the mixture was stirred overnight. The solvent was removed under reduced pressure to afford methyl 6-fluoro-7-hydroxy-3-methyl-2-[3-(trifluoromethyl)phenyl]-4-quinolinecarboxylate. This material was used without further purification in the next step. MS (m/z) 380.1 (M+H$^+$).

methyl 7-(ethyloxy)-6-fluoro-3-methyl-2-[3-(trifluoromethyl)phenyl]-4-quinolinecarboxylate To a mixture of methyl 6-fluoro-7-hydroxy-3-methyl-2-[3-(trifluoromethyl)phenyl]-4-quinolinecarboxylate (9.35 g, 24.64 mmol) and Cs$_2$CO$_3$ (24.08 g, 73.9 mmol) in N,N-dimethylformamide (100 mL) at room temperature was added iodoethane (3.98 mL, 49.3 mmol) slowly. The mixture was stirred at room temperature overnight. The reaction mixture was diluted with saturated aqueous NH$_4$Cl and extracted with methylene chloride. The combined organic extracts were washed with brine, dried over Na$_2$SO$_4$, filtered, and concentrated in vacuo. The crude material was purified via column chromatography (ISCO, 120 g silica, 0-20% ethyl acetate/methylene chloride) to afford methyl 7-(ethyloxy)-6-fluoro-3-methyl-2-[3-(trifluoromethyl)phenyl]-4-quinolinecarboxylate (9.35 g, 93% yield). $^1$H NMR (400 MHz, DMSO-d$_6$) δ7.93-7.99 (m, 2H), 7.88 (d, J=7.78 Hz, 1H), 7.76 (t, J=7.65 Hz, 1H), 7.69 (d, J=8.53 Hz, 1H), 7.63 (d, J=12.30 Hz, 1H), 4.30 (q, J=7.03 Hz, 2H), 4.06 (s, 3H), 2.33 (s, 3H), 1.44 (t, J=6.90 Hz, 3H); MS (m/z) 408.1 (M+H$^+$).

methyl 7-(ethyloxy)-6-(ethylthio)-3-methyl-2-[3-(trifluoromethyl)phenyl]-4-quinolinecarboxylate To a solution of methyl 7-(ethyloxy)-6-fluoro-3-methyl-2-[3-(trifluoromethyl)phenyl]-4-quinolinecarboxylate (9.35 g, 22.95 mmol) in dimethyl sulfoxide (150 mL) was added sodium ethanethiolate (6.44 g, 68.9 mmol) and the resulting mixture was stirred at room temperature overnight. Iodomethane (7.18 mL, 115 mmol) was added, and the mixture was stirred for 2 h. The mixture was diluted with water and extracted with methylene chloride. The organic extracts were washed with brine, dried over Na$_2$SO$_4$, filtered, and concentrated in vacuo to afford methyl 7-(ethyloxy)-6-(ethylthio)-3-methyl-2-[3-(trifluoromethyl)phenyl]-4-quinolinecarboxylate. This material was used without further purification. MS (m/z) 450.1 (M+H$^+$).

methyl 7-(ethyloxy)-6-(ethylsulfonyl)-3-methyl-2-[3-(trifluoromethyl)phenyl]-4-quinolinecarboxylate To a solution of methyl 7-(ethyloxy)-6-(ethylthio)-3-methyl-2-[3-(trifluoromethyl)phenyl]-4-quinolinecarboxylate (10.32 g, 22.95 mmol) in tetrahydrofuran (150 mL) was added oxone (35.3 g, 57.4 mmol) in water (75 mL). The resulting mixture was stirred overnight at room temperature. The mixture was diluted with water and extracted with methylene chloride. The combined organic extracts were washed with brine, dried over Na$_2$SO$_4$, filtered, and concentrated in vacuo. The residue was purified via column chromatography (ISCO, 0-15% ethyl acetate/methylene chloride) to give methyl 7-(ethyloxy)-6-(ethylsulfonyl)-3-methyl-2-[3-(trifluoromethyl)phenyl]-4-quinolinecarboxylate (9.11 g, 82% yield). $^1$H NMR (400 MHz, DMSO-d$_6$) δ8.24 (s, 1H), 7.98-8.05 (m, 2H), 7.92 (d, J=7.78 Hz, 1H), 7.76-7.82 (m, 2H), 4.39 (q, J=6.94 Hz, 2H), 4.09 (s, 3H), 3.56 (q, J=7.28 Hz, 2H), 2.36 (s, 3H), 1.45 (t, J=6.90 Hz, 3H), 1.14 (t, J=7.40 Hz, 3H); MS (m/z) 482.1 (M+H$^+$).

methyl 3-(bromomethyl)-7-(ethyloxy)-6-(ethylsulfonyl)-2-[3-(trifluoromethyl)phenyl]-4-quinolinecarboxylate A mixture of methyl 7-(ethyloxy)-6-(ethylsulfonyl)-3-methyl-2-[3-(trifluoromethyl)phenyl]-4-quinolinecarboxylate (9.11 g, 18.92 mmol), N-bromosuccinimide (4.38 g, 24.60 mmol) and diphenylperoxyanhydride (0.458 g, 1.892 mmol) in carbon tetrachloride (100 mL) was heated to 100° C. overnight. The mixture was cooled to room temperature and the solvent was removed under reduced pressure to afford methyl 3-(bromomethyl)-7-(ethyloxy)-6-(ethylsulfonyl)-2-[3-(trifluoromethyl)phenyl]-4-quinolinecarboxylate. This material was used without further purification. MS (m/z) 562.0 (M+H$^+$).

methyl 7-(ethyloxy)-6-(ethylsulfonyl)-3-{[4-(4-morpholinyl)-1-piperidinyl]methyl}-2-[3-(trifluoromethyl)phenyl]-4-quinolinecarboxylate A suspension of methyl 3-(bromomethyl)-7-(ethyloxy)-6-(ethylsulfonyl)-2-[3-(trifluoromethyl)phenyl]-4-quinolinecarboxylate (3.54 g, 6.31 mmol) and 4-(4-piperidinyl)morpholine (1.397 g, 8.20 mmol) in acetonitrile (30 mL) was stirred for 3 h. The solvent was removed under reduced pressure, and the residue was diluted with NaHCO$_3$ and extracted with methylene chloride (three times). The combined organic extracts were washed with brine, dried over Na$_2$SO$_4$, filtered, and concentrated in vacuo. The residue was dissolved in DMF and purified via HPLC (Biotage RP, 0-50% MeCN/H$_2$O with 0.1% TFA). The fractions containing the product were neutralized with saturated aqueous NaHCO$_3$ and extracted with methylene chloride (three times). The combined organic extracts were washed with brine, dried over Na$_2$SO$_4$, filtered, and concentrated to afford methyl 7-(ethyloxy)-6-(ethylsulfonyl)-3-{[4-(4-morpholinyl)-1-piperidinyl]methyl}-2-[3-(trifluoromethyl)phenyl]-4-quinolinecarboxylate (2.09 g, 51% yield). $^1$H NMR (400 MHz, DMSO-d$_6$) δ8.37 (s, 1H), 7.97 (s, 1H), 7.90 (t, J=8.53 Hz, 2H), 7.76-7.81 (m, 2H), 4.39 (q, J=6.94 Hz, 2H), 4.01 (s, 3H), 3.50-3.64 (m, 9H), 2.63 (d, J=11.29 Hz, 2H), 2.38 (br. s., 4H), 1.95-2.05 (m, 1H), 1.81 (t, J=11.17 Hz, 2H), 1.61 (d, J=11.54 Hz, 2H), 1.45 (t, J=7.03 Hz, 3H), 1.19-1.30 (m, 2H), 1.15 (t, J=7.40 Hz, 3H); MS (m/z) 650.2 (M+H$^+$).

7-(ethyloxy)-6-(ethylsulfonyl)-3-{[4-(4-morpholinyl)-1-piperidinyl]methyl}-2-[3-(trifluoromethyl)phenyl]-4-quinolinecarboxylic acid Potassium hydroxide (1.805 g, 32.2 mmol) was added to a solution of methyl 7-(ethyloxy)-6-(ethylsulfonyl)-3-{[4-(4-morpholinyl)-1-piperidinyl]methyl}-2-[3-(trifluoromethyl)phenyl]-4-quinolinecarboxylate (2.09 g, 3.22 mmol) in methanol (60 mL) and water (20 mL). The mixture was heated to reflux overnight, cooled to room temperature, and diluted with water. The methanol was removed under reduced pressure, and the remaining aqueous solution was acidified to pH 6 and extracted with methylene chloride (three times). The combined organic extracts were washed with brine (two times), dried over Na$_2$SO$_4$, filtered, and concentrated in vacuo to afford 7-(ethyloxy)-6-(ethylsulfonyl)-3-{[4-(4-morpholinyl)-1-piperidinyl]methyl}-2-[3-(trifluoromethyl)phenyl]-4-quinolinecarboxylic acid (1.82 g, 89% yield). $^1$H NMR (400 MHz, DMSO-d$_6$)™ 8.80 (s, 1H), 8.03 (s, 1H), 7.88-7.94 (m, 2H), 7.76-7.82 (m, 1H), 7.67 (s, 1H), 4.37 (q, J=6.94 Hz, 2H), 4.08 (br. s., 2H), 3.50-3.62 (m, 6H), 2.99 (br. s., 2H), 2.31-2.59 (m, 6H), 1.79 (d, J=12.30 Hz, 2H), 1.45 (t, J=6.90 Hz, 3H), 1.23-1.41 (m, 3H), 1.14 (t, J=7.40 Hz, 3H); MS (m/z) 636.2 (M+H$^+$).

7-(ethyloxy)-6-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide T3P (2,4,6-tripropyl-1,3,5,2,4,6-trioxatriphosphorinane 2,4,6-trioxide, 0.262 mL of a 50% solution in ethyl acetate, 0.440 mmol) was added to a solution of 7-(ethyloxy)-6-(ethylsulfonyl)-3-{[4-(4-morpholinyl)-1-piperidinyl]methyl}-2-[3-(trifluoromethyl)phenyl]-4-quinolinecarboxylic acid (0.200 g, 0.315 mmol), (1R)-2,2,2-trifluoro-1-phenylethanamine (0.087 g, 0.409 mmol), N,N-diisopropylethylamine (10.99 µL, 0.063 mmol) in dichloromethane (4 mL) at 0° C. The mixture was stirred at 0° C. for 2 h, warmed to room temperature, and stirred overnight. The solution was diluted with saturated aqueous NaHCO$_3$ and extracted with methylene chloride (three times). The combined organic extracts were washed with brine, dried over Na$_2$SO$_4$, filtered, and concentrated in vacuo. The residue was dissolved in DMSO and purified via HPLC (Waters, Sunfire, 30×75 mm column, 50 mL/min, 20-60% MeCN/H$_2$O with 0.1% TFA). The fractions containing the product were neutralized with saturated aqueous NaHCO$_3$ and extracted with methylene chloride (three times). The combined organic extracts were washed with brine (two times), dried over Na$_2$SO$_4$, filtered, and concentrated in vacuo to afford 7-(ethyloxy)-6-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide (0.165 g, 63% yield). $^1$H NMR (400 MHz, CHLOROFORM-d) δ 9.75 (br. s., 1H), 8.77 (s, 1H), 7.81 (s, 1H), 7.74-7.79 (m, 1H), 7.62-7.70 (m, 2H), 7.52-7.59 (m, 3H), 7.40-7.50 (m, 3H), 6.25 (br. s., 1H), 4.29-4.39 (m, 2H), 3.64-3.71 (m, 4H), 3.53-3.64 (m, 2H), 3.48 (q, J=7.03 Hz, 2H), 2.63 (br. s., 1H), 2.37-2.46 (m, 4H), 2.22 (br. s., 1H), 1.97-2.09 (m, 1H), 1.67 (br. s., 4H), 1.58 (t, J=6.90 Hz, 3H), 1.50 (br. s., 1H), 1.31 (t, J=7.40 Hz, 3H), 1.08-1.24 (m, 1H); MS (m/z) 793.2 (M+H$^+$).

Human TRPV4 FLIPR pIC50=8

The following compounds were prepared using procedures analogous to those described in Example 26 using an appropriate alkyl iodide, substituting 4-morpholinopiperidine with 1,4'-bipiperidine or 4-(1-pyrrolidinyl)piperidine, and replacing (1R)-2,2,2-trifluoro-1-phenylethanamine with (1S)-1-phenylethanamine when necessary. As is appreciated by those skilled in the art, these analogous examples may involve variations in general reaction conditions.

| Ex | Name | Structure | MS (m/z) |
|---|---|---|---|
| 27 | 3-(1,4'-bipiperidin-1'-ylmethyl)-7-(ethyloxy)-6-(ethylsulfonyl)-N-[(1S)-1-phenylethyl]-2-[3-(trifluoromethyl)phenyl]-4-quinolinecarboxamide | 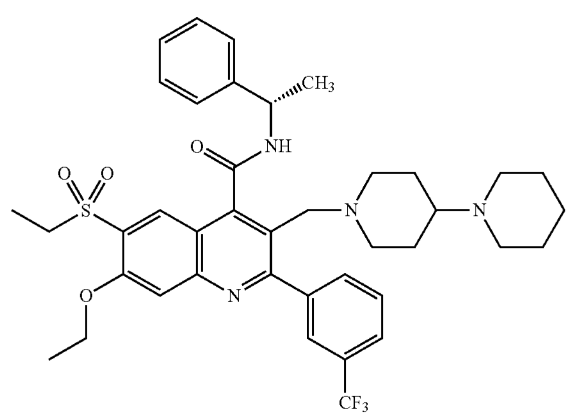 [SMILES: CCOc1cc2nc(-c3cccc(C(F)(F)F)c3)c(CN3CCC(N4CCCCC4)CC3)c(C(=O)N[C@@H](C)c3ccccc3)c2cc1S(=O)(=O)CC] | 737.3 (M + H$^+$) |

-continued

| Ex | Name | Structure | MS (m/z) |
|---|---|---|---|
| 28 | 3-(1,4'-bipiperidin-1'-ylmethyl)-7-(ethyloxy)-6-(ethylsulfonyl)-2-[3-(trifluoromethyl)phenyl]-N-[(1R)-2,2,2-trifluoro-1-phenylethyl]-4-quinolinecarboxamide | 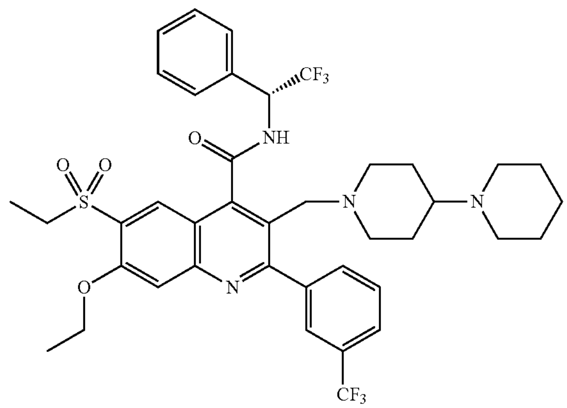 [SMILES: CCOc1cc2nc(-c3cccc(C(F)(F)F)c3)c(CN3CCC(N4CCCCC4)CC3)c(C(=O)N[C@H](c3ccccc3)C(F)(F)F)c2cc1S(=O)(=O)CC] | 791.2 (M + H+) |
| 29 | 7-(ethyloxy)-6-(ethylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide | 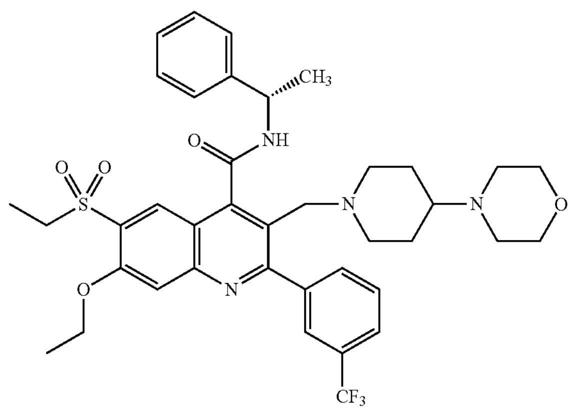 [SMILES: CCOc1cc2nc(-c3cccc(C(F)(F)F)c3)c(CN3CCC(N4CCOCC4)CC3)c(C(=O)N[C@@H](C)c3ccccc3)c2cc1S(=O)(=O)CC] | 739.3 (M + H+) |
| 30 | 7-(ethyloxy)-6-(ethylsulfonyl)-N-[(1S)-1-phenylethyl]-3-{[4-(1-pyrrolidinyl)-1-piperidinyl]methyl}-2-[3-(trifluoromethyl)phenyl]-4-quinolinecarboxamide | 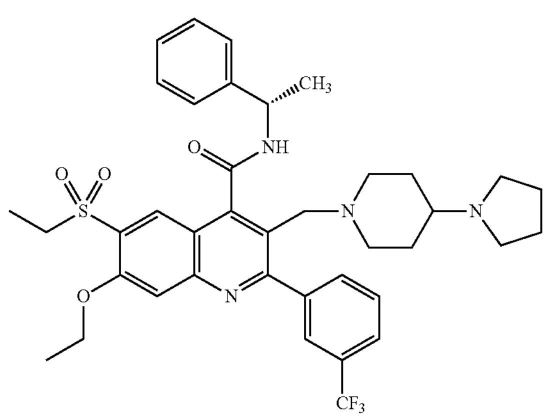 [SMILES: CCOc1cc2nc(-c3cccc(C(F)(F)F)c3)c(CN3CCC(N4CCCC4)CC3)c(C(=O)N[C@@H](C)c3ccccc3)c2cc1S(=O)(=O)CC] | 723.3 (M + H+) |

-continued

| Ex | Name | Structure | MS (m/z) |
|---|---|---|---|
| 31 | 7-(ethyloxy)-6-(ethylsulfonyl)-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide | 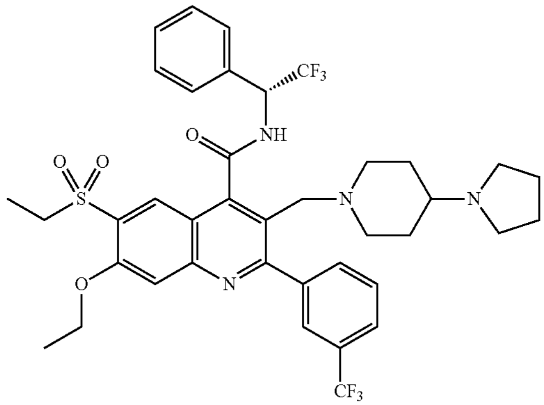 [SMILES: CCOc1cc2nc(-c3cccc(C(F)(F)F)c3)c(CN3CCC(N4CCCC4)CC3)c(C(=O)N[C@H](c3ccccc3)C(F)(F)F)c2cc1S(=O)(=O)CC] | 777.3 (M + H$^+$) |
| 32 | 3-(1,4'-bipiperidin-1'-ylmethyl)-6-(ethylsulfonyl)-7-[(1-methylethyl)oxy]-N-[(1S)-1-phenylethyl]-2-[3-(trifluoromethyl)phenyl]-4-quinolinecarboxamide | 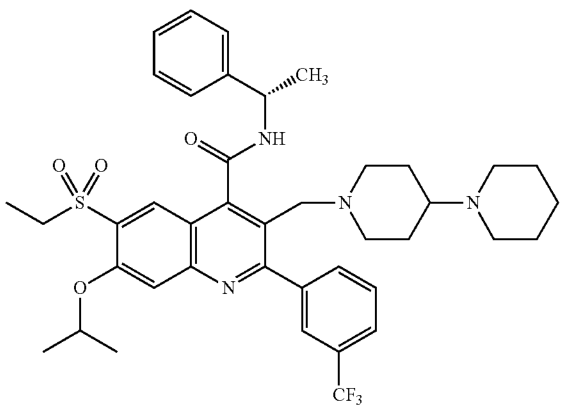 [SMILES: CCS(=O)(=O)c1cc2c(C(=O)N[C@@H](C)c3ccccc3)c(CN3CCC(N4CCCCC4)CC3)c(-c3cccc(C(F)(F)F)c3)nc2cc1OC(C)C] | 751.3 (M + H$^+$) |
| 33 | 3-(1,4'-bipiperidin-1'-ylmethyl)-6-(ethylsulfonyl)-7-[(1-methylethyl)oxy]-2-[3-(trifluoromethyl)phenyl]-N-[(1R)-2,2,2-trifluoro-1-phenylethyl]-4-quinolinecarboxamide | 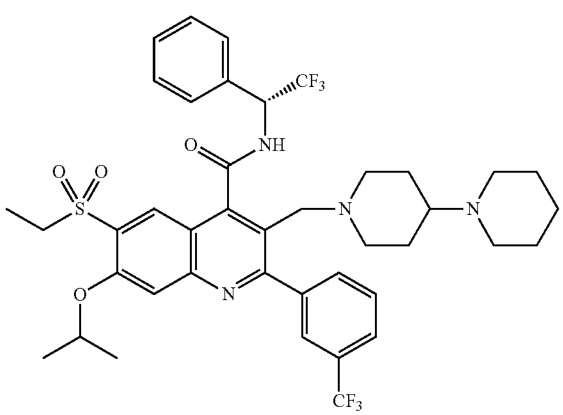 [SMILES: CCS(=O)(=O)c1cc2c(C(=O)N[C@H](c3ccccc3)C(F)(F)F)c(CN3CCC(N4CCCCC4)CC3)c(-c3cccc(C(F)(F)F)c3)nc2cc1OC(C)C] | 805.3 (M + H$^+$) |

-continued

| Ex | Name | Structure | MS (m/z) |
|---|---|---|---|
| 34 | 6-(ethylsulfonyl)-7-[(1-methylethyl)oxy]-3-{[4-(4-morpholinyl)-1-piperidinyl]methyl}-N-[(1S)-1-phenylethyl]-2-[3-(trifluoromethyl)phenyl]-4-quinolinecarboxamide | 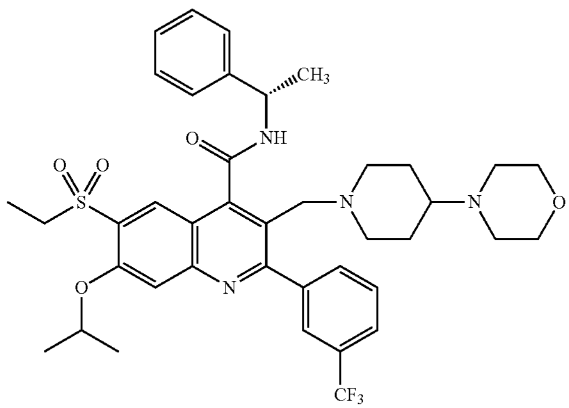 | 753.3 (M + H⁺) |
| 35 | 6-(ethylsulfonyl)-7-[(1-methylethyl)oxy]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide | 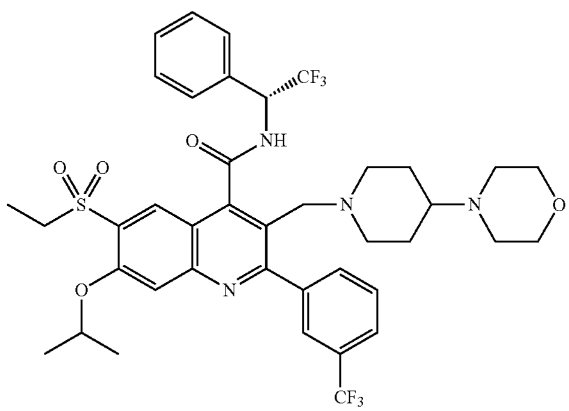 [SMILES: CCS(=O)(=O)c1cc2c(C(=O)N[C@H](c3ccccc3)C(F)(F)F)c(CN3CCC(N4CCOCC4)CC3)c(-c3cccc(C(F)(F)F)c3)nc2cc1OC(C)C] | 807.3 (M + H⁺) |
| 36 | 6-(ethylsulfonyl)-7-[(1-methylethyl)oxy]-N-[(1S)-1-phenylethyl]-3-{[4-(1-pyrrolidinyl)-1-piperidinyl]methyl}-2-[3-(trifluoromethyl)phenyl]-4-quinolinecarboxamide | 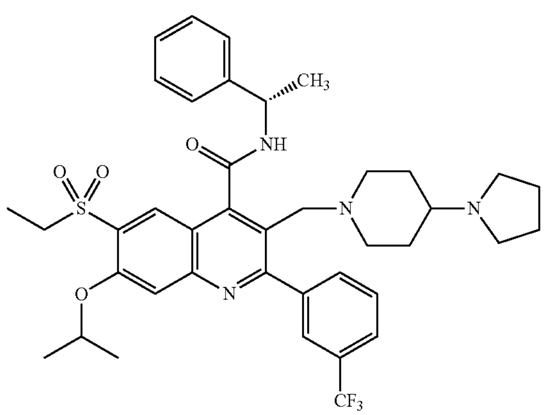 [SMILES: CCS(=O)(=O)c1cc2c(C(=O)N[C@@H](C)c3ccccc3)c(CN3CCC(N4CCCC4)CC3)c(-c3cccc(C(F)(F)F)c3)nc2cc1OC(C)C] | 737.3 (M + H⁺) |

| Ex | Name | Structure | MS (m/z) |
|---|---|---|---|
| 37 | 6-(ethylsulfonyl)-7-[(1-methylethyl)oxy]-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide | 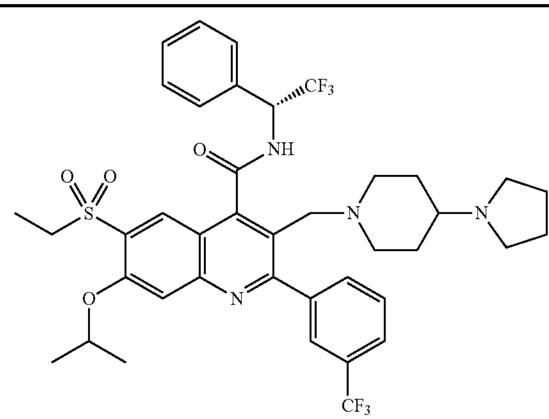 | 791.3 (M + H$^+$) |

Example 38

6-[(1-methylethyl)sulfonyl]-3-{[3-methyl-4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide

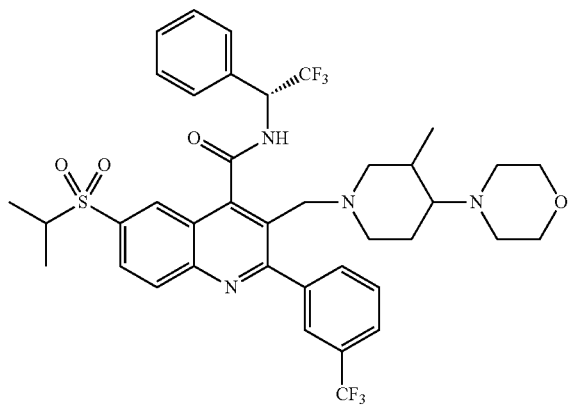 [SMILES: CC1CN(Cc2c(-c3cccc(C(F)(F)F)c3)nc3ccc(S(=O)(=O)C(C)C)cc3c2C(=O)N[C@H](c2ccccc2)C(F)(F)F)CCC1N1CCOCC1]

6-fluoro-3-methyl-2-[3-(trifluoromethyl)phenyl]-4-quinolinecarboxylic acid

5-Fluoroisatin (61.3 g, 371 mmol) was dissolved in ethanol (564 mL) to provide a dark red solution. KOH (125 g, 2226 mmol) was dissolved in water (226 mL) and the solution was added slowly to the isatin solution. 1-[3-(Trifluoromethyl)phenyl]-1-propanone (75 g, 371 mmol) was added, and the solution was heated to reflux for 1 h. The reaction mixture was cooled in an ice bath and neutralized with concentrated HCl (208 mL, 2597 mmol). The precipitate was collected by filtration, washed with water (100 mL), and air dried. The solid material was crushed and resuspended in 1:1 ethanol/water (800 mL). The slurry was refluxed for 30 min. The solid was collected by filtration, washed with 1:1 ethanol/water (100 mL), and dried. The solid material was crushed and resuspended in 1:1 ethanol/water (800 mL). The slurry was refluxed for 30 min. The solid was collected by filtration, washed with 1:1 ethanol/water (100 mL), and dried in a vacuum oven at 50° C. for 6 h to afford 6-fluoro-3-methyl-2-[3-(trifluoromethyl)phenyl]-4-quinolinecarboxylic acid (118.3 g, 91% yield) as an off-white solid. $^1$H NMR (400 MHz, DMSO-d$_6$) δ 14.41 (br. s., 1H), 8.19 (dd, J=5.65, 9.16 Hz, 1H), 7.94-8.00 (m, 2H), 7.89 (d, J=8.03 Hz, 1H), 7.72-7.81 (m, 2H), 7.53 (dd, J=2.76, 9.79 Hz, 1H), 2.41 (s, 3H); MS (m/z) 350.1 (M+H$^+$).

methyl 3-methyl-6-[(1-methylethyl)sulfonyl]-2-[3-(trifluoromethyl)phenyl]-4-quinolinecarboxylate 6-Fluoro-3-methyl-2-[3-(trifluoromethyl)phenyl]-4-quinolinecarboxylic acid (90 g, 258 mmol) was treated with KOH (14.48 g, 258 mmol) in water. The solution was concentrated and azeotroped with toluene (three times). The resulting solid was dissolved in dimethyl sulfoxide (1 L) and sodium 2-propanethiolate (57.0 g, 581 mmol) was added. The mixture was heated to 100° C. and stirred overnight. The solution was cooled to room temperature and MeI (0.048 L, 774 mmol) was added. After stirring for 1 h, water (500 mL) was added slowly with stirring. The solid precipitate was collected by filtration, washed with water, and dried. The filter cake was dissolved in tetrahydrofuran (1.5 L) and cooled in an ice bath. Oxone (317 g, 516 mmol) was added as a solution in water (1.5 L). The ice bath was removed, and stirring was continued for 2 h. The organic phase was separated, and the aqueous phase was extracted with methylene chloride (three times). The THF and methylene chloride extracts were combined, concentrated to approximately 1 L, diluted with methylene chloride (500 mL), and washed with brine. The organic phase was concentrated to afford a brown residue. Methanol was added and the solution was heated to reflux with stirring. The mixture was cooled to room temperature and stirred overnight. The precipitate was collected by filtration, washed with methanol, and dried under reduced pressure to afford methyl 3-methyl-6-[(1-methylethyl)sulfonyl]-2-[3-(trifluoromethyl)phenyl]-4-quinolinecarboxylate (114 g, 97% yield) as an off-white solid. $^1$H NMR (400 MHz, METHANOL-d$_4$) 68.29-8.36 (m, 2H), 8.17 (d, J=8.78 Hz, 1H), 7.97 (s, 1H), 7.91 (d, J=7.53 Hz, 1H), 7.85 (d, J=7.78 Hz, 1H), 7.76 (t, J=7.78 Hz, 1H), 4.13 (s, 3H), 3.47 (quin, J=6.71 Hz, 1H), 2.45 (s, 3H), 1.30 (s, 3H), 1.28 (s, 3H); MS (m/z) 452.1 (M+H$^+$).

methyl 6-[(1-methylethyl)sulfonyl]-3-[(3-methyl-4-oxo-1-piperidinyl)methyl]-2-[3-(trifluoromethyl)phenyl]-4-quinolinecarboxylate A suspension of methyl 3-methyl-6-[(1-methylethyl)sulfonyl]-2-[3-(trifluoromethyl)phenyl]-4-quinolinecarboxylate (1.25 g, 2.77 mmol), N-bromosuccinimide (0.641 g, 3.60 mmol), and benzoyl peroxide (0.067 g, 0.277 mmol) in carbon tetrachloride (27 ml) was heated to 100° C. for 19 h. The mixture was cooled to room temperature, and the solvent was removed under reduced pressure.

The residue was suspended in acetonitrile (20 mL), and 3-methyl-piperidin-4-one hydrochloride (0.497 g, 3.32 mmol) and N,N-diisopropylethylamine (1.209 mL, 6.92 mmol) were added. The mixture was stirred at room temperature for 22 h. The solvent was removed under reduced pressure, and the residue was diluted with 10% $Na_2CO_3$. The aqueous mixture was extracted with ethyl acetate (2×25 mL). The combined organic extracts were dried over $Na_2SO_4$, filtered, and concentrated in vacuo. The crude residue was loaded onto florisil and purified using silica gel chromatography (ISCO, 12 g silica, 5-40% ethyl acetate/hexanes, 12 g silica) to afford methyl 6-[(1-methylethyl)sulfonyl]-3-[(3-methyl-4-oxo-1-piperidinyl)methyl]-2-[3-(trifluoromethyl)phenyl]-4-quinolinecarboxylate (1.24 g, 76% yield). $^1$H NMR (400 MHz, DMSO-$d_6$) δ8.35-8.41 (m, 2H), 8.22 (dd, J=2.01, 8.81 Hz, 1H), 8.03 (s, 1H), 7.93 (t, J=8.94 Hz, 2H), 7.75-7.82 (m, 1H), 4.08 (s, 3H), 3.82 (s, 2H), 3.65 (quin, J=6.74 Hz, 1H), 2.87 (dd, J=5.04, 10.07 Hz, 2H), 2.22-2.47 (m, 3H), 2.06 (d, J=13.60 Hz, 1H), 1.92-2.01 (m, 1H), 1.23 (s, 3H), 1.21 (s, 3H), 0.77 (d, J=6.55 Hz, 3H); MS (m/z) 563.1 (M+H$^+$).

6-[(1-methylethyl)sulfonyl]-3-[(3-methyl-4-oxo-1-piperidinyl)methyl]-2-[3-(trifluoromethyl)phenyl]-4-quinolinecarboxylic acid Sodium hydroxide (11.02 mL of a 2M solution, 22.04 mmol) was added to a yellow solution of methyl 6-[(1-methylethyl)sulfonyl]-3-[(3-methyl-4-oxo-1-piperidinyl)methyl]-2-[3-(trifluoromethyl)phenyl]-4-quinolinecarboxylate (1.24 g, 2.204 mmol) in methanol (11.02 mL) and tetrahydrofuran (11.02 mL). The mixture was heated to 50° C. for 20 h. The mixture was cooled to room temperature, and the solvent was removed under reduced pressure. The residue was diluted with water (5 mL), and the solid precipitate was collected by filtration, washed with water (2×1 mL), and dried in a vacuum oven at 40° C. to afford 6-[(1-methylethyl)sulfonyl]-3-[(3-methyl-4-oxo-1-piperidinyl)methyl]-2-[3-(trifluoromethyl)phenyl]-4-quinolinecarboxylic acid (0.95 g, 72% yield). $^1$H NMR (400 MHz, DMSO-$d_6$) δ8.53 (d, J=1.76 Hz, 1H), 8.10-8.18 (m, 2H), 7.96-8.05 (m, 2H), 7.83 (d, J=7.81 Hz, 1H), 7.72 (t, J=7.68 Hz, 1H), 3.71 (s, 2H), 3.49 (dt, J=6.77, 13.41 Hz, 1H), 2.68-2.78 (m, 2H), 2.08-2.32 (m, 3H), 1.92-2.03 (m, 2H), 1.22 (s, 3H), 1.20 (s, 3H), 0.70 (d, J=6.55 Hz, 3H); MS (m/z) 549.2 (M+H$^+$).

6-[(1-methylethyl)sulfonyl]-3-[(3-methyl-4-oxo-1-piperidinyl)methyl]-2-[3-(trifluoromethyl)phenyl]-N-[(1R)-2,2,2-trifluoro-1-phenylethyl]-4-quinolinecarboxamide T3P (propylphosphonic anhydride) (0.698 mL of a 50% solution in ethyl acetate, 1.185 mmol), N,N-diisopropylethylamine (0.478 mL, 2.73 mmol), and [(1R)-2,2,2-trifluoro-1-phenylethyl]amine (0.251 g, 1.185 mmol) were added to a suspension of 6-[(1-methylethyl)sulfonyl]-3-[(3-methyl-4-oxo-1-piperidinyl)methyl]-2-[3-(trifluoromethyl)phenyl]-4-quinolinecarboxylic acid (0.5 g, 0.911 mmol) in dichloromethane (14.02 mL) at 0° C. After 90 min, additional T3P (propylphosphonic anhydride, 0.349 mL of a 50% solution in ethyl acetate, 0.593 mmol) was added. The mixture was stirred overnight at room temperature. The mixture was diluted with methylene chloride (30 mL), and the solution was washed with 10% $Na_2CO_3$, dried over $Na_2SO_4$, filtered, and concentrated in vacuo. The residue was loaded onto florisil and purified using column chromatography (ISCO, 12 g silica, 5-40% ethyl acetate/hexanes) to afford 6-[(1-methylethyl)sulfonyl]-3-[(3-methyl-4-oxo-1-piperidinyl)methyl]-2-[3-(trifluoromethyl)phenyl]-N-[(1R)-2,2,2-trifluoro-1-phenylethyl]-4-quinolinecarboxamide (0.431 g, 67% yield). MS (m/z) 706.3 (M+H$^+$).

6-[(1-methylethyl)sulfonyl]-3-{[3-methyl-4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide Acetic acid (9.73 µL, 0.170 mmol), morpholine (0.030 g, 0.340 mmol), and sodium triacetoxyborohydride (0.048 g, 0.227 mmol) were added to a suspension of 6-[(1-methylethyl)sulfonyl]-3-[(3-methyl-4-oxo-1-piperidinyl)methyl]-2-[3-(trifluoromethyl)phenyl]-N-[(1R)-2,2,2-trifluoro-1-phenylethyl]-4-quinolinecarboxamide (0.080 g, 0.113 mmol) in dichloromethane (1.5 mL). The mixture was stirred at room temperature for 3 d. The solution was diluted with water (3 mL) and methylene chloride (5 mL) and poured into a hydrophobic frit to separate the phases. The organic phase was concentrated and the residue was purified via HPLC (Waters, Sunfire C18, 30×100 mm, 35-69% $CH_3CN/H_2O$ with 0.1% TFA) to afford 6-[(1-methylethyl)sulfonyl]-3-{[3-methyl-4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide (0.040 g, 45% yield) as a mixture of diastereomers. $^1$H NMR (400 MHz, DMSO-$d_6$) δ10.1250=4 Hz, 0.5H), 10.045 (br d, J=4 Hz, 0.5H), 8.38 (m, 2H), 8.14 (m, 2H), 7.97 (m, 2 H), 7.84 (d, J=8 Hz, 1H), 7.73 (m, 1H), 7.63 (m, 2H), 7.45 (br s, 2H), 6.24 (apparent q, J=6.8 Hz, 1H), 3.50 (m, 4H), 3.17 (m, 1H), 2.40-2.05 (m, 5H), 1.95-0.75 (m, 14H), 0.410 (d, J=6 Hz, 1.7H), 0.295 (br d, J=4 Hz, 1.3H). MS (m/z) 777.3 (M+H$^+$).

Human TRPV4 FLIPR pIC50=8

The following compounds were prepared using procedures analogous to those described in Example 38 substituting pyrrolidine or piperidine for morpholine when necessary. As is appreciated by those skilled in the art, these analogous examples may involve variations in general reaction conditions.

| Ex | Name | Structure | MS (m/z) |
|---|---|---|---|
| 39 | 6-[(1-methylethyl)sulfonyl]-3-{[3-methyl-4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide | 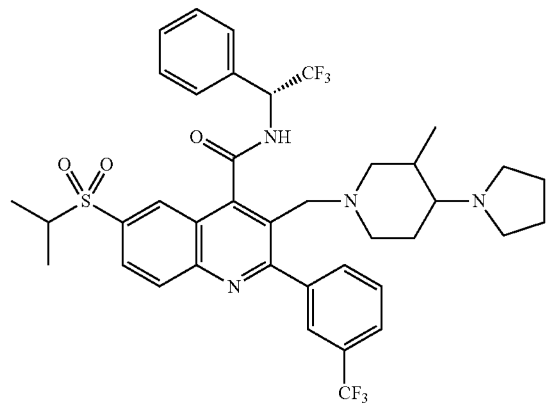 [SMILES: CC1CN(Cc2c(-c3cccc(C(F)(F)F)c3)nc3ccc(S(=O)(=O)C(C)C)cc3c2C(=O)N[C@H](c2ccccc2)C(F)(F)F)CCC1N1CCCC1] | 761.3 (M + H⁺) |
| 40 | 3-[(3'-methyl-1,4'-bipiperidin-1'-yl)methyl]-6-[(1-methylethyl)sulfonyl]-2-[3-(trifluoromethyl)phenyl]-N-[(1R)-2,2,2-trifluoro-1-phenylethyl]-4-quinolinecarboxamide | 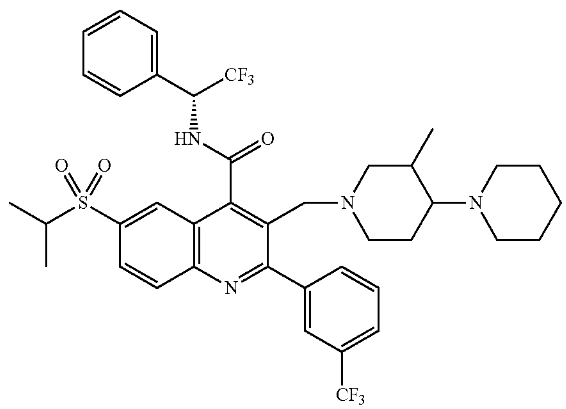 [SMILES: CC1CN(Cc2c(-c3cccc(C(F)(F)F)c3)nc3ccc(S(=O)(=O)C(C)C)cc3c2C(=O)N[C@H](c2ccccc2)C(F)(F)F)CCC1N1CCCCC1] | 775.2 (M + H⁺) |

Example 41

3-(1,4'-bipiperidin-1'-ylmethyl)-7-(methylsulfonyl)-N-[(1S)-1-phenylethyl]-2-[3-(trifluoromethyl)phenyl]-4-quinolinecarboxamide

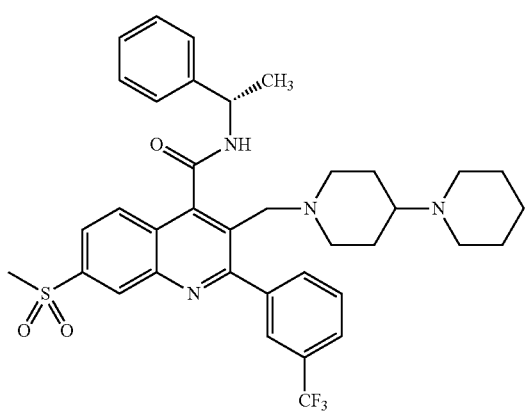 [SMILES: C[C@H](NC(=O)c1c(CN2CCC(N3CCCCC3)CC2)c(-c2cccc(C(F)(F)F)c2)nc2cc(S(C)(=O)=O)ccc12)c1ccccc1]

3-methyl-7-(methylthio)-2-[3-(trifluoromethyl)phenyl]-4-quinolinecarboxylic acid A solution of 3-(methylthio)aniline (1.392 g, 10.0 mmol) and 3-(trifluoromethyl)benzaldehyde (1.741 g, 10.0 mmol) in ethanol (30 mL) was stirred at reflux for 1 h. 2-Oxobutanoic acid (1.021 g, 10.0 mmol) was added portionwise. The reaction mixture was stirred at reflux for additional 3 h, cooled to room temperature, and stirred overnight. The mixture was filtered and the solid material collected to give 3-methyl-7-(methylthio)-2-[3-(trifluoromethyl)phenyl]-4-quinolinecarboxylic acid (0.62 g, 16% yield). MS (m/z) 378.0 (M+H⁺).

methyl 3-methyl-7-(methylsulfonyl)-2-[3-(trifluoromethyl)phenyl]-4-quinolinecarboxylate 3-Methyl-7-(methylthio)-2-[3-(trifluoromethyl)phenyl]-4-quinolinecarboxylic acid (1.67 g, 4.43 mmol) was suspended in methylene chloride (50 mL). DMF (3 drops) was added followed by oxalyl chloride (0.581 mL, 6.64 mmol). The mixture was stirred for 1 h. The solvent was removed under reduced pressure, the residue was redissolved in methanol (50 mL), and triethylamine (1.23 mL, 8.85 mmol) was added slowly. The reaction mixture was stirred overnight at room temperature. The solvent was removed under reduced pressure, the residue was diluted with saturated aqueous sodium bicarbonate, and the aqueous mixture was extracted with ethyl acetate (3 times). The combined organic extracts were washed with brine, dried over $Na_2SO_4$, filtered and concentrated to afford methyl 3-methyl-7-(methylsulfonyl)-2-[3-(trifluoromethyl)phenyl]-4-quinolinecarboxylate (1.75 g). This material was used in the next step without further purification. MS (m/z) 392.1 (M+H$^+$).

methyl 3-methyl-7-(methylsulfonyl)-2-[3-(trifluoromethyl)phenyl]-4-quinolinecarboxylate A solution of methyl 3-methyl-7-(methylsulfonyl)-2-[3-(trifluoromethyl)phenyl]-4-quinolinecarboxylate (1.75 g, 4.47 mmol) and 3-chloroperoxybenzoic acid (1.697 g, 9.84 mmol) in dichloromethane (50 mL) was stirred for 4 h at room temperature. Saturated aqueous sodium bicarbonate was slowly added, and the mixture stirred for 30 min. The mixture was extracted with methylene chloride (3 times). The combined organic extracts were washed with brine, dried over $Na_2SO_4$, filtered, and concentrated in vacuo. The residue was purified via column chromatography (ISCO, 10-40% ethyl acetate/hexanes) to afford methyl 3-methyl-7-(methylsulfonyl)-2-[3-(trifluoromethyl)phenyl]-4-quinolinecarboxylate (1.20 g, 63% yield). MS (m/z) 424.1 (M+H$^+$).

methyl 3-(bromomethyl)-7-(methylsulfonyl)-2-[3-(trifluoromethyl)phenyl]-4-quinolinecarboxylate A mixture of methyl 3-methyl-7-(methylsulfonyl)-2-[3-(trifluoromethyl)phenyl]-4-quinolinecarboxylate (1.20 g, 2.83 mmol), NBS (0.656 g, 3.68 mmol), and diphenylperoxyanhydride (0.069 g, 0.283 mmol) in carbon tetrachloride (20 mL) was heated to 100° C. and stirred overnight. The mixture was cooled to room temperature, and the solvent was removed under reduced pressure to afford methyl 3-(bromomethyl)-7-(methylsulfonyl)-2-[3-(trifluoromethyl)phenyl]-4-quinolinecarboxylate. This material was used directly in the next step without further purification. MS (m/z) 504.0 (M+H$^+$).

methyl 3-(1,4'-bipiperidin-1'-ylmethyl)-7-(methylsulfonyl)-2-[3-(trifluoromethyl)phenyl]-4-quinolinecarboxylate A suspension of methyl 3-(bromomethyl)-7-(methylsulfonyl)-2-[3-(trifluoromethyl)phenyl]-4-quinolinecarboxylate (0.713 g, 1.42 mmol) and 1,4'-bipiperidine (0.311 g, 1.846 mmol) in acetonitrile (25 mL) was stirred at room temperature for 3 h. The solvent was removed under reduced pressure. The residue was diluted with saturated aqueous $NaHCO_3$, and the mixture was extracted with methylene chloride (three time). The combined organic extracts were washed with brine, dried over $Na_2SO_4$, filtered, and concentrated in vacuo. The residue was purified via column chromatography (ISCO, 0-10% MeOH with 0.1% $NH_3/CH_2Cl_2$) to give methyl 3-(1,4'-bipiperidin-1'-ylmethyl)-7-(methylsulfonyl)-2-[3-(trifluoromethyl)phenyl]-4-quinolinecarboxylate (0.730 g, 87% yield). MS (m/z) 590.2 (M+H$^+$).

3-(1,4'-bipiperidin-1'-ylmethyl)-7-(methylsulfonyl)-2-[3-(trifluoromethyl)phenyl]-4-quinolinecarboxylic acid Potassium hydroxide (347 mg, 6.19 mmol) in water (5 mL) was added to a solution of methyl 3-(1,4'-bipiperidin-1'-ylmethyl)-7-(methylsulfonyl)-2-[3-(trifluoromethyl)phenyl]-4-quinolinecarboxylate (0.730 g, 1.24 mmol) in ethanol (15 mL). The mixture was heated to reflux for 5 hours before the solvent was removed under reduced pressure. The residue was acidified to pH 5-6 with 2N HCl and allowed to stand at room temperature overnight. The solid was collected by filtration, washed with water, and dried by azeotrope with benzene to give 3-(1,4'-bipiperidin-1'-ylmethyl)-7-(methylsulfonyl)-2-[3-(trifluoromethyl)phenyl]-4-quinolinecarboxylic acid (0.650 g, 91% yield). MS (m/z) 576.2 (M+H$^+$).

3-(1,4'-bipiperidin-1'-ylmethyl)-7-(methylsulfonyl)-N-[(1S)-1-phenylethyl]-2-[3-(trifluoromethyl)phenyl]-4-quinolinecarboxamide A mixture of 3-(1,4'-bipiperidin-1'-ylmethyl)-7-(methylsulfonyl)-2-[3-(trifluoromethyl)phenyl]-4-quinolinecarboxylic acid (0.100 g, 0.174 mmol), (1S)-1-phenylethanamine (0.032 g, 0.261 mmol), EDC (0.167 g, 0.869 mmol), HOBT (0.027 g, 0.174 mmol), and N,N-diisopropylethylamine (0.303 mL, 1.74 mmol) in N,N-dimethylformamide (2 mL) and 1,2-dichloroethane (2 mL) was stirred at room temperature overnight before it was heated to 50° C. for 4 h. The solvent was removed under reduced pressure. The residue was dissolved in DMSO and purified via HPLC (Waters, 30-80% MeCN/H$_2$O with 0.1% TFA). The fractions containing the product were neutralized with saturated aqueous $NaHCO_3$, acetonitrile was removed under reduced pressure, and the residue was diluted with water. The solid material was collected by filtration, washed with water, and air dried to afford 3-(1,4'-bipiperidin-1'-ylmethyl)-7-(methylsulfonyl)-N-[(1S)-1-phenylethyl]-2-[3-(trifluoromethyl)phenyl]-4-quinolinecarboxamide (0.086 g, 73% yield). MS (m/z) 679.3 (M+H$^+$).

The following compounds were prepared using procedures analogous to those described in Example 41 starting with an appropriate aniline, substituting 1,4'-bipiperidine with 4-morpholinopiperidine, and replacing (1S)-1-phenylethanamine with an appropriate benzylamine when necessary. As is appreciated by those skilled in the art, these analogous examples may involve variations in general reaction conditions.

| Ex | Name | Structure | MS (m/z) |
|---|---|---|---|
| 42 | 3-(1,4'-bipiperidin-1'-ylmethyl)-7-(methylsulfonyl)-2-[3-(trifluoromethyl)phenyl]-N-[(1R)-2,2,2-trifluoro-1-phenylethyl]-4-quinolinecarboxamide | 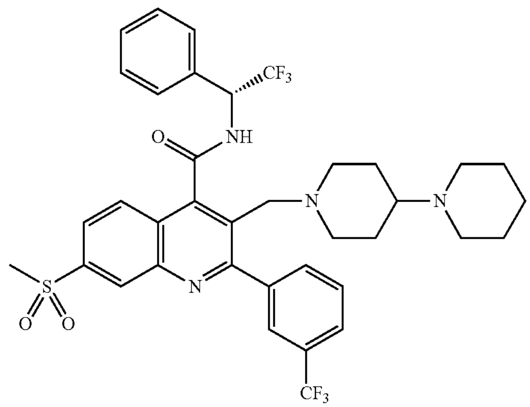 | 679.3 (M + H⁺) |
| 43 | 7-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide | 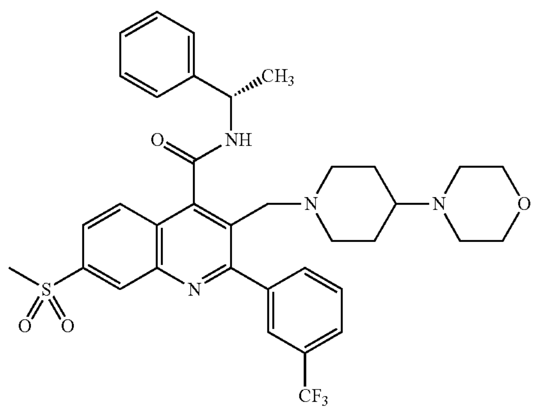 [SMILES: C[C@H](NC(=O)c1c(CN2CCC(N3CCOCC3)CC2)c(-c2cccc(C(F)(F)F)c2)nc2cc(S(C)(=O)=O)ccc12)c1ccccc1] | 681.3 (M + H⁺) |
| 44 | 7-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide | 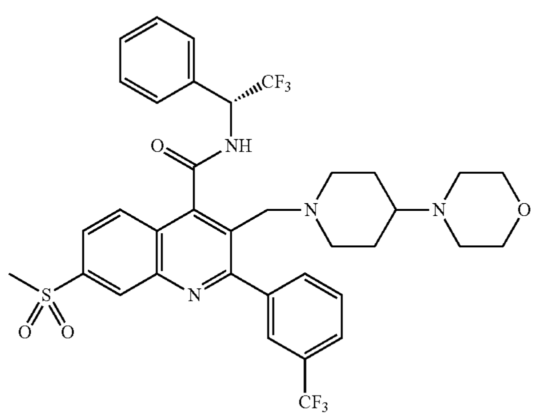 | 735.2 (M + H⁺) |

-continued

| Ex | Name | Structure | MS (m/z) |
|---|---|---|---|
| 45 | 3-(1,4'-bipiperidin-1'-ylmethyl)-7-(ethylsulfonyl)-N-(1-methyl-1-phenylethyl)-2-[3-(trfluoromethyl)phenyl]-4-quinolinecarboxamide | 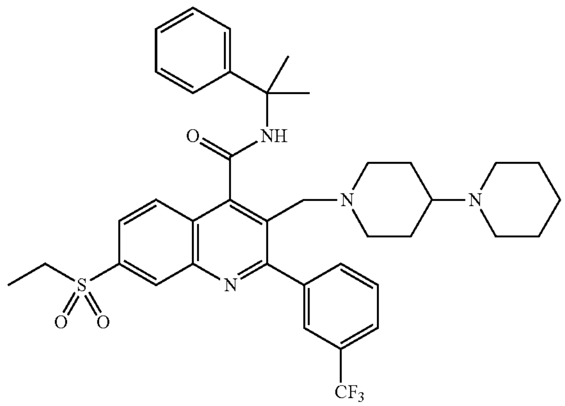 [SMILES: CCS(=O)(=O)c1ccc2c(C(=O)NC(C)(C)c3ccccc3)c(CN3CCC(N4CCCCC4)CC3)c(-c3cccc(C(F)(F)F)c3)nc2c1] | 707.3 (M + H⁺) |
| 46 | 3-(1,4'-bipiperidin-1'-ylmethyl)-7-(ethylsulfonyl)-N-[(1S)-1-phenylethyl]-2-[3-(trifluoromethyl)phenyl]-4-quinolinecarboxamide | 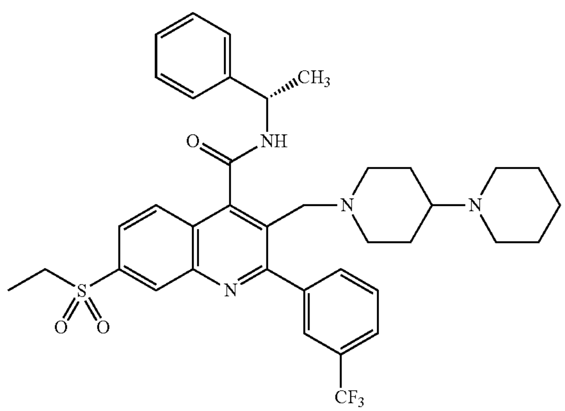 [SMILES: CCS(=O)(=O)c1ccc2c(C(=O)N[C@@H](C)c3ccccc3)c(CN3CCC(N4CCCCC4)CC3)c(-c3cccc(C(F)(F)F)c3)nc2c1] | 693.3 (M + H⁺) |
| 47 | 7-(ethylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide | 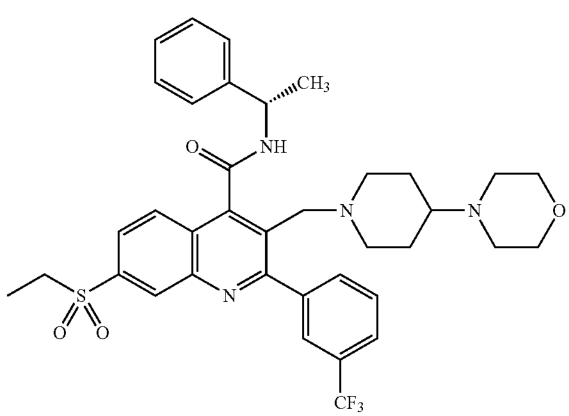 | 695.3 (M + H⁺) |

| Ex | Name | Structure | MS (m/z) |
|---|---|---|---|
| 48 | 7-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide | 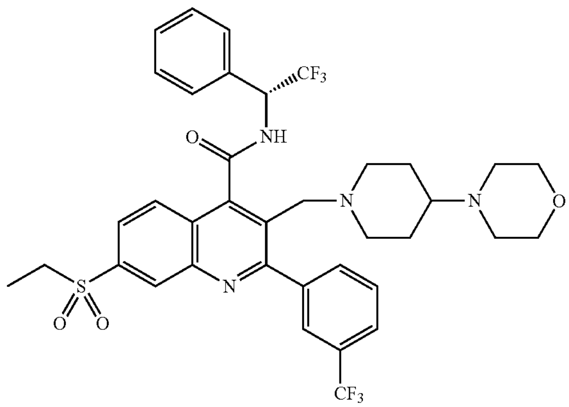 | 749.2 (M + H⁺) |
| 49 | 3-(1,4'-bipiperidin-1'-ylmethyl)-7-(ethylsulfonyl)-2-[3-(trifluoromethyl)phenyl]-N-[(1R)-2,2,2-trifluoro-1-phenylethyl]-4-quinolinecarboxamide | 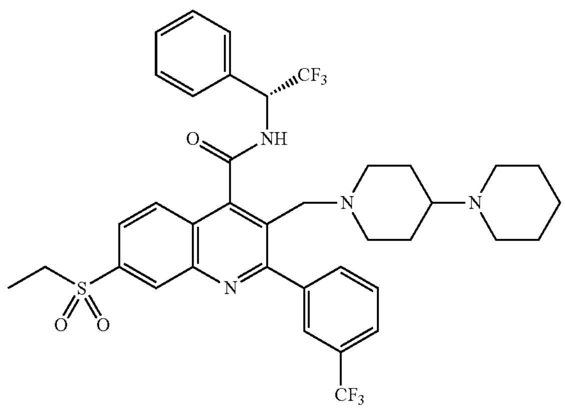 | 747.2 (M + H⁺) |

Example 50

6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide

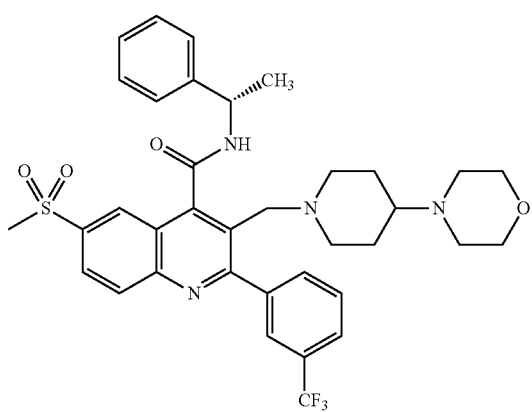 [SMILES: C[C@H](NC(=O)c1c(CN2CCC(N3CCOCC3)CC2)c(-c2cccc(C(F)(F)F)c2)nc2ccc(S(C)(=O)=O)cc12)c1ccccc1]

6-fluoro-3-methyl-2-[3-(trifluoromethyl)phenyl]-4-quinolinecarboxylic acid

Potassium hydroxide (20.39 g, 363 mmol) in water (40 mL) was added to a suspension of 5-fluoro-1H-indole-2,3-dione (10.0 g, 60.6 mmol) in ethanol (100 mL) slowly. 1-[3-(Trifluoromethyl)phenyl]-1-propanone (12.24 g, 60.6 mmol) was added, and the mixture was heated to reflux for 1 h. The solvent was removed under reduced pressure, the residue was dissolved in water, and the mixture was washed with ether (3 times). The aqueous mixture was chilled and adjusted to pH~3 with concentrated HCl. The solid was collected by filtration, washed with water, and air dried to afford 6-fluoro-3-methyl-2-[3-(trifluoromethyl)phenyl]-4-quinolinecarboxylic acid (21.2 g, >99% yield). MS (m/z) 350.1 (M+H⁺).

methyl 6-fluoro-3-methyl-2-[3-(trifluoromethyl)phenyl]-4-quinolinecarboxylate

DMF (5 drops) was added to a suspension of 6-fluoro-3-methyl-2-[3-(trifluoromethyl)phenyl]-4-quinolinecarboxylic acid (11.2 g, 32.1 mmol) in dichloromethane (120 mL) at 0° C. Oxalyl chloride (4.21 mL, 48.1 mmol) was added slowly. The mixture was stirred at 0° C. for 1 h. Methanol (30 mL) was added to the mixture, the mixture was stirred at 0° C. for 2 h and warmed to room temperature overnight. The solvent was removed under reduced pressure, and the residue was diluted with water and treated with saturated aqueous NaHCO$_3$ until basic. The aqueous mixture was extracted with methylene chloride (three times). The combined organic phases were washed with brine (two times), dried over Na$_2$SO$_4$, filtered, and concentrated. The residue was purified via column chromatography (ISCO, 120 g Silica, 0-30% ethyl acetate/hexanes) to give methyl 6-fluoro-3-methyl-2-[3-(trifluoromethyl)phenyl]-4-quinolinecarboxylate (9.6 g, 82% yield). MS (m/z) 364.1 (M+H$^+$).

methyl 3-methyl-6-(methylthio)-2-[3-(trifluoromethyl)phenyl]-4-quinolinecarboxylate A suspension of methyl 6-fluoro-3-methyl-2-[3-(trifluoromethyl)phenyl]-4-quinolinecarboxylate (2.4 g, 6.61 mmol) and sodium thiomethoxide (1.158 g, 16.52 mmol) in N,N-dimethylformamide (40 mL) was stirred at 100° C. overnight. The mixture was cooled to room temperature, treated with NaH (0.264 mg, 6.61 mmol), and stirred for 20 min. Methyl iodide (1.5 g, 9.92 mmol) was added, and the mixture was stirred for 2 h. The mixture was diluted with water and extracted with methylene chloride (three times). The combined organic extracts were washed with brine, dried over Na$_2$SO$_4$, filtered, and concentrated in vacuo. The residue was purified via column chromatography (ISCO, 120 g Silica, 0-30% ethyl acetate/hexanes) to afford methyl 3-methyl-6-(methylthio)-2-[3-(trifluoromethyl)phenyl]-4-quinolinecarboxylate (2.54 g, 95% yield). MS (m/z) 392.1 (M+H$^+$).

methyl 3-methyl-6-(methylsulfonyl)-2-[3-(trifluoromethyl)phenyl]-4-quinolinecarboxylate A solution of methyl 3-methyl-6-(methylthio)-2-[3-(trifluoromethyl)phenyl]-4-quinolinecarboxylate (2.45 g, 6.26 mmol) and 3-chloroperoxybenzoic acid (2.376 g, 13.77 mmol) in dichloromethane (50 mL) was stirred overnight. Saturated aqueous NaHCO$_3$ and Na$_2$S$_2$O$_3$ were added slowly, and the mixture was stirred for 30 min. The mixture was extracted with methylene chloride (three times). The combined organic extracts were washed with brine, dried over Na$_2$SO$_4$, filtered, and concentrated. The residue was purified via column chromatography (ISCO, 10-60% ethyl acetate/hexanes) to give methyl 3-methyl-6-(methylsulfonyl)-2-[3-(trifluoromethyl)phenyl]-4-quinolinecarboxylate (2.59 g, 98% yield). MS (m/z) 424.1 (M+H$^+$).

methyl 3-(bromomethyl)-6-(methylsulfonyl)-2-[3-(trifluoromethyl)phenyl]-4-quinolinecarboxylate A suspension of 3-methyl-6-(methylsulfonyl)-2-[3-(trifluoromethyl)phenyl]-4-quinolinecarboxylate (2.59 g, 6.12 mmol), NBS (1.42 g, 7.95 mmol), and diphenylperoxyanhydride (0.148 g, 0.612 mmol) in carbon tetrachloride (30 mL) was heated to 100° C. overnight. The mixture was cooled to room temperature and concentrated in vacuo to give methyl 3-(bromomethyl)-6-(methylsulfonyl)-2-[3-(trifluoromethyl)phenyl]-4-quinolinecarboxylate. This material was used without further purification. MS (m/z) 504.0 (M+H$^+$).

methyl 6-(methylsulfonyl)-3-{[4-(4-morpholinyl)-1-piperidinyl]methyl}-2-[3-(trifluoromethyl)phenyl]-4-quinolinecarboxylate A suspension of methyl 3-(bromomethyl)-6-(methylsulfonyl)-2-[3-(trifluoromethyl)phenyl]-4-quinolinecarboxylate (3.07 g, 6.12 mmol) and 4-(4-piperidinyl)morpholine (1.36 g, 7.96 mmol) in acetonitrile (10 mL) was stirred for 3 h. The solvent was removed under reduced pressure.

The residue was dissolved in DMSO and purified via reverse phase HPLC (Biotage RP, 0-50% MeCN/H$_2$O with 0.1% TFA). The fractions containing the product were neutralized with saturated aqueous NaHCO$_3$ and extracted with methylene chloride (three times). The combined organic extracts were washed with brine (two times), dried over Na$_2$SO$_4$, filtered, and concentrated to afford methyl 6-(methylsulfonyl)-3-{[4-(4-morpholinyl)-1-piperidinyl]methyl}-2-[3-(trifluoromethyl)phenyl]-4-quinolinecarboxylate (3.0 g, 83% yield). MS (m/z) 592.2 (M+H$^+$).

6-(methylsulfonyl)-3-{[4-(4-morpholinyl)-1-piperidinyl]methyl}-2-[3-(trifluoromethyl)phenyl]-4-quinolinecarboxylic acid Potassium hydroxide (1.42 g, 25.4 mmol) was added to a solution of methyl 6-(methylsulfonyl)-3-{[4-(4-morpholinyl)-1-piperidinyl]methyl}-2-[3-(trifluoromethyl)phenyl]-4-quinolinecarboxylate (3.0 g, 5.07 mmol) in methanol (60 mL) and water (20 mL), and the resulting mixture was heated to reflux for 5 h. The solvent was removed under reduced pressure, and the residue was adjusted to pH~5-6 with 2N HCl and extracted with methylene chloride (three times). The combined organic extracts were washed with brine, dried over Na$_2$SO$_4$, filtered, and concentrated in vacuo to give 6-(methylsulfonyl)-3-{[4-(4-morpholinyl)-1-piperidinyl]methyl}-2-[3-(trifluoromethyl)phenyl]-4-quinolinecarboxylic acid (2.73 g, 81% yield). MS (m/z) 578.2 (M+H$^+$).

6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide A mixture of 6-(methylsulfonyl)-3-{[4-(4-morpholinyl)-1-piperidinyl]methyl}-2-[3-(trifluoromethyl)phenyl]-4-quinolinecarboxylic acid (0.200 g, 0.346 mmol), (1S)-1-phenylethanamine (0.063 g, 0.519 mmol), EDC (0.266 g, 1.39 mmol), HOBT (0.053 g, 0.346 mmol) and N,N-diisopropylethylamine (0.605 mL, 3.46 mmol) in N,N-dimethylformamide (2 mL) and tetrahydrofuran (2 mL) was heated to 50° C. overnight. The solvent was removed under reduced pressure, and the residue was dissolved in DMSO and purified via HPLC (Waters, Sunfire, 30×75 mm column, 50 mL/min, 20-60% MeCN/H$_2$O with 0.1% TFA). The fractions containing the product were neutralized with saturated aqueous NaHCO$_3$ and extracted with methylene chloride (three times). The combined organic extracts were washed with brine (two times), dried over Na$_2$SO$_4$, filtered, and concentrated to afford 6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide (0.116 g, 47% yield). MS (m/z) 681.3 (M+H$^+$).

The following compounds were prepared using procedures analogous to those described in Example 50 using an appropriate 5-fluoro-1H-indole-2,3-dione in the first step, an appropriate thiolate in the third step, substituting 4-morpholinopiperidine with 1,4'-bipiperidine in the sixth step, and replacing (1S)-1-phenylethanamine with an appropriate benzylamine in the last step when necessary. As is appreciated by those skilled in the art, these analogous examples may involve variations in general reaction conditions.

| Ex | Name | Structure | MS (m/z) |
|---|---|---|---|
| 51 | 6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide | 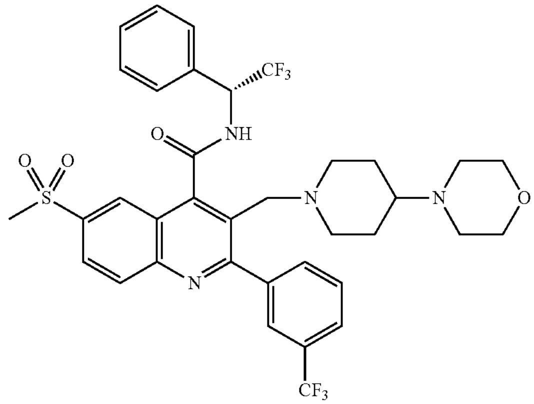 [SMILES: CS(=O)(=O)c1ccc2nc(-c3cccc(C(F)(F)F)c3)c(CN3CCC(N4CCOCC4)CC3)c(C(=O)N[C@H](c3ccccc3)C(F)(F)F)c2c1] | 735.2 (M + H+) |
| 52 | 3-(1,4'-bipiperidin-1'-ylmethyl)-6-(ethylsulfonyl)-N-[(1S)-1-phenylethyl]-2-[3-(trifluoromethyl)phenyl]-4-quinolinecarboxamide | 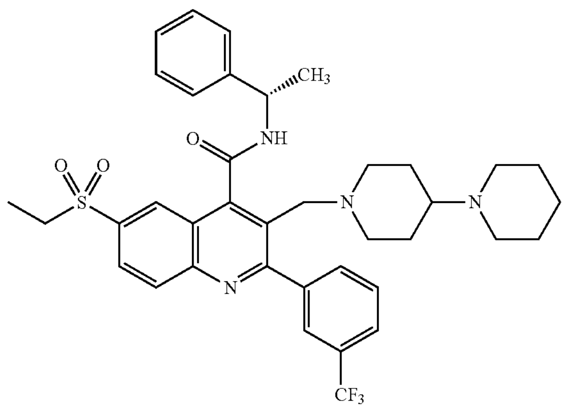 [SMILES: CCS(=O)(=O)c1ccc2nc(-c3cccc(C(F)(F)F)c3)c(CN3CCC(N4CCCCC4)CC3)c(C(=O)N[C@@H](C)c3ccccc3)c2c1] | 693.3 (M + H+) |
| 53 | 3-(1,4'-bipiperidin-1'-ylmethyl)-6-(ethylsulfonyl)-2-[3-(trifluoromethyl)phenyl]-N-[(1R)-2,2,2-trifluoro-1-phenylethyl]-4-quinolinecarboxamide | 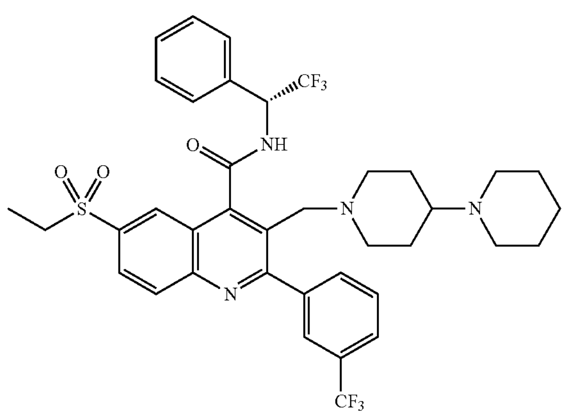 [SMILES: CCS(=O)(=O)c1ccc2nc(-c3cccc(C(F)(F)F)c3)c(CN3CCC(N4CCCCC4)CC3)c(C(=O)N[C@H](c3ccccc3)C(F)(F)F)c2c1] | 747.3 (M + H+) |

-continued

| Ex | Name | Structure | MS (m/z) |
|---|---|---|---|
| 54 | 6-(ethylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide | 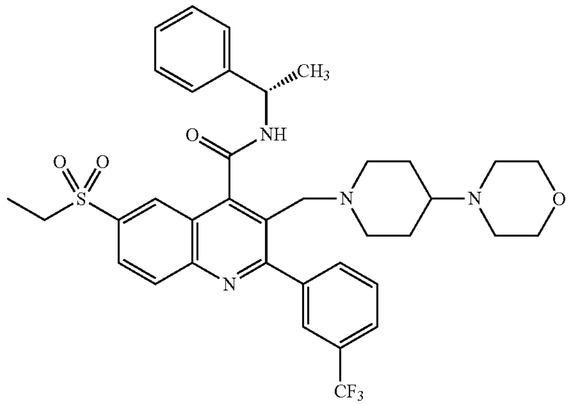 | 695.3 (M + H+) |
| 55 | 6-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide | 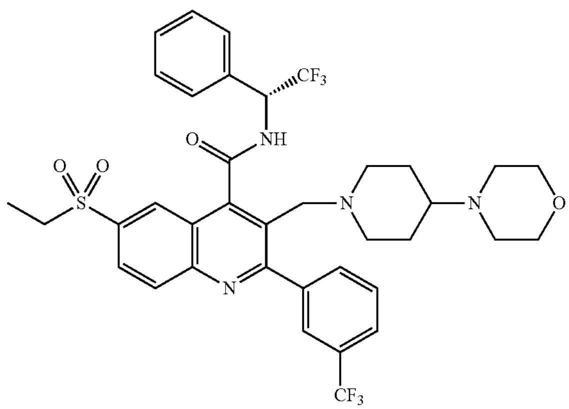 | 749.2 (M + H+) |
| 56 | 3-(1,4'-bipiperidin-1'-ylmethyl)-6-[(1-methylethyl)sulfonyl]-N-[(1S)-1-phenylethyl]-2-[3-(trifluoromethyl)phenyl]-4-quinolinecarboxamide | 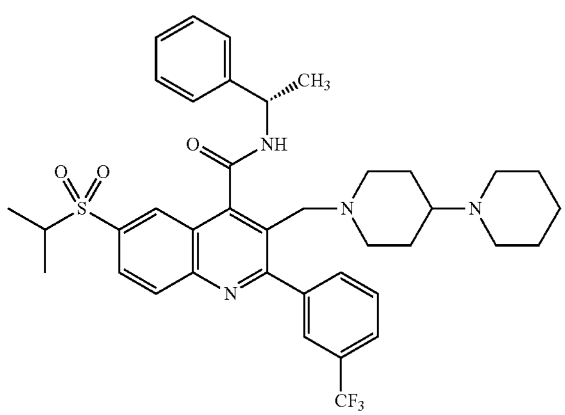 | 707.3 (M + H+) |

-continued

| Ex | Name | Structure | MS (m/z) |
|---|---|---|---|
| 57 | 3-(1,4'-bipiperidin-1'-ylmethyl)-6-[(1-methylethyl)sulfonyl]-2-[3-(trifluoromethyl)phenyl]-N-[(1R)-2,2,2-trifluoro-1-phenylethyl]-4-quinolinecarboxamide | 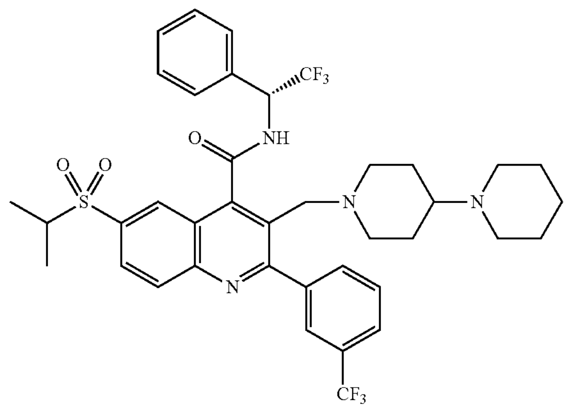 [SMILES: CC(C)S(=O)(=O)c1ccc2nc(-c3cccc(C(F)(F)F)c3)c(CN3CCC(N4CCCCC4)CC3)c(C(=O)N[C@H](c3ccccc3)C(F)(F)F)c2c1] | 761.3 (M + H$^+$) |
| 58 | 6-[(1-methylethyl)sulfonyl]-3-{[4-(4-morpholinyl)-1-piperidinyl]methyl}-N-[(1S)-1-phenylethyl]-2-[3-(trifluoromethyl)phenyl]-4-quinolinecarboxamide | 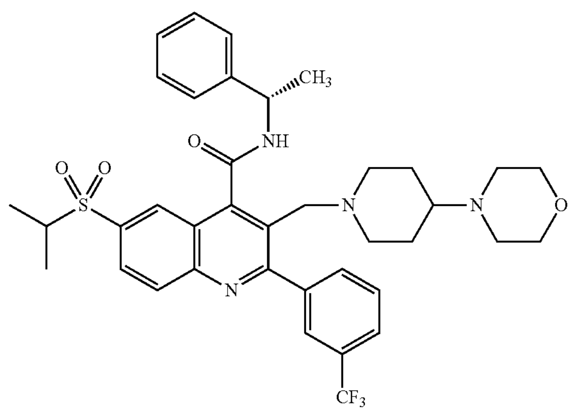 | 709.3 (M + H$^+$) |
| 59 | 7-chloro-6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide | 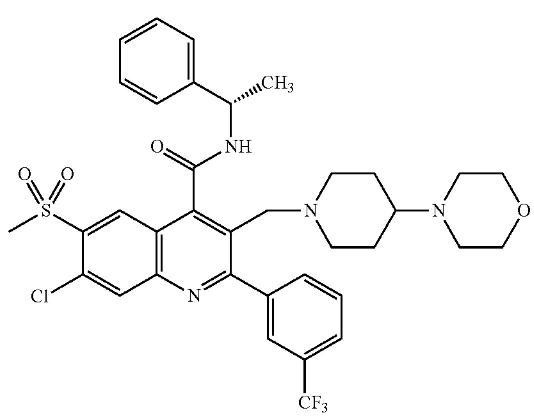 | 716.2 (M + H$^+$) |

-continued

| Ex | Name | Structure | MS (m/z) |
|----|------|-----------|----------|
| 60 | 7-chloro-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide | 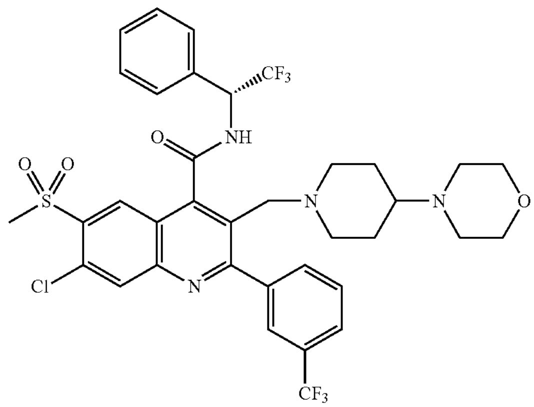 [SMILES: CS(=O)(=O)c1cc2c(C(=O)N[C@H](c3ccccc3)C(F)(F)F)c(CN3CCC(N4CCOCC4)CC3)c(-c3cccc(C(F)(F)F)c3)nc2cc1Cl] | 770.2 (M + H⁺) |
| 61 | 6-[(1-methylethyl)sulfonyl]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide | 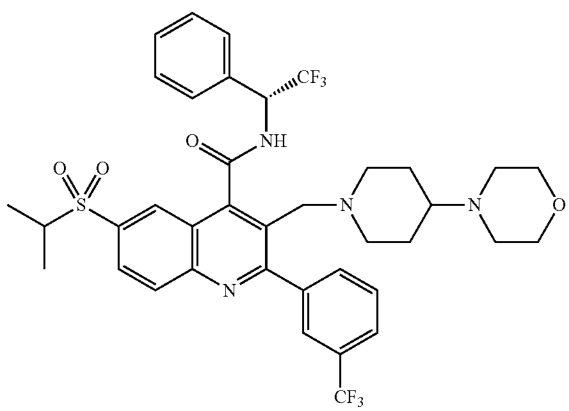 [SMILES: CC(C)S(=O)(=O)c1ccc2nc(-c3cccc(C(F)(F)F)c3)c(CN3CCC(N4CCOCC4)CC3)c(C(=O)N[C@H](c3ccccc3)C(F)(F)F)c2c1] | 763.3 (M + H⁺) |

The following compounds were prepared using procedures analogous to those described in Example 50 substituting an appropriate 5-fluoro-1H-indole-2,3-dione in the first step, selecting an appropriate thiolate in the third step, substituting 4-morpholinopiperidine with 1,4'-bipiperidine in the sixth step, substituting the T3P procedure used in the last step of Example 26 for the EDC/HOBT procedure in the last step, and replacing (1S)-1-phenylethanamine with an appropriate benzylamine in the last step when necessary. As is appreciated by those skilled in the art, these analogous examples may involve variations in general reaction conditions.

| Ex | Name | Structure | MS (m/z) |
|----|------|-----------|----------|
| 62 | 6-[(1-methylethyl)sulfonyl]-3-{[4-(4-morpholinyl)-1-piperidinyl]methyl}-2-[3-(trifluoromethyl)phenyl]-N-[(1S)-2,2,2-trifluoro-1-phenylethyl]-4-quinolinecarboxamide | 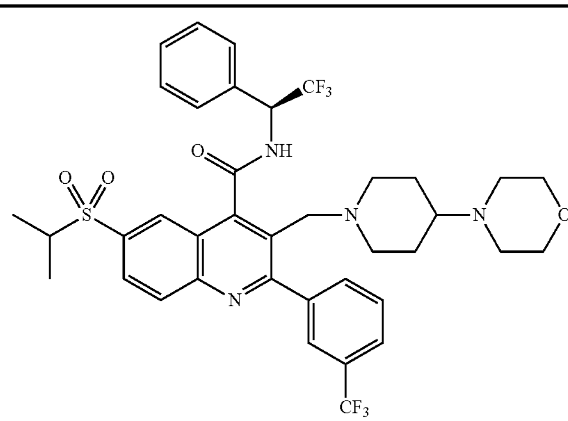 | 762.3 (M + H⁺) |

| Ex | Name | Structure | MS (m/z) |
|---|---|---|---|
| 63 | 3-(1,4'-bipiperidin-1'-ylmethyl)-7-chloro-6-(methylsulfonyl)-2-[3-(trifluoromethyl)phenyl]-N-[(1R)-2,2,2-trifluoro-1-phenylethyl]-4-quinolinecarboxamide | 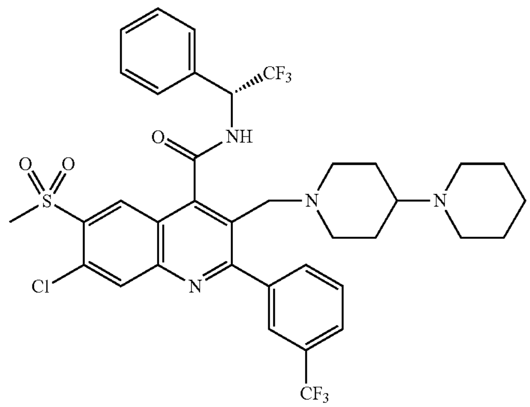 | 767.2 (M + H$^+$) |
| 64 | 3-(1,4'-bipiperidin-1'-ylmethyl)-7-chloro-6-(methylsulfonyl)-N-[(1S)-1-phenylethyl]-2-[3-(trifluoromethyl)phenyl]-4-quinolinecarboxamide | 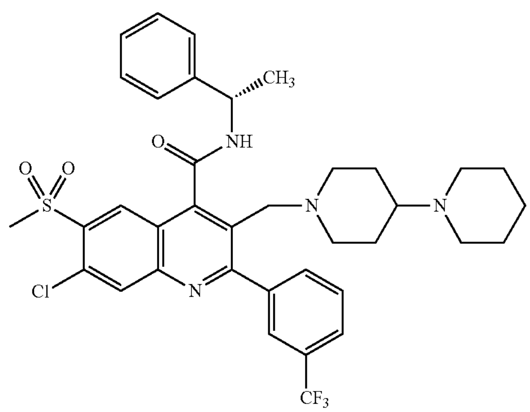 [SMILES: C[C@H](NC(=O)c1c(CN2CCC(N3CCCCC3)CC2)c(-c2cccc(C(F)(F)F)c2)nc2cc(Cl)c(S(C)(=O)=O)cc12)c1ccccc1] | 714.2 (M + H$^+$) |
| 65 | 3-(1,4'-bipiperidin-1'-ylmethyl)-7-chloro-6-(ethylsulfonyl)-N-[(1S)-1-phenylethyl]-2-[3-(trifluoromethyl)phenyl]-4-quinolinecarboxamide | 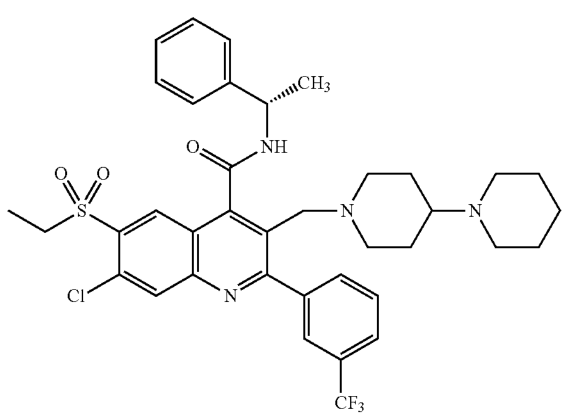 [SMILES: CCS(=O)(=O)c1cc2c(C(=O)N[C@@H](C)c3ccccc3)c(CN3CCC(N4CCCCC4)CC3)c(-c3cccc(C(F)(F)F)c3)nc2cc1Cl] | 728.3 (M + H$^+$) |

-continued

| Ex | Name | Structure | MS (m/z) |
|---|---|---|---|
| 66 | 3-(1,4'-bipiperidin-1'-ylmethyl)-7-chloro-6-(ethylsulfonyl)-2-[3-(trifluoromethyl)phenyl]-N-[(1R)-2,2,2-trifluoro-1-phenylethyl]-4-quinolinecarboxamide | 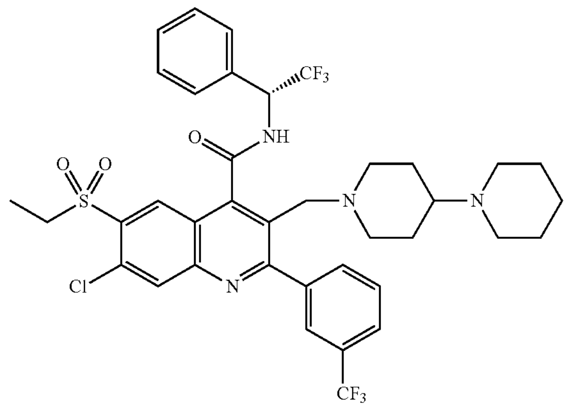 [SMILES: CCS(=O)(=O)c1cc2c(C(=O)N[C@H](c3ccccc3)C(F)(F)F)c(CN3CCC(N4CCCCC4)CC3)c(-c3cccc(C(F)(F)F)c3)nc2cc1Cl] | 781.2 (M + H$^+$) |
| 67 | 7-chloro-6-(ethylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide | 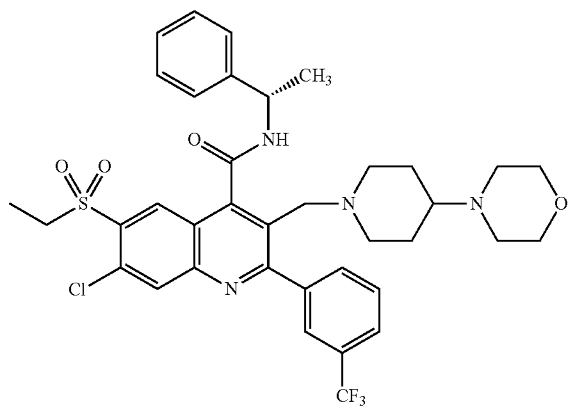 | 730.2 (M + H$^+$) |
| 68 | 7-chloro-6-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide | 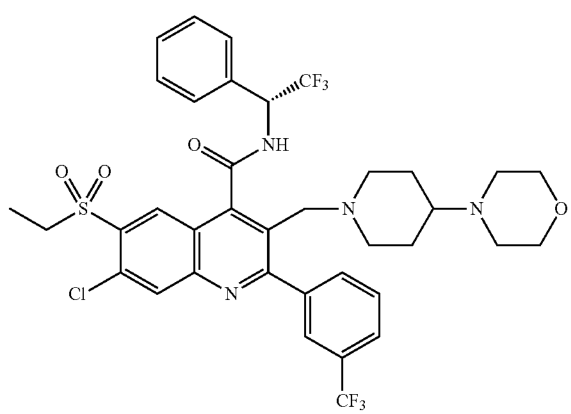 | 784.2 (M + H$^+$) |

-continued

| Ex | Name | Structure | MS (m/z) |
|---|---|---|---|
| 69 | 3-(1,4'-bipiperidin-1'-ylmethyl)-7-chloro-6-[(1-methylethyl)sulfonyl]-N-[(1S)-1-phenylethyl]-2-[3-(trifluoromethyl)phenyl]-4-quinolinecarboxamide | 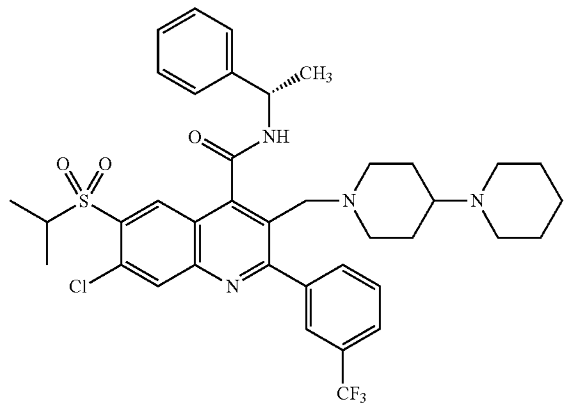 [SMILES: CC(C)S(=O)(=O)c1cc2c(C(=O)N[C@@H](C)c3ccccc3)c(CN3CCC(N4CCCCC4)CC3)c(-c3cccc(C(F)(F)F)c3)nc2cc1Cl] | 742.3 (M + H$^+$) |
| 70 | 3-(1,4'-bipiperidin-1'-ylmethyl)-7-chloro-6-[(1-methylethyl)sulfonyl]-2-[3-(trifluoromethyl)phenyl]-N-[(1R)-2,2,2-trifluoro-1-phenylethyl]-4-quinolinecarboxamide | 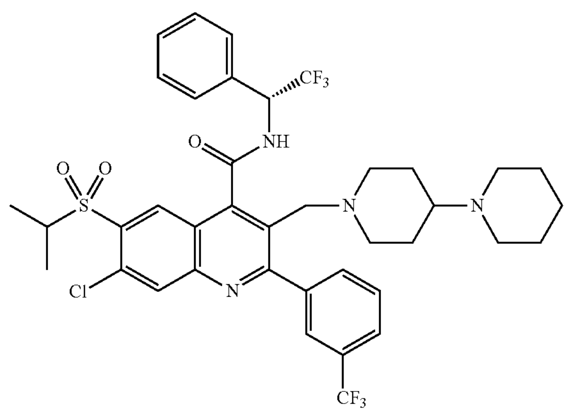 [SMILES: CC(C)S(=O)(=O)c1cc2c(C(=O)N[C@H](c3ccccc3)C(F)(F)F)c(CN3CCC(N4CCCCC4)CC3)c(-c3cccc(C(F)(F)F)c3)nc2cc1Cl] | 796.2 (M + H$^+$) |
| 71 | 7-chloro-6-[(1-methylethyl)sulfonyl]-3-{[4-(4-morpholinyl)-1-piperidinyl]methyl}-N-[(1S)-1-phenylethyl]-2-[3-(trifluoromethyl)phenyl]-4-quinolinecarboxamide | 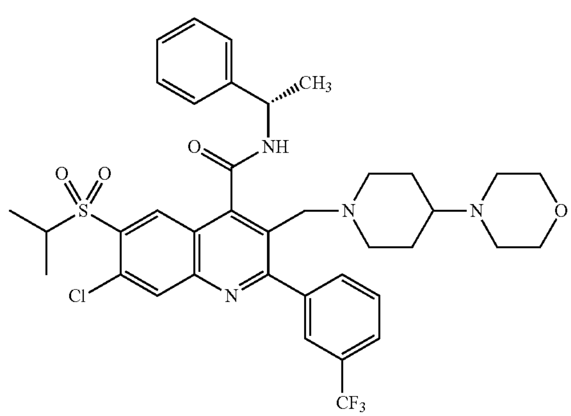 | 744.2 (M + H$^+$) |

| Ex | Name | Structure | MS (m/z) |
|---|---|---|---|
| 72 | 7-chloro-6-[(1-methylethyl)sulfonyl]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide | 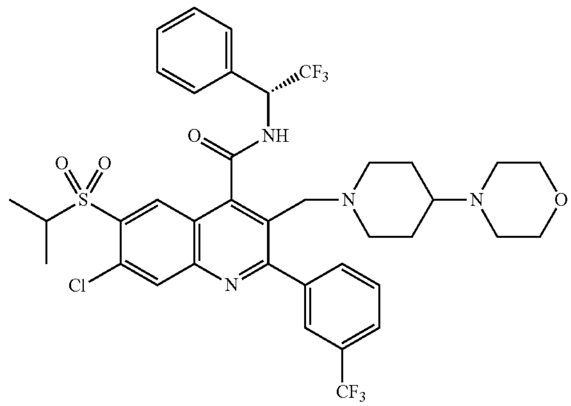 [SMILES: CC(C)S(=O)(=O)c1cc2c(C(=O)N[C@H](c3ccccc3)C(F)(F)F)c(CN3CCC(N4CCOCC4)CC3)c(-c3cccc(C(F)(F)F)c3)nc2cc1Cl] | 798.2 (M + H+) |

Example 73

6-(methylsulfonyl)-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide

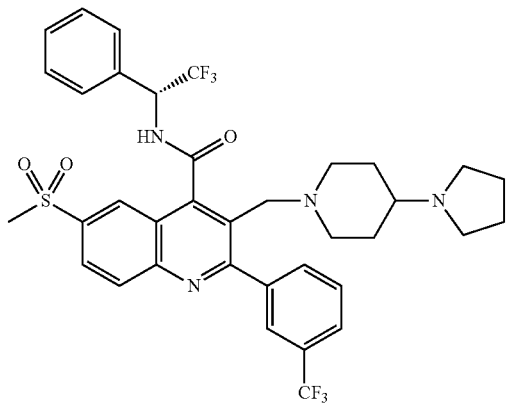 [SMILES: CS(=O)(=O)c1ccc2nc(-c3cccc(C(F)(F)F)c3)c(CN3CCC(N4CCCC4)CC3)c(C(=O)N[C@H](c3ccccc3)C(F)(F)F)c2c1]

methyl 3-(bromomethyl)-6-(methylsulfonyl)-2-[3-(trifluoromethyl)phenyl]-4-quinolinecarboxylate To a suspension of methyl 3-methyl-6-(methylsulfonyl)-2-[3-(trifluoromethyl)phenyl]-4-quinolinecarboxylate (4.5 g, 10.63 mmol) in carbon tetrachloride (53.1 mL) was added N-bromosuccinimide (2.459 g, 13.82 mmol) and benzoyl peroxide (0.257 g, 1.063 mmol). The mixture was heated at 100° C. for 20 h, Additional portions of N-bromosuccinimide (0.3 equiv., 0.568 g, 3.19 mmol) and benzoyl peroxide (0.257 g, 1.063 mmol) were added, and the reaction mixture was heated at 100° C. for 5 h longer. The mixture was cooled to room temperature and concentrated in vacuo to give methyl 3-(bromomethyl)-6-(methylsulfonyl)-2-[3-(trifluoromethyl)phenyl]-4-quinolinecarboxylate. This material was used in the next step without further purification. MS (m/z) 503.9 (M+H+).

methyl 6-(methylsulfonyl)-3-{[4-(1-pyrrolidinyl)-1-piperidinyl]methyl}-2-[3-(trifluoromethyl)phenyl]-4-quinolinecarboxylate An orange suspension of methyl 3-(bromomethyl)-6-(methylsulfonyl)-2-[3-(trifluoromethyl)phenyl]-4-quinolinecarboxylate (1.068 g, 2.126 mmol) and 4-(1-pyrrolidinyl)piperidine (0.492 g, 3.19 mmol) in acetonitrile (14.17 ml) was stirred at room temperature for 16 h. The solvent was removed under reduced pressure. The residue was absorbed onto florisil and was purified via column chromatography (ISCO, 12 g silica, 5-10% methanol/dichloromethane) to give methyl 6-(methylsulfonyl)-3-{[4-(1-pyrrolidinyl)-1-piperidinyl]methyl}-2-[3-(trifluoromethyl)phenyl]-4-quinolinecarboxylate (1.14 g, 88% yield). MS (m/z) 576.2 (M+H+).

6-(methylsulfonyl)-3-{[4-(1-pyrrolidinyl)-1-piperidinyl]methyl}-2-[3-(trifluoromethyl)phenyl]-4-quinolinecarboxylic acid Potassium hydroxide (0.551 g, 9.82 mmol) was added to an orange suspension of methyl 6-(methylsulfonyl)-3-{[4-(1-pyrrolidinyl)-1-piperidinyl]methyl}-2-[3-(trifluoromethyl)phenyl]-4-quinolinecarboxylate (1.13 g, 1.963 mmol) in methanol (19.63 mL) and water (6.54 mL). The mixture was heated to 65° C. Additional methanol (10 mL) was added, and the mixture was heated overnight for 22 h. The mixture was cooled to room temperature, and the solvent was removed under reduced pressure. The mixture was acidified to pH 4-5 with 2N HCl. The solid was collected by filtration and dried to give 6-(methylsulfonyl)-3-{[4-(1-pyrrolidinyl)-1-piperidinyl]methyl}-2-[3-(trifluoromethyl)phenyl]-4-quinolinecarboxylic acid (0.700 g). The filtrate was concentrated to a volume of approximately 3 mL, and the solid precipitate was collected by filtration to afford additional 6-(methylsulfonyl)-3-{[4-(1-pyrrolidinyl)-1-piperidinyl]methyl}-2-[3-(trifluoromethyl)phenyl]-4-quinolinecarboxylic acid (0.153 g; 0.853 g total, 73% combined yield). MS (m/z) 562.2 (M+H+).

6-(methylsulfonyl)-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide A suspension of 6-(methylsulfonyl)-3-{[4-(1-pyrrolidinyl)-1-piperidinyl]methyl}-2-[3-(trifluoromethyl)phenyl]-

4-quinolinecarboxylic acid (0.125 g, 0.223 mmol), [(1R)-2,2,2-trifluoro-1-phenylethyl]amine (0.061 g, 0.289 mmol), N,N-diisopropylethylamine (0.117 mL, 0.668 mmol), and T3P (propylphosphonic anhydride, 0.170 mL of a 50% w/v solution in ethyl acetate, 0.289 mmol) in dichloromethane (3.42 mL) was stirred at room temperature for 20 h. Additional portions of [(1R)-2,2,2-trifluoro-1-phenylethyl]amine (0.031 g, 0.145 mmol) and T3P (propylphosphonic anhydride, 0.085 mL of a 50% w/v solution in ethyl acetate, 0.145 mmol) were added, and the mixture stirred for 2 h. Water (2 mL) was added, and the mixture was poured through a hydrophobic frit. The isolated organic phase was absorbed onto florisil and purified via column chromatography (ISCO, 4 g silica, 1-6% methanol/methylene chloride) to afford 6-(methylsulfonyl)-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide (0.048 g, 28% yield). MS (m/z) 719.2 (M+H$^+$).

The following compounds were prepared using procedures analogous to those described in Example 73 using an appropriate sulfinate in the third step, substituting 4-(1-pyrrolidinyl)piperidine with an appropriate secondary amine and optionally using an amine base (Et$_3$N or DIPEA) if required in the fifth step, and replacing [(1R)-2,2,2-trifluoro-1-phenylethyl]amine with an appropriate benzylamine in the final step when necessary. As is appreciated by those skilled in the art, these analogous examples may involve variations in general reaction conditions.

| Ex | Name | Structure | MS (m/z) |
|---|---|---|---|
| 74 | 6-(methylsulfonyl)-N-[(1S)-1-phenylethyl]-3-{[4-(1-pyrrolidinyl)-1-piperidinyl]methyl}-2-[3-(trifluoromethyl)phenyl]-4-quinolinecarboxamide | 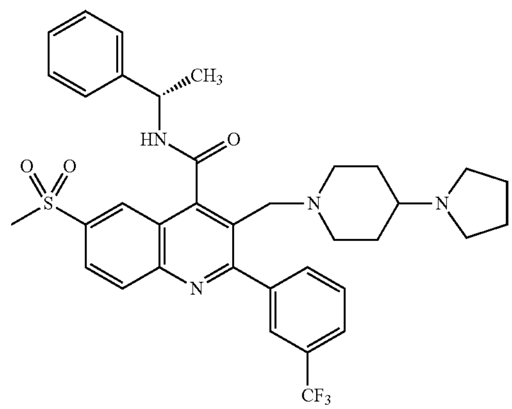 | 665.2 (M + H$^+$) |
| 75 | 3-({4-[(3S)-3-fluoro-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide | 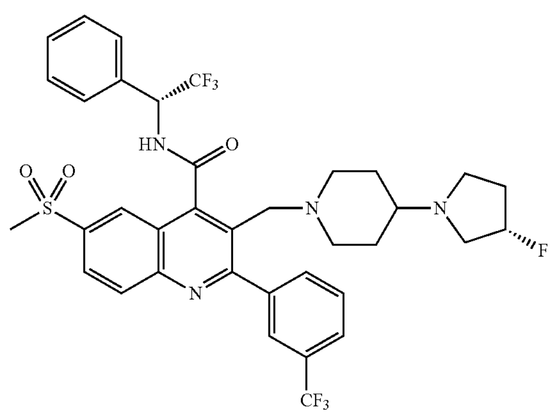 | 737.2 (M + H$^+$) |
| 76 | 3-({4-[(3S)-3-fluoro-1-pyrrolidinyl]-1-piperidinyl}methyl)-6-(methylsulfonyl)-N-[(1S)-1-phenylethyl]-2-[3-(trifluoromethyl)phenyl]-4-quinolinecarboxamide | 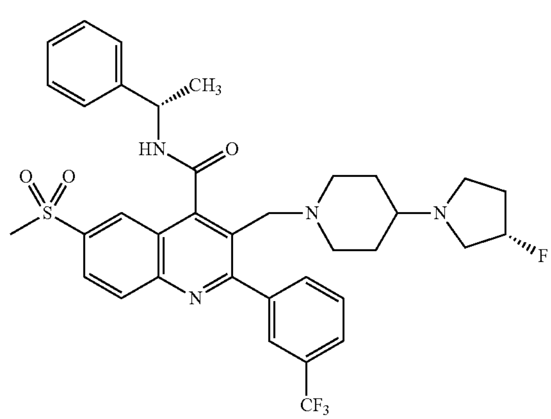 [SMILES: C[C@H](NC(=O)c1c(CN2CCC(N3CC[C@H](F)C3)CC2)c(-c2cccc(C(F)(F)F)c2)nc2ccc(S(C)(=O)=O)cc12)c1ccccc1] | 683.2 (M + H$^+$) |

-continued

| Ex | Name | Structure | MS (m/z) |
|---|---|---|---|
| 77 | 3-[(4,4-difluoro-1,4'-bipiperidin-1'-yl)methyl]-6-(methylsulfonyl)-2-[3-(trifluoromethyl)phenyl]-N-[(1R)-2,2,2-trifluoro-1-phenylethyl]-4-quinolinecarboxamide | 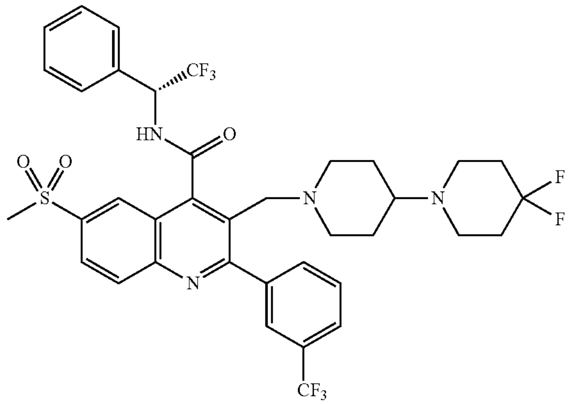 | 769.2 (M + H⁺) |
| 78 | 3-[(4,4-difluoro-1,4'-bipiperidin-1'-yl)methyl]-6-(methylsulfonyl)-N-[(1S)-1-phenylethyl]-2-[3-(trifluoromethyl)phenyl]-4-quinolinecarboxamide | 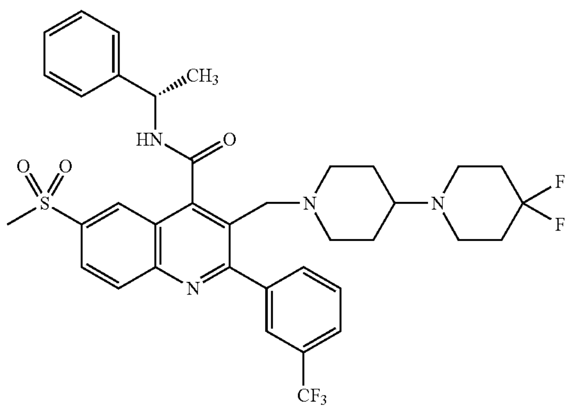 | 715.2 (M + H⁺) |
| 79 | 3-{[(3S)-3-hydroxy-1,4'-bipiperidin-1'-yl]methyl}-6-(methylsulfonyl)-2-[3-(trifluoromethyl)phenyl]-N-[(1R)-2,2,2-trifluoro-1-phenylethyl]-4-quinolinecarboxamide | 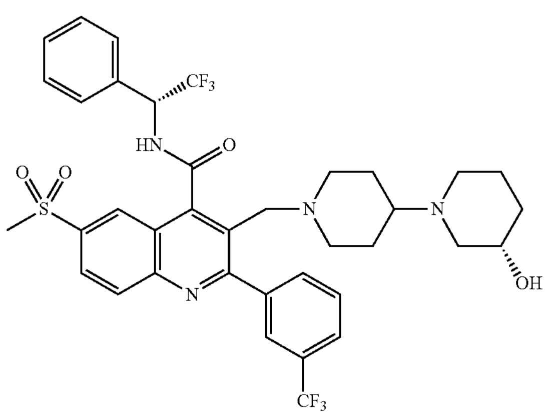 | 749.2 (M + H⁺) |

-continued

| Ex | Name | Structure | MS (m/z) |
|---|---|---|---|
| 80 | 3-{[(3S)-3-hydroxy-1,4'-bipiperidin-1'-yl]methyl}-6-(methylsulfonyl)-N-[(1S)-1-phenylethyl]-2-[3-(trifluoromethyl)phenyl]-4-quinolinecarboxamide | 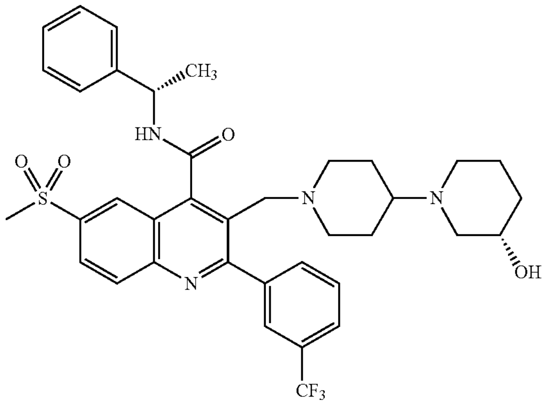 [SMILES: C[C@H](NC(=O)c1c(CN2CCC(N3CCC[C@H](O)C3)CC2)c(-c2cccc(C(F)(F)F)c2)nc2ccc(S(C)(=O)=O)cc12)c1ccccc1] | 695.2 (M + H⁺) |
| 81 | 3-{[(3R)-3-hydroxy-1,4'-bipiperidin-1'-yl]methyl}-6-(methylsulfonyl)-2-[3-(trifluoromethyl)phenyl]-N-[(1R)-2,2,2-trifluoro-1-phenylethyl]-4-quinolinecarboxamide | 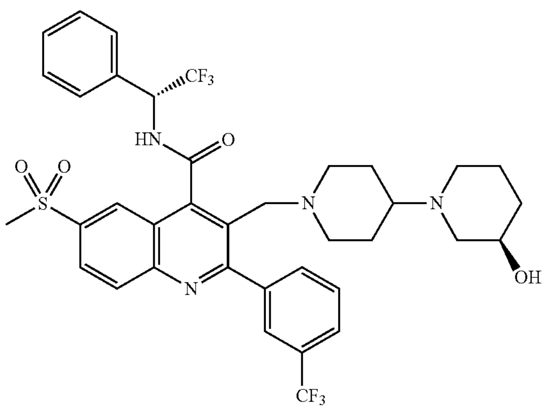 | 749.2 (M + H⁺) |
| 82 | 3-{[(3R)-3-hydroxy-1,4'-bipiperidin-1'-yl]methyl}-6-(methylsulfonyl)-N-[(1S)-1-phenylethyl]-2-[3-(trifluoromethyl)phenyl]-4-quinolinecarboxamide | 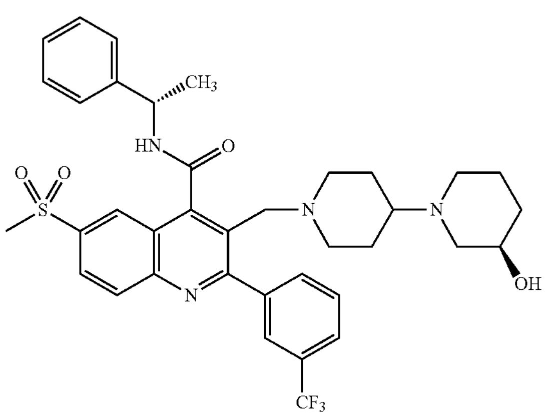 [SMILES: C[C@H](NC(=O)c1c(CN2CCC(N3CCC[C@@H](O)C3)CC2)c(-c2cccc(C(F)(F)F)c2)nc2ccc(S(C)(=O)=O)cc12)c1ccccc1] | 695.2 (M + H⁺) |

-continued

| Ex | Name | Structure | MS (m/z) |
|---|---|---|---|
| 83 | 6-(methylsulfonyl)-2-[3-(trifluoromethyl)phenyl]-3-({4-[2-(trifluoromethyl)-1-pyrrolidinyl]-1-piperidinyl}methyl)-N-[(1R)-2,2,2-trifluoro-1-phenylethyl]-4-quinolinecarboxamide | 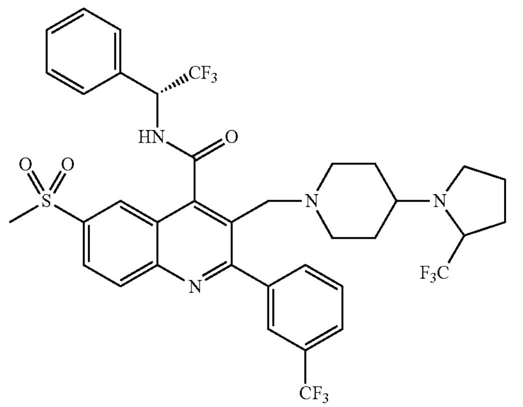 | 787.2 (M + H+) |
| 84 | 6-(methylsulfonyl)-N-[(1S)-1-phenylethyl]-2-[3-(trifluoromethyl)phenyl]-3-({4-[2-(trifluoromethyl)-1-pyrrolidinyl]-1-piperidinyl}methyl)-4-quinolinecarboxamide | 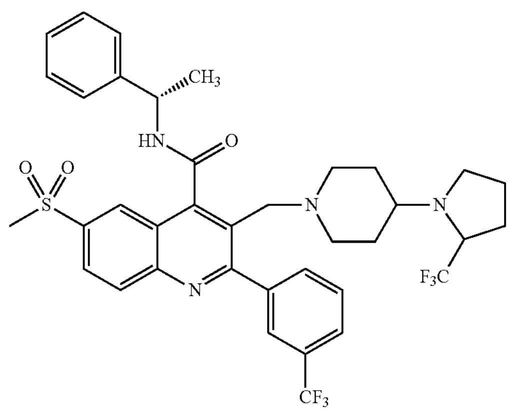 | 733.2 (M + H+) |
| 85 | 3-{[3-(methyloxy)-1,4'-bipiperidin-1'-yl]methyl}-6-(methylsulfonyl)-2-[3-(trifluoromethyl)phenyl]-N-[(1R)-2,2,2-trifluoro-1-phenylethyl]-4-quinolinecarboxamide | 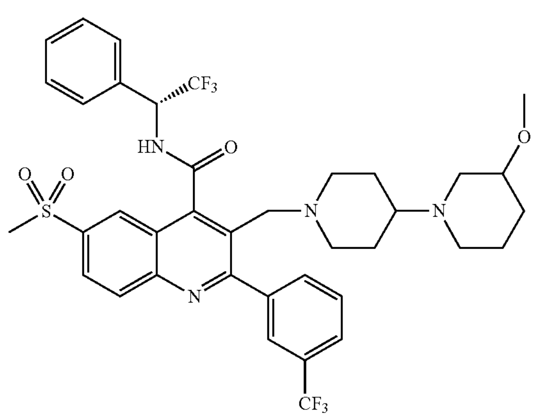 | 763.2 (M + H+) |

| Ex | Name | Structure | MS (m/z) |
|---|---|---|---|
| 86 | 3-[(4-fluoro-1,4'-bipiperidin-1'-yl)methyl]-6-(methylsulfonyl)-2-[3-(trifluoromethyl)phenyl]-N-[(1R)-2,2,2-trifluoro-1-phenylethyl]-4-quinolinecarboxamide | 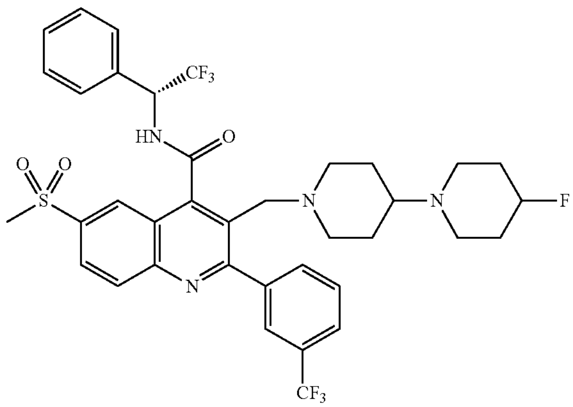 | 751.2 (M + H⁺) |
| 87 | 3-{[4-(diethylamino)-1-piperidinyl]methyl}-6-(methylsulfonyl)-2-[3-(trifluoromethyl)phenyl]-N-[(1R)-2,2,2-trifluoro-1-phenylethyl]-4-quinolinecarboxamide | 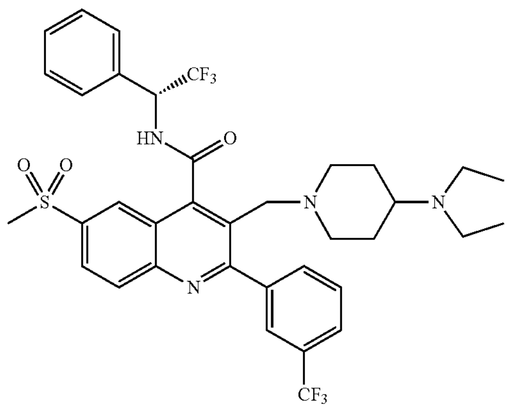 | 721.3 (M + H⁺) |

Example 88

6-(methylsulfonyl)-3-{[4-(4-morpholinyl)-1-piperidinyl]methyl}-2-[4-(trifluoromethyl)phenyl]-N-[(1R)-2,2,2-trifluoro-1-phenylethyl]-4-quinolinecarboxamide

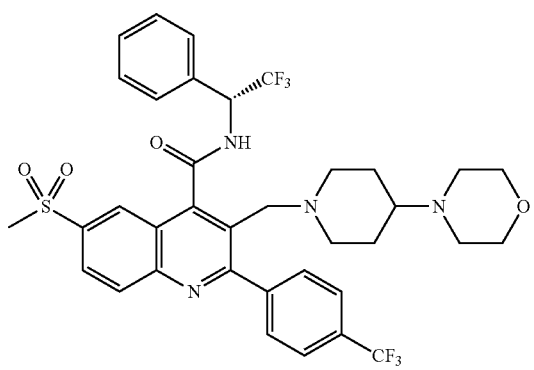 [SMILES: CS(=O)(=O)c1ccc2nc(-c3ccc(C(F)(F)F)cc3)c(CN3CCC(N4CCOCC4)CC3)c(C(=O)N[C@H](c3ccccc3)C(F)(F)F)c2c1]

6-bromo-3-methyl-2-[4-(trifluoromethyl)phenyl]-4-quinolinecarboxylic acid

A solution of potassium hydroxide (13.08 g, 233 mmol) in water (25.2 mL) was added slowly to a solution of 5-bromo-1H-indole-2,3-dione (9.76 g, 38.9 mmol) in ethanol (63.1 mL). 1-[4-(trifluoromethyl)phenyl]-1-propanone (8.64 g, 42.7 mmol) was added and the mixture was heated to reflux for 1 h. The reaction mixture was concentrated to remove the solvent, the residue was dissolved in water, and the mixture was washed three times with Et₂O. The aqueous mixture was chilled, and concentrated HCl was added until the solution was pH 3. The solid was collected by filtration, washed with water, and dried under reduced pressure in a water bath at 100° C. The product was obtained as a light brown powder (15.6 g, 98%). This material was used without further purification. MS (m/z) 412.0 (M+H⁺).

methyl 6-bromo-3-methyl-2-[4-(trifluoromethyl)phenyl]-4-quinolinecarboxylate

6-Bromo-3-methyl-2-[4-(trifluoromethyl)phenyl]-4-quinolinecarboxylic acid (15.6 g, 38.0 mmol), dimethyl sulfoxide (DMSO) (190 ml), methyl iodide (4.76 mL, 76 mmol) and cesium carbonate (12.39 g, 38.0 mmol) were added to a 500 mL flask The mixture was stirred at RT for 2 h. Water (200 mL) was added to the resulting slurry, and the mixture was stirred for 10 min, the solid was collected by filtration, and the filter cake was washed with 500 mL of water. The resulting solid was dried under reduced pressure to afford the desired product as a tan solid (15.75 g, 98%). MS (m/z) 426.0 (M+H⁺).

methyl 3-methyl-6-(methylsulfonyl)-2-[4-(trifluoromethyl)phenyl]-4-quinolinecarboxylate Methyl 6-bromo-3-methyl-2-[4-(trifluoromethyl)phenyl]-4-quinolinecarboxylate (5.1 g, 12.02 mmol) was dissolved in dimethyl sulfoxide (60 mL) and copper(I) iodide (4.58 g, 24.04 mmol) and methanesulfinic acid sodium salt (2.455 g, 24.04 mmol) were added. The reaction vessel was evacuated and flushed with $N_2$ three times, and heated at 120° C. overnight. The reaction mixture was diluted with $CH_2Cl_2$ and $H_2O$, stirred for 30 min, filtered through the Celite, and washed with $CH_2Cl_2$. The filtrate was extracted three times with $CH_2Cl_2$, and the combined organic extracts were washed twice with brine, and dried over $Na_2SO_4$. The residue was purified via silica gel flash chromatography (0%-20% EtOAc/$CH_2Cl_2$) to afford the desired product as an off white solid (3.3 g, 65%). MS (m/z) 424.0 (M+H$^+$).

6-(methylsulfonyl)-3-{[4-(4-morpholinyl)-1-piperidinyl]methyl}-2-[4-(trifluoromethyl)phenyl]-4-quinolinecarboxylic acid Methyl 3-methyl-6-(methylsulfonyl)-2-[4-(trifluoromethyl)phenyl]-4-quinolinecarboxylate (1.11 g, 2.62 mmol) was added to a flask and azeotroped with benzene to remove any residual water. NBS (0.513 g, 2.88 mmol) and diphenylperoxyanhydride (0.064 g, 0.262 mmol) were added, and the solids were suspended in carbon tetrachloride (42 mL). The solutions was heated to reflux for 24 hrs, cooled to room temperature, and concentrated to a minimal volume to afford a light yellow slurry. The slurry was redissolved in acetonitrile (42.0 mL), and 4-(4-piperidinyl)morpholine (0.669 g. 3.93 mmol) was added. The solution was stirred overnight, then concentrated to dryness. The residue was dissolved in 2N HCl and extracted with $CH_2Cl_2$. The phases were separated, and the organic phase was washed with HCl. The combined aqueous extracts were made basic with NaOH (2N) and extracted three times with $CH_2Cl_2$. The combined organic extracts were passed over a phase separator and concentrated to afford a yellow residue. The residue was dissolved in methanol (120 ml), water (21 ml) and KOH (1.471 g, 26.2 mmol), and the mixture was refluxed overnight. The reaction mixture was concentrated under reduced pressure to remove MeOH, additional water was added, and the mixture was stirred at room temperature for 1 h. The solid precipitate was collected by filtration to afford the desired product as an off white solid (1.1 g, 68%). MS (m/z) 578.2 (M+H$^+$).

6-(methylsulfonyl)-3-{[4-(4-morpholinyl)-1-piperidinyl]methyl}-2-[4-(trifluoromethyl)phenyl]-N-[(1R)-2,2,2-trifluoro-1-phenylethyl]-4-quinolinecarboxamide 6-(Methylsulfonyl)-3-{[4-(4-morpholinyl)-1-piperidinyl]methyl}-2-[4-(trifluoromethyl)phenyl]-4-quinolinecarboxylic acid (100 mg, 0.162 mmol), dichloromethane (1621 μL), DIEA (31.2 μL, 0.178 mmol), and [(1R)-2,2,2-trifluoro-1-phenylethyl]amine (37.7 mg, 0.178 mmol) were combined in a round bottom flask. The mixture was cooled to 0° C. and 2,4,6-tripropyl-1,3,5,2,4,6-trioxatriphosphorinane 2,4,6-trioxide (145 μL, 0.243 mmol) (50% in EtOAc) was added dropwise. The mixture was stirred at 0° C. for 2 h, warmed to room temperature, and stirred overnight. The next day 0.1 mL of water and 2 mL of $CH_3CN$ were added, and the solution was concentrated to afford a yellow residue. The residue was dissolved in MeOH/DMSO and purified by reverse phase HPLC to afford the title compound as a white solid (32 mg, 27%). MS (m/z) 735.3 (M+H$^+$).

The following compounds were prepared using procedures analogous to those described in Example 88 using an appropriate ketone in the first step, substituting 4-(1-pyrrolidinyl)piperidine with an appropriate secondary amine in the fifth step, and replacing [(1R)-2,2,2-trifluoro-1-phenylethyl]amine with an appropriate benzylamine in the final step when necessary. As is appreciated by those skilled in the art, these analogous examples may involve variations in general reaction conditions.

| Ex | Name | Structure | MS (m/z) |
|---|---|---|---|
| 89 | 6-(methylsulfonyl)-3-{[4-(4-morpholinyl)-1-piperidinyl]methyl}-N-[(1S)-1-phenylethyl]-2-[4-(trifluoromethyl)phenyl]-4-quinolinecarboxamide | 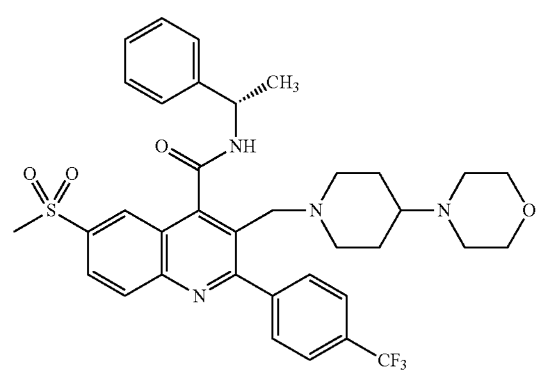 | 681.3 (M + H$^+$) |

| Ex | Name | Structure | MS (m/z) |
|---|---|---|---|
| 90 | 3-(1,4'-bipiperidin-1'-ylmethyl)-6-(methylsulfonyl)-2-[4-(trifluoromethyl)phenyl]-N-[(1R)-2,2,2-trifluoro-1-phenylethyl]-4-quinolinecarboxamide | 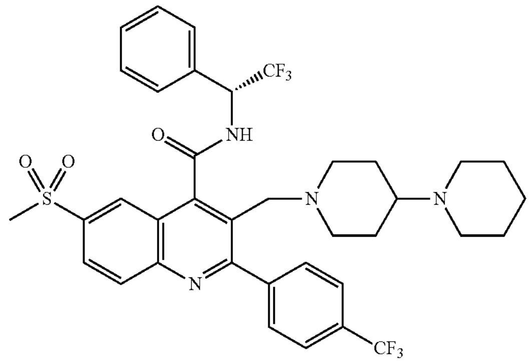 | 733.3 (M + H$^+$) |
| 91 | 3-(1,4'-bipiperidin-1'-ylmethyl)-6-(methylsulfonyl)-N-[(1S)-1-phenylethyl]-2-[4-(trifluoromethyl)phenyl]-4-quinolinecarboxamide | 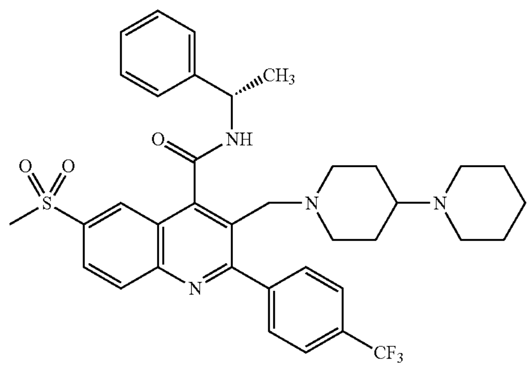 [SMILES: C[C@H](NC(=O)c1c(CN2CCC(N3CCCCC3)CC2)c(-c2ccc(C(F)(F)F)cc2)nc2ccc(S(C)(=O)=O)cc12)c1ccccc1] | 679.3 (M + H$^+$) |
| 92 | 6-(methylsulfonyl)-3-{[4-(1-pyrrolidinyl)-1-piperidinyl]methyl}-2-[4-(trifluoromethyl)phenyl]-N-[(1R)-2,2,2-trifluoro-1-phenylethyl]-4-quinolinecarboxamide | 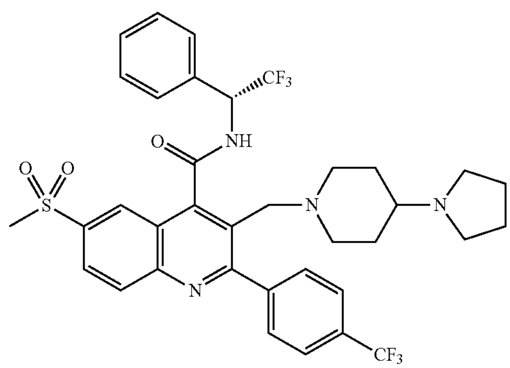 | 719.3 (M + H$^+$) |
| 93 | 6-(methylsulfonyl)-N-[(1S)-1-phenylethyl]-3-{[4-(1-pyrrolidinyl)-1-piperidinyl]methyl}-2-[4-(trifluoromethyl)phenyl]-4-quinolinecarboxamide | 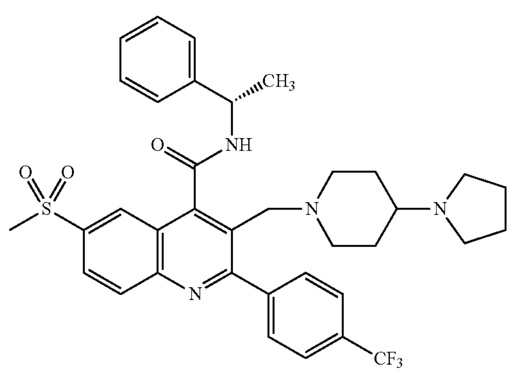 [SMILES: C[C@H](NC(=O)c1c(CN2CCC(N3CCCC3)CC2)c(-c2ccc(C(F)(F)F)cc2)nc2ccc(S(C)(=O)=O)cc12)c1ccccc1] | 665.3 (M + H$^+$) |

-continued

| Ex | Name | Structure | MS (m/z) |
|---|---|---|---|
| 94 | 3-(1,4'-bipiperidin-1'-ylmethyl)-2-[4-(methyloxy)phenyl]-6-(methylsulfonyl)-N-[(1R)-2,2,2-trifluoro-1-phenylethyl]-4-quinolinecarboxamide | 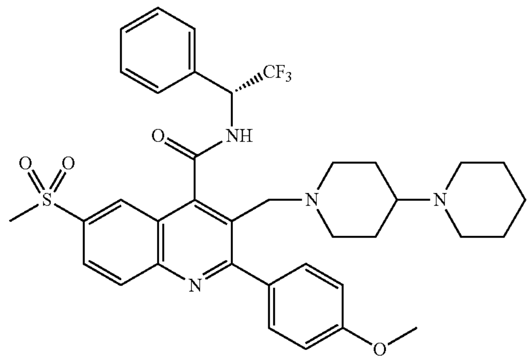 | 695.3 (M + H+) |
| 95 | 2-(3,4-dichlorophenyl)-6-(methylsulfonyl)-3-{[4-(4-morpholinyl)-1-piperidinyl]methyl}-N-[(1R)-2,2,2-trifluoro-1-phenylethyl]-4-quinolinecarboxamide | 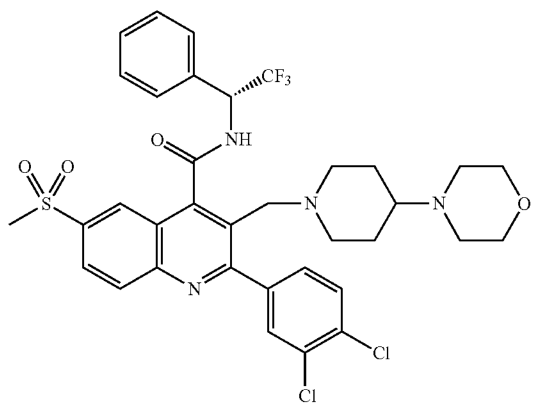 | 737.2 (M + H+) |
| 96 | 2-(3,4-dichlorophenyl)-6-(methylsulfonyl)-3-{[4-(4-morpholinyl)-1-piperidinyl]methyl}-N-[(1S)-1-phenylethyl]-4-quinolinecarboxamide | 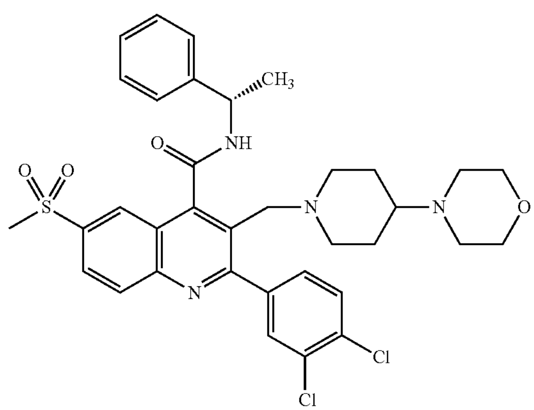 | 683.2 (M + H+) |
| 97 | 3-(1,4'-bipiperidin-1'-ylmethyl)-2-(3,4-dichlorophenyl)-6-(methylsulfonyl)-N-[(1R)-2,2,2-trifluoro-1-phenylethyl]-4-quinolinecarboxamide | 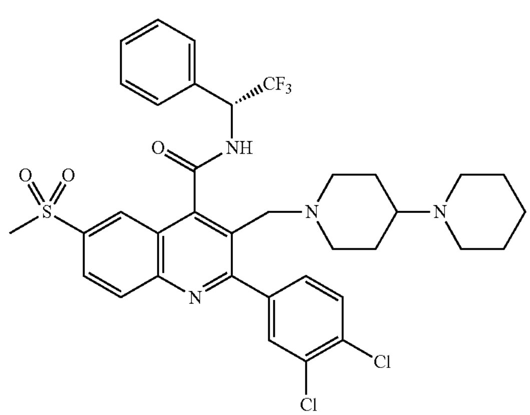 | 733.2 (M + H+) |

-continued

| Ex | Name | Structure | MS (m/z) |
|---|---|---|---|
| 98 | 3-(1,4'-bipiperidin-1'-ylmethyl)-2-(3,4-dichlorophenyl)-6-(methylsulfonyl)-N-[(1S)-1-phenylethyl]-4-quinolinecarboxamide | 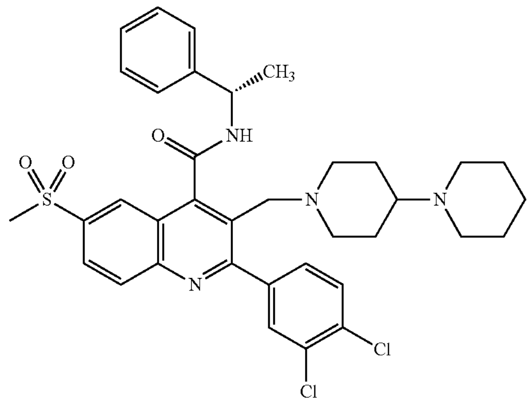 [SMILES: C[C@H](NC(=O)c1c(CN2CCC(N3CCCCC3)CC2)c(-c2ccc(Cl)c(Cl)c2)nc2ccc(S(C)(=O)=O)cc12)c1ccccc1] | 681.3 (M + H⁺) |
| 99 | 2-(3,4-dichlorophenyl)-6-(methylsulfonyl)-3-{[4-(1-pyrrolidinyl)-1-piperidinyl]methyl}-N-[(1R)-2,2,2-trifluoro-1-phenylethyl]-4-quinolinecarboxamide | 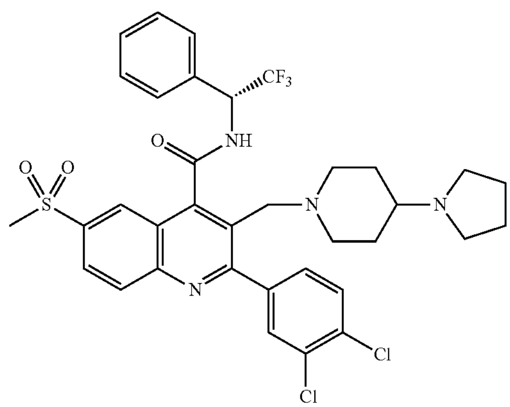 | 721.2 (M + H⁺) |
| 100 | 2-(3,4-dichlorophenyl)-6-(methylsulfonyl)-N-[(1S)-1-phenylethyl]-3-{[4-(1-pyrrolidinyl)-1-piperidinyl]methyl}-4-quinolinecarboxamide | 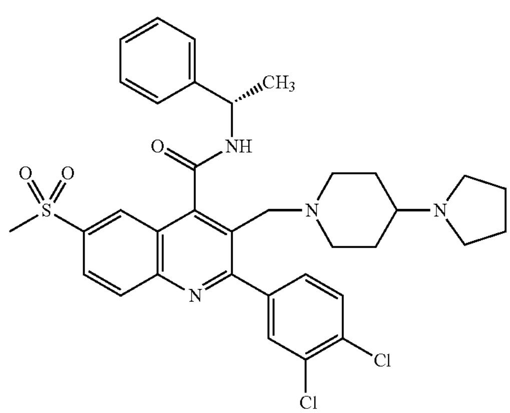 [SMILES: C[C@H](NC(=O)c1c(CN2CCC(N3CCCC3)CC2)c(-c2ccc(Cl)c(Cl)c2)nc2ccc(S(C)(=O)=O)cc12)c1ccccc1] | 667.2 (M + H⁺) |

| Ex | Name | Structure | MS (m/z) |
|---|---|---|---|
| 101 | 6-[(1-methylethyl)sulfonyl]-7-(methyloxy)-3-{[4-(4-morpholinyl)-1-piperidinyl]methyl}-2-[3-(trifluoromethyl)phenyl]-N-[(1S)-2,2,2-trifluoro-1-phenylethyl]-4-quinolinecarboxamide | 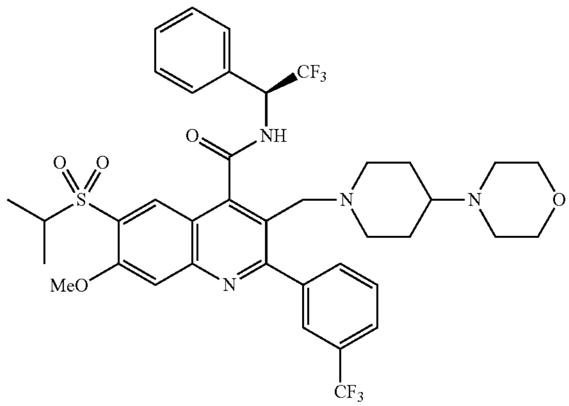 | 793.3 (M + H+) |

Example 102

3-{[4-(3,3-difluoro-1-pyrrolidinyl)-1-piperidinyl]methyl}-6-(methylsulfonyl)-2-[3-(trifluoromethyl)phenyl]-N-[(1R)-2,2,2-trifluoro-1-phenylethyl]-4-quinolinecarboxamide

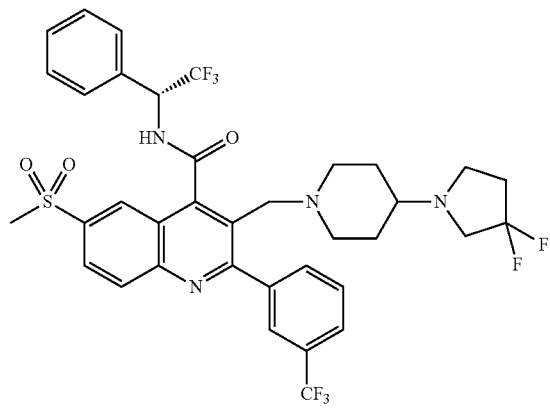 [SMILES: CS(=O)(=O)c1ccc2nc(-c3cccc(C(F)(F)F)c3)c(CN3CCC(N4CCC(F)(F)C4)CC3)c(C(=O)N[C@H](c3ccccc3)C(F)(F)F)c2c1]

6-bromo-3-methyl-2-[3-(trifluoromethyl)phenyl]-4-quinolinecarboxylic acid

Potassium hydroxide (29.8 g, 531 mmol) in water (49.2 mL) was added to an orange suspension of 5-bromoisatin (20 g, 88 mmol) in ethanol (172 mL). 1-[3-(Trifluoromethyl)phenyl]-1-propanone (19.68 g, 97 mmol) was added and the mixture was heated to 85° C. for 3 h. The solvent was removed under reduced pressure. The residue was diluted with water (400 mL) and stirred overnight. The aqueous mixture was cooled to 0° C. and adjusted to pH~3 with concentrated HCl. The solid was collected by filtration and dried in a vacuum oven at 70° C. for 3 days to afford 6-bromo-3-methyl-2-[3-(trifluoromethyl)phenyl]-4-quinolinecarboxylic acid (42 g, >99% yield). This material was used without further purification. MS (m/z) 411.8 (M+H+).

3-methyl-6-(methylsulfonyl)-2-[3-(trifluoromethyl)phenyl]-4-quinolinecarboxylic acid To a suspension of 6-bromo-3-methyl-2-[3-(trifluoromethyl)phenyl]-4-quinolinecarboxylic acid (10 g, 21.94 mmol) in dimethyl sulfoxide (146 mL) was added copper(I) iodide (8.36 g, 43.9 mmol) and sodium methanesulfinate (5.27 g, 43.9 mmol). The reaction mixture was alternately evacuated and purged with nitrogen three times and heated to 120° C. for 18 h. Additional copper(I) iodide (8.36 g, 43.9 mmol) and sodium methanesulfinate (5.27 g, 43.9 mmol) was added, and the mixture was stirred for an additional 22 h. The mixture was cooled to room temperature and diluted with ethyl acetate and water. The mixture was acidified to pH 2-3 with 2N HCl, filtered through Celite®, and rinsed with ethyl acetate. The organic layer was separated, washed with water, dried over MgSO4, filtered, and concentrated in vacuo to give 3-methyl-6-(methylsulfonyl)-2-[3-(trifluoromethyl)phenyl]-4-quinolinecarboxylic acid (4.07 g, 30% yield) as an orange solid. MS (m/z) 410.0 (M+H+).

methyl 3-methyl-6-(methylsulfonyl)-2-[3-(trifluoromethyl)phenyl]-4-quinolinecarboxylate To a suspension of 3-methyl-6-(methylsulfonyl)-2-[3-(trifluoromethyl)phenyl]-4-quinolinecarboxylic acid (4.07 g, 9.94 mmol) at 0° C. was added oxalyl chloride (1.305 mL, 14.91 mmol) and N,N-dimethylformamide (0.1 mL). The resulting mixture was stirred at 0° C. for 1 h. Methanol (5 mL) was added, and the mixture was warmed to room temperature and stirred overnight. The solvent was removed under reduced pressure, and the residue diluted with saturated aqueous NaHCO3. The aqueous mixture was extracted with methylene chloride, dried over MgSO4, filtered, and concentrated in vacuo. The crude material was absorbed onto florisil and purified via column chromatography (ISCO, 5-100% ethyl acetate/hexanes) to afford methyl 3-methyl-6-(methylsulfonyl)-2-[3-(trifluoromethyl)phenyl]-4-quinolinecarboxylate (2.665 g, 60% yield). MS (m/z) 424.0 (M+H+).

methyl 3-(bromomethyl)-6-(methylsulfonyl)-2-[3-(trifluoromethyl)phenyl]-4-quinolinecarboxylate To a suspension of methyl 3-methyl-6-(methylsulfonyl)-2-[3-(trifluoromethyl)phenyl]-4-quinolinecarboxylate (2.66 g, 6.28 mmol) in carbon tetrachloride (41.9 mL) was added N-bromosuccinimide (1.454 g, 8.17 mmol) and benzoyl peroxide (0.152 g, 0.628 mmol). The resulting mixture was heated at 100° C. for 18 h. The mixture was cooled to room temperature and concentrated in vacuo to afford methyl 3-(bromomethyl)-6-(methylsulfonyl)-2-[3-(trifluoromethyl)phenyl]-4-quinolinecarboxylate. This material was used without further purification.

methyl 3-{[4-(3,3-difluoro-1-pyrrolidinyl)-1-piperidinyl]methyl}-6-(methylsulfonyl)-2-[3-(trifluoromethyl)phenyl]-4-quinolinecarboxylate To a suspension of methyl 3-(bromomethyl)-6-(methylsulfonyl)-2-[3-(trifluoromethyl)phenyl]-4-quinolinecarboxylate (1.05 g, 2.090 mmol) in acetonitrile (13.94 mL) was added 4-(3,3-difluoro-1-pyrrolidinyl)piperidine (0.517 g, 2.72 mmol). After 15 h, additional 4-(3,3-difluoro-1-pyrrolidinyl)piperidine (0.188 g, 0.988 mmol, 0.47 equiv.) was added. The mixture was stirred at room temperature for 4 days. The solvent was removed, and the residue was absorbed onto florisil and purified via column chromatography (ISCO 0.5-3% methanol/methylene chloride) to give methyl 3-{[4-(3,3-difluoro-1-pyrrolidinyl)-1-piperidinyl]methyl}-6-(methylsulfonyl)-2-[3-(trifluoromethyl)phenyl]-4-quinolinecarboxylate (0.976 g, 73% yield) as a yellow foam. MS (m/z) 612.2 (M+H$^+$).

3-{[4-(3,3-difluoro-1-pyrrolidinyl)-1-piperidinyl]methyl}-6-(methylsulfonyl)-2-[3-(trifluoromethyl)phenyl]-4-quinolinecarboxylic acid To a solution of methyl 3-{[4-(3,3-difluoro-1-pyrrolidinyl)-1-piperidinyl]methyl}-6-(methylsulfonyl)-2-[3-(trifluoromethyl)phenyl]-4-quinolinecarboxylate (0.970 g, 1.586 mmol) in methanol (15.86 mL) was added water (5.29 mL) and potassium hydroxide (0.445 g, 7.93 mmol). The mixture was heated to 65° C. for 15 h. The mixture was cooled to room temperature and concentrated. The residue was acidified to pH 4-5 with 2N HCl. The resulting precipitate was collected by filtration, washed with water (2×1 mL), and dried in the vacuum oven (35° C.) overnight to provide 3-{[4-(3,3-difluoro-1-pyrrolidinyl)-1-piperidinyl]methyl}-6-(methylsulfonyl)-2-[3-(trifluoromethyl)phenyl]-4-quinolinecarboxylic acid (0.718 g, 72% yield) as a yellow solid. MS (m/z) 598.1 (M+H$^+$).

3-{[4-(3,3-difluoro-1-pyrrolidinyl)-1-piperidinyl]methyl}-6-(methylsulfonyl)-2-[3-(trifluoromethyl)phenyl]-N-[(1R)-2,2,2-trifluoro-1-phenylethyl]-4-quinolinecarboxamide A suspension of 3-{[4-(3,3-difluoro-1-pyrrolidinyl)-1-piperidinyl]methyl}-6-(methylsulfonyl)-2-[3-(trifluoromethyl)phenyl]-4-quinolinecarboxylic acid (0.100 g, 0.167 mmol), [(1R)-2,2,2-trifluoro-1-phenylethyl]amine (0.046 g, 0.218 mmol), N,N-diisopropylethylamine (0.088 mL, 0.502 mmol), and propylphosphonic anhydride (0.128 mL of a 50% solution in ethyl acetate, 0.218 mmol) in dichloromethane (2.57 mL) was stirred at room temperature for 30 min. Water (2 mL) was added, and the mixture was poured into a hydrophobic frit to separate the layers. The organic phase was concentrated in vacuo, and the residue was loaded onto florisil and purified via column chromatography (ISCO, 4 g silica, 0-10% methanol/methylene chloride) to afford 3-{[4-(3,3-difluoro-1-pyrrolidinyl)-1-piperidinyl]methyl}-6-(methylsulfonyl)-2-[3-(trifluoromethyl)phenyl]-N-[(1R)-2,2,2-trifluoro-1-phenylethyl]-4-quinolinecarboxamide (0.110 g, 83% yield). MS (m/z) 755.2 (M+H$^+$).

The following compounds were prepared using procedures analogous to those described in Example 102, substituting 4-(1-pyrrolidinyl)piperidine with an appropriate secondary amine and replacing [(1R)-2,2,2-trifluoro-1-phenylethyl]amine with an appropriate benzylamine when necessary. As is appreciated by those skilled in the art, these analogous examples may involve variations in general reaction conditions.

| Ex | Name | Structure | MS (m/z) |
|---|---|---|---|
| 103 | 3-{[4-(3,3-difluoro-1-pyrrolidinyl)-1-piperidinyl]methyl}-6-(methylsulfonyl)-N-[(1S)-1-phenylethyl]-2-[3-(trifluoromethyl)phenyl]-4-quinolinecarboxamide | 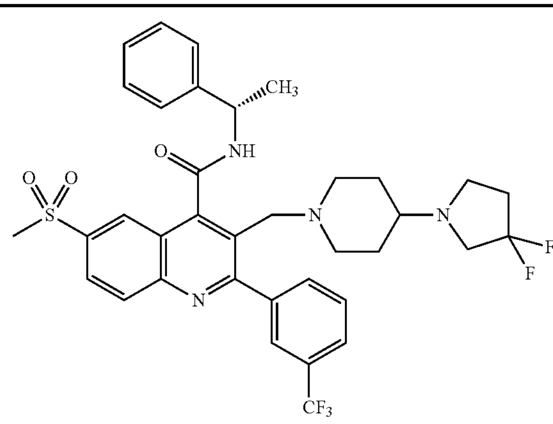 | 701.2 (M + H$^+$) |

| Ex | Name | Structure | MS (m/z) |
|---|---|---|---|
| 104 | 3-({4-[(3R)-3-hydroxy-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide | 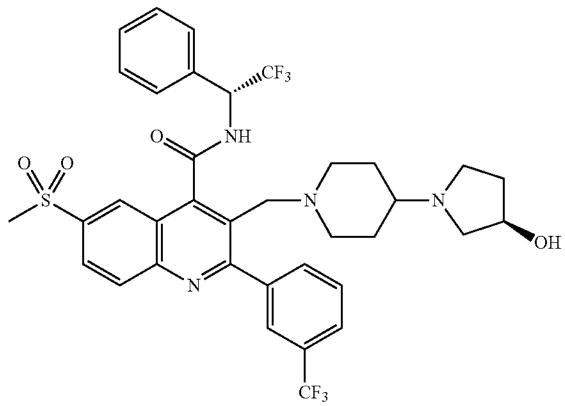 | 735.2 (M + H+) |
| 105 | 3-({4-[(3S)-3-hydroxy-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide | 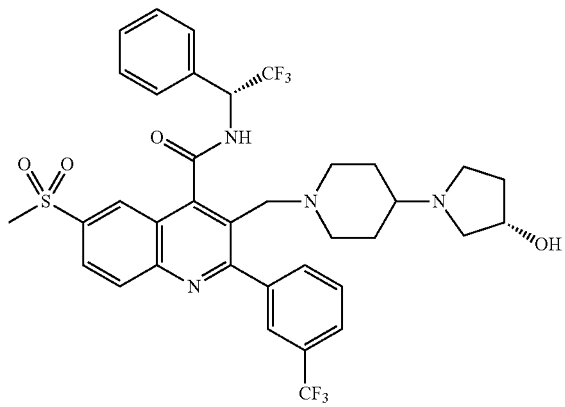 | 735.2 (M + H+) |

Example 106

2-(3-bromophenyl)-6-(methylsulfonyl)-3-{[4-(4-morpholinyl)-1-piperidinyl]methyl}-N-[(1R)-2,2,2-trifluoro-1-phenylethyl]-4-quinolinecarboxamide

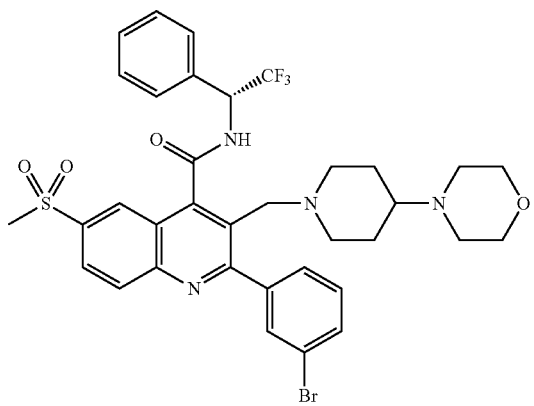 [SMILES: CS(=O)(=O)c1ccc2nc(-c3cccc(Br)c3)c(CN3CCC(N4CCOCC4)CC3)c(C(=O)N[C@H](c3ccccc3)C(F)(F)F)c2c1]

2-(3-bromophenyl)-6-fluoro-3-methyl-4-quinolinecarboxylic acid

Potassium hydroxide (19.98 g, 356 mmol) was added to a suspension of 5-fluoro-1H-indole-2,3-dione (10 g, 59.4 mmol) in ethanol (96 mL). 1-(3-Bromophenyl)-1-propanone (13.91 g, 65.3 mmol) was added and the mixture was heated to reflux for 1 h. The reaction mixture was cooled to room temperature and acidified to pH 3 with concentrated HCl. The solid was collected by filtration, washed with water, and dried to afford 2-(3-bromophenyl)-6-fluoro-3-methyl-4-quinolinecarboxylic acid (20.9 g, 98% yield). This material was used without further purification. MS (m/z) 360.0 (M+H+).

methyl 2-(3-bromophenyl)-3-methyl-6-(methylsulfonyl)-4-quinolinecarboxylate

Potassium hydroxide (1.32 g, 23.60 mmol) in water was added to 2-(3-bromophenyl)-6-fluoro-3-methyl-4-quinolinecarboxylic acid (8.5 g, 23.60 mmol). The solution was concentrated and then azeotroped 3 times with toluene. The resulting solid was dissolved in dimethyl sulfoxide (120 mL) and sodium thiomethoxide (4.96 g, 70.8 mmol) was added. The mixture was heated to 65° C. and stirred overnight. The solution was cooled to room temperature, MeI (4.43 mL, 70.8 mmol) was added, and the mixture was stirred for 1 h. The solid was collected by filtration and dried.

The solid material was dissolved in tetrahydrofuran (400 mL) and Oxone (43.5 g, 70.8 mmol) in water (300 mL) was added. The solution was stirred for 2 h at room temperature, and the mixture was partitioned between water and methylene chloride. The organic phase was separated, and the aqueous phase was extracted with methylene chloride. The combined organic extracts were concentrated and purified via column chromatography (ISCO, 330 g column, 0-20% ethyl acetate/ methylene chloride). The fractions containing the product were concentrated. The residue was dissolved in methanol and heated to reflux, and the resulting mixture was cooled to room temperature and stirred overnight. The solid was collected by filtration and dried to afford methyl 2-(3-bromophenyl)-3-methyl-6-(methylsulfonyl)-4-quinolinecarboxylate (5.78 g, 75% yield) as a white powder. MS (m/z) 436.0 (M+H$^+$).

2-(3-bromophenyl)-6-(methylsulfonyl)-3-{[4-(4-morpholinyl)-1-piperidinyl]methyl}-4-quinolinecarboxylic acid Methyl 2-(3-bromophenyl)-3-methyl-6-(methylsulfonyl)-4-quinolinecarboxylate (1.92 g, 4.42 mmol) was azeotropically dried with benzene to remove any residual water. NBS (0.984 g, 5.53 mmol) and diphenylperoxyanhydride (0.107 g, 0.442 mmol) were added, followed by carbon tetrachloride (150 mL). The resulting solution was heated to reflux. Additional NBS (8.84 mmol) was added and the reaction mixture was stirred at reflux overnight. The mixture was cooled to room temperature, and the solvent was removed under reduced pressure. The residue was dissolved in acetonitrile (16 mL) and 4-(4-piperidinyl)morpholine (1.23 g, 6.63 mmol) was added. The reaction mixture was stirred at room temperature overnight. The solvent was removed under reduced pressure, and the residue was partitioned between 2N HCl and methylene chloride. The organic layer was removed and extracted with 2N HCl. The combined aqueous extracts were neutralized with 2N NaOH and were extracted with methylene chloride (five times). The combined organic extracts were passed over a phase separator and concentrated to afford a yellow residue. This residue was dissolved in methanol (100 mL) and water (21 mL), and KOH (2.480 g, 44.2 mmol) was added. The mixture was heated to reflux overnight. The solvent was removed under reduced pressure, and the residue was diluted with water and stirred for 1 h at room temperature. The solid precipitate was collected by filtration to afford 2-(3-bromophenyl)-6-(methylsulfonyl)-3-{[4-(4-morpholinyl)-1-piperidinyl]methyl}-4-quinolinecarboxylic acid as the potassium salt (1.8 g, 65% yield). MS (m/z) 590.1 (M+H$^+$).

2-(3-bromophenyl)-6-(methylsulfonyl)-3-{[4-(4-morpholinyl)-1-piperidinyl]methyl}-N-[(1R)-2,2,2-trifluoro-1-phenylethyl]-4-quinolinecarboxamide A mixture of 2-(3-bromophenyl)-6-(methylsulfonyl)-3-{[4-(4-morpholinyl)-1-piperidinyl]methyl}-4-quinolinecarboxylic acid (0.250 g, 0.398 mmol), [(1R)-2,2,2-trifluoro-1-phenylethyl]amine (0.093 g, 0.438 mmol), and N,N-diisopropylethylamine (77 µL, 0.438 mmol) in dichloromethane (3.98 mL) was cooled to 0° C., and 2,4,6-tripropyl-1,3,5,2,4,6-trioxatriphosphorinane 2,4,6-trioxide (0.356 mL of 50% solution in ethyl acetate, 0.597 mmol) was added dropwise. The mixture was stirred at 0° C. for 2 h, warmed to room temperature, and stirred overnight. The mixture was diluted with water (2 mL) and saturated aqueous NaHCO$_3$ (1 mL) was added. After stirring for 30 min, the organic phase was removed, passed over a phase separator, and concentrated in vacuo. The residue was dissolved in acetonitrile, and water was added slowly until the mixture became cloudy. The solid precipitate was collected by filtration, washed with water, and dried to afford 2-(3-bromophenyl)-6-(methylsulfonyl)-3-{[4-(4-morpholinyl)-1-piperidinyl]methyl}-N-[(1R)-2,2,2-trifluoro-1-phenylethyl]-4-quinolinecarboxamide (0.260 g, 88% yield). MS (m/z) 747.1 (M+H$^+$).

The following compounds were prepared using procedures analogous to those described in Example 106 starting with an appropriate ketone in the first step, using an appropriate thiolate, substituting 4-morpholinopiperidine with either 4-(1-pyrrolidinyl)piperidine or 1,4'-bipiperidine and replacing [(1R)-2,2,2-trifluoro-1-phenylethyl]amine with an appropriate benzylamine when necessary. As is appreciated by those skilled in the art, these analogous examples may involve variations in general reaction conditions.

| Ex | Name | Structure | MS (m/z) |
|---|---|---|---|
| 107 | 6-[(1-methylethyl)sulfonyl]-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide | 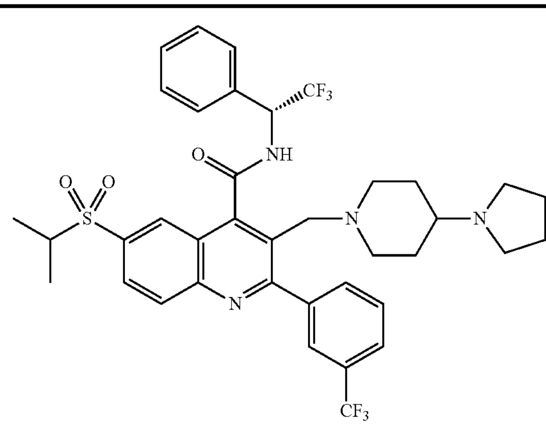 | 747.2 (M + H$^+$) |

| Ex | Name | Structure | MS (m/z) |
|---|---|---|---|
| 108 | 6-[(1-methylethyl)sulfonyl]-N-[(1S)-1-phenylethyl]-3-{[4-(1-pyrrolidinyl)-1-piperidinyl]methyl}-2-[3-(trifluoromethyl)phenyl]-4-quinolinecarboxamide | 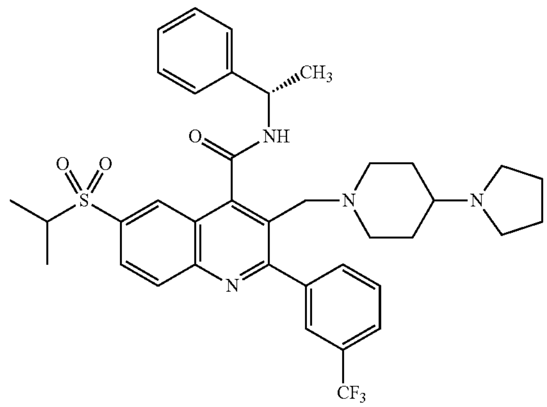 | 693.3 (M + H⁺) |
| 109 | 2-(3-bromophenyl)-6-(methylsulfonyl)-3-{[4-(4-morpholinyl)-1-piperidinyl]methyl}-N-[(1S)-1-phenylethyl]-4-quinolinecarboxamide | 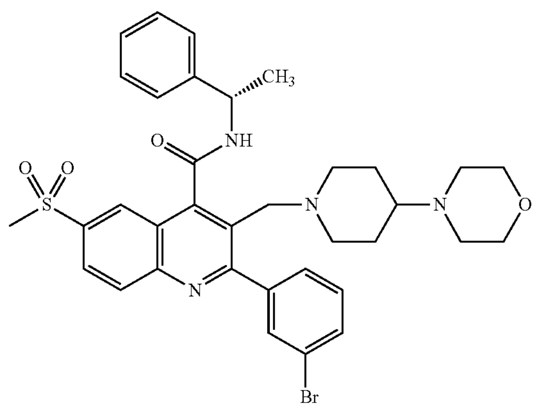 | 693.2 (M + H⁺) |
| 110 | 3-(1,4'-bipiperidin-1'-ylmethyl)-2-(3-bromophenyl)-6-(methylsulfonyl)-N-[(1R)-2,2,2-trifluoro-1-phenylethyl]-4-quinolinecarboxamide | 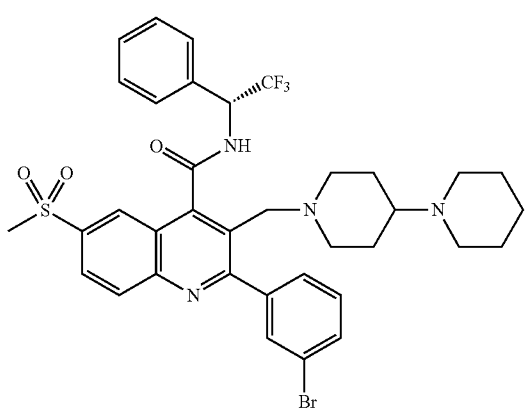 | 745.2 (M + H⁺) |

| Ex | Name | Structure | MS (m/z) |
|---|---|---|---|
| 111 | 3-(1,4'-bipiperidin-1'-ylmethyl)-2-(3-bromophenyl)-6-(methylsulfonyl)-N-[(1S)-1-phenylethyl]-4-quinolinecarboxamide | 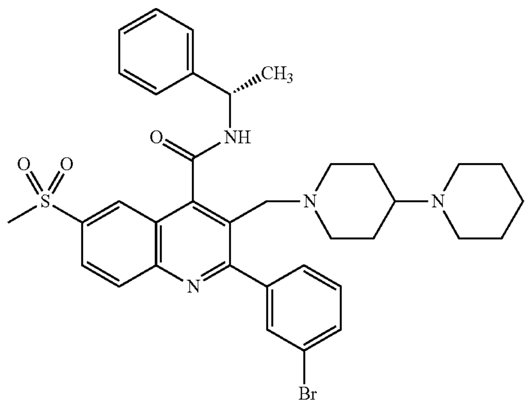 | 691.2 (M + H$^+$) |
| 112 | 2-(3-bromophenyl)-6-(methylsulfonyl)-3-{[4-(1-pyrrolidinyl)-1-piperidinyl]methyl}-N-[(1R)-2,2,2-trifluoro-1-phenylethyl]-4-quinolinecarboxamide | 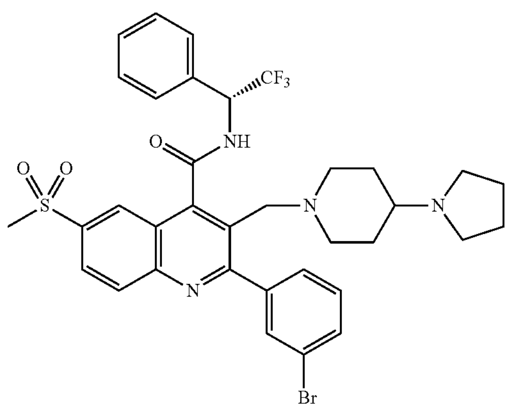 | 731.2 (M + H$^+$) |
| 113 | 2-(3-bromophenyl)-6-(methylsulfonyl)-N-[(1S)-1-phenylethyl]-3-{[4-(1-pyrrolidinyl)-1-piperidinyl]methyl}-4-quinolinecarboxamide | 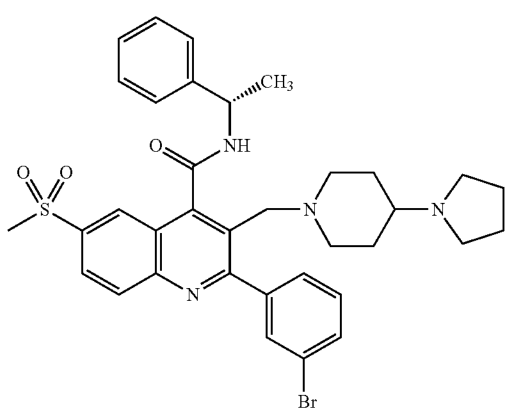 | 677.2 (M + H$^+$) |

The following compound was prepared using procedures analogous to those described in Example 106 starting with 1-[3-(trifluoromethyl)phenyl]-1-propanone instead of 1-(3-bromophenyl)-1-propanone, using m-CPBA as the oxidant in place of Oxone according to the procedure described in Example 50, substituting 4-morpholinopiperidine with 1,4'-bipiperidine, and replacing [(1R)-2,2,2-trifluoro-1-phenylethyl]amine with [(1S)-2,2,2-trifluoro-1-phenylethyl]amine. As is appreciated by those skilled in the art, this analogous example may involve variations in general reaction conditions.

| Ex | Name | Structure | MS (m/z) |
|---|---|---|---|
| 114 | 3-(1,4'-bipiperidin-1'-ylmethyl)-6-(methylsulfonyl)-2-[3-(trifluoromethyl)phenyl]-N-[(1S)-2,2,2-trifluoro-1-phenylethyl]-4-quinolinecarboxamide | 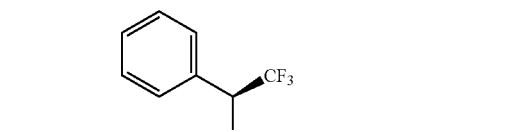 | 733.2 (M + H+) |

Example 115

3-({4-[(2R)-2-methyl-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide

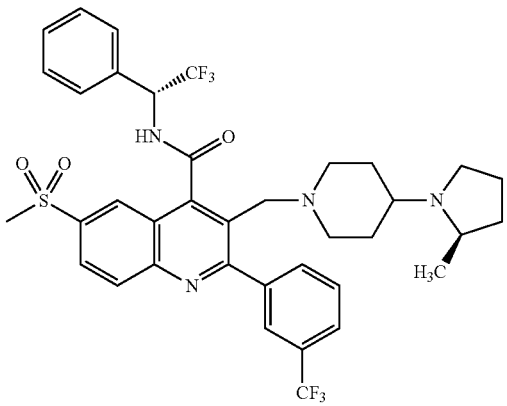 [SMILES: C[C@@H]1CCCN1C1CCN(Cc2c(-c3cccc(C(F)(F)F)c3)nc3ccc(S(C)(=O)=O)cc3c2C(=O)N[C@H](c2ccccc2)C(F)(F)F)CC1]

methyl 3-(bromomethyl)-6-(methylsulfonyl)-2-[3-(trifluoromethyl)phenyl]-4-quinolinecarboxylate A mixture of methyl 3-methyl-6-(methylsulfonyl)-2-[3-(trifluoromethyl)phenyl]-4-quinolinecarboxylate (2 g, 4.72 mmol), benzoyl peroxide (0.114 g, 0.472 mmol) and NBS (1.093 g, 6.14 mmol) was suspended in carbon tetrachloride (31.5 mL) and heated to reflux for 4 h. Additional benzoyl peroxide (0.571 g, 2.36 mmol) was added, and the mixture was stirred at 100° C. for 24 h. Additional benzoyl peroxide (0.571 g, 2.36 mmol) was added, and the mixture stirred for 3 h. Additional benzoyl peroxide (0.571 g, 2.36 mmol) and NBS (0.250 g, 1.42 mmol) were added, and the mixture was heated for 2.5 h. The mixture was cooled to room temperature, and the solvent was removed under reduced pressure to afford methyl 3-(bromomethyl)-6-(methylsulfonyl)-2-[3-(trifluoromethyl)phenyl]-4-quinolinecarboxylate. This material was used without further purification. MS (m/z) 502.0 (M+H+).

methyl 6-(methylsulfonyl)-3-[(4-oxo-1-piperidinyl)methyl]-2-[3-(trifluoromethyl)phenyl]-4-quinolinecarboxylate Methyl 3-(bromomethyl)-6-(methylsulfonyl)-2-[3-(trifluoromethyl)phenyl]-4-quinolinecarboxylate (2 g, 3.98 mmol), 4-piperidone HCl salt (0.648 g, 4.78 mmol), N,N-diisopropylethylamine (1.53 mL, 8.76 mmol) in acetonitrile (13.27 mL) was heated to 50° C. overnight. The solvent was removed under reduced pressure. The residue was diluted with Na$_2$CO$_3$ and extracted with methylene chloride (four times). The combined organic extracts were washed with brine, dried over Na$_2$SO$_4$, filtered and concentrated in vacuo. The residue was purified via column chromatography (ISCO, 40 g silica, 5-100% ethyl acetate/hexanes) to afford methyl 6-(methylsulfonyl)-3-[(4-oxo-1-piperidinyl)methyl]-2-[3-(trifluoromethyl)phenyl]-4-quinolinecarboxylate (1.051 g, 51% yield). MS (m/z) 521.0 (M+H+).

6-(methylsulfonyl)-3-[(4-oxo-1-piperidinyl)methyl]-2-[3-(trifluoromethyl)phenyl]-4-quinolinecarboxylic acid Methyl 6-(methylsulfonyl)-3-[(4-oxo-1-piperidinyl)methyl]-2-[3-(trifluoromethyl)phenyl]-4-quinolinecarboxylate (0.796 g, 1.529 mmol) and 3N NaOH (5.097 mL, 15.29 mmol) were suspended in tetrahydrofuran (5.097 mL) and methanol (5.097 mL) and heated to 50° C. for 20 h. The tetrahydrofuran and methanol were removed under reduced pressure, and the residue was diluted with water. The mixture was purified via Oasis SPE cartridge to afford 6-(methylsulfonyl)-3-[(4-oxo-1-piperidinyl)methyl]-2-[3-(trifluoromethyl)phenyl]-4-quinolinecarboxylic acid (0.977 g). This material was used without further purification. MS (m/z) 507.2 (M+H+).

6-(methylsulfonyl)-3-[(4-oxo-1-piperidinyl)methyl]-2-[3-(trifluoromethyl)phenyl]-N-[(1R)-2,2,2-trifluoro-1-phenylethyl]-4-quinolinecarboxamide A mixture of 6-(methylsulfonyl)-3-[(4-oxo-1-piperidinyl)methyl]-2-[3-(trifluoromethyl)phenyl]-4-quinolinecarboxylic acid (0.977 g, 1.929 mmol), [(1R)-2,2,2-trifluoro-1-phenylethyl]amine (0.449 g, 2.12 mmol), N,N-diisopropylethylamine (0.404 mL, 2.315 mmol), and 2,4,6-tripropyl-1,3,5,2,4,6-trioxatriphosphorinane 2,4,6-trioxide (1.705 mL of a 50% solution in ethyl acetate, 2.89 mmol) in dichloromethane (19.29 mL) was stirred at 0° C. for 2 h, warmed to room temperature, and stirred at room temperature overnight. The mixture was diluted with 10% Na$_2$CO$_3$, and extracted with methylene chloride (four times). The combined organic extracts were washed with brine, dried over Na$_2$SO$_4$, filtered, and concentrated in vacuo. The residue was purified via column chromatography (ISCO, 40 g silica, 5-100% ethyl acetate hexanes) to afford 6-(methylsulfonyl)-3-[(4-oxo-1-piperidinyl)methyl]-2-[3-(trifluoromethyl)phenyl]-N-[(1R)-2,2,2-trifluoro-1-phenylethyl]-4-quinolinecarboxamide (0.570 g, 31% yield). MS (m/z) 664.1 (M+H$^+$).

3-({4-[(2R)-2-methyl-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide 6-(Methylsulfonyl)-3-[(4-oxo-1-piperidinyl)methyl]-2-[3-(trifluoromethyl)phenyl]-N-[(1R)-2,2,2-trifluoro-1-phenylethyl]-4-quinolinecarboxamide (0.093 g, 0.140 mmol) was dissolved in dichloromethane (1.4 mL) and acetic acid (0.012 mL, 0.210 mmol). (S)-2-Methylpyrrolidine (0.036 g, 0.420 mmol) was added followed by sodium triacetoxyborohydride (59.4 mg, 0.280 mmol). The mixture was stirred at room temperature for 2 d. The solvent was removed under reduced pressure, and the residue was purified via HPLC (Waters, Sunfire 30×100 mm, 26-60% CH$_3$CN/H$_2$O with 0.1% TFA) to afford 3-({4-[(2R)-2-methyl-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide (0.035 g, 32% yield). MS (m/z) 733.3 (M+H$^+$).

The following compounds were prepared using procedures analogous to those described in Example 115 substituting (S)-2-methylpyrrolidine with an appropriate amine. As is appreciated by those skilled in the art, these analogous examples may involve variations in general reaction conditions.

| Ex | Name | Structure | MS (m/z) |
|---|---|---|---|
| 116 | 3-[(3-fluoro-1,4'-bipiperidin-1'-yl)methyl]-6-(methylsulfonyl)-2-[3-(trifluoromethyl)phenyl]-N-[(1R)-2,2,2-trifluoro-1-phenylethyl]-4-quinolinecarboxamide | 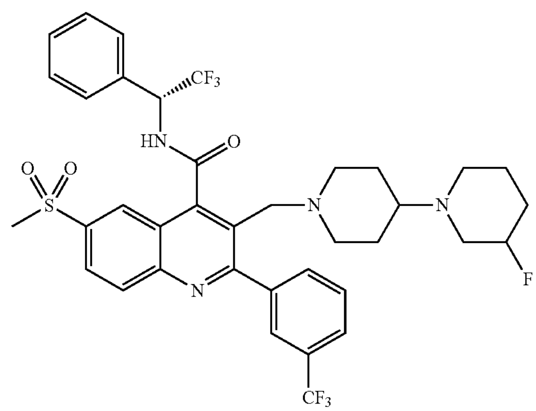 | 751.2 (M + H$^+$) |
| 117 | 3-({4-[(2S)-2-methyl-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide | 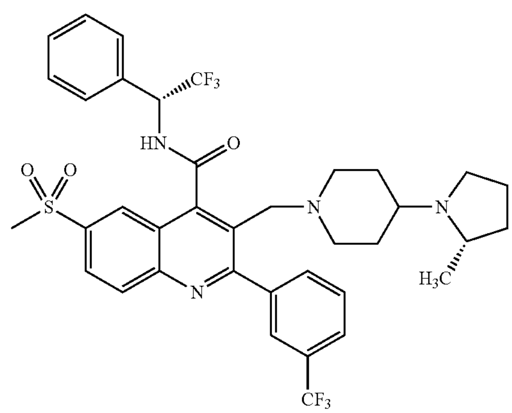 | 733.2 (M + H$^+$) |

| Ex | Name | Structure | MS (m/z) |
|---|---|---|---|
| 118 | 3-({4-[(2S)-2-(hydroxymethyl)-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide | 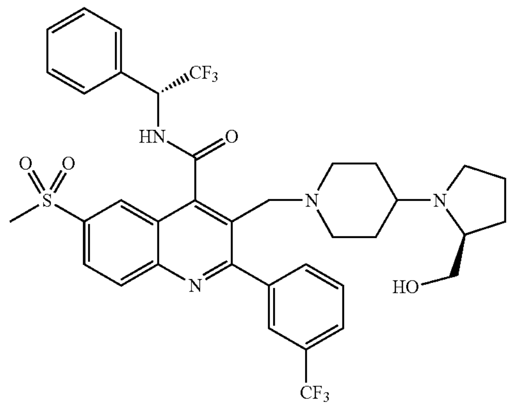 | 749.2 (M + H$^+$) |
| 119 | 3-({4-[(2R)-2-(hydroxymethyl)-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide | 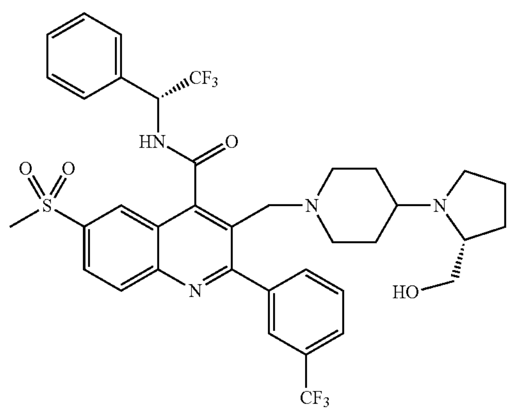 | 749.2 (M + H$^+$) |
| 120 | 3-{[3-(hydroxymethyl)-1,4'-bipiperidin-1'-yl]methyl}-6-(methylsulfonyl)-2-[3-(trifluoromethyl)phenyl]-N-[(1R)-2,2,2-trifluoro-1-phenylethyl]-4-quinolinecarboxamide | 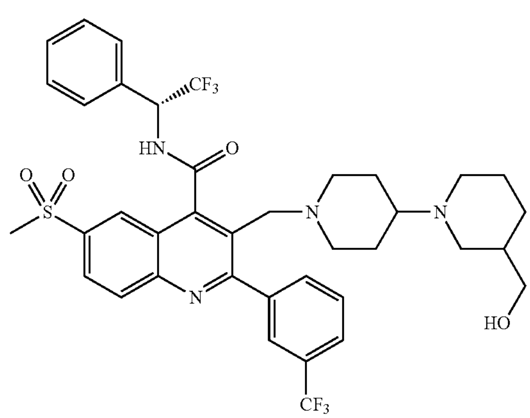 | 763.3 (M + H$^+$) |

| Ex | Name | Structure | MS (m/z) |
|---|---|---|---|
| 121 | 3-[(4-{methyl[2-(methyloxy)ethyl]amino}-1-piperidinyl)methyl]-6-(methylsulfonyl)-2-[3-(trifluoromethyl)phenyl]-N-[(1R)-2,2,2-trifluoro-1-phenylethyl]-4-quinolinecarboxamide | 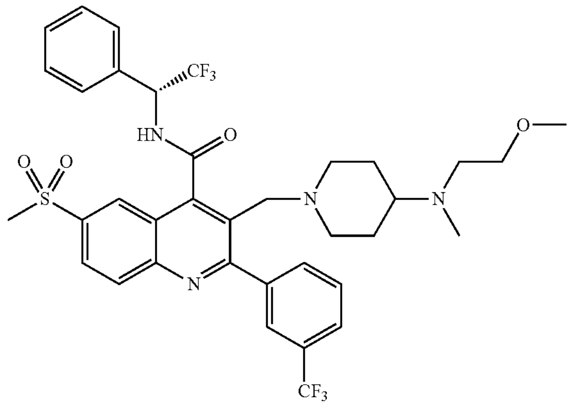 | 737.3 (M + H+) |
| 122 | 3-({4-[ethyl(propyl)amino]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide | 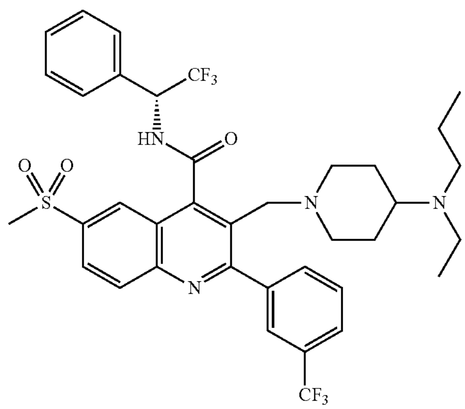 [SMILES: CCCN(CC)C1CCN(Cc2c(-c3cccc(C(F)(F)F)c3)nc3ccc(S(C)(=O)=O)cc3c2C(=O)N[C@H](c2ccccc2)C(F)(F)F)CC1] | 735.3 (M + H+) |
| 123 | 3-({4-[methyl(2-methylpropyl)amino]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide | 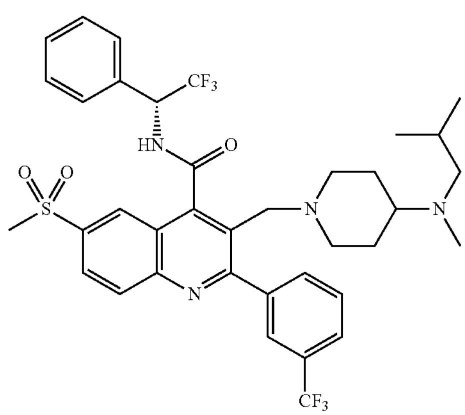 [SMILES: CC(C)CN(C)C1CCN(Cc2c(-c3cccc(C(F)(F)F)c3)nc3ccc(S(C)(=O)=O)cc3c2C(=O)N[C@H](c2ccccc2)C(F)(F)F)CC1] | 735.3 (M + H+) |

-continued

| Ex | Name | Structure | MS (m/z) |
|---|---|---|---|
| 124 | 3-{[4-(hexahydro-1H-azepin-1-yl)-1-piperidinyl]methyl}-6-(methylsulfonyl)-2-[3-(trifluoromethyl)phenyl]-N-[(1R)-2,2,2-trifluoro-1-phenylethyl]-4-quinolinecarboxamide | 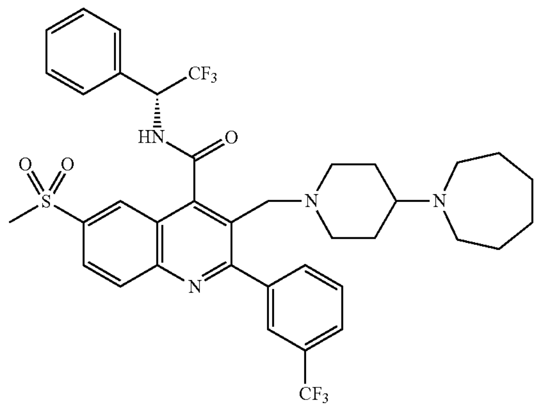 [SMILES: CS(=O)(=O)c1ccc2nc(-c3cccc(C(F)(F)F)c3)c(CN3CCC(N4CCCCCC4)CC3)c(C(=O)N[C@H](c3ccccc3)C(F)(F)F)c2c1] | 747.3 (M + H⁺) |
| 125 | 3-{[4-(methyloxy)-1,4'-bipiperidin-1'-yl]methyl}-6-(methylsulfonyl)-2-[3-(trifluoromethyl)phenyl]-N-[(1R)-2,2,2-trifluoro-1-phenylethyl]-4-quinolinecarboxamide | 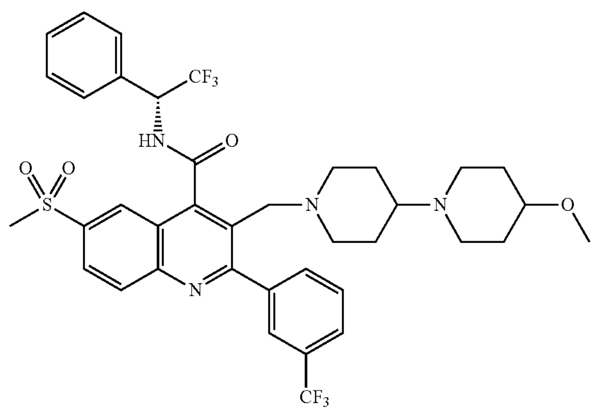 | 763.3 (M + H⁺) |
| 126 | 3-({4-[methyl(propyl)amino]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide | 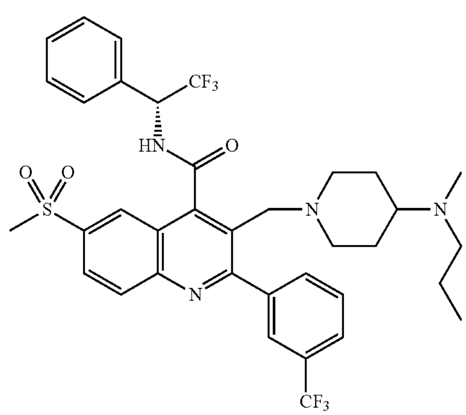 [SMILES: CCCN(C)C1CCN(Cc2c(-c3cccc(C(F)(F)F)c3)nc3ccc(S(C)(=O)=O)cc3c2C(=O)N[C@H](c2ccccc2)C(F)(F)F)CC1] | 721.3 (M + H⁺) |

-continued

| Ex | Name | Structure | MS (m/z) |
|---|---|---|---|
| 127 | 3-[(4-{(2S)-2-[(methyloxy)methyl]-1-pyrrolidinyl}-1-piperidinyl)methyl]-6-(methylsulfonyl)-2-[3-(trifluoromethyl)phenyl]-N-[(1R)-2,2,2-trifluoro-1-phenylethyl]-4-quinolinecarboxamide | 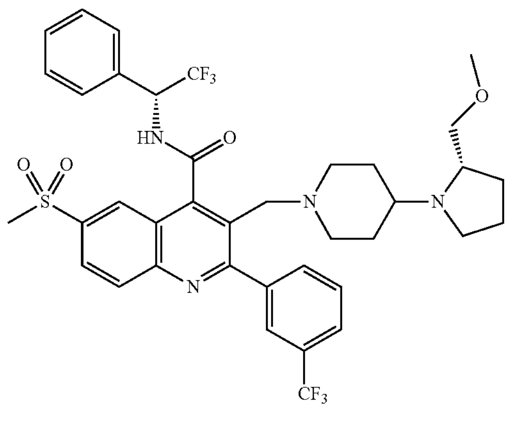 [SMILES: COC[C@@H]1CCCN1C1CCN(Cc2c(-c3cccc(C(F)(F)F)c3)nc3ccc(S(C)(=O)=O)cc3c2C(=O)N[C@H](c2ccccc2)C(F)(F)F)CC1] | 763.3 (M + H+) |
| 128 | 3-({4-[(2-hydroxyethyl)(methyl)amino]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide | 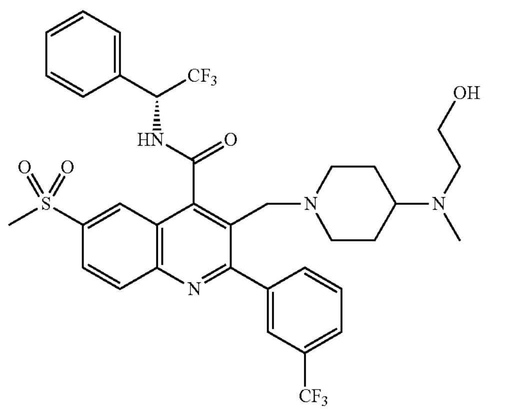 [SMILES: CN(CCO)C1CCN(Cc2c(-c3cccc(C(F)(F)F)c3)nc3ccc(S(C)(=O)=O)cc3c2C(=O)N[C@H](c2ccccc2)C(F)(F)F)CC1] | 723.3 (M + H+) |

Example 129

6-(ethylsulfonyl)-7-(methyloxy)-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide

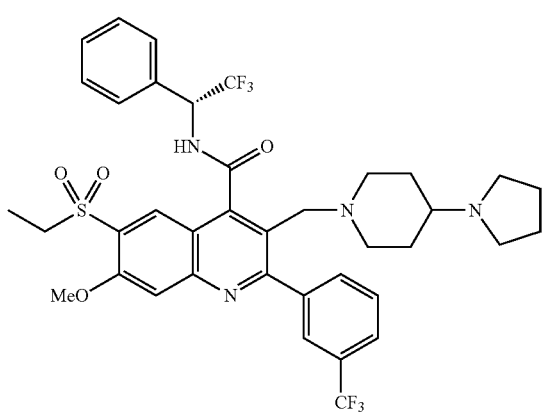

6-bromo-3-methyl-7-(methyloxy)-2-[3-(trifluoromethyl)phenyl]-4-quinolinecarboxylic acid A solution of the 4-bromo-3-(methyloxy)aniline (25 g, 124 mmol) and 3-(trifluoromethyl)benzaldehyde (21.54 g, 124 mmol) in ethanol (300 mL) was stirred at reflux for 1 h. 2-Oxobutanoic acid (12.63 g, 124 mmol) was added portionwise. The reaction mixture was stirred at reflux for additional 3 h, warmed to room temperature, and stirred overnight. The solid precipitate was collected by filtration, washed with ethanol, and air dried to give 6-bromo-3-methyl-7-(methyloxy)-2-[3-(trifluoromethyl)phenyl]-4-quinolinecarboxylic acid (42.6 g, 78% yield). MS (m/z) 441.0 (M+H+).

methyl 6-bromo-3-methyl-7-(methyloxy)-2-[3-(trifluoromethyl)phenyl]-4-quinolinecarboxylate DMF (5 drops) was added to a suspension of 6-bromo-3-methyl-7-(methyloxy)-2-[3-(trifluoromethyl)phenyl]-4-quinolinecarboxylic acid (42.6 g, 97 mmol) in dichloromethane (500 mL) at 0° C. Oxalyl chloride (12.71 mL, 145 mmol) was added slowly, and the mixture was stirred at 0° C. for 1 h. Methanol (30 mL) was added, and the resulting mixture was stirred at 0° C. for 2 h and allowed to warm to room temperature overnight. The solvent was removed under reduced pressure, and the residue was diluted with water and neutralized with saturated aqueous NaHCO$_3$. The mixture was extracted with methylene chloride, and the organic extracts were washed with brine, dried over Na$_2$SO$_4$, filtered, and concentrated in vacuo. The residue was purified via column chromatography (ISCO, 330 g silica, 40-100% methylene chloride/hexanes) to give methyl 6-bromo-3-methyl-7-(methyloxy)-2-[3-(trifluoromethyl)phenyl]-4-quinolinecarboxylate (29.8 g, 68% yield). MS (m/z) 455.0 (M+H$^+$).

methyl 6-(ethylsulfonyl)-3-methyl-7-(methyloxy)-2-[3-(trifluoromethyl)phenyl]-4-quinolinecarboxylate To a solution of methyl 6-bromo-3-methyl-7-(methyloxy)-2-[3-(trifluoromethyl)phenyl]-4-quinolinecarboxylate (2 g, 4.40 mmol) in N-methyl-2-pyrrolidone (15 mL) and DMSO (30 mL) was added copper(I) iodide (2.52 g, 13.21 mmol) followed by ethanesulfinic acid, sodium salt (1.534 g, 13.21 mmol). The mixture was evacuated and purged with N$_2$ three times and heated at 120° C. for 16 h. The mixture was cooled to room temperature, and iodomethane (1.377 mL, 22.01 mmol) was added. After 90 min, additional iodomethane (1.377 mL, 22.01 mmol) was added and the mixture was stirred for an additional hour. The mixture was diluted with methylene chloride and water, and the biphasic solution was filtered through Celite®. The phases were separated, and the aqueous phase was extracted with methylene chloride (50 mL). The combined organic extracts were washed with water (3×50 mL), dried over MgSO$_4$, filtered and concentrated in vacuo. The residue was loaded onto florisil and purified via column chromatography (ISCO, 40 g silica, 5-55% ethyl acetate/hexanes) to give methyl 6-(ethylsulfonyl)-3-methyl-7-(methyloxy)-2-[3-(trifluoromethyl)phenyl]-4-quinolinecarboxylate (1.95 g, 76% yield). MS (m/z) 468.0 (M+H$^+$).

methyl 6-(ethylsulfonyl)-7-(methyloxy)-3-{[4-(1-pyrrolidinyl)-1-piperidinyl]methyl}-2-[3-(trifluoromethyl)phenyl]-4-quinolinecarboxylate A suspension of methyl 6-(ethylsulfonyl)-3-methyl-7-(methyloxy)-2-[3-(trifluoromethyl)phenyl]-4-quinolinecarboxylate (1 g, 2.139 mmol), N-bromosuccinimide (0.495 g, 2.78 mmol) and benzoyl peroxide (0.052 g, 0.214 mmol) in carbon tetrachloride (20 mL) was heated to 100° C. for 16 h. Additional N-bromosuccinimide (0.65 equiv., 0.248 g, 1.39 mmol) and benzoyl peroxide (0.052 g, 0.214 mmol) were added and heating was continued. Additional portions of N-bromosuccinimide (0.65 equiv., 0.248 g, 1.39 mmol) and benzoyl peroxide (0.052 g, 0.214 mmol) were again added after 1 h. After 1 h, additional portions of N-bromosuccinimide (0.248 g, 1.39 mmol) and benzoyl peroxide (0.052 g, 0.214 mmol) were added. The mixture was stirred for an additional hour, cooled to room temperature and concentrated in vacuo.

The residue was dissolved in acetonitrile (15 mL) and 4-(1-pyrrolidinyl)piperidine (0.429 g, 2.78 mmol) was added. The mixture was stirred at room temperature for 3 d. The solvent was removed under reduced pressure and diluted with ethyl acetate. The resulting solution was washed with 10% Na$_2$CO$_3$ (15 mL) and water, dried over MgSO$_4$, filtered, and concentrated in vacuo. The crude material was absorbed onto florisil and purified via column chromatography (50-100% ethyl acetate/hexanes, 5-10% methanol/dichloromethane) to afford methyl 6-(ethylsulfonyl)-7-(methyloxy)-3-{[4-(1-pyrrolidinyl)-1-piperidinyl]methyl}-2-[3-(trifluoromethyl)phenyl]-4-quinolinecarboxylate (0.812 g, 58% yield). MS (m/z) 620.2 (M+H$^+$).

6-(ethylsulfonyl)-7-(methyloxy)-3-{[4-(1-pyrrolidinyl)-1-piperidinyl]methyl}-2-[3-(trifluoromethyl)phenyl]-4-quinolinecarboxylic acid Potassium hydroxide (0.364 g, 6.50 mmol) was added to a suspension of methyl 6-(ethylsulfonyl)-7-(methyloxy)-3-{[4-(1-pyrrolidinyl)-1-piperidinyl]methyl}-2-[3-(trifluoromethyl)phenyl]-4-quinolinecarboxylate (0.805 g, 1.299 mmol) in methanol (12.99 mL) and water (4.33 mL). The mixture was heated to 65° C. for 3 d. The reaction mixture was cooled to room temperature, concentrated in vacuo, diluted with water (5 mL), and acidified to pH 4-5 with 2N HCl. The resulting precipitate was collected by filtration and dried to afford 6-(ethylsulfonyl)-7-(methyloxy)-3-{[4-(1-pyrrolidinyl)-1-piperidinyl]methyl}-2-[3-(trifluoromethyl)phenyl]-4-quinolinecarboxylic acid (0.487 g, 59% yield) as a tan solid. MS (m/z) 606.2 (M+H$^+$).

6-(ethylsulfonyl)-7-(methyloxy)-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide N,N-Diisopropylethylamine (0.087 mL, 0.495 mmol), [(1R)-2,2,2-trifluoro-1-phenylethyl]amine (0.045 g, 0.215 mmol), and propylphosphonic anhydride (0.126 mL of a 50% solution in ethyl acetate, 0.215 mmol) were added to a suspension of 6-(ethylsulfonyl)-7-(methyloxy)-3-{[4-(1-pyrrolidinyl)-1-piperidinyl]methyl}-2-[3-(trifluoromethyl)phenyl]-4-quinolinecarboxylic acid (0.100 g, 0.165 mmol) in dichloromethane (2.54 mL). The mixture was stirred for 15 h, diluted with 10% Na$_2$CO$_3$ (2 mL) and methylene chloride (5 mL), and poured into a hydrophobic frit to separate the phases. The organic phase was absorbed onto florisil and purified via column chromatography (ISCO, 1-10% methanol/methylene chloride). The material was dissolved in methylene chloride, and the organic phase was washed with 10% Na$_2$CO$_3$ (2×10 mL), dried over MgSO$_4$, filtered, and concentrated in vacuo to afford 6-(ethylsulfonyl)-7-(methyloxy)-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide as a light orange solid (0.068 g, 51% yield). MS (m/z) 763.2 (M+H$^+$).

The following compounds were prepared using procedures analogous to those described in Example 129 substituting 4-(1-pyrrolidinyl)piperidine with 4-fluoro-1,4'-bipiperidine and replacing [(1R)-2,2,2-trifluoro-1-phenylethyl]amine with (1S)-1-phenylethanamine when necessary. As is appreciated by those skilled in the art, these analogous examples may involve variations in general reaction conditions.

| Ex | Name | Structure | MS (m/z) |
|---|---|---|---|
| 130 | 6-(ethylsulfonyl)-7-(methyloxy)-N-[(1S)-1-phenylethyl]-3-{[4-(1-pyrrolidinyl)-1-piperidinyl]methyl}-2-[3-(trifluoromethyl)phenyl]-4-quinolinecarboxamide | 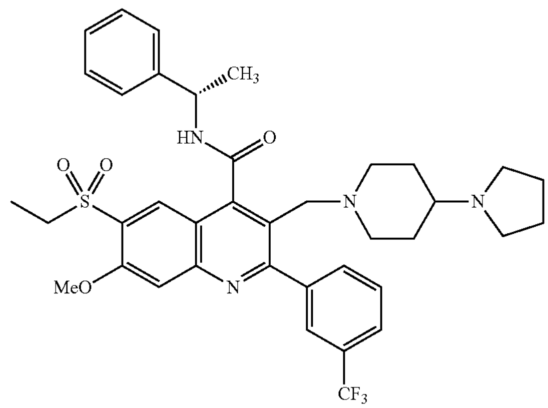 | 709.3 (M + H+) |
| 131 | 6-(ethylsulfonyl)-3-[(4-fluoro-1,4'-bipiperidin-1'-yl)methyl]-7-(methyloxy)-2-[3-(trifluoromethyl)phenyl]-N-[(1R)-2,2,2-trifluoro-1-phenylethyl]-4-quinolinecarboxamide | 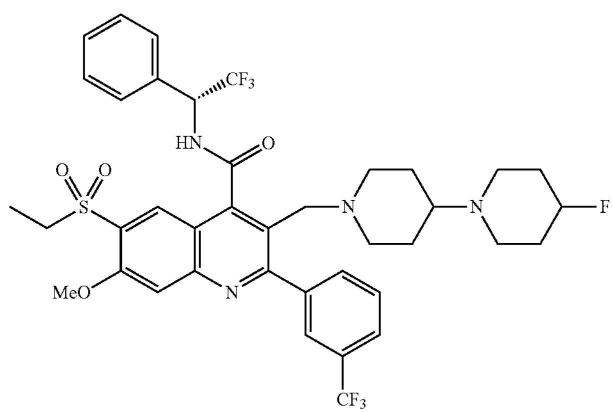 | 795.3 (M + H+) |
| 132 | 6-(ethylsulfonyl)-3-[(4-fluoro-1,4'-bipiperidin-1'-yl)methyl]-7-(methyloxy)-N-[(1S)-1-phenylethyl]-2-[3-(trifluoromethyl)phenyl]-4-quinolinecarboxamide | 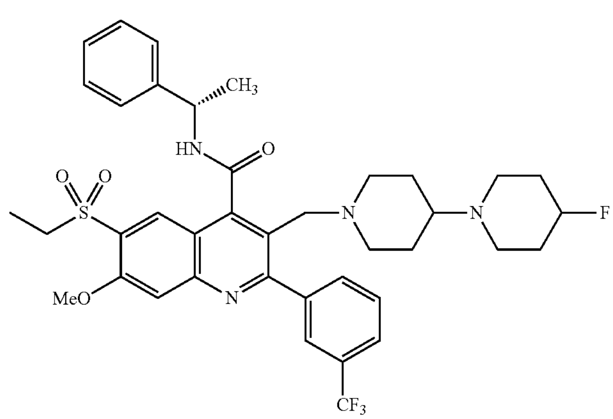 | 741.3 (M + H+) |

The invention claimed is:
1. A compound of Formula I:

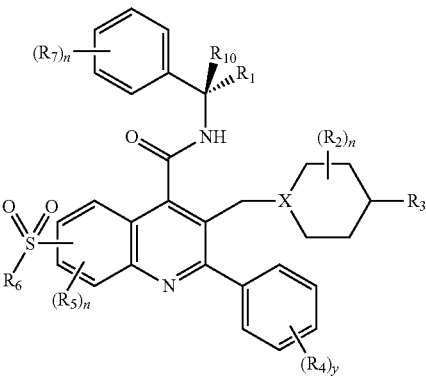

wherein:
R₁ is independently H, CF₃, or Me;
R₂ is independently OH, OC₁₋₄ alkyl, C₁₋₄ alkyl, CH₂OH, F, CH₂OC₁₋₄ alkyl, CF₃, or CF₂H;
R₃ is morpholinyl, piperidinyl, pyrrolidinyl, or hexahydroazepinyl; all of which may be unsubstituted or substituted by one or two R₈;
or R₃ is N(C₁₋₆ alkyl)₂, wherein C₁₋₆ alkyl may be unsubstituted or substituted by OH or —OCH₃;
R₄ is CF₃, halo, OMe, or C₁₋₃ alkyl;
R₅ is

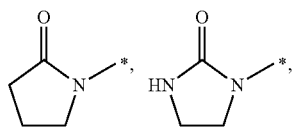

halo, cyano, CF₃, C₁₋₅ alkyl, C₂₋₄ alkenyl, pyrrolidinyl, morpholinyl, piperidinyl, phenyl, pyridyl, pyrazolyl, pyrrolyl, piperazinyl, pyrimidinyl, OH, O—C₁₋₄alkyl-OR₆, OCF₃, OCH₂CF₃, OCH₂CN, OR₆, or CH₂R₉;
wherein the

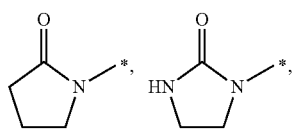

pyrrolidinyl, morpholinyl, piperidinyl, phenyl, pyridyl, pyrazolyl, pyrrolyl, piperazinyl or pyrimidinyl may be unsubstituted or substituted with one or two halo, OH, OR₆ or R₆;
R₆ is independently C₁₋₄ alkyl, C₃₋₆ cycloalkyl;
R₇ is independently halo, methyl, or OMe;
R₈ is independently OH, OC₁₋₄ alkyl, C₁₋₄ alkyl, CH₂OH, F, CH₂OC₁₋₄ alkyl, CF₃, or CF₂H;
R₉ is independently pyrrolidinyl, morpholinyl, or piperidinyl;
R₁₀ is independently H, CF₃, or Me;
n is independently 0, 1, or 2;
X is N or C;
y is 1 or 2;
or a pharmaceutically acceptable salt thereof.

2. A compound of Formula (I) of claim 1 wherein:
R₁ is independently CF₃, or Me;
R₂ is independently OH, OC₁₋₄ alkyl, C₁₋₄ alkyl, CH₂OH, F, CH₂OC₁₋₄ alkyl, CF₃, or CF₂H;
R₃ is morpholinyl, piperidinyl, pyrrolidinyl, or hexahydroazepinyl; all of which may be unsubstituted or substituted by one or two R₈;
or R₃ is N(C₁₋₆ alkyl)₂, wherein C₁₋₆ alkyl may be unsubstituted or substituted by OH or —OCH₃;
R₄ is CF₃ or halo;
R₅ is

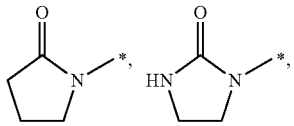

halo, cyano, CF₃, C₁₋₅ alkyl, C₂₋₄ alkenyl, pyrrolidinyl, morpholinyl, piperidinyl, phenyl, pyridyl, pyrazolyl, pyrrolyl, piperazinyl, pyrimidinyl, OH, O—C₁₋₄alkyl-OR₆, OCF₃, OCH₂CF₃, OCH₂CN, OR₆, or CH₂R₉;
wherein the

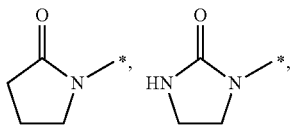

pyrrolidinyl, morpholinyl, piperidinyl, phenyl, pyridyl, pyrazolyl, pyrrolyl, piperazinyl or pyrimidinyl may be unsubstituted or substituted with one or two, OR₆ or R₆;
R₆ is independently C₁₋₄ alkyl or C₃₋₆ cycloalkyl;
R₇ is independently halo, methyl, or OMe;
R₈ is independently OH, OC₁₋₄ alkyl, C₁₋₄ alkyl, CH₂OH, F, CH₂OC₁₋₄ alkyl, CF₃, or CF₂H;
R₉ is independently pyrrolidinyl, morpholinyl, or piperidinyl;
R₁₀ is H;
n is independently 0, or 1;
X is N or C; and
y is 1 or 2;
or a pharmaceutically acceptable salt thereof.

3. A compound of Formula (I) of claim 1 wherein:
R₁ is independently CF₃, or Me;
R₂ is independently C₁₋₄ alkyl, CF₃, or CF₂H;
R₃ is morpholinyl, piperidinyl, pyrrolidinyl, or hexahydroazepinyl; all of which may be unsubstituted or substituted by one or two R₈;
or R₃ is N(C₁₋₆ alkyl)₂, wherein C₁₋₆ alkyl may be unsubstituted or substituted by OH or —OCH₃;
R₄ is CF₃ or halo;
R₅ is halo, cyano, CF₃, C₁₋₅ alkyl, C₂₋₄ alkenyl, OH, O—C₁₋₄alkyl-OR₆, OCF₃, OCH₂CF₃, OCH₂CN, or OR₆,
R₆ is independently C₁₋₄ alkyl, or C₃₋₆ cycloalkyl;
R₇ is independently halo, methyl, or OMe;
R₈ is independently OH, OC₁₋₄ alkyl, C₁₋₄ alkyl, CH₂OH, F, CH₂OC₁₋₄ alkyl, CF₃, or CF₂H;
R₁₀ is H;
n is independently 0, or 1;
X is N; and
y is 1 or 2;
or a pharmaceutically acceptable salt thereof.

4. A compound of Formula (I) of claim 1 wherein:
R₁ is independently CF₃, or Me;
R₂ is independently C₁₋₄ alkyl;
R₃ is morpholinyl, piperidinyl, pyrrolidinyl, or hexahydroazepinyl; all of which may be unsubstituted or substituted by one or two R₈;
R₄ is CF₃ or halo;
R₅ is halo, cyano, CF₃, C₁₋₅ alkyl, C₂₋₄ alkenyl, OH, O—C₁₋₄alkyl-OR₆, OCF₃, OCH₂CF₃, OCH₂CN, or OR₆,
R₆ is independently C₁₋₄ alkyl, or C₃₋₆ cycloalkyl;
N is 0 for R₇;
R₈ is independently OH, C₁₋₄ alkyl, F, CF₃, or CF₂H;
R₁₀ is H;
n is independently 0, or 1;
X is N; and
y is 1 or 2
or a pharmaceutically acceptable salt thereof.

5. A compound of claim 1 selected from the group consisting of:
3-(1,4'-bipiperidin-1'-ylmethyl)-6-(methylsulfonyl)-2-[3-(trifluoromethyl)phenyl]-N-[(1R)-2,2,2-trifluoro-1-phenylethyl]-4-quinolinecarboxamide;
3-(1,4'-bipiperidin-1'-ylmethyl)-6-(methylsulfonyl)-N-[(1S)-1-phenylethyl]-2-[3-(trifluoromethyl)phenyl]-4-quinolinecarboxamide;
3-(1,4'-bipiperidin-1'-ylmethyl)-6-(ethylsulfonyl)-7-(methyloxy)-2-[3-(trifluoromethyl)phenyl]-N-[(1R)-2,2,2-trifluoro-1-phenylethyl]-4-quinolinecarboxamide;
3-(1,4'-bipiperidin-1'-ylmethyl)-7-(methyloxy)-6-(methylsulfonyl)-N-[(1S)-1-phenylethyl]-2-[3-(trifluoromethyl)phenyl]-4-quinolinecarboxamide;
3-(1,4'-bipiperidin-1'-ylmethyl)-7-(methyloxy)-6-(methylsulfonyl)-2-[3-trifluoromethyl)phenyl]-N-[(1R)-2,2,2-trifluoro-1-phenylethyl]-4-quinolinecarboxamide;
7-(methyloxy)-6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;
7-(methyloxy)-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;
3-(1,4'-bipiperidin-1'-ylmethyl)-6-(ethylsulfonyl)-7-(methyloxy)-N-[(1S)-1-phenylethyl]-2-[3-(trifluoromethyl)phenyl]-4-quinolinecarboxamide;
6-(ethylsulfonyl)-7-(methyloxy)-3-{[4-(4-morpholinyl)-1-piperidinyl]methyl}-N-[(1S)-1-phenylethyl]-2-[3-(trifluoromethyl)phenyl]-4-quinolinecarboxamide;
3-(1,4'-bipiperidin-1'-ylmethyl)-6-[(1-methylethyl)sulfonyl]-7-(methyloxy)-N-[(1S)-1-phenylethyl]-2-[3-(trifluoromethyl)phenyl]-4-quinolinecarboxamide;
6-[(1-methylethyl)sulfonyl]-7-(methyloxy)-3-{[4-(4-morpholinyl)-1-piperidinyl]methyl}-N-[(1S)-1-phenylethyl]-2-[3-(trifluoromethyl)phenyl]-4-quinolinecarboxamide;
6-(ethylsulfonyl)-7-(methyloxy)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;
7-(ethyloxy)-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;
3-(1,4'-bipiperidin-1'-ylmethyl)-7-(ethyloxy)-6-(methylsulfonyl)-N-[(1S)-1-phenylethyl]-2-[3-(trifluoromethyl)phenyl]-4-quinolinecarboxamide;
3-(1,4'-bipiperidin-1'-ylmethyl)-7-(ethyloxy)-6-(methylsulfonyl)-2-[3-(trifluoromethyl)phenyl]-N-[(1R)-2,2,2-trifluoro-1-phenylethyl]-4-quinolinecarboxamide;
7-(ethyloxy)-6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;
(3-(1,4'-bipiperidin-1'-ylmethyl)-7-[(1-methylethyl)oxy]-6-(methylsulfonyl)-N-[(1S)-1-phenylethyl]-2-[3-(trifluoromethyl)phenyl]-4-quinolinecarboxamide;
3-(1,4'-bipiperidin-1'-ylmethyl)-7-[(1-methylethyl)oxy]-6-(methylsulfonyl)-2-[3-(trifluoromethyl)phenyl]-N-[(1R)-2,2,2-trifluoro-1-phenylethyl]-4-quinolinecarboxamide;
7-[(1-methylethyl)oxy]-6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;
7-[(1-methylethyl)oxy]-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;
3-(1,4'-bipiperidin-1'-ylmethyl)-6-[(1-methylethyl)sulfonyl]-7-(methyloxy)-2-[3-(trifluoromethyl)phenyl]-N-[(1R)-2,2,2-trifluoro-1-phenylethyl]-4-quinolinecarboxamide;
6-[(1-methylethyl)sulfonyl]-7-(methyloxy)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;
7-(ethyloxy)-6-[(1-methylethyl)sulfonyl]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;
3-(1,4'-bipiperidin-1'-ylmethyl)-7-(ethyloxy)-6-[(1-methylethyl)sulfonyl]-2-[3-(trifluoromethyl)phenyl]-N-[(1R)-2,2,2-trifluoro-1-phenylethyl]-4-quinolinecarboxamide;
7-(ethyloxy)-6-[(1-methylethyl)sulfonyl]-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;
7-(ethyloxy)-6-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;
3-(1,4'-bipiperidin-1'-ylmethyl)-7-(ethyloxy)-6-(ethylsulfonyl)-N-[(1S)-1-phenylethyl]-2-[3-(trifluoromethyl)phenyl]-4-quinolinecarboxamide;
3-(1,4'-bipiperidin-1'-ylmethyl)-7-(ethyloxy)-6-(ethylsulfonyl)-2-[3-(trifluoromethyl)phenyl]-N-[(1R)-2,2,2-trifluoro-1-phenylethyl]-4-quinolinecarboxamide;
7-(ethyloxy)-6-(ethylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;
7-(ethyloxy)-6-(ethylsulfonyl)-N-[(1S)-1-phenylethyl]-3-{[4-(1-pyrrolidinyl)-1-piperidinyl]methyl}-2-[3-(trifluoromethyl)phenyl]-4-quinolinecarboxamide;
7-(ethyloxy)-6-(ethylsulfonyl)-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;
3-(1,4'-bipiperidin-1'-ylmethyl)-6-(ethylsulfonyl)-7-[(1-methylethyl)oxy]-N-[(1S)-1-phenylethyl]-2-[3-(trifluoromethyl)phenyl]-4-quinolinecarboxamide;

3-(1,4'-bipiperidin-1'-ylmethyl)-6-(ethylsulfonyl)-7-[(1-methylethyl)oxy]-2-[3-(trifluoromethyl)phenyl]-N-[(1R)-2,2,2-trifluoro-1-phenylethyl]-4-quinolinecarboxamide;

6-(ethylsulfonyl)-7-[(1-methylethyl)oxy]-3-{[4-(4-morpholinyl)-1-piperidinyl]methyl}-N-[(1S)-1-phenylethyl]-2-[3-(trifluoromethyl)phenyl]-4-quinolinecarboxamide;

6-(ethylsulfonyl)-7-[(1-methylethyl)oxy]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

6-(ethylsulfonyl)-7-[(1-methylethyl)oxy]-N-[(1S)-1-phenylethyl]-3-{[4-(1-pyrrolidinyl)-1-piperidinyl]methyl}-2-[3-(trifluoromethyl)phenyl]-4-quinolinecarboxamide;

6-(ethylsulfonyl)-7-[(1-methylethyl)oxy]-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;

6-[(1-methylethyl)sulfonyl]-3-{[3-methyl-4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

6-[(1-methylethyl)sulfonyl]-3-{[3-methyl-4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;

3-[(3'-methyl-1,4'-bipiperidin-1'-yl)methyl]-6-[(1-methylethyl)sulfonyl]-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-7-(methylsulfonyl)-N-[(1S)-1-phenylethyl]-2-[3-(trifluoromethyl)phenyl]-4-quinolinecarboxamide;

3-(1,4'-bipiperidin-1'-ylmethyl)-7-(methylsulfonyl)-2-[3-(trifluoromethyl)phenyl]-N-[(1R)-2,2,2-trifluoro-1-phenylethyl]-4-quinolinecarboxamide;

7-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

7-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-7-(ethylsulfonyl)-N-(1-methyl-1-phenylethyl)-2-[3-(trifluoromethyl)phenyl]-4-quinolinecarboxamide;

3-(1,4'-bipiperidin-1'-ylmethyl)-7-(ethylsulfonyl)-N-[(1S)-1-phenylethyl]-2-[3-(trifluoromethyl)phenyl]-4-quinolinecarboxamide;

7-(ethylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

7-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-7-(ethylsulfonyl)-2-[3-(trifluoromethyl)phenyl]-N-[(1R)-2,2,2-trifluoro-1-phenylethyl]-4-quinolinecarboxamide;

6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-6-(ethylsulfonyl)-N-[(1S)-1-phenylethyl]-2-[3-(trifluoromethyl)phenyl]-4-quinolinecarboxamide;

3-(1,4'-bipiperidin-1'-ylmethyl)-6-(ethylsulfonyl)-2-[3-(trifluoromethyl)phenyl]-N-[(1R)-2,2,2-trifluoro-1-phenylethyl]-4-quinolinecarboxamide;

6-(ethylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

6-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-6-[(1-methylethyl)sulfonyl]-N-[(1S)-1-phenylethyl]-2-[3-(trifluoromethyl)phenyl]-4-quinolinecarboxamide;

3-(1,4'-bipiperidin-1'-ylmethyl)-6-[(1-methylethyl)sulfonyl]-2-[3-(trifluoromethyl)phenyl]-N-[(1R)-2,2,2-trifluoro-1-phenylethyl]-4-quinolinecarboxamide;

6-[(1-methylethyl)sulfonyl]-3-{[4-(4-morpholinyl)-1-piperidinyl]methyl}-N-[(1S)-1-phenylethyl]-2-[3-(trifluoromethyl)phenyl]-4-quinolinecarboxamide;

7-chloro-6-(methylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

7-chloro-6-(methylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

6-[(1-methylethyl)sulfonyl]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

6-[(1-methylethyl)sulfonyl]-3-{[4-(4-morpholinyl)-1-piperidinyl]methyl}-2-[3-(trifluoromethyl)phenyl]-N-[(1S)-2,2,2-trifluoro-1-phenylethyl]-4-quinolinecarboxamide;

3-(1,4'-bipiperidin-1'-ylmethyl)-7-chloro-6-(methylsulfonyl)-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-7-chloro-6-(methylsulfonyl)-N-[(1S)-1-phenylethyl]-2-[3-(trifluoromethyl)phenyl]-4-quinolinecarboxamide;

3-(1,4'-bipiperidin-1'-ylmethyl)-7-chloro-6-(ethylsulfonyl)-N-[(1S)-1-phenylethyl]-2-[3-(trifluoromethyl)phenyl]-4-quinolinecarboxamide;

3-(1,4'-bipiperidin-1'-ylmethyl)-7-chloro-6-(ethylsulfonyl)-2-[3-(trifluoromethyl)phenyl]-N-[(1R)-2,2,2-trifluoro-1-phenylethyl]-4-quinolinecarboxamide;

7-chloro-6-(ethylsulfonyl)-3-{[4-(4-morpholinyl)-1-piperidinyl]methyl}-N-[(1S)-1-phenylethyl]-2-[3-(trifluoromethyl)phenyl]-4-quinolinecarboxamide;

7-chloro-6-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-7-chloro-6-[(1-methylethyl)sulfonyl]-N-[(1S)-1-phenylethyl]-2-[3-(trifluoromethyl)phenyl]-4-quinolinecarboxamide;

3-(1,4'-bipiperidin-1'-ylmethyl)-7-chloro-6-[(1-methylethyl)sulfonyl]-2-[3-(trifluoromethyl)phenyl]-N-[(1R)-2,2,2-trifluoro-1-phenylethyl]-4-quinolinecarboxamide;

7-chloro-6-[(1-methylethyl)sulfonyl]-3-{[4-(4-morpholinyl)-1-piperidinyl]methyl}-N-[(1S)-1-phenylethyl]-2-[3-(trifluoromethyl)phenyl]-4-quinolinecarboxamide;

72) 7-chloro-6-[(1-methylethyl)sulfonyl]-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

6-(methylsulfonyl)-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;

6-(methylsulfonyl)-N-[(1S)-1-phenylethyl]-3-{[4-(1-pyrrolidinyl)-1-piperidinyl]methyl}-2-[3-(trifluoromethyl)phenyl]-4-quinolinecarboxamide;

3-({4-[(3S)-3-fluoro-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-({4-[(3S)-3-fluoro-1-pyrrolidinyl]-1-piperidinyl}methyl)-6-(methylsulfonyl)-N-[(1S)-1-phenylethyl]-2-[3-(trifluoromethyl)phenyl]-4-quinolinecarboxamide;

3-[(4,4-difluoro-1,4'-bipiperidin-1'-yl)methyl]-6-(methylsulfonyl)-2-[3-(trifluoromethyl)phenyl]-N-[(1R)-2,2,2-trifluoro-1-phenylethyl]-4-quinolinecarboxamide;

3-[(4,4-difluoro-1,4'-bipiperidin-1'-yl)methyl]-6-(methylsulfonyl)-N-[(1S)-1-phenylethyl]-2-[3-(trifluoromethyl)phenyl]-4-quinolinecarboxamide;

3-{[(3S)-3-hydroxy-1,4'-bipiperidin-1'-yl]methyl}-6-(methylsulfonyl)-2-[3-(trifluoromethyl)phenyl]-N-[(1R)-2,2,2-trifluoro-1-phenylethyl]-4-quinolinecarboxamide;

3-{[(3S)-3-hydroxy-1,4'-bipiperidin-1'-yl]methyl}-6-(methylsulfonyl)-N-[(1S)-1-phenylethyl]-2-[3-(trifluoromethyl)phenyl]-4-quinolinecarboxamide;

3-{[(3R)-3-hydroxy-1,4'-bipiperidin-1'-yl]methyl}-6-(methylsulfonyl)-2-[3-(trifluoromethyl)phenyl]-N-[(1R)-2,2,2-trifluoro-1-phenylethyl]-4-quinolinecarboxamide;

3-{[(3R)-3-hydroxy-1,4'-bipiperidin-1'-yl]methyl}-6-(methylsulfonyl)-N-[(1S)-1-phenylethyl]-2-[3-(trifluoromethyl)phenyl]-4-quinolinecarboxamide;

6-(methylsulfonyl)-2-[3-(trifluoromethyl)phenyl]-3-({4-[2-(trifluoromethyl)-1-pyrrolidinyl]-1-piperidinyl}methyl)-N-[(1R)-2,2,2-trifluoro-1-phenylethyl]-4-quinolinecarboxamide;

6-(methylsulfonyl)-N-[(1S)-1-phenylethyl]-2-[3-(trifluoromethyl)phenyl]-3-({4-[2-(trifluoromethyl)-1-pyrrolidinyl]-1-piperidinyl}methyl)-4-quinolinecarboxamide;

3-{[3-(methyloxy)-1,4'-bipiperidin-1'-yl]methyl}-6-(methylsulfonyl)-2-[3-(trifluoromethyl)phenyl]-N-[(1R)-2,2,2-trifluoro-1-phenylethyl]-4-quinolinecarboxamide;

3-[(4-fluoro-1,4'-bipiperidin-1'-yl)methyl]-6-(methylsulfonyl)-2-[3-(trifluoromethyl)phenyl]-N-[(1R)-2,2,2-trifluoro-1-phenylethyl]-4-quinolinecarboxamide;

3-{[4-(diethylamino)-1-piperidinyl]methyl}-6-(methylsulfonyl)-2-[3-(trifluoromethyl)phenyl]-N-[(1R)-2,2,2-trifluoro-1-phenylethyl]-4-quinolinecarboxamide;

6-(methylsulfonyl)-3-{[4-(4-morpholinyl)-1-piperidinyl]methyl}-2-[4-(trifluoromethyl)phenyl]-N-[(1R)-2,2,2-trifluoro-1-phenylethyl]-4-quinolinecarboxamide;

6-(methylsulfonyl)-3-{[4-(4-morpholinyl)-1-piperidinyl]methyl}-N-[(1S)-1-phenyl ethyl]-2-[4-(trifluoromethyl)phenyl]-4-quinolinecarboxamide;

3-(1,4'-bipiperidin-1'-ylmethyl)-6-(methylsulfonyl)-2-[4-(trifluoromethyl)phenyl]-N-[(1R)-2,2,2-trifluoro-1-phenylethyl]-4-quinolinecarboxamide;

3-(1,4'-bipiperidin-1'-ylmethyl)-6-(methylsulfonyl)-N-[(1S)-1-phenylethyl]-2-[4-(trifluoromethyl)phenyl]-4-quinolinecarboxamide;

6-(methylsulfonyl)-3-{[4-(1-pyrrolidinyl)-1-piperidinyl]methyl}-2-[4-(trifluoromethyl)phenyl]-N-[(1R)-2,2,2-trifluoro-1-phenylethyl]-4-quinolinecarboxamide;

6-(methylsulfonyl)-N-[(1S)-1-phenylethyl]-3-{[4-(1-pyrrolidinyl)-1-piperidinyl]methyl}-2-[4-(trifluoromethyl)phenyl]-4-quinolinecarboxamide;

3-(1,4'-bipiperidin-1'-ylmethyl)-2-[4-(methyloxy)phenyl]-6-(methylsulfonyl)-N-[(1R)-2,2,2-trifluoro-1-phenylethyl]-4-quinolinecarboxamide;

2-(3,4-dichlorophenyl)-6-(methylsulfonyl)-3-{[4-(4-morpholinyl)-1-piperidinyl]methyl}-N-[(1R)-2,2,2-trifluoro-1-phenylethyl]-4-quinolinecarboxamide;

2-(3,4-dichlorophenyl)-6-(methylsulfonyl)-3-{[4-(4-morpholinyl)-1-piperidinyl]methyl}-N-[(1S)-1-phenylethyl]-4-quinolinecarboxamide;

3-(1,4'-bipiperidin-1'-ylmethyl)-2-(3,4-dichlorophenyl)-6-(methylsulfonyl)-N-[(1R)-2,2,2-trifluoro-1-phenylethyl]-4-quinolinecarboxamide;

3-(1,4'-bipiperidin-1'-ylmethyl)-2-(3,4-dichlorophenyl)-6-(methylsulfonyl)-N-[(1S)-1-phenylethyl]-4-quinolinecarboxamide;

2-(3,4-dichlorophenyl)-6-(methylsulfonyl)-3-{[4-(1-pyrrolidinyl)-1-piperidinyl]methyl}-N-[(1R)-2,2,2-trifluoro-1-phenylethyl]-4-quinolinecarboxamide;

2-(3,4-dichlorophenyl)-6-(methylsulfonyl)-N-[(1S)-1-phenylethyl]-3-{[4-(1-pyrrolidinyl)-1-piperidinyl]methyl}-4-quinolinecarboxamide;

6-[(1-methylethyl)sulfonyl]-7-(methyloxy)-3-{[4-(4-morpholinyl)-1-piperidinyl]methyl}-2-[3-(trifluoromethyl)phenyl]-N-[(1S)-2,2,2-trifluoro-1-phenylethyl]-4-quinolinecarboxamide;

3-{[4-(3,3-difluoro-1-pyrrolidinyl)-1-piperidinyl]methyl}-6-(methylsulfonyl)-2-[3-(trifluoromethyl)phenyl]-N-[(1R)-2,2,2-trifluoro-1-phenylethyl]-4-quinolinecarboxamide;

3-{[4-(3,3-difluoro-1-pyrrolidinyl)-1-piperidinyl]methyl}-6-(methylsulfonyl)-N-[(1S)-1-phenylethyl]-2-[3-(trifluoromethyl)phenyl]-4-quinolinecarboxamide;

3-({4-[(3R)-3-hydroxy-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-({4-[(3S)-3-hydroxy-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

2-(3-bromophenyl)-6-(methylsulfonyl)-3-{[4-(4-morpholinyl)-1-piperidinyl]methyl}-N-[(1R)-2,2,2-trifluoro-1-phenylethyl]-4-quinolinecarboxamide;

6-[(1-methylethyl)sulfonyl]-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;

6-[(1-methylethyl)sulfonyl]-N-[(1S)-1-phenylethyl]-3-{[4-(1-pyrrolidinyl)-1-piperidinyl]methyl}-2-[3-(trifluoromethyl)phenyl]-4-quinolinecarboxamide;

2-(3-bromophenyl)-6-(methylsulfonyl)-3-{[4-(4-morpholinyl)-1-piperidinyl]methyl}-N-[(1S)-1-phenylethyl]-4-quinolinecarboxamide;

3-(1,4'-bipiperidin-1'-ylmethyl)-2-(3-bromophenyl)-6-(methylsulfonyl)-N-[(1R)-2,2,2-trifluoro-1-phenylethyl]-4-quinolinecarboxamide;

3-(1,4'-bipiperidin-1'-ylmethyl)-2-(3-bromophenyl)-6-(methylsulfonyl)-N-[(1S)-1-phenylethyl]-4-quinolinecarboxamide;

2-(3-bromophenyl)-6-(methylsulfonyl)-3-{[4-(1-pyrrolidinyl)-1-piperidinyl]methyl}-N-[(1R)-2,2,2-trifluoro-1-phenylethyl]-4-quinolinecarboxamide;

2-(3-bromophenyl)-6-(methylsulfonyl)-N-[(1S)-1-phenylethyl]-3-{[4-(1-pyrrolidinyl)-1-piperidinyl]methyl}-4-quinolinecarboxamide;

3-(1,4'-bipiperidin-1'-ylmethyl)-6-(methylsulfonyl)-2-[3-(trifluoromethyl)phenyl]-N-[(1S)-2,2,2-trifluoro-1-phenylethyl]-4-quinolinecarboxamide;

3-({4-[(2R)-2-methyl-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-[(3-fluoro-1,4'-bipiperidin-1'-yl)methyl]-6-(methylsulfonyl)-2-[3-(trifluoromethyl)phenyl]-N-[(1R)-2,2,2-trifluoro-1-phenylethyl]-4-quinolinecarboxamide;

3-({4-[(2S)-2-methyl-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-({4-[(2S)-2-(hydroxymethyl)-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-({4-[(2R)-2-(hydroxymethyl)-1-pyrrolidinyl]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-{[3-(hydroxymethyl)-1,4'-bipiperidin-1'-yl]methyl}-6-(methylsulfonyl)-2-[3-(trifluoromethyl)phenyl]-N-[(1R)-2,2,2-trifluoro-1-phenylethyl]-4-quinolinecarboxamide;

3-[(4-{methyl[2-(methyloxy)ethyl]amino}-1-piperidinyl)methyl]-6-(methylsulfonyl)-2-[3-(trifluoromethyl)phenyl]-N-[(1R)-2,2,2-trifluoro-1-phenylethyl]-4-quinolinecarboxamide;

3-({4-[ethyl(propyl)amino]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-({4-[methyl(2-methylpropyl)amino]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-{[4-(hexahydro-1H-azepin-1-yl)-1-piperidinyl]methyl}-6-(methylsulfonyl)-2-[3-(trifluoromethyl)phenyl]-N-[(1R)-2,2,2-trifluoro-1-phenylethyl]-4-quinolinecarboxamide;

3-{[4-(methyloxy)-1,4'-bipiperidin-1'-yl]methyl}-6-(methylsulfonyl)-2-[3-(trifluoromethyl)phenyl]-N-[(1R)-2,2,2-trifluoro-1-phenylethyl]-4-quinolinecarboxamide;

3-({4-[methyl(propyl)amino]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

3-[(4-{(2S)-2-[(methyloxy)methyl]-1-pyrrolidinyl}-1-piperidinyl)methyl]-6-(methylsulfonyl)-2-[3-(trifluoromethyl)phenyl]-N-[(1R)-2,2,2-trifluoro-1-phenylethyl]-4-quinolinecarboxamide;

3-({4-[(2-hydroxyethyl)(methyl)amino]-1-piperidinyl}methyl)-6-(methylsulfonyl)-2-[3-(trifluoromethyl)phenyl]-N-[(1R)-2,2,2-trifluoro-1-phenylethyl]-4-quinolinecarboxamide;

6-(ethylsulfonyl)-7-(methyloxy)-3-{[4-(1-pyrrolidinyl)-1-piperidinyl]methyl}-2-[3-(trifluoromethyl)phenyl]-N-[(1R)-2,2,2-trifluoro-1-phenylethyl]-4-quinolinecarboxamide;

6-(ethylsulfonyl)-7-(methyloxy)-N-[(1S)-1-phenylethyl]-3-{[4-(1-pyrrolidinyl)-1-piperidinyl]methyl}-2-[3-(trifluoromethyl)phenyl]-4-quinolinecarboxamide;

6-(ethylsulfonyl)-3-[(4-fluoro-1,4'-bipiperidin-1'-yl)methyl]-7-(methyloxy)-2-[3-(trifluoromethyl)phenyl]-N-[(1R)-2,2,2-trifluoro-1-phenylethyl]-4-quinolinecarboxamide; and 6-(ethylsulfonyl)-3-[(4-fluoro-1,4'-bipiperidin-1'-yl)methyl]-7-(methyloxy)-N-[(1S)-1-phenylethyl]-2-[3-(trifluoromethyl)phenyl]-4-quinolinecarboxamide; or a pharmaceutically acceptable salt thereof.

6. A compound of claim 1 selected from the group consisting of:

3-(1,4'-bipiperidin-1'-ylmethyl)-6-(methylsulfonyl)-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-6-(ethylsulfonyl)-7-(methyloxy)-2-[3-(trifluoromethyl)phenyl]-N-[(1R)-2,2,2-trifluoro-1-phenylethyl]-4-quinolinecarboxamide;

7-[(1-methylethyl)oxy]-6-(methylsulfonyl)-3-[4-(4-morpholinyl)-1-piperidinyl]methyl-2-[3-(trifluoromethyl)phenyl]-N-[(1R)-2,2,2-trifluoro-1-phenylethyl]-4-quinolinecarboxamide;

3-(1,4'-bipiperidin-1'-ylmethyl)-6-[(1-methylethyl)sulfonyl]-7-(methyloxy)-2-[3-(trifluoromethyl)phenyl]-N-[(1R)-2,2,2-trifluoro-1-phenylethyl]-4-quinolinecarboxamide;

6-[(1-methylethyl)sulfonyl]-7-(methyloxy)-3-[4-(4-morpholinyl)-1-piperidinyl]methyl-2-[3-(trifluoromethyl)phenyl]-N-[(1R)-2,2,2-trifluoro-1-phenylethyl]-4-quinolinecarboxamide;

7-(ethyloxy)-6-[(1-methylethyl)sulfonyl]-3-{[4-(4-morpholinyl)-1-piperidinyl]methyl}-2-[3-(trifluoromethyl)phenyl]-N-[(1R)-2,2,2-trifluoro-1-phenylethyl]-4-quinoline carboxamide;

7-(ethyloxy)-6-(ethylsulfonyl)-3-{[4-(4-morpholinyl)-1-piperidinyl]methyl}-2-[3-(trifluoromethyl)phenyl]-N-[(1R)-2,2,2-trifluoro-1-phenylethyl]-4-quinoline carboxamide;

6-[(1-methylethyl)sulfonyl]-3-{[3-methyl-4-(4-morpholinyl)-1-piperidinyl]methyl}-2-[3-(trifluoromethyl)phenyl]-N-[(1R)-2,2,2-trifluoro-1-phenylethyl]-4-quinoline carboxamide;

or a pharmaceutically acceptable salt thereof.

7. A compound of claim 1 selected from the group consisting of:

3-(1,4'-bipiperidin-1'-ylmethyl)-6-[(1-methylethyl)sulfonyl]-7-(methyloxy)-2-[3-(trifluoromethyl)phenyl]-N-[(1R)-2,2,2-trifluoro-1-phenylethyl]-4-quinolinecarboxamide;

6-[(1-methylethyl)sulfonyl]-7-(methyloxy)-3-{[4-(4-morpholinyl)-1-piperidinyl]methyl}-2-[3-(trifluoromethyl)phenyl]-N-[(1R)-2,2,2-trifluoro-1-phenylethyl]-4-quinolinecarboxamide;

or a pharmaceutically acceptable salt thereof.

8. A pharmaceutical composition comprising a compound of claim 1 and a pharmaceutically acceptable carrier or excipient.

* * * * *